US007557200B2

(12) United States Patent
Wu et al.

(10) Patent No.: US 7,557,200 B2
(45) Date of Patent: Jul. 7, 2009

(54) SUPERIOR MOLECULAR VACCINE BASED ON SELF-REPLICATING RNA, SUICIDAL DNA OR NAKED DNA VECTOR, THAT LINKS ANTIGEN WITH POLYPEPTIDE THAT PROMOTES ANTIGEN PRESENTATION

(75) Inventors: Tzyy-Choou Wu, Stevenson, MD (US); Chien-Fu Hung, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 175 days.

(21) Appl. No.: 10/470,543

(22) PCT Filed: Feb. 1, 2002

(86) PCT No.: PCT/US02/02598

§ 371 (c)(1),
(2), (4) Date: Mar. 5, 2004

(87) PCT Pub. No.: WO02/061113

PCT Pub. Date: Aug. 8, 2002

(65) Prior Publication Data

US 2005/0277605 A1 Dec. 15, 2005

(51) Int. Cl.
*C07H 21/04* (2006.01)
(52) U.S. Cl. .................................... 536/23.4; 536/23.7
(58) Field of Classification Search ........................ None
See application file for complete search history.

(56) References Cited

U.S. PATENT DOCUMENTS

| 5,844,089 | A * | 12/1998 | Hoffman et al. ............. 530/385 |
| 6,734,173 | B1 * | 5/2004 | Wu et al. ...................... 514/44 |
| 2004/0028693 | A1 | 2/2004 | Wu et al. |
| 2004/0086845 | A1 | 5/2004 | Wu et al. |
| 2005/0277605 | A1 | 12/2005 | Wu et al. |
| 2007/0026076 | A1 | 2/2007 | Wu et al. |

FOREIGN PATENT DOCUMENTS

| WO | WO 9907860 A1 * | 2/1999 |
| WO | WO-01/29233 | 4/2001 |
| WO | WO-02/09645 | 2/2002 |
| WO | WO-02/12281 | 2/2002 |
| WO | WO-02/061113 | 8/2002 |
| WO | WO-03/085085 | 10/2003 |
| WO | WO-2004/098526 | 11/2004 |
| WO | WO-2005/047501 | 5/2005 |
| WO | WO-2005/081716 | 9/2005 |
| WO | WO-2006/073970 | 7/2006 |
| WO | WO-2006/081323 | 8/2006 |

OTHER PUBLICATIONS

Suzue et al. 1996, J. Immunol. vol. 156: 873-879.*
Rouse et al., 1994, J. Virol. vol. 68: 5685-5689. Eisenbraun et al., 1993, DNA and Cell Biology, vol. 12: 791-797.*
Bredenbeek et al., 1993, J. Virol. vol. 67: 6439-6446. Mikayama et al., 1993, PNAS, vol. 90: 10056-10060.*
Whisstock et al., 2003, Quarterly Reviews of Biophysics, vol. 3: 307-340. Lazar et al., 1988, Mol. Cell. Biol. vol. 8: 1247-1252.*
Burgess et al., 1990, J. Cell. Biol. vol. 111: 2129-2138. Meinkoth et al., 1984, Annalytical Biochemistry, vol. 138: 267-284.*
Wang et al., 2001, J. Biol. Chem. vol. 276: 49213-49220.*
Hung, C.F. et al., Enhancement of DNA Vaccine Potency by Linkage of Antigen Gene to a Gene Encoding the Extracellular Domain of Fms-like Tyrosine Kinase 3-ligand. Cancer Research, Feb. 2001, vol. 61, pp. 1080-1088.
Cheng et al., Enhancement of Sindbis Virus Self-Replicating RNA Vaccine Potency by Linkage of *Mycobacterium tuberculosis* Heat Shock Protein 70 Gene to an Antigen Gene, J. Immunology, 2001, vol. 166, pp. 6218-6226.
Suzue, K. et al., Heat Shock fusion proteins as vehicles for antigen delivery into the Major Histocompatibility complex Class I presentation pathway, PNAS USA, 1997, vol. 94, pp. 13146-13151.
Chu, N.R. et al., Immunotherapy of a human papilloma virus (HPV) type 16 E7, expressing tumour by administration of a fusion protein comprising *Mycobacterium bovis* bacilli Calmette-Guerin (BCG) hsp65 and HPV 16 E7, Clin. Exp. Immun. 2000, vol. 121, pp. 216-225.
More, S. et al., Activation of cytotoxic T cells in vitro by recombinant gp96 fusion proteins irrespective of the fused antigenic peptide sequence. Immunology Letters, 1991, vol. 69, pp. 275-282.
Leitner, W. et al., DNA and RNA-based Vaccines: Principles, Progress and Prospects, Vaccine, 2000, vol. 18, pp. 765-777.
Chen, C-H. et al., Enhancement of DNA Vaccine Potency by Linkage of Antigen Gene to an HSP70 Gene, Cancer Research, 2000, vol. 60, pp. 1035-1042.
Hsu, K-F. et al., Enhancement of suicidal DNA vaccine potency by linking *Mycobacterium tuberculosis* heat shock protein 70 to an antigen, Gene Therapy, 2001, vol. 8, pp. 376-383.

* cited by examiner

*Primary Examiner*—G. R Ewoldt
*Assistant Examiner*—Amy E Juedes
(74) *Attorney, Agent, or Firm*—Foley Hoag LLP

(57) ABSTRACT

Improved molecular vaccines comprise nucleic acid vectors that encode a fusion polypeptide that includes polypeptide or peptide physically linked to an antigen. The linked polypeptide is one that (a) promotes processing of the expressed fusion polypeptide via the MHC class I pathway and/or (b) promotes development or activity of antigen presenting cells, primarily dendritic cells. These vaccines employ one of several types of nucleic acid vectors, each with its own relative advantages: naked DNA plasmids, self-replicating RNA replicons and suicidal DNA-based on viral RNA replicons. Administration of such a vaccine results in enhance immune responses, primarily those mediated by CD8+ cytotoxic T lymphocytes, directed against the immunizing antigen part of the fusion polypeptide. Such vaccines are useful against tumor antigens, viral antigens and antigens of other pathogenic microorganisms and can be used in the prevention or treatment of diseases that include cancer and infections.

36 Claims, 28 Drawing Sheets

(*: corrected by transfection efficiency)

Days after TC-1 challenge

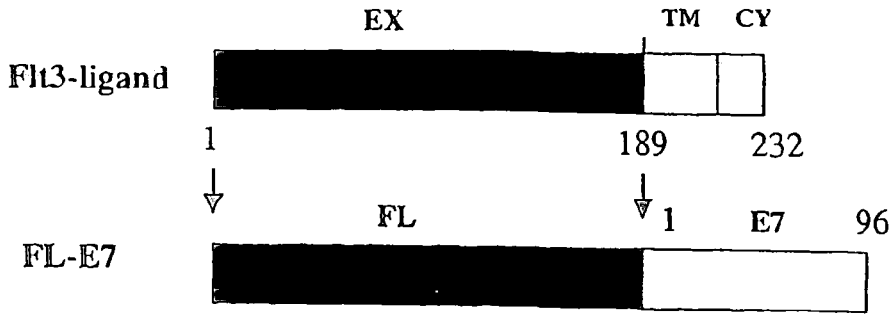

(B)

```
1/1                                          31/11
atg aca gtg ctg gcg cca gcc tgg agc cca aat tcc tcc ctg ttg ctg ctg ttg ctg ctg
Met thr val leu ala pro ala trp ser pro asn ser ser leu leu leu leu leu leu leu
61/21                                        91/31
ctg agt cct tgc ctg cgg ggg aca cct gac tgt tac ttc agc cac agt ccc atc tcc tcc
leu ser pro cys leu arg gly thr pro asp cys tyr phe ser his ser pro ile ser ser
121/41                                       151/51
aac ttc aaa gtg aag ttt aga gag ttg act gac cac ctg ctt aaa gat tac cca gtc act
asn phe lys val lys phe arg glu leu thr asp his leu leu lys asp tyr pro val thr
181/61                                       211/71
gtg gcc gtc aat ctt cag gac gag aag cac tgc aag gcc ttg tgg agc ctc ttc cta gcc
val ala val asn leu gln asp glu lys his cys lys ala leu trp ser leu phe leu ala
241/81                                       271/91
cag cgc tgg ata gag caa ctg aag act gtg gca ggg tct aag atg caa acg ctt ctg gag
gln arg trp ile glu gln leu lys thr val ala gly ser lys met gln thr leu leu glu
301/101                                      331/111
gac gtc aac acc gag ata cat ttt gtc acc tca tgt acc ttc cag ccc cta cca gaa tgt
asp val asn thr glu ile his phe val thr ser cys thr phe gln pro leu pro glu cys
361/121                                      391/131
ctg cga ttc gtc cag acc aac atc tcc cac ctc ctg aag gac acc tgc aca cag ctg ctt
leu arg phe val gln thr asn ile ser his leu leu lys asp thr cys thr gln leu leu
421/141                                      451/151
gct ctg aag ccc tgt atc ggg aag gcc tgc cag aat ttc tct cgg tgc ctg gag gtg cag
ala leu lys pro cys ile gly lys ala cys gln asn phe ser arg cys leu glu val gln
481/161                                      511/171
tgc cag ccg gac tcc tcc acc ctg ctg ccc cca agg agt ccc ata gcc cta gaa gcc acg
cys gln pro asp ser ser thr leu leu pro pro arg ser pro ile ala leu glu ala thr
541/181                                      571/191
gag ctc cca gag cct cgg ccc agg cag gga tcc atg cat gga gat aca cct aca ttg cat
glu leu pro glu pro arg pro arg gln gly ser met his gly asp thr pro thr leu his
601/201                                      631/211
gaa tat atg tta gat ttg caa cca gag aca act gat ctc tac tgt tat gag caa tta aat
glu tyr met leu asp leu gln pro glu thr thr asp leu tyr cys tyr glu gln leu asn
661/221                                      691/231
gac agc tca gag gag gag gat gaa ata gat ggt cca gct gga caa gca gaa ccg gac aga
asp ser ser glu glu glu asp glu ile asp gly pro ala gly gln ala glu pro asp arg
721/241                                      751/251
gcc cat tac aat att gta acc ttt tgt tgc aag tgt gac tct acg ctt cgg ttg tgc gta
ala his tyr asn ile val thr phe cys cys lys cys asp ser thr leu arg leu cys val
781/261                                      811/271
caa agc aca cac gta gac att cgt act ttg gaa gac ctg tta atg ggc aca cta gga att
gln ser thr his val asp ile arg thr leu glu asp leu leu met gly thr leu gly ile
841/281                                      871/291
gtg tgc ccc atc tgt tct cag gat aag ctt aag ttt aaa ccg ctg atc agc ctc gac tgt
val cys pro ile cys ser gln asp lys leu lys phe lys pro leu ile ser leu asp cys
901/301
gcc ttc tag
ala phe AMB
```

Days after TC-1 challenge

FIG. 22
(A)
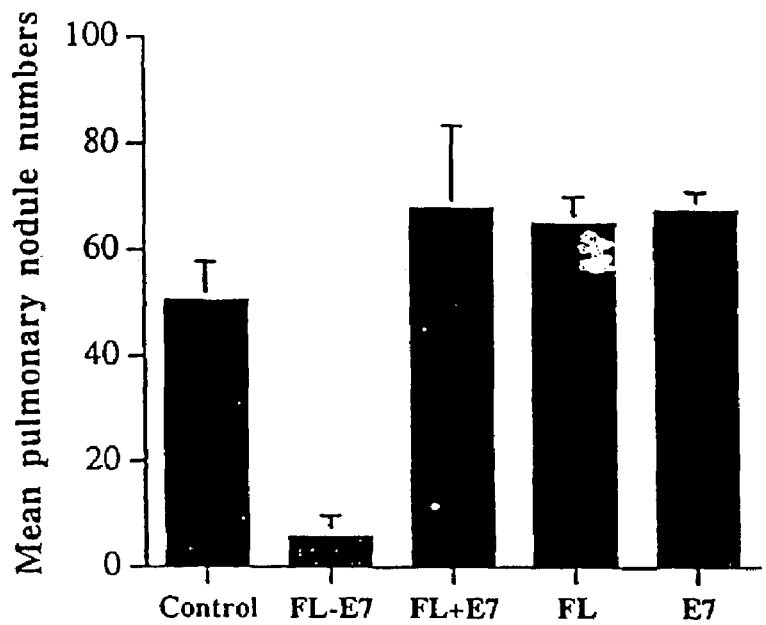
(B)
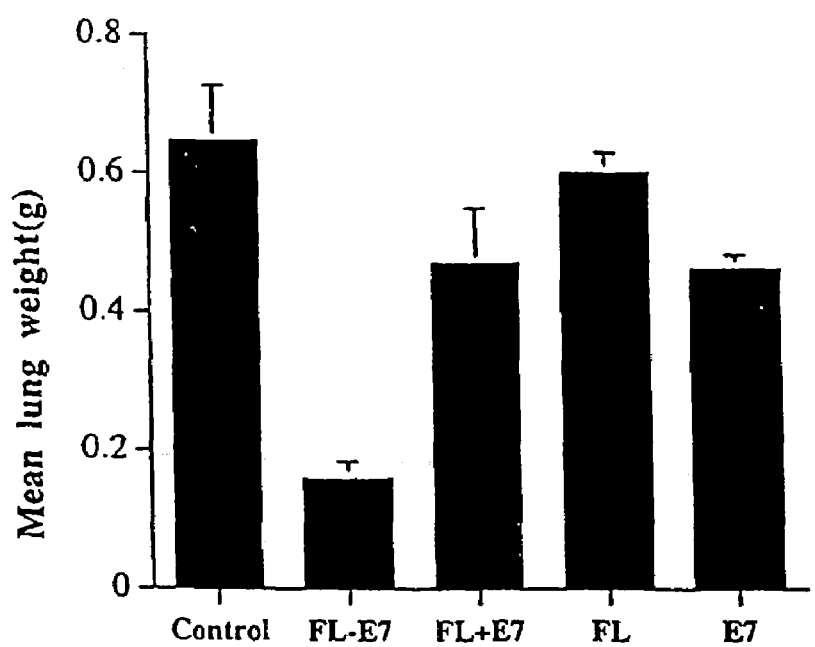

SUPERIOR MOLECULAR VACCINE BASED ON SELF-REPLICATING RNA, SUICIDAL DNA OR NAKED DNA VECTOR, THAT LINKS ANTIGEN WITH POLYPEPTIDE THAT PROMOTES ANTIGEN PRESENTATION

BACKGROUND OF THE INVENTION

1. Field of the Invention

The present invention in the fields of molecular biology, immunology and medicine relates to chimeric nucleic acids encoding fusion proteins and their use as vaccines to enhance immune responses, primarily cytotoxic T lymphocyte (CTL) responses to specific antigens such as tumor antigens. The fusion proteins comprise an antigenic polypeptide fused to a protein that promotes processing via the MHC class I pathway and/or promotes development or activity of antigen presenting cells (APCs), primarily dendritic cells (DCs). Preparation of the foregoing nucleic acid constructs as naked DNA plasmids, self-replicating RNA replicons and suicidal DNA-based viral RNA replicons confer various advantages on these molecular vaccines.

2. Description of the Background Art

Antigen-specific cancer immunotherapy has emerged as a promising approach because it is capable of engendering specific immunity against neoplastic cells while sparing normal cells. Increasing evidence suggests that professional antigen-presenting cells (APCs), particularly dendritic cells (DCs), are central players in this process. An effective vaccine strategy includes targeting the tumor antigen to professional APCs that in turn activate antigen-specific T cells (for review, see (Chen, CH et al., *J Biomed Sci.* 5:231-52, 1998.).

Recently, DNA vaccines have become attractive as an approach for generating antigen-specific immunotherapy (for review, see (Robinson, H L *Vaccine* 15:785-778, 1997; Robinson, H L et al., *Semin Immunol.* 9:271-83, 1997; Pardoll, D M et al., *Immunity.* 3:165-9, 1995; Donnelly, J J et al., *Annu Rev Immunol.* 15: 617-48, 1997). The advantages of naked DNA include purity, ease of preparation and stability. In addition, DNA-based vaccines can be prepared inexpensively and rapidly in large-scale. Furthermore, multiple DNA vaccines can be administered simultaneously. However, naked DNA vaccines raise concerns such as potential integration into the host genome and cell transformation. Because they do not have the intrinsic ability to amplify in vivo as do viral vaccines, DNA vaccines may be more limited in their potency.

The present inventors conceived that a directing a DNA vaccine encoding an antigen (in the form of a fusion protein) to cells which activate immune responses, such as DCs, would enhance the vaccine's potency. Others demonstrated that linking DNA encoding the cytokine GM-CSF gene to DNA encoding an HIV or hepatitis C antigen enhanced the potency of DNA vaccines (Lee, A H et al., *Vaccine* 17: 473-9, 1999; Lee, S W et al., *J Virol.* 72: 8430- 6, 1998). The chigmeric GM-CSF/antigen is believed to act as an immunostimulatory signal to DCs, inducing their differentiation from an immature form (Banchereau, J et al., *Nature* 392: 245-52, 1998). Since DCs and their precursors express high levels of GM-CSF receptors, the chimeric GM-CSF/antigen should target and concentrate the linked antigen to the DCs and further improve the vaccine's potency.

Use of self-replicating RNA vaccines (RNA replicons) has also been identified as an important strategy in nucleic acid vaccine development. RNA replicon vaccines may be derived from alphavirus vectors, such as Sindbis virus (Hariharan, M J et al., 1998. *J Virol* 72:950-8.), Semliki Forest virus (Berglund, P M et al., 1997. *AIDS Res Hum Retroviruses* 13:1487-95; Ying, H T et al., 1999. *Nat Med* 5:823-7) or Venezuelan equine encephalitis virus (Pushko, P M et al., 1997. *Virology* 239:389-401). These self-replicating and self-limiting vaccines may be administered as either (1) RNA or (2) DNA which is then transcribed into RNA replicons in cells transfected in vitro or in vivo (Berglund, P C et al., 1998. *Nat Biotechnol* 16:562-5; Leitner, W W et al., 2000. *Cancer Res* 60:51-5).

Self-replicating RNA infects a diverse range of cell types and allows the expression of a linked antigen of interest at high levels (Huang, H V 1996. *Curr Opin Biotechnol* 7:531-5) Because viral replication is toxic to infected host cells, such self-replicating RNA preparations eventually causes lysis of the transfected cells (Frolov, I et al., 1996. *J Virol* 70:1182-90). These vectors cannot integrate into the host genome, and therefore do not raise concerns of associated with naked DNA vaccines. This is particularly important for vaccine development where target proteins are potentially oncogenic, such as human papillomavirus (HPV) E6 and E7 proteins.

The present inventors and their colleagues recently demonstrated that linkage of HPV-16 E7 antigen to Mtb heat shock protein 70 (Hsp70) leads to the enhancement of DNA vaccine potency (Chen, CH et al., 2000. *Cancer Research* 60:1035-1042). (See also co-pending patent applications U.S. Ser. No. 09/501,097, filed 9 Feb. 2000; and U.S. Ser. No. 099/421,608, filed 20 Oct. 1999, all of which are incorporated by reference in their entirety.) Immunization with HSP complexes isolated from tumor or virus-infected cells induced potent anti-tumor immunity (Janetzki, S et al., 1998. *J Immunother* 21:269-76) or antiviral immunity (Heikema, A E et al, *Immunol Lett* 57:69-74). In addition, immunogenic HSP-peptide complexes dould be reconstituted in vitro by mixing the peptides with HSPs (Ciuputu, AM et al., 1998. *J Exp Med* 187:685-91). Furthermore, HSP-based protein vaccines have been created by fusing antigens to HSPs (Suzue, K et al., 1996. *J Immunol* 156:873-9). The results of these investigations point to HSPs a attractive candidates for use in immunotherapy. However, prior to the present inventors' work, HSP vaccines were all peptide/protein-based vaccines or, in more recent cases, were in the form of naked DNA. To date, there have been no reports of HSPs incorporated into self-replicating RNA vaccines.

Another molecule that stimulates growth of DC precursors and can help in generating large numbers of DCs in vivo is Flt3-ligand ("FL") (Maraskovsky, E et al., *J Exp Med* 184: 1953-62, 1996, Shurin, M R et al., *Cell Lmmunol.* 179: 174-84, 1997). FL has emerged as an important molecule in the development of tumor vaccines that augment numbers and action of DCs in vivo. Flt3, a murine tyrosine kinase receptor, first described in 1991 (Rosnet, O et al., *Oncogene.* 6: 1641-50, 1991), was found to be a member of the type III receptor kinase family which includes -kit and c-fms (for review, see (Lyman, S D *Curr Opin Hematol.* 5:192-6, 1998). In hematopoietic tissues, the Flt3expression is restricted to the CD34+ progenitor population. Flt3 has been used to identify and subsequently clone the corresponding ligand, Flt3-ligand or "FL" (Lyman, S D et al., *Cell.* 75: 1157-67, 1993; Hannum, C et al., *Nature.* 368: 643-8, 1994).

The predominant form of FL is synthesized as a transmembrane protein from which the soluble form is believed to be generated by proteolytic cleavage. The soluble form of FL (the extracellular domain or "ECD") is functionally similar to intact FL (Lyman, S D et al., *Cell.* 75: 1157-67, 1993). These proteins function by binding to and activating unique tyrosine kinase receptors. Expression of the Flt3 receptor is primarily restricted, among hematopoietic cells, to the most primitive progenitor cells, including DC precursors. The soluble ECD of FL induced strong anti-tumor effects against several murine model tumors including fibrosarcoma (Lynch, D H et al., *Nat Med.* 3: 625-31, 1997), breast cancer (Chen, K et al *Cancer Res.* 57: 3511-6, 1997; Braun, S E et al., *Hum Gene*

*Ther.* 10: 2141-51, 1999), liver cancer (Peron, J M et al., *J Immunol.* 161: 6164-70, 1998), lung cancer (Chakravarty, P K et al., *Cancer Res.* 59: 6028-32, 1999), melanoma and lymphoma (Esche, C et al., *Cancer Res.* 58: 380-3, 1998).

There is a need in the art for improved molecular vaccines, such as nucleic acid vaccines, that combine potency and safety. The present invention helps meet this need by its design of novel fusion or chimeric polypeptides and nucleic acids coding therefor, that link the antigen with specialized polypeptides that promote antigen presentation by various mechanisms and that exploit delivery of these constructs by various nucleic acid vectors.

Partial List of Abbreviations Used

APC, antigen presenting cell; BHK, baby hamster kidney; CMV, cytomegalovirus; CTL, cytotoxic T lymphocyte; DC, dendritic cell; ECD, extracellular domain; ELISA, enzyme-linked immunosorbent assay; FL, Flt3 ligand; GFP, green fluorescent protein; HPV, human papillomavirus; HSP, heat shock protein; Hsp70, mycobacterial heat shock protein 70; IFN-γ, interferon-γ; i.m., intramuscular(ly); i.v., intravenous (ly); MHC, major histocompatibility complex; PBS, phosphate-buffered saline; PCR, polymerase chain reaction; β-gal, β-galactosidase

SUMMARY OF THE INVENTION

Self-replicating RNA vaccines (RNA replicons) have emerged as an important strategy for nucleic acid vaccine development. The present inventors evaluated the effect of linking HPV type 16 (HPV-16) E7 as a model antigen to *Mycobacterium tuberculosis* (Mtb) heat shock protein 70 (Hsp70) on the potency of antigen-specific immunity generated by a Sindbis virus self-replicating RNA vector, SINrep5. The results indicated that this RNA replicon vaccine containing E7/Hsp70 fusion genes generated significantly greater E7-specific T cell-mediated immunity than vaccines comprising wild type E7 DNA.

HPV-16 E7 was selected as a model antigen for vaccine development because .HPVs, particularly HPV-16, are associated with most cervical cancers. HPV oncogenic proteins, E6 and E7, are co-expressed in most HPV-containing cervical cancers and are important in the induction and maintenance of cell transformation. Therefore, vaccines targeting E6 or E7 provide an opportunity to prevent and treat HPV-associated cervical malignancies. HPV-16 E7 is a well-characterized cytoplasmic/nuclear protein that is more conserved than E6 in HPV-associated cancer cells; E7 has been tested in a variety of HPV vaccines.

Furthermore, in vitro studies demonstrated that E7 antigen from apoptotic cells that have been transfected with E7/Hsp70 RNA replicons is taken up by bone marrow-derived dendritic cells (DC's) and presented more efficiently through the MHC class I pathway compared to antigen from than apoptotic cells transfected by wild-type E7 RNA replicons.

Importantly, the fusion of Hsp70 to E7 converted a less effective vaccine into one with significant potency against E7-expressing tumors. This antitumor effect involved NK cells and CD8$^+$ T cells. Thus, fusion of a nucleic acid sequence encoding Hsp70 to nucleic acid encoding an antigen of interest in the form of a self-replicating RNA vaccine greatly enhances the potency of this vaccine.

Naked DNA vaccines represent an attractive approach for generating antigen-specific immunity because of their stability and simplicity of delivery. Concerns with DNA vaccines include potential integration into the host genome, cell transformation, and limited potency. The use of DNA-based alphaviral RNA replicons ("suicidal DNA vectors"), as disclosed herein, may alleviate concerns surrounding DNA integration or cell transformation since suicidal DNA vectors eventually cause lysis of the cells they transfect.

To further improve the potency of suicidal DNA vaccines, the present inventors linked Hsp70 to E7 (as a model antigen) using DNA-based Semliki Forest virus (SFV) RNA vector, pSCA1. This suicidal DNA vaccine containing E7/Hsp70 fusion DNA produced a significantly greater E7-specific T cell-mediated immune response in mice than did vaccines containing the wild type E7 DNA alone. Importantly, this fusion converted a less effective vaccine into one with significant therapeutic potency against established E7-expressing metastatic tumors. The antitumor effect was dependent upon CD8+ T cells. Thus, linkage of Hsp70 to an antigen enhances the potency of a suicidal DNA vaccine.

Flt3 (fms-like tyrosine kinase 3)-ligand is an important cytokine in the development and differentiation of professional APCs, particularly DCs. A recombinant chimeric or fusion polypeptide molecule comprising the extracellular domain (ECD) of Flt3-ligand (FL) linked to an antigen targets the antigen to DCs and their precursors. Using HPV-16 E7 as a model antigen, the present inventors linked FL to E7 and caused stimulation of an antigen-specific immune response by a naked DNA vaccine administered intradermally via gene gun. Vaccines that included DNA encoding a chimeric FL-E7 fusion polypeptide dramatically increased the frequency of E7-specific CD8$^+$ T cells when compared to vaccines of only E7 DNA. Cells transfected in vitro with FL-E7 DNA presented E7 via the MHC class I pathway more efficiently than did cells transfected with wild-type E7 DNA. Furthermore, bone marrow-derived DCs pulsed with lysates of cells that had been transfected to express an FL-E7 fusion protein presented E7 (via the MHC class I pathway) more efficiently than did DCs pulsed with lysates of cells expresssing (after transfection) E7 protein alone. More importantly, this fusion construct rendered a less effective vaccine highly potent in inducing a therapeutic response against established E7-expressing metastatic tumors. The FL-E7 fusion vaccines mainly targeted CD8$^+$ T cells as anti-tumor effects were completely independent of CD4+ T cells. Thus, fusion of DNA encoding the ECD of FL to DNA encoding an antigen markedly enhances the potency of a DNA vaccine acting via CD8-dependent pathways.

In one embodiment, the antigen (e.g., the MHC class I-binding peptide epitope) is derived from a pathogen, e.g., it comprises a peptide expressed by a pathogen. The pathogen can be a virus, such as, e.g., a papilloma virus, a herpesvirus, a retrovirus (e.g., an immunodeficiency virus, such as HIV-1), an adenovirus, and the like. The papilloma virus can be a human papilloma virus; for example, the antigen (e.g., the Class I-binding peptide) can be derived from an HPV-16 E7 polypeptide. In one embodiment, the HPV-16 E7 polypeptide is substantially non-oncogenic, i.e., it does not bind retinoblastoma polypeptide (pRB) or binds pRB with such low affinity that the HPV-16 E7 polypeptide is effectively non-oncogenic when expressed or delivered in vivo.

In alternative embodiments, the pathogen is a bacteria, such as *Bordetella pertussis; Ehrlichia chaffeensis; Staphylococcus aureus; Toxoplasma gondii; Legionella pneumophila; Brucella suis; Salmonella enterica; Mycobacterium avium; Mycobacterium tuberculosis; Listeria monocytogenes; Chlamydia trachomatis; Chlamydia pneumoniae; Rickettsia rickettsii;* or, a fungi, such as, e.g., *Paracoccidioides brasiliensis;* or other pathogen, e.g., *Plasmodium falciparum.*

In another embodiment, the MHC class I-binding peptide epitope is derived from a tumor cell. The tumor cell-derived peptide epitope can comprise a tumor associated antigen, e.g., a tumor specific antigen, such as, e.g., a HER-2/neu antigen.

In one embodiment, the isolated or recombinant nucleic acid molecule is operatively linked to a promoter, such as, e.g., a constitutive, an inducible or a tissue-specific promoter.

The promoter can be expressed in any cell, including cells of the immune system, including, e.g., antigen presenting cells (APCs), e.g., in a constitutive, an inducible or a tissue-specific manner.

In alternative embodiments, the APCs are dendritic cells, keratinocytes, astrocytes, monocytes, macrophages, B lymphocytes, a microglial cell, or activated endothelial cells, and the like.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

FIG. 8A shows numbers of NK cells in mice immunized with various self-replicating RNA vaccines. The percentage of NK cells among the spleen cells is indicated in the upper left corner. FIG. 8B is a histogram demonstratinge the percentages of NK cells in vaccinated mice. The percentage of NK cells in mice immunized with self-replicating RNA vaccines was higher than in unimmunized controls. There was no significant difference between the percentage of NK cells among mice given various self-replicating RNA vaccines. These results are from one representative experiment of two performed.

FIG. 12A): splenocytes from vaccinated mice were cultured with E7 peptide RAHYNIVTF (SEQ ID 22, see above) overnight, stained for both CD8 and intracellular IFN-.gamma., and analyzed by flow cytometry. Mice vaccinated with E7/Hsp70 DNA generated the highest number of IFNγ-secreting CD8$^+$ "double positive" T cells compared to other groups. (FIG. 12B). Flow cytometry was performed in the presence (solid, columns) and absence (open columns) of RAHYNIVTF (SEQ ID NO: 22) peptide. Results are expressed as the mean number of IFN-γ-secreting CD8$^+$ T cells/3×10$^5$ splenocytes (±SEM). Results shown here are from one representative experiment of two performed.

FIG. 13B: Splenocytes from vaccinated mice were cultured in vitro with the above E7 peptide overnight and stained for both CD4 and intracellular IL-4. The number of IL-4 secreting CD4$^+$ T cells was analyzed by flow cytometry. No significant difference in the frequency of IL-4 secreting E7-specific CD4$^+$ cells was observed among mice immunized with various recombinant DNA vaccines. This figure represents the mean value of three experiments ±SEM.

FIG. 16A shows that the pSCA1-E7/Hsp70 group had the lowest number of pulmonary metastatic nodules of all the groups (ANOVA, P<0.001). Results are from one representative experiment of two performed. FIG. 16B shows representive lung tumors in each vaccinated group. Multiple grossly visible lung tumors were observed in unvaccinated control mice and mice vaccinated with Hsp70, E7, or vector DNA alone. No lung tumors were observed at this maginification in the pSCA1-E7/Hsp70 vaccinated group.

FIGS. 18A and 18B show aschematic domain structure of the Flt3-ligand protein and FL-E7 fusion peptide (FIG. 18A) and the sequence of the FL-E7 construct, comprising the ECD of FL (FIG. 18B; SEQ ID NO:11 and 12). Residues 1-189 are FL-derived, residues 191-287 are E7-derived. The remaining residues (e.g.,, 288-302) are from the vector DNA.

(FIG. 19A) Splenocytes from vaccinated mice were cultured in vitro with E7 peptide (aa 49-57) overnight and were stained for both CD8 and intracellular IFN-γ. The number of IFN-γ secreting CD8$^+$ T cell precursors in mice immunized with various recombinant DNA vaccines was analyzed by flow cytometry. Mice vaccinated with FL-E7 DNA generated the highest IFN-γ$^+$ CD8$^+$ double positive T cells compared to other groups. (FIG. 19B) The number of EFN-γ-producing E7-specific CD8$^+$ T cells was determined using flow cytometry in the presence (solid columns) and absence (open columns) of E7 peptide (aa 49-57). Data are expressed as mean number of CD8$^+$ IFN-γ$^+$ cells/3×10$^5$ splenocytes ±SEM. The data from intracellular cytokine staining shown here are from one representative experiment of two performed.

(FIG. 20A) Splenocytes from vaccinated mice were cultured in vitro with E7 peptide (aa 30-67) overnight and were stained for both CD4 and intracellular IFN-γ. The number of IFN-γ-secreting CD4$^+$ T cells was analyzed using flow cytometry. No significant difference in the frequency of E7-specific IFN-γ-secreting CD4$^+$ cells was observed in mice immunized with various recombinant DNA vaccines. (FIG. 20B) Splenocytes from vaccinated mice were cultured in vitro with E7 peptide (aa 30-67) overnight and stained for both CD4 and intracellular IL-4. The percentage of IL-4 secreting CD4+ T cells was analyzed by flow cytometry. The IL-4 secreting activated mouse splenocytes (MiCK-2) from PharMingen were used as positive controls to assure the success of intracytoplasmic IL-4 staining for this study. The specificity of IL-4 staining was demonstrated by the absence of CD4+ IL-4+ T cells when the IL-4 antibody was omitted. No significant difference in the frequency of IL-4 secreting E7-specific CD4+ cells was observed in mice immunized with various recombinant DNA vaccines. The intracellular cytokine staining shown here are from one representative experiment of two performed.

FIGS. 22A and 22B. In vivo tumor treatment experiments against pre-existing metastatic TC-1 tumor cells. The mice were intravenously challenged with $1\times10^4$ cells/mouse TC-1 tumor cells in the tail vein on day 0. Three days after challenge with TC-1 tumor cells, mice received 2 μg of FL DNA, E7 DNA, FL-E7 DNA, FL mixed with E7 (FL+E7), via gene gun or unvaccinated. One week later, these mice were boosted with the same regimen as the first vaccination. The mice were sacrificed on day 25. The FL-E7 group has (FIG. 22A) the least number of pulmonary metastatic nodules and (FIG. 22B) the lowest lung weight as compared with the other vaccinated groups (one-way ANOVA, P<0.001). The data obtained from these in vivo treatment experiments are from one representative experiment of two performed.

DESCRIPTION OF THE PREFERRED EMBODIMENTS

Figure 1:
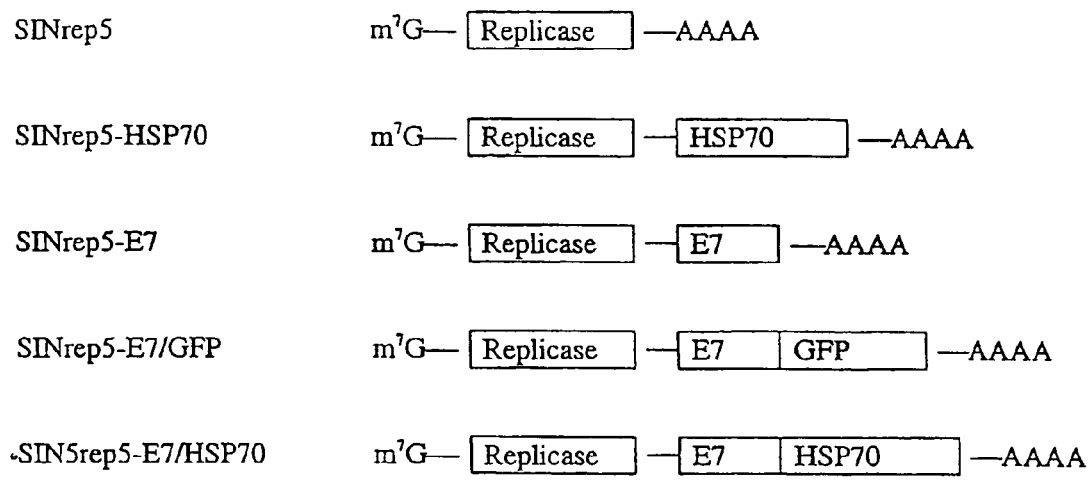
FIG. 1 is a schematic diagram showing the SINrep5 self-replicating RNA transcripts. A methylated $M^7G$, "cap" is located at the 5' end of the mRNA, followed by a sequence responsible for the self-replication (replicase), the gene of interest (i.e. E7, Hsp70, E7/GFP or E7/Hsp70), and a polyadenylated tail (AAAA).

The invention provides compositions and methods for enhancing the immune responses, particularly cytotoxic T cell immune responses, induced by ex vivo or in vivo administration of chimeric polypeptides or, preferably, nucleic acid vaccines that encode these chimeric polypeptides. The preferred chimeric or fusion polypeptide comprises (1) at least one first polypeptide or peptide that, upon introduction to cells of the host immune system, in vitro or in vivo, promotes (a) processing via the MHC class I pathway and/or (b) development or activity of APCs, primarily DCs, and (2) at least one second polypeptide or peptide that is an antigenic polypeptide or peptide in the host. As noted, in a preferred embodiment, the chimeric or fusion polypeptides are "indirectly" administered by administration of a nucleic acid that encodes the chimeric molecule; the nucleic acid construct, and thus the fusion protein, is expressed in vivo. The chimeric nucleic acids are administered in the form of DNA vaccines, either naked DNA or suicidal DNA, or a self-replicating RNA replicons.

The fusion protein comprises at least two domains or repeats thereof. The first domain again comprises a polypeptide that promotes (a) processing via the MHC class I pathway and/or (b) development or activity of APCs, and the second domain comprises a peptide or polypeptide, that includes one or several epitopes, derived from an antigen against which it is desired to induce an immune response.

For convenience, a polypeptide or peptide that promotes processing via the MHC class I pathway is abbreviated herein as "MHC-I-PP." A polypeptide or peptide that promotes development or activity of APCs, preferably DC's, is abbreviated DC-PP.

The exemplary MHC-I-PP protein describec herein is Hsp70. However, it is understood that any protein, or functional fragment or variant thereof, that has this activity can be used in the invention. A preferred fragment is a C-terminal domain ("CD") of Hsp70, which is designated "Hsp70$_{CD}$". One Hsp70$_{CD}$ spans from about residue 312 to the C terminus of Hsp70 (SEQ ID NO:4). A preferred shorter polypeptide spans from about residue 517 to the C-terminus of SEQ ID NO:4. Shorter peptides from that sequence that have the ability to promote protein processing via the MHC-1 class I pathway are also included, and may be defined by routine experimentation.

The second type of domain of the chimeric molecule comprises an antigenic peptide, which can be derived from a pathogen, a cancer cell, or any source to which induction, enhancement or suppression of an immune response is desired. In a preferred embodiment, the peptide comprises at least one MHC class I-binding peptide epitope that helps stimulate CD8+ CTLs and is recognized by such cells and their precursors.

The order in which the two (or more) component polypeptides of the fusion protein are arranged, and therefore, the order of the encoding nucleic acid fragments in the nucleic acid vector, can be altered without affecting immunogenicity of the fusion polypeptides proteins and the utility of the composition. For example, the Hsp70-encoding (or FL-encoding) DNA sequences may be located 5' or 3' to the target antigen-encoding sequences. In one embodiment, these polypeptide-encoding nucleic acid domains are in-frame so that the DNA construct encodes a recombinant fusion polypeptide in which the antigen is located N-terminal to the Hsp70 or FL derived polypeptide.

The vaccines of the present invention include, the antigenic epitope itself and an MHC-I-PP such as Hsp70 or its active domain (CD), or DC-PP intercellular spreading protein such as FL. In addition to the specific antigens and vectors employed in the Examples, the present invention is intended to encompass a vector such as naked DNA, naked RNA, self replicating RNA replicons and viruses including vaccinia, adenoviruses, adeno-associated virus (AAV), lentiviruses and RNA alphaviruses.

In addition to the MHC-I-PP and/or DC-PP, the vaccine construct of the present invention optionally, may also include (a) an additional antigen targeting or processing signal such as proteins that promote intercellular transport, e.g., VP22 protein from herpes simplex virus and related herpes viruses; an endoplasmic reticulum chaperone polypeptide such as calreticulin, ER60, GRP94 or gp96, well-characterized ER chaperone polypeptide that representatives of the HSP90 family of stress-induced proteins (Argon (1999) *Semin. Cell Dev.Biol.* 10:495-505; Sastry (1999) *J. Biol. Chem.* 274:12023-12035; Nicchitta (1998) *Curr. Opin. Immunol.* 10:103-109; U.S. Pat. No. 5,981,706)); cytoplasmic translocation polypeptide domains of pathogen toxins, such as domain II of *Pseudomonas* exotoxin ETA (ETAdII) or of similar toxins from *Diptheria, Clostridium, Botulinum, Bacillus, Yersinia, Vibrio cholerae*, or *Bordetella pertussis*; or active fragments or domains of any of the foregoing polypeptides.

(b) an immunostimulatory cytokine, preferably those that target APCs, preferably DC's, such as granulocyte macrophage colony stimulating factor (GM-CSF), or active fragments or domains thereof; and (c) a costimulatory signal, such as a B7 family protein, including B7-DC (see commonly assigned U.S. patent application Ser. No. 09/794,210), B7.1, B7.2, soluble CD40, etc.).

(For description of some of the foregoin, see, for example, commonly owned Interanational patent applications PCT/US01/23966, PCT/US01/24134, PCTUS/00/41422))

In the methods of the invention, the chimeric polypeptide or nucleic acid that encodes it are employed to induce or enhance immune responses. In one embodiment, the compositions of the invention synergistically enhance immune responses and antitumor effects through both immunological and anti-angiogenic mechanisms.

The experiments described herein demonstrate that the methods of the invention can enhance a cellular immune response, particularly, tumor-destructive CTL reactivity, induced by a DNA vaccine encoding an epitope of a human pathogen. Human HPV-16 E7 was used as a model antigen for vaccine development because human papillomaviruses (HPVs), particularly HPV-16, are associated with most human cervical cancers. The oncogenic HPV protein E7 is important in the induction and maintenance of cellular trans-formation and co-expressed in most HPV-containing cervical cancers and their precursor lesions. Therefore, cancer vaccines, such as the compositions of the invention, that target E7 can be used to control of HPV-associated neoplasms (Wu (1994) *Curr. Opin. Immunol.* 6:746-754).

Unless defined otherwise, all technical and scientific terms used herein have the meaning commonly understood by a person skilled in the art of this invention. As used herein, the following terms have the meanings ascribed to them unless specified otherwise.

The term "antigen" or "immunogen" as used herein refers to a compound or composition comprising a peptide, polypeptide or protein which is "antigenic" or "immunogenic" when administered (or expressed in vivo by an administered nucleic acid, e.g., a DNA vaccine) in an appropriate amount (an "immunogenically effective amount"), i.e., capable of inducing, eliciting, augmenting or boosting a cellular and/or humoral immune response either alone or in combination or linked or fused to another substance (which can be administered at once or over several intervals). An immunogenic composition can comprise an antigenic peptide of at least about 5 amino acids, a peptide of 10 amino acids in length, a polypepide fragment of 15 amino acids in length, 20 amino acids in length or longer. Smaller immunogens may require presence of a "carrier" polypeptide e.g., as a fusion protein, aggregate, conjugate or mixture, preferablyl linked (chemically or otherwise) to the immunogen. The immunogen can be recombinantly expressed from a vaccine vector, which can be naked DNA comprising the immunogen's coding sequence operably linked to a promoter, e.g., an expression cassette as described herein. The immunogen includes one or more antigenic determinants or epitopes which may vary in size from about 3 to about 15 amino acids.

The term "epitope" as used herein refers to an antigenic determinant or antigenic site that interacts with an antibody or a T cell receptor (TCR), e.g., the MHC class I-binding peptide compositions (or expressed products of the nucleic acid compositions of the invention) used in the methods of the invention. An "antigen" is a molecule or chemical structure that either induces an immune response or is specifically recognized or bound by the product or mediator of an immune response, such as an antibody or a CTL. The specific conformational or stereochemical "domain" to which an antibody or a TCR bind is an "antigenic determinant" or "epitope." TCRs bind to peptide epitopes which are physically associated with a third molecule, a major histocompatibility complex (MHC) class I or class II protein.

The term "recombinant" refers to (1) a nucleic acid or polynucleotide synthesized or otherwise manipulated in vitro, (2) methods of using recombinant DNA technology to produce gene products in cells or other biological systems, or (3) a polypeptide encoded by a recombinant nucleic acid. For example, the FL-encoding nucleic acid or polypeptide, the nucleic acid encoding an MHC class I-binding peptide epitope (antigen) or the peptide itself can be rececombinant. "Recombinant means" includes ligation of nucleic acids having various coding regions or domains or promoter sequences from different sources into a single unit in the form of an expression cassette or vector for expression of the coding sequences in the vectors resulting in production of the encoded polypeptide.

The term "self-replicating RNA replicon" refers to a construct based on an RNA viruses, such as alphavirus genome RNAs (e.g., Sindbis virus, Semliki Forest virus, etc.), that have been engineered to allow expression of heterologous RNAs and proteins. These recombinant vectors are self-replicating ("replicons") which can be introduced into cells as naked RNA or DNA, as described in detail, below. In a preferred embodiment, the self-replicating RNA replicon comprises a Sindbis virus self-replicating RNA vector SINrep5, which is described in detail in U.S. Pat. No. 5,217,879.

Sequences of Polypeptides and Nucleic Acids

The section that follows lists the sequences of the MHC-I-PP and DC-PP polypeptides alone or in fusion with E7 antigen, the nucleic acids encoding some of these peptides and nucleic acids of the vectors into which the sequences encoding these polypeptides are cloned.

HPV-E7 (nucleic acid is SEQ ID NO:1; amino acids are SEQ ID NO:2)

```
1/1                                    31/11
atg cat gga gat aca cct aca ttg cat gaa tat atg tta gat ttg caa cca gag aca act
Met his gly asp thr pro thr leu his glu tyr met leu asp leu gln pro glu thr thr 61/21                                  91/31
gat ctc tac tgt tat gag caa tta aat gac agc tca gag gag gag gat gaa ata gat ggt
asp leu tyr cys tyr glu gln leu asn asp ser ser glu glu glu asp glu ile asp gly 121/41                                 151/51
cca gct gga caa gca gaa ccg gac aga gcc cat tac aat att gta acc ttt tgt tgc aag
pro ala gly gln ala glu pro asp arg ala his tyr asn ile val thr phe cys cys lys 181/61                                 211/71
tgt gac tct acg ctt cgg ttg tgc gta caa agc aca cac gta gac att cgt act ttg gaa
cys asp ser thr leu arg leu cys val gln ser thr his val asp ile arg thr leu glu 241/81                                 271/91
gac ctg tta atg ggc aca cta gga att gtg tgc ccc atc tgt tct cag gat aag ctt
asp leu leu met gly thr leu gly ile val cys pro ile cys ser gln asp lys leu
```

GENBANK Accession No. AAD33353 ("native" sequence). After cloning the last 9 nucleotides (3 amino acids were modified, as shown above underscored and/or bold.

The original GENBANK sequence has a Lys-Pro after the Gln in position 96 (encoded by aaa/cca/taa, rather than Asp-Lys-Leu (encoded by gat/aag/ctt).

Hsp70 from *M. tuberculosis*

(nucleic acid is SEQ ID NO:3; amino acids are SEQ ID NO:4)

```
1/1                                    31/11
atg gct cgt gcg gtc ggg atc gac ctc ggg acc acc aac tcc gtc gtc tcg gtt ctg gaa
Met ala arg ala val gly ile asp leu gly thr thr asn ser val val ser val leu glu 61/21                                  91/31
ggt ggc gac ccg gtc gtc gtc gcc aac tcc gag ggc tcc agg acc acc ccg tca att gtc
gly gly asp pro val val val ala asn ser glu gly ser arg thr thr pro ser ile val 121/41                                 151/51
gcg ttc gcc cgc aac ggt gag gtg ctg gtc ggc cag ccc gcc aag aac cag gca gtg acc
ala phe ala arg asn gly glu val leu val gly gln pro ala lys asn gln ala val thr 181/61                                 211/71
aac gtc gat cgc acc gtg cgc tcg gtc aag cga cac atg ggc agc gac tgg tcc ata gag
asn val asp arg thr val arg ser val lys arg his met gly ser asp trp ser ile glu 241/81                                 271/91
att gac ggc aag aaa tac acc gcg ccg gag atc agc gcc cgc att ctg atg aag ctg aag
ile asp gly lys lys tyr thr ala pro glu ile ser ala arg ile leu met lys leu lys 301/101                                331/111
cgc gac gcc gag gcc tac ctc ggt gag gac att acc gac gcg gtt atc acg acg ccc gcc
arg asp ala glu ala tyr leu gly glu asp ile thr asp ala val ile thr thr pro ala 361/121                                391/131
tac ttc aat gac gcc cag cgt cag gcc acc aag gac gcc ggc cag atc gcc ggc ctc aac
tyr phe asn asp ala gln arg gln ala thr lys asp ala gly gln ile ala gly leu asn 421/141                                451/151
gtg ctg cgg atc gtc aac gag ccg acc gcg gcc gcg ctg gcc tac ggc ctc gac aag ggc
val leu arg ile val asn glu pro thr ala ala ala leu ala tyr gly leu asp lys gly 481/161                                511/171
gag aag gag cag cga atc ctg gtc ttc gac ttg ggt ggt ggc act ttc gac gtt tcc ctg
glu lys glu gln arg ile leu val phe asp leu gly gly gly thr phe asp val ser leu
```

-continued

```
541/181                              571/191
ctg gag atc ggc gag ggt gtg gtt gag gtc cgt gcc act tcg ggt gac aac cac ctc ggc
leu glu ile gly glu gly val val glu val arg ala thr ser gly asp asn his leu gly 601/201                              631/211
ggc gac gac tgg gac cag cgg gtc gtc gat tgg ctg gtg gac aag ttc aag ggc acc agc
gly asp asp trp asp gln arg val val asp trp leu val asp lys phe lys gly thr ser 661/221                              691/231
ggc atc gat ctg acc aag gac aag atg gcg atg cag cgg ctg cgg gaa gcc gcc gag aag
gly ile asp leu thr lys asp lys met ala met gln arg leu arg glu ala ala glu lys 721/241                              751/251
gca aag atc gag ctg agt tcg agt cag tcc acc tcg atc aac ctg ccc tac atc acc gtc
ala lys ile glu leu ser ser ser gln ser thr ser ile asn leu pro tyr ile thr val 781/261                              811/271
gac gcc gac aag aac ccg ttg ttc tta gac gag cag ctg acc cgc gcg gag ttc caa cgg
asp ala asp lys asn pro leu phe leu asp glu gln leu thr arg ala glu phe gln arg 841/281                              871/291
atc act cag gac ctg ctg gac cgc act cgc aag ccg ttc cag tcg gtg atc gct gac acc
ile thr gln asp leu leu asp arg thr arg lys pro phe gln ser val ile ala asp thr 901/301                              931/311
ggc att tcg gtg tcg gag atc gat cac gtt gtg ctc gtg ggt ggt tcg acc cgg atg ccc
gly ile ser val ser glu ile asp his val val leu val gly gly ser thr arg met pro 961/321                              991/331
gcg gtg acc gat ctg gtc aag gaa ctc acc ggc aag gaa ccc aac aag ggc gtc aac
ala val thr asp leu val lys glu leu thr gly gly lys glu pro asn lys gly val asn 1021/341                             1051/351
ccc gat gag gtt gtc gcg gtg gga gcc gct ctg cag gcc ggc gtc ctc aag ggc gag gtg
pro asp glu val val ala val gly ala ala leu gln ala gly val leu lys gly glu val 1081/361                             1111/371
aaa gac gtt ctg ctg ctt gat gtt acc ccg ctg agc ctg ggt atc gag acc aag ggc ggg
lys asp val leu leu leu asp val thr pro leu ser leu gly ile glu thr lys gly gly 1141/381                             1171/391
gtg atg acc agg ctc atc gag cgc aac acc acg atc ccc acc aag cgg tcg gag act ttc
val met thr arg leu ile glu arg asn thr thr ile pro thr lys arg ser glu thr phe 1201/401                             1231/411
acc acc gcc gac gac aac caa ccg tcg gtg cag atc cag gtc tat cag ggg gag cgt gag
thr thr ala asp asp asn gln pro ser val gln ile gln val tyr gln gly glu arg glu 1261/421                             1291/431
atc gcc gcg cac aac aag ttg ctc ggg tcc ttc gag ctg acc ggc atc ccg ccg gcg ccg
ile ala ala his asn lys leu leu gly ser phe glu leu thr gly ile pro pro ala pro 1321/441                             1351/451
cgg ggg att ccg cag atc gag gtc act ttc gac atc gac gcc aac ggc att gtg cac gtc
arg gly ile pro gln ile glu val thr phe asp ile asp ala asn gly ile val his val 1381/461                             1411/471
acc gcc aag gac aag ggc acc ggc aag gag aac acg atc cga atc cag gaa ggc tcg ggc
thr ala lys asp lys gly thr gly lys glu asn thr ile arg ile gln glu gly ser gly 1441/481                             1471/491
ctg tcc aag gaa gac att gac cgc atg atc aag gac gcc gaa gcg cac gcc gag gag gat
leu ser lys glu asp ile asp arg met ile lys asp ala glu ala his ala glu glu asp 1501/501                             1531/511
cgc aag cgt cgc gag gag gcc gat gtt cgt aat caa gcc gag aca ttg gtc tac cag acg
arg lys arg arg glu glu ala asp val arg asn gln ala glu thr leu val tyr gln thr 1561/521                             1591/531
gag aag ttc gtc aaa gaa cag cgt gag gcc gag ggt ggt tcg aag gta cct gaa gac acg
gly lys phe val lys glu gln arg glu ala glu gly gly ser lys val pro glu asp thr    540

1621/541                             1651/551
ctg aac aag gtt gat gcc gcg gtg gcg gaa gcg aag gcg gca ctt ggc gga tcg gat att
leu asn lys val asp ala ala val ala glu ala lys ala ala leu gly gly ser asp ile    560

1681/561                             1711/571
tcg gcc atc aag tcg gcg atg gag aag ctg ggc cag gag tcg cag gct ctg ggg caa gcg
ser ala ile lys ser ala met glu lys leu gly gln glu ser gln ala leu gly gln ala    580
```

-continued

```
1741/581                            1771/591
atc tac gaa gca gct cag gct gcg tca cag gcc act ggc gct gcc cac ccc ggc tcg gct
ile tyr glu ala ala gln ala ala ser gln ala thr gly ala ala his pro gly ser ala 1801/601
gat gaA AGC
asp glu ser
```

GENBANK Z95324 AL123456; encoded by nucleotides 10633-12510 of *Mycobacterium tuberculosis* genome). As a result of cloning, this has been modified from the original GENTBANK sequence which had at its 3' end:

```
ggc gag ccg ggc ggt gcc cac ccc ggc    (SEQ ID NO:5)

tcg gct gat gac gtt gtg gac gcg gag gtg gtc gac gac ggc cgg gag gcc aag
``` which was replaced in the cloned version used herein, by tcg gct gat gaa agc (SEQ ID NO:6) which is bold and underlined above.

E7-Hsp70 Fusion (nucleic acid is SEQ ID NO:7; amino acids are SEQ ID NO:8)

E7 coding sequence is capitalized and underscored.

```
1/1                                 31/11
ATG CAT GGA GAT ACA CCT ACA TTG CAT GAA TAT ATG TTA GAT TTG CAA CCA GAG ACA ACT
Met his gly asp thr pro thr leu his glu tyr met leu asp leu gln pro glu thr thr 61/21                               91/31
GAT CTC TAC TGT TAT GAG CAA TTA AAT GAC AGC TCA GAG GAG GAG GAT GAA ATA GAT GGT
asp leu tyr cys tyr glu gln leu asn asp ser ser glu glu glu asp glu ile asp gly 121/41                              151/51
CCA GCT GGA CAA GCA GAA CCG GAC AGA GCC CAT TAC AAT ATT GTA ACC TTT TGT TGC AAG
pro ala gly gln ala glu pro asp arg ala his tyr asn ile val thr phe cys cys lys 181/61                              211/71
TGT GAC TCT ACG CTT CGG TTG TGC GTA CAA AGC ACA CAC GTA GAC ATT CGT ACT TTG GAA
cys asp ser thr leu arg leu cys val gln ser thr his val asp ile arg thr leu glu 241/81                              271/91
GAC CTG TTA ATG GGC ACA CTA GGA ATT GTG TGC CCC ATC TGT TCT CAA GAA TCC atg gct
asp leu leu met gly thr leu gly ile val cys pro ile cys ser gln glu ser met ala 301/101                             331/111
cgt gcg gtc ggg atc gac ctc ggg acc acc aac tcc gtc gtc tcg gtt ctg gaa ggt ggc
arg ala val gly ile asp leu gly thr thr asn ser val val ser val leu glu gly gly 361/121                             391/131
gac ccg gtc gtc gtc gcc aac tcc gag ggc tcc agg acc acc ccg tca att gtc gcg ttc
asp pro val val val ala asn ser glu gly ser arg thr thr pro ser ile val ala phe 421/141                             451/151
gcc cgc aac ggt gag gtg ctg gtc ggc cag ccc gcc aag aac cag gca gtg acc aac gtc
ala arg asn gly glu val leu val gly gln pro ala lys asn gln ala val thr asn val 481/161                             511/171
gat cgc acc gtg cgc tcg gtc aag cga cac atg ggc agc gac tgg tcc ata gag att gac
asp arg thr val arg ser val lys arg his met gly ser asp trp ser ile glu ile asp 541/181                             571/191
ggc aag aaa tac acc gcg ccg gag atc agc gcc cgc att ctg atg aag ctg aag cgc gac
gly lys lys tyr thr ala pro glu ile ser ala arg ile leu met lys leu lys arg asp 601/201                             631/211
gcc gag gcc tac ctc ggt gag gac att acc gac gcg gtt atc acg acg ccc gcc tac ttc
ala glu ala tyr leu gly glu asp ile thr asp ala val ile thr thr pro ala tyr phe 661/221                             691/231
aat gac tcc cag cgt cag gcc acc aag gac gcc ggc cag atc gcc ggc ctc aac gtg ctg
asn asp ala gln arg gln ala thr lys asp ala gly gln ile ala gly leu asn val leu 721/241                             751/251
cgg atc gtc aac gag ccg acc gcg gcc gcg ctg gcc tac ggc ctc gac aag ggc gag aag
arg ile val asn glu pro thr ala ala ala leu ala tyr gly leu asp lys gly glu lys 781/261                             811/271
gag cag cga atc ctg gtc ttc gac ttg ggt ggt ggc act ttc gac gtt tcc ctg ctg gag
```

-continued glu gln arg ile leu val phe asp leu gly gly gly thr phe asp val ser leu leu glu 841/281                                         871/291
atc ggc gag ggt gtg gtt gag gtc cgt gcc act tcg ggt gac aac cac ctc ggc ggc gac
ile gly glu gly val val glu val arg ala thr ser gly asp asn his leu gly gly asp 901/301                                         931/311
gac tgg gac cag cgg gtc gtc gat tgg ctg gtg gac aag ttc aag ggc acc agc ggc atc
asp trp asp gln arg val val asp trp leu val asp lys phe lys gly thr ser gly ile 961/321                                         991/331
gat ctg acc aag gac aag atg gcg atg cag cgg ctg cgg gaa gcc gcc gag aag gca aag
asp leu thr lys asp lys met ala met gln arg leu arg glu ala ala glu lys ala lys 1021/341                                        1051/351
atc gag ctg agt tcg agt cag tcc acc tcg atc aac ctg ccc tac atc acc gtc gac gcc
ile glu leu ser ser ser gln ser thr ser ile asn leu pro tyr ile thr val asp ala 1081/361                                        1111/371
gac aag aac ccg ttg ttc tta gac gag cag ctg acc cgc gcg gag ttc caa cgg atc act
asp lys asn pro leu phe leu asp glu gln leu thr arg ala glu phe gln arg ile thr 1141/381                                        1171/391
cag gac ctg ctg gac cgc act cgc aag ccg ttc cag tcg gtg atc gct gac acc ggc att
gln asp leu leu asp arg thr arg lys pro phe gln ser val ile ala asp thr gly ile 1201/401                                        1231/411
tcg gtg tcg gag atc gat cac gtt gtg ctc gtg ggt ggt tcg acc cgg atg ccc gcg gtg
ser val ser glu ile asp his val val leu val gly gly ser thr arg met pro ala val 1261/421                                        1291/431
acc gat ctg gtc aag gaa ctc acc ggc ggc aag gaa ccc aac aag ggc gtc aac ccc gat
thr asp leu val lys glu leu thr gly gly lys glu pro asn lys gly val asn pro asp 1321/441                                        1351/451
gag gtt gtc gcg gtg gga gcc gct ctg cag gcc ggc gtc ctc aag ggc gag gtg aaa gac
glu val val ala val gly ala ala leu gln ala gly val leu lys gly glu val lys asp 1381/461                                        1411/471
gtt ctg ctg ctt gat gtt acc ccg ctg agc ctg ggt atc gag acc aag ggc ggg gtg atg
val leu leu leu asp val thr pro leu ser leu gly ile glu thr lys gly gly val met 1441/481                                        1471/491
acc agg ctc atc gag cgc aac acc acg atc ccc acc aag cgg tcg gag act ttc acc acc
thr arg leu ile glu arg asn thr thr ile pro thr lys arg ser glu thr phe thr thr 1501/501                                        1531/511
gcc gac gac aac caa ccg tcg gtg cag atc cag gtc tat cag ggg gag cgt gag atc gcc
ala asp asp asn gln pro ser val gln ile gln val tyr gln gly glu arg glu ile ala 1561/521                                        1591/531
gcg cac aac aag ttg ctc ggg tcc ttc gag ctg acc ggc atc ccg ccg gcg ccg cgg ggg
ala his asn lys leu leu gly ser phe glu leu thr gly ile pro pro ala pro arg gly 1621/541                                        1651/551
att ccg cag atc gag gtc act ttc gac atc gac gcc aac ggc att gtg cac gtc acc gcc
ile pro gln ile glu val thr phe asp ile asp ala asn gly ile val his val thr ala 1681/561                                        1711/571
aag gac aag ggc acc ggc aag gag aac acg atc cga atc cag gaa ggc tcg ggc ctg tcc
lys asp lys gly thr gly lys glu asn thr ile arg ile gln glu gly ser gly leu ser 1741/581                                        1771/591
aag gaa gac att gac cgc atg atc aag gac gcc gaa gcg cac gcc gag gag gat cgc aag
lys glu asp ile asp arg met ile lys asp ala glu ala his ala glu glu asp arg lys 1801/601                                        1831/611
cgt cgc gag gag gcc gat gtt cgt aat caa gcc gag aca ttg gtc tac cag acg gag aag
arg arg glu glu ala asp val arg asn gln ala glu thr leu val tyr gln thr glu lys 1861/621                                        1891/631
ttc gtc aaa gaa cag cgt gag gcc gag ggt ggt tcg aag gta cct gaa gac acg ctg aac
phe val lys glu gln arg glu ala glu gly gly ser lys val pro glu asp thr leu asn 1921/641                                        1951/651
aag gtt gat gcc gcg gtg gcg gaa gcg aag gcg ctt ggc gga tcg gat att tcg gcc
lys val asp ala ala val ala glu ala lys ala leu gly gly ser asp ile ser ala 1981/661                                        2011/671
atc aag tcg gcg atg gag aag ctg ggc cag gag tcg cag gct ctg ggg caa gcg atc tac -continued
```
                                           ile lys ser ala met glu lys leu gly gln glu ser gln ala leu gly gln ala ile tyr 2041/681                                   2071/691
gaa gca gct cag gct gcg tca cag gcc act ggc gct gcc cac ccc ggc tcg gct gat gaA
glu ala ala gln ala ala ser gln ala thr gly ala ala his pro gly ser ala asp glu 2101/701
AGC a
ser
```

Flt3 Ligand (FL) extracellular domain (nucleic acid is SEQ ID NO:9; amino acids are SEQ ID NO: 10)

```
1/1                                        31/11
atg aca gtg ctg gcg cca gcc tgg agc cca aat tcc tcc ctg ttg ctg ctg ttg ctg ctg
Met thr val leu ala pro ala trp ser pro asn ser ser leu leu leu leu leu leu leu 61/21                                      91/31
ctg agt cct tgc ctg cgg ggg aca cct gac tgt tac ttc agc cac agt ccc atc tcc tcc
leu ser pro cys leu arg gly thr pro asp cys tyr phe ser his ser pro ile ser ser 121/41                                     151/51
aac ttc aaa gtg aag ttt aga gag ttg act gac cac ctg ctt aaa gat tac cca gtc act
asn phe lys val lys phe arg glu leu thr asp his leu leu lys asp tyr pro val thr 181/61                                     211/71
gtg gcc gtc aat ctt cag gac gag aag cac tgc aag gcc ttg tgg agc ctc ttc cta gcc
val ala val asn leu gln asp glu lys his cys lys ala leu trp ser leu phe leu ala 241/81                                     271/91
cag cgc tgg ata gag caa ctg aag act gtg gca ggg tct aag atg caa acg ctt ctg gag
gln arg trp ile glu gln leu lys thr val ala gly ser lys met gln thr leu leu glu 301/101                                    331/111
gac gtc aac acc gag ata cat ttt gtc acc tca tgt acc ttc cag ccc cta cca gaa tgt
asp val asn thr glu ile his phe val thr ser cys thr phe gln pro leu pro glu cys 361/121                                    391/131
ctg cga ttc gtc cag acc aac atc tcc cac ctc ctg aag gac acc tgc aca cag ctg ctt
leu arg phe val gln thr asn ile ser his leu leu lys asp thr cys thr gln leu leu 421/141                                    451/151
gct ctg aag ccc tgt atc ggg aag gcc tgc cag aat ttc tct cgg tgc ctg gag gtg cag
ala leu lys pro cys ile gly lys ala cys gln asn phe ser arg cys leu glu val gln 481/161                                    511/171
tgc cag ccg gac tcc tcc acc ctg ctg ccc cca agg agt ccc ata gcc cta gaa gcc acg
cys gln pro asp ser ser thr leu leu pro pro arg ser pro ile ala leu glu ala thr 541/181
gag ctc cca gag cct cgg ccc agg cag
glu leu pro glu pro arg pro arg gln
```

FL-E7 Fusion Polypeptide (nucleic acid is SEQ ID NO:11; amino acids are SEQ ID NO:12)

N-terminal sequence is FL, followed by E7 (underscored, cap)

```
1/1                                        31/11
atg aca gtg ctg gcg cca gcc tgg agc cca aat tcc tcc ctg ttg ctg ctg ttg ctg ctg
Met thr val leu ala pro ala trp ser pro asn ser ser leu leu leu leu leu leu leu 61/21                                      91/31
cgt agt cct tgc ctg cgg ggg aca cct gac tgt tac ttc agc cac agt ccc atc tcc tcc
leu ser pro cys leu arg gly thr pro asp cys tyr phe ser his ser pro ile ser ser 121/41                                     151/51
aac ttc aaa gtg aag ttt aga gag ttg act gac cac ctg ctt aaa gat tac cca gtc act
```

-continued

```
                                             211/71
181/61
gtg gcc gtc aat ctt cag gac gag aag cac tgc aag gcc ttg tgg agc ctc ttc cta gcc
val ala val asn leu gln asp glu lys his cys lys ala leu trp ser leu phe leu ala 241/81                                       271/91
cag cgc tgg ata gag caa ctg aag act gtg gca ggg tct aag atg caa acg ctt ctg gag
gln arg trp ile glu gln leu lys thr val ala gly ser lys met gln thr leu leu glu 301/101                                      331/111
gac gtc aac acc gag ata cat ttt gtc acc tca tgt acc ttc cag ccc cta cca gaa tgt
asp val asn thr glu ile his phe val thr ser cys thr phe gln pro leu pro glu cys 361/121                                      391/131
ctg cga ttc gtc cag acc aac atc tcc cac ctc ctg aag gac acc tgc aca cag ctg ctt
leu arg phe val gln thr asn ile ser his leu leu lys asp thr cys thr gln leu leu 421/141                                      451/151
gct ctg aag ccc tgt atc ggg aag gcc tgc cag aat ttc tct cgg tgc ctg gag gtg cag
ala leu lys pro cys ile gly lys ala cys gln asn phe ser arg cys leu glu val gln 481/161                                      511/171
tgc cag ccg gac tcc tcc acc ctg ctg ccc cca agg agt ccc ata gcc cta gaa gcc acg
cys gln pro asp ser ser thr leu leu pro pro arg ser pro ile ala leu glu ala thr 541/181                                      571/191
gag ctc cca gag cct cgg ccc agg cag gaa ttc ATG CAT GGA GAT ACA CCT ACA TTG CAT
glu leu pro glu pro arg pro arg gln glu phe met his gly asp thr pro thr leu his 601/201                                      631/211
GAA TAT ATG TTA GAT TTG CAA CCA GAG ACA ACT GAT CTC TAC TGT TAT GAG CAA TTA AAT
glu tyr met leu asp leu gln pro glu thr thr asp leu tyr cys tyr glu gln leu asn 661/221                                      691/231
GAC AGC TCA GAG GAG GAG GAT GAA ATA GAT GGT CCA GCT GGA CAA GCA GAA CCG GAC AGA
asp ser ser glu glu glu asp glu ile asp gly pro ala gly gln ala glu pro asp arg 721/241                                      751/251
GCC CAT TAC AAT ATT GTA ACC TTT TGT TGC AAG TGT GAC TCT ACG CTT CGG TTG TGC GTA
ala his tyr asn ile val thr phe cys cys lys cys asp ser thr leu arg leu cys val 781/261                                      811/271
CAA AGC ACA CAC GTA GAC ATT CGT ACT TTG GAA GAC CTG TTA ATG GGC ACA CTA GGA ATT
gln ser thr his val asp ile arg thr leu glu asp leu leu met gly thr leu gly ile 841/281
GTG TGC CCC ATC TGT TCT CAA GGA TCC
val cys pro ile cys ser gln gly ser
```

FL-E7-GFP Fusion Polypeptide (nucleic acid is SEQ ID NO:13; amino acids are SEQ ID NO: 14

N-terminal sequence is FL, followed by E7 (underscored, cap) followed by GFP (italic)

```
1/1                                          31/11
atg aca gtg ctg gcg cca gcc tgg agc cca aat tcc tcc ctg ttg ctg ctg ttg ctg ctg
Met thr val leu ala pro ala trp ser pro asn ser ser leu leu leu leu leu leu leu 61/21                                        91/31
ctg agt cct tgc ctg cgg ggg aca cct gac tgt tac ttc agc cac agt ccc atc tcc tcc
leu ser pro cys leu arg gly thr pro asp cys tyr phe ser his ser pro ile ser ser 121/41                                       151/51
aac ttc aaa gtg aag ttt aga gag ttg act gac cac ctg ctt aaa gat tac cca gtc act
asn phe lys val lys phe arg glu leu thr asp his leu leu lys asp tyr pro val thr 181/61                                       211/71
gtg gcc gtc aat ctt cag gac gag aag cac tgc aag gcc ttg tgg agc ctc ttc cta gcc
val ala val asn leu gln asp glu lys his cys lys ala leu trp ser leu phe leu ala 241/81                                       271/91
cag cgc tgg ata gag caa ctg aag act gtg gca ggg tct aag atg caa acg ctt ctg gag
```

```
                              -continued
gln arg trp ile glu gln leu lys thr val ala gly ser lys met gln thr leu leu glu 301/101                              331/111
gac gtc aac acc gag ata cat ttt gtc acc tca tgt acc ttc cag ccc cta cca gaa tgt
asp val asn thr glu ile his phe val thr ser cys thr phe gln pro leu pro glu cys 361/121                              391/131
ctg cga ttc gtc cag acc aac atc tcc cac ctc ctg aag gac acc tgc aca cag ctg ctt
leu arg phe val gln thr asn ile ser his leu leu lys asp thr cys thr gln leu leu 421/141                              451/151
gct ctg aag ccc tgt atc ggg aag gcc tgc cag aat ttc tct cgg tgc ctg gag gtg cag
ala leu lys pro cys ile gly lys ala cys gln asn phe ser arg cys leu glu val gln 481/161                              511/171
tgc cag ccg gac tcc tcc acc ctg ctg ccc cca agg agt ccc ata gcc cta gaa gcc acg
cys gln pro asp ser ser thr leu leu pro pro arg ser pro ile ala leu glu ala thr 541/181                              571/191
gag ctc cca gag cct cgg ccc agg cag gaa ttc ATG CAT GGA GAT ACA CCT ACA TTG CAT
glu leu pro glu pro arg pro arg gln glu phe met his gly asp thr pro thr leu his 601/201                              631/211
GAA TAT ATG TTA GAT TTG CAA CCA GAG ACA ACT GAT CTC TAC TGT TAT GAG CAA TTA AAT
glu tyr met leu asp leu gln pro glu thr thr asp leu tyr cys tyr glu gln leu asn 661/221                              691/231
GAC AGC TCA GAG GAG GAG GAT GAA ATA GAT GGT CCA GCT GGA CAA GCA GAA CCG GAC AGA
asp ser ser glu glu glu asp glu ile asp gly pro ala gly gln ala glu pro asp arg 721/241                              751/251
GCC CAT TAC AAT ATT GTA ACC TTT TGT TGC AAG TGT GAC TCT ACG CTT CGG TTG TGC GTA
ala his tyr asn ile val thr phe cys cys lys cys asp ser thr leu arg leu cys val 781/261                              811/271
CAA AGC ACA CAC GTA GAC ATT CGT ACT TTG GAA GAC CTG TTA ATG GGC ACA CTA GGA ATT
gln ser thr his val asp ile arg thr leu glu asp leu leu met gly thr leu gly ile 841/281                              871/291
GTG TGC CCC ATC TGT TCT CAA GGA TCC atg gtg agc aag ggc gag gag ctg ttc acc ggg
val cys pro ile cys ser gln gly ser met val ser lys gly glu glu leu phe thr gly 901/301                              931/311
gtg gtg ccc atc ctg gtc gag ctg gac ggc gac gta aac ggc cac aag ttc agc gtg tcc
val val pro ile leu val glu leu asp gly asp val asn gly his lys phe ser val ser 961/321                              991/331
ggc gag ggc gag ggc gat gcc acc tac ggc aag ctg acc ctg aag ttc atc tgc acc acc
gly glu gly glu gly asp ala thr tyr gly lys leu thr leu lys phe ile cys thr thr 1021/341                             1051/351
ggc aag ctg ccc gtg ccc tgg ccc acc ctc gtg acc acc ttc acc tac ggc gtg cag tgc
gly lys leu pro val pro trp pro thr leu val thr thr phe thr tyr gly val gln cys 1081/361                             1111/371
ttc agc cgc tac ccc gac cac atg aag cag cac gac ttc ttc aag tcc gcc atg ccc gaa
phe ser arg tyr pro asp his met lys gln his asp phe phe lys ser ala met pro glu 1141/381                             1171/391
ggc tac gtc cag gag cgc acc atc ttc ttc aag gac gac ggc aac tac aag acc cgc gcc
gly tyr val gln glu arg thr ile phe phe lys asp asp gly asn tyr lys thr arg ala 1201/401                             1231/411
gag gtg aag ttc gag ggc gac acc ctg gtg aac cgc atc gag ctg aag ggc atc gac ttc
glu val lys phe glu gly asp thr leu val asn arg ile glu leu lys gly ile asp phe 1261/421                             1291/431
aag gag gac ggc aac atc ctg ggg cac aag ctg gag tac aac tac aac agc cac aac gtc
lys glu asp gly asn ile leu gly his lys leu glu tyr asn tyr asn ser his asn val 1321/441                             1351/451
tat atc atg gcc gac aag cag aag aac ggc atc aag gtg aac ttc aag atc cgc cac aac
tyr ile met ala asp lys gln lys asn gly ile lys val asn phe lys ile arg his asn 1381/461                             1411/471
atc gag gac ggc agc gtg cag ctc gcc gac cac tac cag cag aac acc ccc atc ggc gac
ile glu asp gly ser val gln leu ala asp his tyr gln gln asn thr pro ile gly asp 1441/481                             1471/491
ggc ccc gtg ctg ctg ccc gac aac cac tac ctg agc acc cag tcc gcc ctg agc aaa gac
```

-continued gly pro val leu leu pro asp asn his tyr leu ser thr gln ser ala leu ser lys asp 1501/501                          1531/511
ccc aac gag aag cgc gat cac atg gtc ctg ctg gag ttc gtg acc gcc gcc ggg atc act
pro asn glu lys arg asp his met val leu leu glu phe val thr ala ala gly ile thr 1561/521
ctc ggc atg gac gag ctg tac aag
leu gly met asp glu leu tyr lys pcDNA3 plasmid vector: (SEQ ID NO: 15)

```
GACGGATCGG GAGATCTCCC GATCCCCTAT GGTCGACTCT CAGTACAATC TGCTCTGATG CCGCATAGTT

AAGCCAGTAT CTGCTCCCTG CTTGTGTGTT GGAGGTCGCT GAGTAGTGCG CGAGCAAAAT TTAAGCTACA

ACAAGGCAAG GCTTGACCGA CAATTGCATG AAGAATCTGC TTAGGGTTAG GCGTTTTGCG CTGCTTCGCG

ATGTACGGGC CAGATATACG CGTTGACATT GATTATTGAC TAGTTATTAA TAGTAATCAA TTACGGGGTC

ATTAGTTCAT AGCCCATATA TGGAGTTCCG CGTTACATAA CTTACGGTAA ATGGCCCGCC TGGCTGACCG

CCCAACGACC CCCGCCCATT GACGTCAATA ATGACGTATG TTCCCATAGT AACGCCAATA GGGACTTTCC

ATTGACGTCA ATGGGTGGAC TATTTACGGT AAACTGCCCA CTTGGCAGTA CATCAAGTGT ATCATATGCC

AAGTACGCCC CCTATTGACG TCAATGACGG TAAATGGCCC GCCTGGCATT ATGCCCAGTA CATGACCTTA

TGGGACTTTC CTACTTGGCA GTACATCTAC GTATTAGTCA TCGCTATTAC CATGGTGATG CGGTTTTGGC

AGTACATCAA TGGGCGTGGA TAGCGGTTTG ACTCACGGGG ATTTCCAAGT CTCCACCCCA TTGACGTCAA

TGGGAGTTTG TTTTGGCACC AAAATCAACG GGACTTTCCA AAATGTCGTA ACAACTCCGC CCCATTGACG

CAAATGGGCG GTAGGCGTGT ACGGTGGGAG GTCTATATAA GCAGAGCTCT CTGGCTAACT AGAGAACCCA

CTGCTTACTG GCTTATCGAA ATTAATACGA CTCACTATAG GGAGACCCAA GCTGGCTAGC GTTTAAACGG

GCCCTCTAGA CTCGAGCGGC CGCCACTGTG CTGGATATCT GCAGAATTCC ACCACACTGG ACTAGTGGAT

CCGAGCTCGG TACCAAGCTT AAGTTTAAAC CGCTGATCAG CCTCGACTGT GCCTTCTAGT TGCCAGCCAT

CTGTTGTTTG CCCCTCCCCC GTGCCTTCCT TGACCCTGGA AGGTGCCACT CCCACTGTCC TTTCCTAATA

AAATGAGGAA ATTGCATCGC ATTGTCTGAG TAGGTGTCAT TCTATTCTGG GGGTGGGGT GGGGCAGGAC

AGCAAGGGGG AGGATTGGGA AGACAATAGC AGGCATGCTG GGGATGCGGT GGGCTCTATG GCTTCTGAGG

CGGAAAGAAC CAGCTGGGGC TCTAGGGGGT ATCCCCACGC GCCCTGTAGC GGCGCATTAA GCGCGGCGGG

TGTGGTGGTT ACGCGCAGCG TGACCGCTAC ACTTGCCAGC GCCCTAGCGC CCGCTCCTTT CGCTTTCTTC

CCTTCCTTTC TCGCCACGTT CGCCGGCTTT CCCCGTCAAG CTCTAAATCG GGGCATCCCT TTAGGGTTCC

GATTTAGTGC TTTACGGCAC CTCGACCCCA AAAAACTTGA TTAGGGTGAT GGTTCACGTA GTGGGCCATC

GCCCTGATAG ACGGTTTTTC GCCCTTTGAC GTTGGAGTCC ACGTTCTTTA ATAGTGGACT CTTGTTCCAA

ACTGGAACAA CACTCAACCC TATCTCGGTC TATTCTTTTG ATTTATAAGG GATTTTGGGG ATTTCGGCCT

ATTGGTTAAA AAATGAGCTG ATTTAACAAA AATTTAACGC GAATTAATTC TGTGGAATGT GTGTCAGTTA

GGGTGTGGAA AGTCCCCAGG CTCCCCAGGC AGGCAGAAGT ATGCAAAGCA TGCATCTCAA TTAGTCAGCA

ACCAGGTGTG GAAAGTCCCC AGGCTCCCCA GCAGGCAGAA GTATGCAAAG CATGCATCTC AATTAGTCAG

CAACCATAGT CCCGCCCCTA ACTCCGCCCA TCCCGCCCCT AACTCCGCCC AGTTCCGCCC ATTCTCCGCC

CCATGGCTGA CTAATTTTTT TTATTTATGC AGAGGCCGAG GCCGCCTCTG CCTCTGAGCT ATTCCAGAAG

TAGTGAGGAG GCTTTTTTGG AGGCCTAGGC TTTTGCAAAA AGCTCCCGGG AGCTTGTATA TCCATTTTCG

GATCTGATCA AGAGACAGGA TGAGGATCGT TTCGCATGAT TGAACAAGAT GGATTGCACG CAGGTTCTCC

GGCCGCTTGG GTGGAGAGGC TATTCGGCTA TGACTGGGCA CAACAGACAA TCGGCTGCTC TGATGCCGCC
```

-continued

```
GTGTTCCGGC TGTCAGCGCA GGGGCGCCCG GTTCTTTTTG TCAAGACCGA CCTGTCCGGT GCCCTGAATG
AACTGCAGGA CGAGGCAGCG CGGCTATCGT GGCTGGCCAC GACGGGCGTT CCTTGCGCAG CTGTGCTCGA
CGTTGTCACT GAAGCGGGAA GGGACTGGCT GCTATTGGGC GAAGTGCCGG GGCAGGATCT CCTGTCATCT
CACCTTGCTC CTGCCAGAAA AGTATCCATC ATGGCTGATG CAATGCGGCG GCTGCATACG CTTGATCCGG
CTACCTGCCC ATTCGACCAC CAAGCGAAAC ATCGCATCGA GCGAGCACGT ACTCGGATGG AAGCCGGTCT
TGTCGATCAG GATGATCTGG ACGAAGAGCA TCAGGGGCTC GCGCCAGCCG AACTGTTCGC CAGGCTCAAG
GCGCGCATGC CCGACGGCGA GGATCTCGTC GTGACCCATG GCGATGCCTG CTTGCCGAAT ATCATGGTGG
AAAATGGCCG CTTTTCTGGA TTCATCGACT GTGGCCGGCT GGGTGTGGCG GACCGCTATC AGGACATAGC
GTTGGCTACC CGTGATATTG CTGAAGAGCT TGGCGGCGAA TGGGCTGACC GCTTCCTCGT GCTTTACGGT
ATCGCCGCTC CCGATTCGCA GCGCATCGCC TTCTATCGCC TTCTTGACGA GTTCTTCTGA GCGGGACTCT
GGGGTTCGAA ATGACCGACC AAGCGACGCC CAACCTGCCA TCACGAGATT TCGATTCCAC CGCCGCCTTC
TATGAAAGGT TGGGCTTCGG AATCGTTTTC CGGGACGCCG GCTGGATGAT CCTCCAGCGC GGGGATCTCA
TGCTGGAGTT CTTCGCCCAC CCCAACTTGT TTATTGCAGC TTATAATGGT TACAAATAAA GCAATAGCAT
CACAAATTTC ACAAATAAAG CATTTTTTTC ACTGCATTCT AGTTGTGGTT TGTCCAAACT CATCAATGTA
TCTTATCATG TCTGTATACC GTCGACCTCT AGCTAGAGCT TGGCGTAATC ATGGTCATAG CTGTTTCCTG
TGTGAAATTG TTATCCGCTC ACAATTCCAC ACAACATACG AGCCGGAAGC ATAAAGTGTA AAGCCTGGGG
TGCCTAATGA GTGAGCTAAC TCACATTAAT TGCGTTGCGC TCACTGCCCG CTTTCCAGTC GGGAAACCTG
TCGTGCCAGC TGCATTAATG AATCGGCCAA CGCGCGGGGA GAGGCGGTTT GCGTATTGGG CGCTCTTCCG
CTTCCTCGCT CACTGACTCG CTGCGCTCGG TCGTTCGGCT GCGGCGAGCG GTATCAGCTC ACTCAAAGGC
GGTAATACGG TTATCCACAG AATCAGGGGA TAACGCAGGA AGAACATGT GAGCAAAAGG CCAGCAAAAG
GCCAGGAACC GTAAAAAGGC CGCGTTGCTG GCGTTTTTCC ATAGGCTCCG CCCCCCTGAC GAGCATCACA
AAAATCGACG CTCAAGTCAG AGGTGGCGAA ACCCGACAGG ACTATAAAGA TACCAGGCGT TTCCCCCTGG
AAGCTCCCTC GTGCGCTCTC CTGTTCCGAC CCTGCCGCTT ACCGGATACC TGTCCGCCTT TCTCCCTTCG
GGAAGCGTGG CGCTTTCTCA ATGCTCACGC TGTAGGTATC TCAGTTCGGT GTAGGTCGTT CGCTCCAAGC
TGGGCTGTGT GCACGAACCC CCCGTTCAGC CCGACCGCTG CGCCTTATCC GGTAACTATC GTCTTGAGTC
CAACCCGGTA AGACACGACT TATCGCCACT GGCAGCAGCC ACTGGTAACA GGATTAGCAG AGCGAGGTAT
GTAGGCGGTG CTACAGAGTT CTTGAAGTGG TGGCCTAACT ACGGCTACAC TAGAAGGACA GTATTTGGTA
TCTGCGCTCT GCTGAAGCCA GTTACCTTCG GAAAAAGAGT TGGTAGCTCT TGATCCGGCA ACAAACCAC
CGCTGGTAGC GGTGGTTTTT TTGTTTGCAA GCAGCAGATT ACGCGCAGAA AAAAAGGATC TCAAGAAGAT
CCTTTGATCT TTTCTACGGG GTCTGACGCT CAGTGGAACG AAAACTCACG TTAAGGGATT TTGGTCATGA
GATTATCAAA AAGGATCTTC ACCTAGATCC TTTTAAATTA AAAATGAAGT TTTAAATCAA TCTAAAGTAT
ATATGAGTAA ACTTGGTCTG ACAGTTACCA ATGCTTAATC AGTGAGGCAC CTATCTCAGC GATCTGTCTA
TTTCGTTCAT CCATAGTTGC CTGACTCCCC GTCGTGTAGA TAACTACGAT ACGGGAGGGC TTACCATCTG
GCCCCAGTGC TGCAATGATA CCGCGAGACC CACGCTCACC GGCTCCAGAT TTATCAGCAA TAAACCAGCC
AGCCGGAAGG GCCGAGCGCA GAAGTGGTCC TGCAACTTTA TCCGCCTCCA TCCAGTCTAT TAATTGTTGC
CGGGAAGCTA GAGTAAGTAG TTCGCCAGTT AATAGTTTGC GCAACGTTGT TGCCATTGCT ACAGGCATCG
TGGTGTCACG CTCGTCGTTT GGTATGGCTT CATTCAGCTC CGGTTCCCAA CGATCAAGGC GAGTTACATG
ATCCCCCATG TTGTGCAAAA AAGCGGTTAG CTCCTTCGGT CCTCCGATCG TTGTCAGAAG TAAGTTGGCC
GCAGTGTTAT CACTCATGGT TATGGCAGCA CTGCATAATT CTCTTACTGT CATGCCATCC GTAAGATGCT
TTTCTGTGAC TGGTGAGTAC TCAACCAAGT CATTCTGAGA ATAGTGTATG CGGCGACCGA GTTGCTCTTG
```

-continued

```
CCCGGCGTCA ATACGGGATA ATACCGCGCC ACATAGCAGA ACTTTAAAAG TGCTCATCAT GGAAAACGT

TCTTCGGGGC GAAAACTCTC AAGGATCTTA CCGCTGTTGA GATCCAGTTC GATGTAACCC ACTCGTGCAC

CCAACTGATC TTCAGCATCT TTTACTTTCA CCAGCGTTTC TGGGTGAGCA AAAACAGGAA GGCAAAATGC

CGCAAAAAAG GGAATAAGGG CGACACGGAA ATGTTGAATA CTCATACTCT TCCTTTTTCA ATATTATTGA

AGCATTTATC AGGGTTATTG TCTCATGAGC GGATACATAT TTGAATGTAT TTAGAAAAAT AAACAAATAG

GGGTTCCGCG CACATTTCCC CGAAAAGTGC CACCTGACGT C
```

SINrep5 self replicating replicon (SEQ ID NO:16)

(includes cloning sites)

```
ATTGACGGCG TAGTACACAC TATTGAATCA AACAGCCGAC CAATTGCACT ACCATCACAA TGGAGAAGCC

AGTAGTAAAC GTAGACGTAG ACCCCCAGAG TCCGTTTGTC GTGCAACTGC AAAAAAGCTT CCCGCAATTT

GAGGTAGTAG CACAGCAGGT CACTCCAAAT GACCATGCTA ATGCCAGAGC ATTTTCGCAT CTGGCCAGTA

AACTAATCGA GCTGGAGGTT CCTACCACAG CGACGATCTT GGACATAGGC AGCGCACCGG CTCGTAGAAT

GTTTTCCGAG CACCAGTATC ATTGTGTCTG CCCCATGCGT AGTCCAGAAG ACCCGGACCG CATGATGAAA

TACGCCAGTA AACTGGCGGA AAAAGCGTGC AAGATTACAA ACAAGAACTT GCATGAGAAG ATTAAGGATC

TCCGGACCGT ACTTGATACG CCGGATGCTG AAACACCATC GCTCTGCTTT CACAACGATG TTACCTGCAA

CATGCGTGCC GAATATTCCG TCATGCAGGA CGTGTATATC AACGCTCCCG AACTATCTA TCATCAGGCT

ATGAAAGGCG TGCGGACCCT GTACTGGATT GGCTTCGACA CCACCCAGTT CATGTTCTCG GCTATGGCAG

GTTCGTACCC TGCGTACAAC ACCAACTGGG CCGACGAGAA AGTCCTTGAA GCGCGTAACA TCGGACTTTG

CAGCACAAAG CTGAGTGAAG GTAGGACAGG AAAATTGTCG ATAATGAGGA AGAAGGAGTT GAAGCCCGGG

TCGCGGGTTT ATTTCTCCGT AGGATCGACA CTTTATCCAG AACACAGAGC CAGCTTGCAG AGCTGGCATC

TTCCATCGGT GTTCCACTTG AATGGAAAGC AGTCGTACAC TTGCCGCTGT GATACAGTGT TGAGTTGCGA

AGGCTACGTA GTGAAGAAAA TCACCATCAG TCCCGGGATC ACGGGAGAAA CCGTGGGATA CGCGGTTACA

CACAATAGCG AGGGCTTCTT GCTATGCAAA GTTACTGACA CAGTAAAAGG AGAACGGGTA TCGTTCCCTG

TGTGCACGTA CATCCCGGCC ACCATATGCG ATCAGATGAC TGGTATAATG GCCACGGATA TATCACCTGA

CGATGCACAA AAACTTCTGG TTGGGCTCAA CCAGCGAATT GTCATTAACG GTAGGACTAA CAGGAACACC

AACACCATGC AAAATTACCT TCTGCCGATC ATAGCACAAG GGTTCAGCAA ATGGGCTAAG GAGCGCAAGG

ATGATCTTGA TAACGAGAAA ATGCTGGGTA CTAGAGAACG CAAGCTTACG TATGGCTGCT TGTGGGCGTT

TCGCACTAAG AAAGTACATT CGTTTTATCG CCCACCTGGA ACGCAGACCT GCGTAAAAGT CCCAGCCTCT

TTTAGCGCTT TTCCCATGTC GTCCGTATGG ACGACCTCTT TGCCCATGTC GCTGAGGCAG AAATTGAAAC

TGGCATTGCA ACCAAAGAAG GAGGAAAAAC TGCTGCAGGT CTCGGAGGAA TTAGTCATGG AGGCCAAGGC

TGCTTTTGAG GATGCTCAGG AGGAAGCCAG AGCGGAGAAG CTCCGAGAAG CACTTCCACC ATTAGTGGCA

GACAAAGGCA TCGAGGCAGC CGCAGAAGTT GTCTGCGAAG TGGAGGGGCT CCAGGCGGAC ATCGGAGCAG

CATTAGTTGA AACCCCGCGC GGTCACGTAA GGATAATACC TCAAGCAAAT GACCGTATGA TCGGACAGTA

TATCGTTGTC TCGCCAAACT CTGTGCTGAA GAATGCCAAA CTCGCACCAG CGCACCCGCT AGCAGATCAG

GTTAAGATCA TAACACACTC CGGAAGATCA GGAAGGTACG CGGTCGAACC ATACGACGCT AAAGTACTGA

TGCCAGCAGG AGGTGCCGTA CCATGGCCAG AATTCCTAGC ACTGAGTGAG AGCGCCACGT TAGTGTACAA

CGAAAGAGAG TTTGTGAACC GCAAACTATA CCACATTGCC ATGCATGGCC CGCCAAGAA TACAGAAGAG

GAGCAGTACA AGGTTACAAA GGCAGAGCTT GCAGAAACAG AGTACGTGTT TGACGTGGAC AAGAAGCGTT
```

-continued

```
GCGTTAAGAA GGAAGAAGCC TCAGGTCTGG TCCTCTCGGG AGAACTGACC AACCCTCCCT ATCATGAGCT

AGCTCTGGAG GGACTGAAGA CCCGACCTGC GGTCCCGTAC AAGGTCGAAA CAATAGGAGT GATAGGCACA

CCGGGGTCGG GCAAGTCAGC TATTATCAAG TCAACTGTCA CGGCACGAGA TCTTGTTACC AGCGGAAAGA

AAGAAAATTG TCGCGAAATT GAGGCCGACG TGCTAAGACT GAGGGGTATG CAGATTACGT CGAAGACAGT

AGATTCGGTT ATGCTCAACG GATGCCACAA AGCCGTAGAA GTGCTGTACG TTGACGAAGC GTTCGCGTGC

CACGCAGGAG CACTACTTGC CTTGATTGCT ATCGTCAGGC CCCGCAAGAA GGTAGTACTA TGCGGAGACC

CCATGCAATG CGGATTCTTC AACATGATGC AACTAAAGGT ACATTTCAAT CACCCTGAAA AGACATATG

CACCAAGACA TTCTACAAGT ATATCTCCCG GCGTTGCACA CAGCCAGTTA CAGCTATTGT ATCGACACTG

CATTACGATG GAAAGATGAA ACCACGAAC CCGTGCAAGA AGAACATTGA ATCGATATT ACAGGGGCCA

CAAAGCCGAA GCCAGGGGAT ATCATCCTGA CATGTTTCCG CGGGTGGGTT AAGCAATTGC AAATCGACTA

TCCCGGACAT GAAGTAATGA CAGCCGCGGC CTCACAAGGG CTAACCAGAA AAGGAGTGTA TGCCGTCCGG

CAAAAAGTCA ATGAAAACCC ACTGTACGCG ATCACATCAG AGCATGTGAA CGTGTTGCTC ACCCGCACTG

AGGACAGGCT AGTGTGGAAA ACCTTGCAGG GCGACCCATG GATTAAGCAG CCCACTAACA TACCTAAAGG

AAACTTTCAG GCTACTATAG AGGACTGGGA AGCTGAACAC AAGGGAATAA TTGCTGCAAT AAACAGCCCC

ACTCCCCGTG CCAATCCGTT CAGCTGCAAG ACCAACGTTT GCTGGGCGAA AGCATTGGAA CCGATACTAG

CCACGGCCGG TATCGTACTT ACCGGTTGCC AGTGGAGCGA ACTGTTCCCA CAGTTTGCGG ATGACAAACC

ACATTCGGCC ATTTACGCCT TAGACGTAAT TTGCATTAAG TTTTTCGGCA TGGACTTGAC AAGCGGACTG

TTTTCTAAAC AGAGCATCCC ACTAACGTAC CATCCCGCCG ATTCAGCGAG GCCGGTAGCT CATTGGGACA

ACAGCCCAGG AACCCGCAAG TATGGGTACG ATCACGCCAT TGCCGCCGAA CTCTCCCGTA GATTTCCGGT

GTTCCAGCTA GCTGGGAAGG GCACACAACT TGATTTGCAG ACGGGGAGAA CCAGAGTTAT CTCTGCACAG

CATAACCTGG TCCCGGTGAA CCGCAATCTT CCTCACGCCT TAGTCCCCGA GTACAAGGAG AAGCAACCCG

GCCCGGTCAA AAAATTCTTG AACCAGTTCA ACACCACTC AGTACTTGTG GTATCAGAGG AAAAAATTGA

AGCTCCCCGT AAGAGAATCG AATGGATCGC CCCGATTGGC ATAGCGGTG CAGATAAGAA CTACAACCTG

GCTTTCGGGT TTCCGCCGCA GGCACGGTAC GACCTGGTGT TCATCAACAT TGGAACTAAA TACAGAAACC

ACCACTTTCA GCAGTGCGAA GACCATGCGG CGACCTTAAA AACCCTTTCG CGTTCGGCCC TGAATTGCCT

TAACCCAGGA GGCACCCTCG TGGTGAAGTC CTATGGCTAC GCCGACCGCA ACAGTGAGGA CGTAGTCACC

GCTCTTGCCA GAAAGTTTGT CAGGGTGTCT GCAGCGAGAC CAGATTGTGT CTCAAGCAAT ACAGAAATGT

ACCTGATTTT CCGACAACTA GACAACAGCC GTACACGGCA ATTCACCCCG CACCATCTGA ATTGCGTGAT

TTCGTCCGTG TATGAGGGTA CAAGAGATGG AGTTGGAGCC GCGCCGTCAT ACCGCACCAA AAGGGAGAAT

ATTGCTGACT GTCAAGAGGA AGCAGTTGTC AACGCAGCCA ATCCGCTGGG TAGACCAGGC GAAGGAGTCT

GCCGTGCCAT CTATAAACGT TGGCCGACCA GTTTTACCGA TTCAGCCACG GAGACAGGCA CCGCAAGAAT

GACTGTGTGC CTAGGAAAGA AAGTGATCCA CGCGGTCGGC CCTGATTTCC GGAAGCACCC AGAAGCAGAA

GCCTTGAAAT TGCTACAAAA CGCCTACCAT GCAGTGGCAG ACTTAGTAAA TGAACATAAC ATCAAGTCTG

TCGCCATTCC ACTGCTATCT ACAGGCATTT ACGCAGCCGG AAAAGACCGC CTTGAAGTAT CACTTAACTG

CTTGACAACC GCGCTAGACA GAACTGACGC GGACGTAACC ATCTATTGCC TGGATAAGAA GTGGAAGGAA

AGAATCGACG CGGCACTCCA ACTTAAGGAG TCTGTAACAG AGCTGAAGGA TGAAGATATG GAGATCGACG

ATGAGTTAGT ATGGATTCAT CCAGACAGTT GCTTGAAGGG AAGAAAGGGA TTCAGTACTA CAAAAGGAAA

ATTGTATTCG TACTTCGAAG GCACCAAATT CCATCAAGCA GCAAAAGACA TGGCGGAGAT AAAGGTCCTG

TTCCCTAATG ACCAGGAAAG TAATGAACAA CTGTGTGCCT ACATATTGGG TGAGACCATG GAAGCAATCC

GCGAAAAGTG CCCGGTCGAC CATAACCCGT CGTCTAGCCC GCCCAAAACG TTGCCGTGCC TTTGCATGTA
```

-continued
```
TGCCATGACG CCAGAAAGGG TCCACAGACT TAGAAGCAAT AACGTCAAAG AAGTTACAGT ATGCTCCTCC
ACCCCCCTTC CTAAGCACAA AATTAAGAAT GTTCAGAAGG TTCAGTGCAC GAAAGTAGTC CTGTTTAATC
CGCACACTCC CGCATTCGTT CCCGCCCGTA AGTACATAGA AGTGCCAGAA CAGCCTACCG CTCCTCCTGC
ACAGGCCGAG GAGGCCCCCG AAGTTGTAGC GACACCGTCA CCATCTACAG CTGATAACAC CTCGCTTGAT
GTCACAGACA TCTCACTGGA TATGGATGAC AGTAGCGAAG GCTCACTTTT TTCGAGCTTT AGCGGATCGG
ACAACTCTAT TACTAGTATG GACAGTTGGT CGTCAGGACC TAGTTCACTA GAGATAGTAG ACCGAAGGCA
GGTGGTGGTG GCTGACGTTC ATGCCGTCCA AGAGCCTGCC CCTATTCCAC CGCCAAGGCT AAAGAAGATG
GCCCGCCTGG CAGCGGCAAG AAAAGAGCCC ACTCCACCGG CAAGCAATAG CTCTGAGTCC CTCCACCTCT
CTTTTGGTGG GGTATCCATG TCCCTCGGAT CAATTTTCGA CGGAGAGACG GCCCGCCAGG CAGCGGTACA
ACCCCTGGCA ACAGGCCCCA CGGATGTGCC TATGTCTTTC GGATCGTTTT CCGACGGAGA GATTGATGAG
CTGAGCCGCA GAGTAACTGA GTCCGAACCC GTCCTGTTTG GATCATTTGA ACCGGGCGAA GTGAACTCAA
TTATATCGTC CCGATCAGCC GTATCTTTTC CACTACGCAA GCAGAGACGT AGACGCAGGA GCAGGAGGAC
TGAATACTGA CTAACCGGGG TAGGTGGGTA CATATTTTCG ACGGACACAG GCCCTGGGCA CTTGCAAAAG
AAGTCCGTTC TGCAGAACCA GCTTACAGAA CCGACCTTGG AGCGCAATGT CCTGGAAAGA ATTCATGCCC
CGGTGCTCGA CACGTCGAAA GAGGAACAAC TCAAACTCAG GTACCAGATG ATGCCCACCG AAGCCAACAA
AAGTAGGTAC CAGTCTCGTA AAGTAGAAAA TCAGAAAGCC ATAACCACTG AGCGACTACT GTCAGGACTA
CGACTGTATA ACTCTGCCAC AGATCAGCCA GAATGCTATA AGATCACCTA TCCGAAACCA TTGTACTCCA
GTAGCGTACC GGCGAACTAC TCCGATCCAC AGTTCGCTGT AGCTGTCTGT AACAACTATC TGCATGAGAA
CTATCCGACA GTAGCATCTT ATCAGATTAC TGACGAGTAC GATGCTTACT TGGATATGGT AGACGGGACA
GTCGCCTGCC TGGATACTGC AACCTTCTGC CCCGCTAAGC TTAGAAGTTA CCCGAAAAAA CATGAGTATA
GAGCCCCGAA TATCCGCAGT GCGGTTCCAT CAGCGATGCA GAACACGCTA CAAAATGTGC TCATTGCCGC
AACTAAAAGA AATTGCAACG TCACGCAGAT GCGTGAACTG CCAACACTGG ACTCAGCGAC ATTCAATGTC
GAATGCTTTC GAAAATATGC ATGTAATGAC GAGTATTGGG AGGAGTTCGC TCGGAAGCCA ATTAGGATTA
CCACTGAGTT TGTCACCGCA TATGTAGCTA GACTGAAAGG CCCTAAGGCC GCCGCACTAT TTGCAAAGAC
GTATAATTTG GTCCCATTGC AAGAAGTGCC TATGGATAGA TTCGTCATGG ACATGAAAAG AGACGTGAAA
GTTACACCAG GCACGAAACA CACAGAAGAA AGACCGAAAG TACAAGTGAT ACAAGCCGCA GAACCCCTGG
CGACTGCTTA CTTATGCGGG ATTCACCGGG AATTAGTGCG TAGGCTTACG GCCGTCTTGC TTCCAAACAT
TCACACGCTT TTTGACATGT CGGCGGAGGA TTTTGATGCA ATCATAGCAG AACACTTCAA GCAAGGCGAC
CCGGTACTGG AGACGGATAT CGCATCATTC GACAAAAGCC AAGACGACGC TATGGCGTTA ACCGGTCTGA
TGATCTTGGA GGACCTGGGT GTGGATCAAC CACTACTCGA CTTGATCGAG TGCGCCTTTG GAGAAATATC
ATCCACCCAT CTACCTACGG GTACTCGTTT TAAATTCGGG GCGATGATGA AATCCGGAAT GTTCTTCACA
CTTTTTGTCA ACACAGTTTT GAATGTCGTT ATCGCCAGCA GAGTACTAGA AGAGCGGCTT AAAACGTCCA
GATGTGCAGC GTTCATTGGC GACGACAACA TCATACATGG AGTAGTATCT GACAAAGAAA TGGCTGAGAG
GTGCGCCACC TGGCTCAACA TGGAGGTTAA GATCATCGAC GCAGTCATCG GTGAGAGACC ACCTTACTTC
TGCGGCGGAT TTATCTTGCA AGATTCGGTT ACTTCCACAG CGTGCCGCGT GGCGGATCCC CTGAAAAGGC
TGTTTAAGTT GGGTAAACCG CTCCCAGCCG ACGACGAGCA AGACGAAGAC AGAAGACGCG CTCTGCTAGA
TGAAACAAAG GCGTGGTTTA GAGTAGGTAT AACAGGCACT TTAGCAGTGG CCGTGACGAC CCGGTATGAG
GTAGACAATA TTACACCTGT CCTACTGGCA TTGAGAACTT TGCCCAGAG CAAAAGAGCA TTCCAAGCCA
TCAGAGGGGA AATAAAGCAT CTCTACGGTG GTCCTAAATA GTCAGCATAG TACATTTCAT CTGACTAATA
CTACAACACC ACCACCTCTA GACGCGTAGA TCTCACGTGA GCATGCAGGC CTTGGGCCCA ATGATCCGAC
```

-continued

```
CAGCAAAACT CGATGTACTT CCGAGGAACT GATGTGCATA ATGCATCAGG CTGGTACATT AGATCCCCGC
TTACCGCGGG CAATATAGCA ACACTAAAAA CTCGATGTAC TTCCGAGGAA GCGCAGTGCA TAATGCTGCG
CAGTGTTGCC ACATAACCAC TATATTAACC ATTTATCTAG CGGACGCCAA AAACTCAATG TATTTCTGAG
GAAGCGTGGT GCATAATGCC ACGCAGCGTC TGCATAACTT TTATTATTTC TTTTATTAAT CAACAAAATT
TTGTTTTTAA CATTTCAAAA AAAAAAAAAA AAAAAAAAAA AAAAAAAAAA AAAGGGAATT CCTCGATTAA
TTAAGCGGCC GCTCGAGGGG AATTAATTCT TGAAGACGAA AGGGCCAGGT GGCACTTTTC GGGGAAATGT
GCGCGGAACC CCTATTTGTT TATTTTTCTA AATACATTCA AATATGTATC CGCTCATGAG ACAATAACCC
TGATAAATGC TTCAATAATA TTGAAAAAGG AAGAGTATGA GTATTCAACA TTTCCGTGTC GCCCTTATTC
CCTTTTTTGC GGCATTTTGC CTTCCTGTTT TTGCTCACCC AGAAACGCTG GTGAAAGTAA AAGATGCTGA
AGATCAGTTG GGTGCACGAG TGGGTTACAT CGAACTGGAT CTCAACAGCG GTAAGATCCT TGAGAGTTTT
CGCCCCGAAG AACGTTTTCC AATGATGAGC ACTTTTAAAG TTCTGCTATG TGGCGCGGTA TTATCCCGTG
TTGACGCCGG GCAAGAGCAA CTCGGTCGCC GCATACACTA TTCTCAGAAT GACTTGGTTG AGTACTCACC
AGTCACAGAA AAGCATCTTA CGGATGGCAT GACAGTAAGA GAATTATGCA GTGCTGCCAT AACCATGAGT
GATAACACTG CGGCCAACTT ACTTCTGACA ACGATCGGAG GACCGAAGGA GCTAACCGCT TTTTTGCACA
ACATGGGGGA TCATGTAACT CGCCTTGATC GTTGGGAACC GGAGCTGAAT GAAGCCATAC CAAACGACGA
GCGTGACACC ACGATGCCTG TAGCAATGGC AACAACGTTG CGCAAACTAT TAACTGGCGA ACTACTTACT
CTAGCTTCCC GGCAACAATT AATAGACTGG ATGGAGGCGG ATAAAGTTGC AGGACCACTT CTGCGCTCGG
CCCTTCCGGC TGGCTGGTTT ATTGCTGATA AATCTGGAGC CGGTGAGCGT GGGTCTCGCG GTATCATTGC
AGCACTGGGG CCAGATGGTA AGCCCTCCCG TATCGTAGTT ATCTACACGA CGGGGAGTCA GGCAACTATG
GATGAACGAA ATAGACAGAT CGCTGAGATA GGTGCCTCAC TGATTAAGCA TTGGTAACTG TCAGACCAAG
TTTACTCATA TATACTTTAG ATTGATTTAA AACTTCATTT TTAATTTAAA AGGATCTAGG TGAAGATCCT
TTTTGATAAT CTCATGACCA AAATCCCTTA ACGTGAGTTT TCGTTCCACT GAGCGTCAGA CCCCGTAGAA
AAGATCAAAG GATCTTCTTG AGATCCTTTT TTTCTGCGCG TAATCTGCTG CTTGCAAACA AAAAAACCAC
CGCTACCAGC GGTGGTTTGT TGCCGGATC AAGAGCTACC AACTCTTTTT CCGAAGGTAA CTGGCTTCAG
CAGAGCGCAG ATACCAAATA CTGTCCTTCT AGTGTAGCCG TAGTTAGGCC ACCACTTCAA GAACTCTGTA
GCACCGCCTA CATACCTCGC TCTGCTAATC CTGTTACCAG TGGCTGCTGC CAGTGGCGAT AAGTCGTGTC
TTACCGGGTT GGACTCAAGA CGATAGTTAC CGGATAAGGC GCAGCGGTCG GGCTGAACGG GGGGTTCGTG
CACACAGCCC AGCTTGGAGC GAACGACCTA CACCGAACTG AGATACCTAC AGCGTGAGCA TTGAGAAAGC
GCCACGCTTC CCGAAGGGAG AAAGGCGGAC AGGTATCCGG TAAGCGGCAG GGTCGGAACA GGAGAGCGCA
CGAGGGAGCT TCCAGGGGGA AACGCCTGGT ATCTTTATAG TCCTGTCGGG TTTCGCCACC TCTGACTTGA
GCGTCGATTT TTGTGATGCT CGTCAGGGGG CGGAGCCTA TGGAAAAACG CCAGCAACGC GAGCTCGTAT
GGACATATTG TCGTTAGAAC GCGGCTACAA TTAATACATA ACCTTATGTA TCATACACAT ACGATTTAGG
GGACACTATA G
```

55 pSCA1 suicide DNA vector SEQ ID NO:17:
(includes cloning sites

```
ATGGCGGATG TGTGACATAC ACGACGCCAA AAGATTTTGT TCCAGCTCCT GCCACCTCCG CTACGCGAGA
GATTAACCAC CCACGATGGC CGCCAAAGTG CATGTTGATA TTGAGGCTGA CAGCCCATTC ATCAAGTCTT
TGCAGAAGGC ATTTCCGTCG TTCGAGGTGG AGTCATTGCA GGTCACACCA AATGACCATG CAAATGCCAG
```

-continued

```
AGCATTTTCG CACCTGGCTA CCAAATTGAT CGAGCAGGAG ACTGACAAAG ACACACTCAT CTTGGATATC
GGCAGTGCGC CTTCCAGGAG AATGATGTCT ACGCACAAAT ACCACTGCGT ATGCCCTATG CGCAGCGCAG
AAGACCCCGA AAGGCTCGAT AGCTACGCAA AGAAACTGGC AGCGGCCTCC GGGAAGGTGC TGGATAGAGA
GATCGCAGGA AAAATCACCG ACCTGCAGAC CGTCATGGCT ACGCCAGACG CTGAATCTCC TACCTTTTGC
CTGCATACAG ACGTCACGTG TCGTACGGCA GCCGAAGTGG CCGTATACCA GGACGTGTAT GCTGTACATG
CACCAACATC GCTGTACCAT CAGGCGATGA AAGGTGTCAG AACGGCGTAT TGGATTGGGT TTGACACCAC
CCCGTTTATG TTTGACGCGC TAGCAGGCGC GTATCCAACC TACGCCACAA ACTGGGCCGA CGAGCAGGTG
TTACAGGCCA GGAACATAGG ACTGTGTGCA GCATCCTTGA CTGAGGGAAG ACTCGGCAAA CTGTCCATTC
TCCGCAAGAA GCAATTGAAA CCTTGCGACA CAGTCATGTT CTCGGTAGGA TCTACATTGT ACACTGAGAG
CAGAAAGCTA CTGAGGAGCT GGCACTTACC CTCCGTATTC CACCTGAAAG GTAAACAATC CTTTACCTGT
AGGTGCGATA CCATCGTATC ATGTGAAGGG TACGTAGTTA AGAAAATCAC TATGTGCCCC GGCCTGTACG
GTAAAACGGT AGGGTACGCC GTGACGTATC ACGCGGAGGG ATTCCTAGTG TGCAAGACCA CAGACACTGT
CAAAGGAGAA AGAGTCTCAT TCCCTGTATG CACCTACGTC CCCTCAACCA TCTGTGATCA AATGACTGGC
ATACTAGCGA CCGACGTCAC ACCGGAGGAC GCACAGAAGT TGTTAGTGGG ATTGAATCAG AGGATAGTTG
TGAACGGAAG AACACAGCGA AACACTAACA CGATGAAGAA CTATCTGCTT CCGATTGTGG CCGTCGCATT
TAGCAAGTGG GCGAGGGAAT ACAAGGCAGA CCTTGATGAT GAAAAACCTC TGGGTGTCCG AGAGAGGTCA
CTTACTTGCT GCTGCTTGTG GGCATTTAAA ACGAGGAAGA TGCACACCAT GTACAAGAAA CCAGACACCC
AGACAATAGT GAAGGTGCCT TCAGAGTTTA ACTCGTTCGT CATCCCGAGC CTATGGTCTA CAGGCCTCGC
AATCCCAGTC AGATCACGCA TTAAGATGCT TTTGGCCAAG AAGACCAAGC GAGAGTTAAT ACCTGTTCTC
GACGCGTCGT CAGCCAGGGA TGCTGAACAA GAGGAGAAGG AGAGGTTGGA GGCCGAGCTG ACTAGAGAAG
CCTTACCACC CCTCGTCCCC ATCGCGCCGG CGGAGACGGG AGTCGTCGAC GTCGACGTTG AAGAACTAGA
GTATCACGCA GGTGCAGGGG TCGTGGAAAC ACCTCGCAGC GCGTTGAAAG TCACCGCACA GCCGAACGAC
GTACTACTAG GAAATTACGT AGTTCTGTCC CCGCAGACCG TGCTCAAGAG CTCCAAGTTG GCCCCCGTGC
ACCCTCTAGC AGAGCAGGTG AAAATAATAA CACATAACGG GAGGGCCGGC GGTTACCAGG TCGACGGATA
TGACGGCAGG GTCCTACTAC CATGTGGATC GGCCATTCCG GTCCCTGAGT TTCAAGCTTT GAGCGAGAGC
GCCACTATGG TGTACAACGA AAGGGAGTTC GTCAACAGGA AACTATACCA TATTGCCGTT CACGGACCGT
CGCTGAACAC CGACGAGGAG AACTACGAGA AAGTCAGAGC TGAAAGAACT GACGCCGAGT ACGTGTTCGA
CGTAGATAAA AAATGCTGCG TCAAGAGAGA GGAAGCGTCG GGTTTGGTGT TGGTGGGAGA GCTAACCAAC
CCCCCGTTCC ATGAATTCGC CTACGAAGGG CTGAAGATCA GGCCGTCGGC ACCATATAAG ACTACAGTAG
TAGGAGTCTT TGGGGTTCCG GGATCAGGCA AGTCTGCTAT TATTAAGAGC CTCGTGACCA ACACGATCT
GGTCACCAGC GGCAAGAAGG AGAACTGCCA GGAAATAGTT AACGACGTGA AGAAGCACCG CGGGAAGGGG
ACAAGTAGGG AAAACAGTGA CTCCATCCTG CTAAACGGGT GTCGTCGTGC CGTGGACATC CTATATGTGG
ACGAGGCTTT CGCTaGCCAT TCCGGTACTC TGCTGGCCCT AATTGCTCTT GTTAAACCTC GGAGCAAAGT
GGTGTTATGC GGAGACCCCA AGCAATGCGG ATTCTTCAAT ATGATGCAGC TTAAGGTGAA CTTCAACCAC
AACATCTGCA CTGAAGTATG TCATAAAAGT ATATCCAGAC GTTGCACGCG TCCAGTCACG GCCATCGTGT
CTACGTTGCA CTACGGAGGC AAGATGCGCA CGACCAACCC GTGCAACAAA CCCATAATCA TAGACACCAC
AGGACAGACC AAGCCCAAGC CAGGAGACAT CGTGTTAACA TGCTTCCGAG CTGGGCAAA GCAGCTGCAG
TTGGACTACC GTGGACACGA AGTCATGACA GCAGCAGCAT CTCAGGGCCT CACCCGCAAA GGGGTATACG
CCGTAAGGCA GAAGGTGAAT GAAAATCCCT TGTATGCCCC TGCGTCGGAG CACGTGAATG TACTGCTGAC
GCGCACTGAG GATAGGCTGG TGTGGAAAAC GCTGGCCGGC GATCCCTGGA TTAAGGTCCT ATCAAACATT
```

-continued

```
CCACAGGGTA ACTTTACGGC CACATTGGAA GAATGGCAAG AAGAACACGA CAAAATAATG AAGGTGATTG
AAGGACCGGC TGCGCCTGTG GACGCGTTCC AGAACAAAGC GAACGTGTGT TGGGCGAAAA GCCTGGTGCC
TGTCCTGGAC ACTGCCGGAA TCAGATTGAC AGCAGAGGAG TGGAGCACCA TAATTACAGC ATTTAAGGAG
GACAGAGCTT ACTCTCCAGT GGTGGCCTTG AATGAAATTT GCACCAAGTA CTATGGAGTT GACCTGGACA
GTGGCCTGTT TTCTGCCCCG AAGGTGTCCC TGTATTACGA GAACAACCAC TGGGATAACA GACCTGGTGG
AAGGATGTAT GGATTCAATG CCGCAACAGC TGCCAGGCTG GAAGCTAGAC ATACCTTCCT GAAGGGGCAG
TGGCATACGG GCAAGCAGGC AGTTATCGCA GAAAGAAAAA TCCAACCGCT TTCTGTGCTG GACAATGTAA
TTCCTATCAA CCGCAGGCTG CCGCACGCCC TGGTGGCTGA GTACAAGACG GTTAAAGGCA GTAGGGTTGA
GTGGCTGGTC AATAAAGTAA GAGGGTACCA CGTCCTGCTG GTGAGTGAGT ACAACCTGGC TTTGCCTCGA
CGCAGGGTCA CTTGGTTGTC ACCGCTGAAT GTCACAGGCG CCGATAGGTG CTACGACCTA AGTTTAGGAC
TGCCGGCTGA CGCCGGCAGG TTCGACTTGG TCTTTGTGAA CATTCACACG GAATTCAGAA TCCACCACTA
CCAGCAGTGT GTCGACCACG CCATGAAGCT GCAGATGCTT GGGGGAGATG CGCTACGACT GCTAAAACCC
GGCGGCATCT TGATGAGAGC TTACGGATAC GCCGATAAAA TCAGCGAAGC CGTTGTTTCC TCCTTAAGCA
GAAAGTTCTC GTCTGCAAGA GTGTTGCGCC CGGATTGTGT CACCAGCAAT ACAGAAGTGT TCTTGCTGTT
CTCCAACTTT GACAACGGAA AGAGACCCTC TACGCTACAC CAGATGAATA CCAAGCTGAG TGCCGTGTAT
GCCGGAGAAG CCATGCACAC GGCCGGGTGT GCACCATCCT ACAGAGTTAA GAGAGCAGAC ATAGCCACGT
GCACAGAAGC GGCTGTGGTT AACGCAGCTA ACGCCCGTGG AACTGTAGGG GATGGCGTAT GCAGGGCCGT
GGCGAAGAAA TGGCCGTCAG CCTTTAAGGG AGCAGCAACA CCAGTGGGCA CAATTAAAAC AGTCATGTGC
GGCTCGTACC CCGTCATCCA CGCTGTAGCG CCTAATTTCT CTGCCACGAC TGAAGCGGAA GGGGACCGCG
AATTGGCCGC TGTCTACCGG GCAGTGGCCC CCGAAGTAAA CAGACTGTCA CTGAGCAGCA TAGCCATCCC
GCTGCTGTCC ACAGGAGTGT TCAGCGGCGG AAGAGATAGG CTGCAGCAAT CCCTCAACCA TCTATTCACA
GCAATGGACG CCACGGACGC TGACGTGACC ATCTACTGCA GAGACAAAAG TTGGGAGAAG AAAATCCAGG
AAGCCATTGA CATGAGGACG GCTGTGGAGT TGCTCAATGA TGACGTGGAG CTGACCACAG ACTTGGTGAG
AGTGCACCCG GACAGCAGCC TGGTGGGTCG TAAGGGCTAC AGTACCACTG ACGGGTCGCT GTACTCGTAC
TTTGAAGGTA CGAAATTCAA CCAGGCTGCT ATTGATATGG CAGAGATACT GACGTTGTGG CCCAGACTGC
AAGAGGCAAA CGAACAGATA TGCCTATACG CGCTGGGCGA AACAATGGAC AACATCAGAT CCAAATGTCC
GGTGAACGAT TCCGATTCAT CAACACCTCC CAGGACAGTG CCCTGCCTGT GCCGCTACGC AATGACAGCA
GAACGGATCG CCCGCCTTAG GTCACACCAA GTTAAAAGCA TGGTGGTTTG CTCATCTTTT CCCCTCCCGA
AATACCATGT AGATGGGGTG CAGAAGGTAA AGTGCGAGAA GGTTCTCCTG TTCGACCCGA CGGTACCTTC
AGTGGTTAGT CCGCGGAAGT ATGCCGCATC TACGACGGAC CACTCAGATC GGTCGTTACG AGGGTTTGAC
TTGGACTGGA CCACCGACTC GTCTTCCACT GCCAGCGATA CCATGTCGCT ACCCAGTTTG CAGTCGTGTG
ACATCGACTC GATCTACGAG CCAATGGCTC CCATAGTAGT GACGGCTGAC GTACACCCTG AACCCGCAGG
CATCGCGGAC CTGGCGGCAG ATGTGCACCC TGAACCCGCA GACCATGTGG ACCTCGAAGA CCCGATTCCT
CCACCGCGCC CGAAGAGAGC TGCATACCTT GCCTCCCGCG CGGCGGAGCG ACCGGTGCCG GCGCCGAGAA
AGCCGACGCC TGCCCCAAGG ACTGCGTTTA GGAACAAGCT GCCTTTGACG TTCGGCGACT TTGACGAGCA
CGAGGTCGAT GCGTTGGCCT CCGGGATTAC TTTCGGAGAC TTCGACGACG TCCTGCGACT AGGCCGCGCG
GGTGCATATA TTTTCTCCTC GGACACTGGC AGCGGACATT ACAACAAAA ATCCGTTAGG CAGCACAATC
TCCAGTGCGC ACAACTGGAT GCGGTCCAGG AGGAGAAAAT GTACCCGCCA AAATTGGATA CTGAGAGGGA
GAAGCTGTTG CTGCTGAAAA TGCAGATGCA CCCATCGGAG GCTAATAAGA GTCGATACCA GTCTCGCAAA
GTGGAGAACA TGAAAGCCAC GGTGGTGGAC AGGCTCACAT CGGGGGCCAG ATTGTACACG GGAGCGGACG
```

-continued

```
TAGGCCGCAT ACCAACATAC GCGGTTCGGT ACCCCCGCCC CGTGTACTCC CCTACCGTGA TCGAAAGATT

CTCAAGCCCC GATGTAGCAA TCGCAGCGTG CAACGAATAC CTATCCAGAA ATTACCCAAC AGTGGCGTCG

TACCAGATAA CAGATGAATA CGACGCATAC TTGGACATGG TTGACGGGTC GGATAGTTGC TTGGACAGAG

CGACATTCTG CCCGGCGAAG CTCCGGTGCT ACCCGAAACA TCATGCGTAC CACCAGCCGA CTGTACGCAG

TGCCGTCCCG TCACCCTTTC AGAACACACT ACAGAACGTG CTAGCGGCCG CCACCAAGAG AAACTGCAAC

GTCACGCAAA TGCGAGAACT ACCCACCATG GACTCGGCAG TGTTCAACGT GGAGTGCTTC AAGCGCTATG

CCTGCTCCGG AGAATATTGG AAGAATATG CTAAACAACC TATCCGGATA ACCACTGAGA ACATCACTAC

CTATGTGACC AAATTGAAAG GCCCGAAAGC TGCTGCCTTG TTCGCTAAGA CCCACAACTT GGTTCCGCTG

CAGGAGGTTC CCATGGACAG ATTCACGGTC GACATGAAAC GAGATGTCAA AGTCACTCCA GGGACGAAAC

ACACAGAGGA AAGACCCAAA GTCCAGGTAA TTCAAGCAGC GGAGCCATTG GCGACCGCTT ACCTGTGCGG

CATCCACAGG GAATTAGTAA GGAGACTAAA TGCTGTGTTA CGCCCTAACG TGCACACATT GTTTGATATG

TCGGCCGAAG ACTTTGACGC GATCATCGCC TCTCACTTCC ACCCAGGAGA CCCGGTTCTA GAGACGGACA

TTGCATCATT CGACAAAAGC CAGGACGACT CCTTGGCTCT TACAGGTTTA ATGATCCTCG AAGATCTAGG

GGTGGATCAG TACCTGCTGG ACTTGATCGA GGCAGCCTTT GGGGAAATAT CCAGCTGTCA CCTACCAACT

GGCACGCGCT TCAAGTTCGG AGCTATGATG AAATCGGGCA TGTTTCTGAC TTTGTTTATT AACACTGTTT

TGAACATCAC CATAGCAAGC AGGGTACTGG AGCAGAGACT CACTGACTCC GCCTGTGCGG CCTTCATCGG

CGACGACAAC ATCGTTCACG GAGTGATCTC CGACAAGCTG ATGGCGGAGA GGTGCGCGTC GTGGGTCAAC

ATGGAGGTGA AGATCATTGA CGCTGTCATG GGCGAAAAAC CCCCATATTT TTGTGGGGGA TTCATAGTTT

TTGACAGCGT CACACAGACC GCCTGCCGTG TTTCAGACCC ACTTAAGCGC CTGTTCAAGT TGGGTAAGCC

GCTAACAGCT GAAGACAAGC AGGACGAAGA CAGGCGACGA GCACTGAGTG ACGAGGTTAG CAAGTGGTTC

CGGACAGGCT TGGGGGCCGA ACTGGAGGTG GCACTAACAT CTAGGTATGA GGTAGAGGGC TGCAAAAGTA

TCCTCATAGC CATGGCCACC TTGGCGAGGG ACATTAAGGC GTTTAAGAAA TTGAGAGGAC CTGTTATACA

CCTCTACGGC GGTCCTAGAT TGGTGCGTTA ATACACAGAA TTCTGATTgg atccCGGGTA ATTAATTGAA

TTACATCCCT ACGCAAACGT TTTACGGCCG CCGGTGGCGC CCGCGCCCGG CGGCCCGTCC TTGGCCGTTG

CAGGCCACTC CGGTGGCTCC CGTCGTCCCC GACTTCCAGG CCCAGCAGAT GCAGCAACTC ATCAGCGCCG

TAAATGCGCT GACAATGAGA CAGAACGCAA TTGCTCCTGC TAGGCCTCCC AAACCAAAGA AGAAGAAGAC

AACCAAACCA AAGCCGAAAA CGCAGCCCAA GAAGATCAAC GGAAAAACGC AGCAGCAAAA GAAGAAAGAC

AAGCAAGCCG ACAAGAAGAA GAAGAAACCC GGAAAAAGAG AAAGAATGTG CATGAAGATT GAAAATGACT

GTATCTTCGT ATGCGGCTAG CCACAGTAAC GTAGTGTTTC CAGACATGTC GGGCACCGCA CTATCATGGG

TGCAGAAAAT CTCGGGTGGT CTGGGGGCCT TCGCAATCGG CGCTATCCTG GTGCTGGTTG TGGTCACTTG

CATTGGGCTC CGCAGATAAG TTAGGGTAGG CAATGGCATT GATATAGCAA GAAAATTGAA AACAGAAAAA

GTTAGGGTAA GCAATGGCAT ATAACCATAA CTGTATAACT TGTAACAAAG CGCAACAAGA CCTGCGCAAT

TGGCCCCGTG GTCCGCCTCA CGGAAACTCG GGGCAACTCA TATTGACACA TTAATTGGCA ATAATTGGAA

GCTTACATAA GCTTAATTCG ACGAATAATT GGATTTTTAT TTTATTTTGC AATTGGTTTT TAATATTTCC

AAAAAAAAAA AAAAAAAAAA AAAAAAAAAA AAAAAAAAAA AAAAAAAAAA AAAAAAAAAA AAAAAAAAAA

CTAGTgatca taatcagcca taccacattt gtagaggttt tacttgcttt aaaaaacctc ccacacctcc ccctgaacct gaaacataaa atgaatgcaa ttgttgttgt taacttgttt attgcagctt ataatggtta caaataaagc aatagcatca caaatttcac aaataaagca ttttttttcac tgcattctag ttgtggtttg tccaaactca tcaatgtatc ttatcatgtc tggaTCTAGT CTGCATTAAT GAATCGGCCA ACGCGCGGGG

AGAGGCGGTT TGCGTATTGG GCGCTCTTCC GCTTCCTCGC TCACTGACTC GCTGCGCTCG GTCGTTCGGC
```

-continued

```
TGCGGCGAGC GGTATCAGCT CACTCAAAGG CGGTAATACG GTTATCCACA GAATCAGGGG ATAACGCAGG
AAAGAACATG TGAGCAAAAG GCCAGCAAAA GGCCAGGAAC CGTAAAAAGG CCGCGTTGCT GGCGTTTTTC
CATAGGCTCC GCCCCCCTGA CGAGCATCAC AAAAATCGAC GCTCAAGTCA GAGGTGGCGA AACCCGACAG
GACTATAAAG ATACCAGGCG TTTCCCCCTG GAAGCTCCCT CGTGCGCTCT CCTGTTCCGA CCCTGCCGCT
TACCGGATAC CTGTCCGCCT TTCTCCCTTC GGGAAGCGTG GCGCTTTCTC AATGCTCGCG CTGTAGGTAT
CTCAGTTCGG TGTAGGTCGT TCGCTCCAAG CTGGGCTGTG TGCACGAACC CCCCGTTCAG CCCGACCGCT
GCGCCTTATC CGGTAACTAT CGTCTTGAGT CCAACCCGGT AAGACACGAC TTATCGCCAC TGGCAGCAGC
CACTGGTAAC AGGATTAGCA GAGCGAGGTA TGTAGGCGGT GCTACAGAGT TCTTGAAGTG GTGGCCTAAC
TACGGCTACA CTAGAAGGAC AGTATTTGGT ATCTGCGCTC TGCTGAAGCC AGTTACCTTC GGAAAAAGAG
TTGGTAGCTC TTGATCCGGC AAACAAACCA CCGCTGGTAG CGGTGGTTTT TTTGTTTGCA AGCAGCAGAT
TACGCGCAGA AAAAAAGGAT CTCAAGAAGA TCCTTTGATC TTTTCTACGG GGcatTCTGA CGCTCAGTGG
AACGAAAACT CACGTTAAGG GATTTTGGTC ATGAGATTAT CAAAAAGGAT CTTCACCTAG ATCCTTTTAA
ATTAAAAATG AAGTTTTAAA TCAATCTAAA GTATATATGA GTAAACTTGG TCTGACAGTT ACCAATGCTT
AATCAGTGAG GCACCTATCT CAGCGATCTG TCTATTTCGT TCATCCATAG TTGCCTGACT CCCCGTCGTG
TAGATAACTA CGATACGGGA GGGCTTACCA TCTGGCCCCA GTGCTGCAAT GATACCGCGA GACCCACGCT
CACCGGCTCC AGATTTATCA GCAATAAACC AGCCAGCCGG AAGGGCCGAG CGCAGAAGTG GTCCTGCAAC
TTTATCCGCC TCCATCCAGT CTATTAATTG TTGCCGGGAA GCTAGAGTAA GTAGTTCGCC AGTTAATAGT
TTGCGCAACG TTGTTGCCAT TGCTACAGGC ATCGTGGTGT CACGCTCGTC GTTTGGTATG GCTTCATTCA
GCTCCGGTTC CCAACGATCA AGGCGAGTTA CATGATCCCC CATGTTGTGC AAAAAAGCGG TTAGCTCCTT
CGGTCCTCCG ATCGTTGTCA GAAGTAAGTT GGCCGCAGTG TTATCACTCA TGGTTATGGC AGCACTGCAT
AATTCTCTTA CTGTCATGCC ATCCGTAAGA TGCTTTTCTG TGACTGGTGA GTACTCAACC AAGTCATTCT
GAGAATAGTG TATGCGGCGA CCGAGTTGCT CTTGCCCGGC GTCAATACGG GATAATACCG CGCCACATAG
CAGAACTTTA AAAGTGCTCA TCATTGGAAA ACGTTCTTCG GGGCGAAAAC TCTCAAGGAT CTTACCGCTG
TTGAGATCCA GTTCGATGTA ACCCACTCGT GCACCCAACT GATCTTCAGC ATCTTTTACT TCACCAGCG
TTTCTGGGTG AGCAAAAACA GGAAGGCAAA ATGCCGCAAA AAAGGGAATA AGGGCGACAC GGAAATGTTG
AATACTCATA CTCTTCCTTT TTCAATATTA TTGAAGCATT TATCAGGGTT ATTGTCTCAT GAGCGGATAC
ATATTTGAAT GTATTTAGAA AAATAAACAA ATAGGGGTTC CGCGCACATT TCCCCGAAAA GTGCCACCTG
ACGTCTAAGA AACCATTATT ATCATGACAT TAACCTATAA AAATAGGCGT ATCACGAGGC CCTTTCGTCT
CGCGCGTTTC GGTGATGACG GTGAAAACCT CTGACACATG CAGCTCCCGG AGACGGTCAC AGCTTCTGTC
TAAGCGGATG CCGGGAGCAG ACAAGCCCGT CAGGGCGCGT CAGCGGGTGT TGGCGGGTGT CGGGGCTGGC
TTAACTATGC GGCATCAGAG CAGATTGTAC TGAGAGTGCA CCATATCGAC GCTCTCCCTT ATGCGACTCC
TGCATTAGGA AGCAGCCCAG TACTAGGTTG AGGCCGTTGA GCACCGCCGC CGCAAGGAAT GGTGCATGCG
TAATCAATTA CGGGGTCATT AGTTCATAGC CCATATATGG AGTTCCGCGT TACATAACTT ACGGTAAATG
GCCCGCCTGG CTGACCGCCC AACGACCCCC GCCCATTGAC GTCAATAATG ACGTATGTTC CCATAGTAAC
GCCAATAGGG ACTTTCCATT GACGTCAATG GGTGGAGTAT TTACGGTAAA CTGCCCACTT GGCAGTACAT
CAAGTGTATC ATATGCCAAG TACGCCCCCT ATTGACGTCA ATGACGGTAA ATGGCCCGCC TGGCATTATG
CCCAGTACAT GACCTTATGG GACTTTCCTA CTTGGCAGTA CATCTACGTA TTAGTCATCG CTATTACCAT
GGTGATGCGG TTTTGGCAGT ACATCAATGG GCGTGGATAG CGGTTTGACT CACGGGGATT TCCAAGTCTC
CACCCCATTG ACGTCAATGG GAGTTTGTTT TGGCACCAAA ATCAACGGGA CTTTCCAAAA TGTCGTAACA
```

-continued

```
ACTCCGCCCC ATTGACGCAA ATGGGCGGTA GGCGTGTACG GTGGGAGGTC TATATAAGCA GAGCTCTCTG
GCTAACTAGA GAACCCACTG CTTAACTGGC TTATCGAAAT TAATACGACT CACTATAGGG AGACCGGAAG CTTGAATTC
``` pcDNA3-E7-Hsp70 SEQ ID NO:18 The E7-Hsp70 fusion
sequence is shown in bold, caps

```
              |    10     |    20     |    30     |    40     |    50     |    60     |    70     |    80     |
     1  gacggatcgg gagatctccc gatccctat ggtcgactct cagtacaatc tgctctgatg ccgcatagtt aagccagtat     80
    81  ctgctccctg cttgtgtgtt ggaggtcgct gagtagtgcg cgagcaaaat ttaagctaca acaaggcaag gcttgaccga   160
   161  caattgcatg aagaatctgc ttaggggttag gcgttttgcg ctgcttcgcg atgtacgggc cagatatacg cgttgacatt   240
   241  gattattgac tagttattaa tagtaatcaa ttacgggtc attagttcat agcccatata tggagttccg cgttacataa   320
   321  cttacggtaa atggcccgcc tggctgaccg cccaacgacc cccgcccatt gacgtcaata atgacgtatg ttcccatagt   400
   401  aacgccaata gggactttcc attgacgtca atgggtggac tatttacggt aaactgccca cttggcagta tcaagtgt   480
   481  atcatatgcc aagtacgccc cctattgacg tcaatgacgg taaatggccc gcctggcatt atgcccagta catgacctta   560
   561  tgggactttc ctacttggca gtacatctac gtattagtca tcgctattac catggtgatg cggttttggc agtacatcaa   640
   641  tgggcgtgga tagcggtttg actcacgggg atttccaagt ctccaccca ttgacgtcaa tgggagtttg ttttggcacc   720
   721  aaaatcaacg ggactttcca aaatgtcgta acaactccgc cccattgacg caaatgggcg taggcgtgt acggtgggag   800
   801  gtctatataa gcagagctct ctggctaact agagaaccca ctgcttactg gcttatcgaa attaatacga ctcactatag   880
   881  ggagacccaa gctggctagc gtttaaacgg gccctctaga ctcgagcggc cgccactgtg ctggatatct gcagaattcc   960
   961  accacactgg actagtggat ccATGCATGG AGATACACCT ACATTGCATG AATATATGTT AGATTTGCAA CCAGAGACAA  1040
  1041  CTGATCTCTA CTGTTATGAG CAATTAAATG ACAGCTCAGA GGAGGAGGAT GAAATAGATG GTCCAGCTGG ACAAGCAGAA  1120
  1121  CCGGACAGAG CCCATTACAA TATTGTAACC TTTTGTTGCA AGTGTGACTC TACGCTTCGG TTGTGCGTAC AAAGCACACA  1200
  1201  CGTAGACATT CGTACTTTGG AAGACCTGTT AATGGGCACA CTAGGAATTG TGTGCCCCAT CTGTTCTCAA GGATCCATGG  1280
  1281  CTCGTGCGGT CGGGATCGAC CTCGGGACCA CCAACTCCGT CGTCTCGGTT CTGGAAGGTG GCGACCCGGT CGTCGTCGCC  1360
  1361  AACTCCGAGG GCTCCAGGAC CACCCCGTCA ATTGTCGCGT TCGCCCGCAA CGGTGAGGTG CTGGTCGGCC AGCCCGCCAA  1440
  1441  GAACCAGGCA GTGACCAACG TCGATCGCAC CGTGCGCTCG GTCAAGCGAC ACATGGGCAG CGACTGGTCC ATAGAGATTG  1520
  1521  ACGGCAAGAA ATACACCGCG CCGGAGATCA GCGCCCGCAT TCTGATGAAG CTGAAGCGCG ACGCCGAGGC CTACCTCGGT  1600
  1601  GAGGACATTA CCGACGCGGT TATCACGACG CCCGCCTACT TCAATGACGC CCAGCGTCAG GCCACCAAGG ACGCCGGCCA  1680
  1681  GATCGCCGGC CTCAACGTGC TGCGGATCGT CAACGAGCCG ACCGCGGCCG CGCTGGCCTA CGGCCTCGAC AAGGGCGAGA  1760
  1761  AGGAGCAGCG AATCCTGGTC TTCGACTTGG GTGGTGGCAC TTTCGACGTT TCCCTGCTGG AGATCGGCGA GGGTGTGGTT  1840
  1841  GAGGTCCGTG CCACTTCGGG TGACAACCAC CTCGGCGGCG ACGACTGGGA CCAGCGGGTC GTCGATTGGC TGGTGGACAA  1920
  1921  GTTCAAGGGC ACCAGCGGCA TCGATCTGAC CAAGGACAAG ATGGCGATGC AGCGGCTGCG GGAAGCCGCC GAGAAGGCAA  2000
  2001  AGATCGAGCT GAGTTCGAGT CAGTCCACCT CGATCAACCT GCCCTACATC ACCGTCGACG CCGACAAGAA CCCGTTGTTC  2080
  2081  TTAGACGAGC AGCTGACCCG CGCGGAGTTC AACGGATCA CTCAGGACCT GCTGGACCGC ACTCGCAAGC CGTTCCAGTC  2160
  2161  GGTGATCGCT GACACCGGCA TTTCGGTGTC GGAGATCGAT CACGTTGTGC TCGTGGGTGG TTCGACCCGG ATGCCCGCG  2240
  2241  TGACCGATCT GGTCAAGGAA CTCACCGGCG GCAAGGAACC CAACAAGGGC GTCAACCCCG ATGAGGTTGT CGCGGTGGGA  2320
  2321  GCCGCTCTGC AGGCCGGCGT CCTCAAGGGC GAGGTGAAAG ACGTTCTGCT GCTTGATGTT ACCCCGCTGA GCCTGGGTAT  2400
  2401  CGAGACCAAG GGCGGGGTGA TGACCAGGCT CATCGAGCGC AACACCACGA TCCCCACCAA GCGGTCGGAG ACTTTCACCA  2480
  2481  CCGCCGACGA CAACCAACCG TCGGTGCAGA TCCAGGTCTA TCAGGGGGAG CGTGAGATCG CCGCGCACAA CAAGTTGCTC  2560
  2561  GGGTCCTTCG AGCTGACCGG CATCCCGCCG GCGCCGCGGG GGATTCCGCA GATCGAGGTC ACTTTCGACA TCGACGCCAA  2640
  2641  CGGCATTGTG CACGTCACCG CCAAGGACAA GGGCACCGGC AAGGAGAACA CGATCCGAAT CCAGGAAGGC TCGGGCCTGT  2720
```

-continued

```
2721 CCAAGGAAGA CATTGACCGC ATGATCAAGG ACGCCGAAGC GCACGCCGAG GAGGATCGCA AGCGTCGCGA GGAGGCCGAT 2800
2801 GTTCGTAATC AAGCCGAGAC ATTGGTCTAC CAGACGGAGA AGTTCGTCAA AGAACAGCGT GAGGCCGAGG GTGGTTCGAA 2880
2881 GGTACCTGAA GACACGCTGA ACAAGGTTGA TGCCGCGGTG GCGGAAGCGA AGGCGGCACT TGGCGGATCG GATATTTCGG 2960
2961 CCATCAAGTC GGCGATGGAG AAGCTGGGCC AGGAGTCGCA GGCTCTGGGG CAAGCGATCT ACGAAGCAGC TCAGGCTGCG 3040
3041 TCACAGGCCA CTGGCGCTGC CCACCCCGGC TCGGCTGATG AAAGCTTaag tttaaaccgc tgatcagcct cgactgtgcc 3120
3121 ttctagttgc cagccatctg ttgtttgccc ctccccgtg ccttccttga ccctggaagg tgccactccc actgtccttt 3200
3201 cctaataaaa tgaggaaatt gcatcgcatt gtctgagtag gtgtcattct attctggggg gtggggtggg gcaggacagc 3280
3281 aaggggggag attgggaaga caatagcagg catgctgggg atgcggtggg ctctatggct tctgaggcgg aaagaaccag 3360
3361 ctggggctct aggggggtatc cccacgcgcc ctgtagcggc gcattaagcg cggcgggtgt ggtggttacg cgcagcgtga 3440
3441 ccgctacact tgccagcgcc ctagcgcccg ctcctttcgc tttcttccct tcctttctcg ccacgttcgc cggctttccc 3520
3521 cgtcaagctc taaatcgggg catcccttta gggttccgat ttagtgcttt acggcacctc gaccccaaaa aacttgatta 3600
3601 gggtgatggt tcacgtagtg ggccatcgcc ctgatagacg ttttttcgcc ctttgacgtt ggagtccacg ttctttaata 3680
3681 gtggactctt gttccaaact ggaacaacac tcaaccctat ctcggtctat tctttgatt tataagggat tttggggatt 3760
3761 tcggcctatt ggttaaaaaa tgagctgatt taacaaaaat ttaacgcgaa ttaattctgt ggaatgtgtg tcagttaggg 3840
3841 tgtggaaagt ccccaggctc cccaggcagg cagaagtatg caaagcatgc atctcaatta gtcagcaacc aggtgtggaa 3920
3921 agtccccagg ctccccagca ggcagaagta tgcaaagcat gcatctcaat tagtcagcaa ccatagtccc gcccctaact 4000
4001 ccgcccatcc cgcccctaac tccgcccagt tccgcccatt ctccgcccca tggctgacta attttttttta tttatgcaga 4080
4081 ggccgaggcc gcctctgcct ctgagctatt ccagaagtag tgaggaggct ttttttggagg cctaggcttt tgcaaaaagc 4160
4161 tcccgggagc ttgtatatcc attttcggat ctgatcaaga acaggatga ggatcgtttc gcatgattga acaagatgga 4240
4241 ttgcacgcag gttctccggc cgcttgggtg gagaggctat tcggctatga ctgggcacaa cagacaatcg gctgctctga 4320
4321 tgccgccgtg ttccggctgt cagcgcaggg gcgcccggtt ctttttgtca agaccgacct gtccggtgcc ctgaatgaac 4400
4401 tgcaggacga ggcagcgcgg ctatcgtggc tggccacgac gggcgttcct tgcgcagctg tgctcgacgt tgtcactgaa 4480
4481 gcgggaaggg actggctgct attgggcgaa gtgccggggc aggatctcct gtcatctcac cttgctcctg ccgagaaagt 4560
4561 atccatcatg gctgatgcaa tgcggcggct gcatacgctt gatccggcta cctgcccatt cgaccaccaa gcgaaacatc 4640
4641 gcatcgagcg agcacgtact cggatggaag ccggtcttgt cgatcaggat gatctggacg aagagcatca ggggctcgcg 4720
4721 ccagccgaac tgttcgccag gctcaaggcg cgcatgcccg acggcgagga tctcgtcgtg acccatggcg atgcctgctt 4800
4801 gccgaatatc atggtggaaa atggccgctt ttctggattc atcgactgtg gccggctggg tgtggcggac cgctatcagg 4880
4881 acatagcgtt ggctacccgt gatattgctg aagagcttgg cggcgaatgg gctgaccgct tcctcgtgct ttacggtatc 4960
4961 gccgctcccg attcgcagcg catcgccttc tatcgccttc ttgacgagtt cttctgagcg ggactctggg gttcgaaatg 5040
5041 accgaccaag cgacgcccaa cctgccatca cgagatttcg attccaccgc cgccttctat gaaaggttgg gcttcggaat 5120
5121 cgttttccgg gacgccggct ggatgatcct ccagcgcggg gatctcatgc tggagttctt cgcccacccc aacttgttta 5200
5201 ttgcagctta taatggttac aaataaagca atagcatcac aaatttcaca aataaagcat ttttttcact gcattctagt 5280
5281 tgtggtttgt ccaaactcat caatgtatct tatcatgtct gtataccgtc gacctctagc tagagcttgg cgtaatcatg 5360
5361 gtcatagctg tttcctgtgt gaaattgtta tccgctcaca attccacaca acatacgagc cggaagcata aagtgtaaag 5440
5441 cctggggtgc ctaatgagtg agctaactca cattaattgc gttgcgctca ctgcccgctt tccagtcggg aaacctgtcg 5520
5521 tgccagctgc attaatgaat cggccaacgc gcggggagag gcggtttgcg tattgggcgc tcttccgctt cctcgctcac 5600
5601 tgactcgctg cgctcggtcg ttcggctgcg gcgagcggta tcagctcact caaaggcggt aatacggtta tccacagaat 5680
5681 caggggataa cgcaggaaag aacatgtgag caaaaggcca gcaaaaggcc aggaaccgta aaaaggccgc gttgctggcg 5760
5761 tttttccata ggctccgccc ccctgacgag catcacaaaa atcgacgctc aagtcagagg tggcgaaacc cgacaggact 5840
5841 ataaagatac caggcgtttc cccctggaag ctccctcgtg cgctctcctg ttccgaccct gccgcttacc ggatacctgt 5920
```

-continued

```
5921 ccgcctttct cccttcggga agcgtggcgc tttctcaatg ctcacgctgt aggtatctca gttcggtgta ggtcgttcgc 6000
6001 tccaagctgg gctgtgtgca cgaaccccc gttcagcccg accgctgcgc cttatccggt aactatcgtc ttgagtccaa 6080
6081 cccggtaaga cacgacttat cgccactggc agcagccact ggtaacagga ttagcagagc gaggtatgta ggcggtgcta 6160
6161 cagagttctt gaagtggtgg cctaactacg gctacactag aaggacagta tttggtatct gcgctctgct gaagccagtt 6240
6241 accttcggaa aaagagttgg tagctcttga tccggcaaac aaaccaccgc tggtagcggt ggtttttttg tttgcaagca 6320
6321 gcagattacg cgcagaaaaa aaggatctca agaagatcct ttgatctttt ctacggggtc tgacgctcag tggaacgaaa 6400
6401 actcacgtta agggattttg gtcatgagat tatcaaaaag gatcttcacc tagatccttt taaattaaaa atgaagtttt 6480
6481 aaatcaatct aaagtatata tgagtaaact tggtctgaca gttaccaatg cttaatcagt gaggcaccta tctcagcgat 6560
6561 ctgtctattt cgttcatcca tagttgcctg actccccgtc gtgtagataa ctacgatacg ggagggctta ccatctggcc 6640
6641 ccagtgctgc aatgataccg cgagacccac gctcaccggc tccagattta tcagcaataa accagccagc cggaagggcc 6720
6721 gagcgcagaa gtggtcctgc aactttatcc gcctccatcc agtctattaa ttgttgccgg gaagctagag taagtagttc 6800
6801 gccagttaat agtttgcgca acgttgttgc cattgctaca ggcatcgtgg tgtcacgctc gtcgtttggt atggcttcat 6880
6881 tcagctccgg ttcccaacga tcaaggcgag ttacatgatc ccccatgttg tgcaaaaaag cggttagctc cttcggtcct 6960
6961 ccgatcgttg tcagaagtaa gttggccgca gtgttatcac tcatggttat ggcagcactg cataattctc ttactgtcat 7040
7041 gccatccgta agatgctttt ctgtgactgg tgagtactca accaagtcat tctgagaata gtgtatgcgg cgaccgagtt 7120
7121 gctcttgccc ggcgtcaata cgggataata ccgcgccaca tagcagaact ttaaaagtgc tcatcattgg aaaacgttct 7200
7201 tcggggcgaa aactctcaag gatcttaccg ctgttgagat ccagttcgat gtaacccact cgtgcaccca actgatcttc 7280
7281 agcatctttt actttcacca gcgtttctgg gtgagcaaaa acaggaaggc aaaatgccgc aaaaaaggga ataagggcga 7360
7361 cacggaaatg ttgaatactc atactcttcc tttttcaata ttattgaagc atttatcagg gttattgtcc catgagcgga 440
7441 tacatatttg aatgtattta gaaaaataaa caaatagggg ttccgcgcac atttccccga aagtgccac ctgacgtc    7518
              |  10      |   20      |   30      |   40      |   50      |   60      |   70      |   80      |
```

SINrep5-E7-Hsp70 SEQ ID NO:19 The E7-Hsp70 fusion
sequence is shown in bold, caps

```
              |  10      |   20      |   30      |   40      |   50      |   60      |   70      |   80      |
   1 attgacggcg tagtacacac tattgaatca aacagccgac caattgcact accatcacaa tggagaagcc agtagtaaac   80
  81 gtagacgtag accccagag tccgtttgtc gtgcaactgc aaaaaagctt cccgcaattt gaggtagtag cacagcaggt  160
 161 cactccaaat gaccatgcta atgccagagc attttcgcat ctggccagta aactaatcga gctggaggtt cctaccacag  240
 241 cgacgatctt ggacataggc agcgcaccgg ctcgtagaat gttttccgag caccagtatc attgtgtctg ccccatgcgt  320
 321 agtccagaag acccggaccg catgatgaaa tacgccagta aactggcgga aaaagcgtgc aagattacaa acaagaactt  400
 401 gcatgagaag attaaggatc tccggaccgt acttgatacg ccggatgctg aaacaccatc gctctgcttt cacaacgatg  480
 481 ttacctgcaa catgcgtgcc gaatattccg tcatgcagga cgtgtatatc aacgctcccg gaactatcta tcatcaggct  560
 561 atgaaaggcg tgcggaccct gtactggatt ggcttcgaca ccacccagtt catgttctcg gctatggcag gttcgtaccc  640
 641 tgcgtacaac accaactggg ccgacgagaa agtccttgaa gcgcgtaaca tcggactttg cagcacaaag ctgagtgaag  720
 721 gtaggacagg aaaattgtcg ataatgagga agaaggagtt gaagcccggg tcgcgggttt atttctccgt aggatcgaca  800
 801 cttatccag aacacagagc cagcttgcag agctggcatc ttccatcggt gttccacttg aatggaaagc agtcgtacac  880
 881 ttgccgctgt gatacagtgg tgagttgcga aggctacgta gtgaagaaaa tcaccatcag tcccgggatc acggagaaa   960
 961 ccgtgggata cgcggttaca cacaatagcg agggcttctt gctatgcaaa gttactgaca cagtaaaagg agaacgggta 1040
1041 tcgttccctg tgtgcacgta catcccggcc accatatgcg atcagatgac tggtataatg ccacggata tatcacctga 1120
1121 cgatgcacaa aaacttctgg ttgggctcaa ccagcgaatt gtcattaacg gtaggactaa caggaacacc aacaccatgc 1200
```

-continued

```
1201 aaaattacct tctgccgatc atagcacaag ggttcagcaa atgggctaag gagcgcaagg atgatcttga taacgagaaa 1280
1281 atgctgggta ctagagaacg caagcttacg tatggctgct tgtgggcgtt tcgcactaag aaagtacatt cgttttatcg 1360
1361 cccacctgga acgcagacct gcgtaaaagt cccagcctct tttagcgctt ttcccatgtc gtccgtatgg acgacctctt 1440
1441 tgcccatgtc gctgaggcag aaattgaaac tggcattgca accaaagaag gaggaaaaac tgctgcaggt ctcggaggaa 1520
1521 ttagtcatgg aggccaaggc tgcttttgag gatgctcagg aggaagccag agcggagaag ctccgagaag cacttccacc 1600
1601 attagtggca gacaaaggca tcgaggcagc cgcagaagtt gtctgcgaag tggaggggct ccaggcggac atcgagcag 1680
1681 cattagttga aaccccgcgc ggtcacgtaa ggataatacc tcaagcaaat gaccgtatga tcggacagta tatcgttgtc 1760
1761 tcgccaaact ctgtgctgaa gaatgccaaa ctcgcaccag cgcaccgct agcagatcag gttaagatca taacacactc 1840
1841 cggaagatca ggaaggtacg cggtcgaacc atacgacgct aaagtactga tgccagcagg aggtgccgta ccatggccag 1920
1921 aattcctagc actgagtgag agcgccacgt tagtgtacaa cgaaagagag tttgtgaacc gcaaactata ccacattgcc 2000
2001 atgcatggcc ccgccaagaa tacagaagag gagcagtaca aggttacaaa ggcagagctt gcagaaacag agtacgtgtt 2080
2081 tgacgtggac aagaagcgtt gcgttaagaa ggaagaagcc tcaggtctgg tcctctcggg agaactgacc aaccctccct 2160
2161 atcatgagct agctctggag ggactgaaga cccgacctgc ggtcccgtac aaggtcgaaa caataggagt gataggcaca 2240
2241 ccggggtcgg gcaagtcagc tattatcaag tcaactgtca cggcacgaga tcttgttacc agcggaaaga agaaaattg 2320
2321 tcgcgaaatt gaggccgacg tgctaagact gaggggtatg cagattacgt cgaagacagt agattcggtt atgctcaacg 2400
2401 gatgccacaa agccgtagaa gtgctgtacg ttgacgaagc gttcgcgtgc cacgcaggag cactacttgc cttgattgct 2480
2481 atcgtcaggc cccgcaagaa ggtagtacta tgcggagacc ccatgcaatg cggattcttc aacatgatgc aactaaaggt 2560
2561 acatttcaat caccctgaaa aagacatatg caccaagaca ttctacaagt atatctcccg gcgttgcaca cagccagtta 2640
2641 cagctattgt atcgacactg cattacgatg gaaagatgaa aaccacgaac ccgtgcaaga gaacattga atcgatatt 2720
2721 acaggggcca caaagccgaa gccaggggat atcatcctga catgtttccg cgggtgggtt aagcaattgc aaatcgacta 2800
2801 tcccggacat gaagtaatga cagccgcggc ctcacaaggg ctaaccagaa aaggagtgta tgccgtccgg caaaagtca 2880
2881 atgaaaaccc actgtacgcg atcacatcag agcatgtgaa cgtgttgctc acccgcactg aggacaggct agtgtggaaa 2960
2961 accttgcagg gcgacccatg gattaagcag cccactaaca tacctaaagg aaacttcag gctactatag gggactggga 3040
3041 agctgaacac aagggaataa ttgctgcaat aaacagcccc actcccgtg ccaatccgtt cagctgcaag accaacgttt 3120
3121 gctgggcgaa agcattggaa ccgatactag ccacggccgg tatcgtactt accggttgcc agtggagcga actgttccca 3200
3201 cagtttgcgg atgacaaacc acattcggcc atttacgcct tagacgtaat ttgcattaag ttttcggca tggacttgac 3280
3281 aagcggactg ttttctaaac agagcatccc actaacgtac catcccgccg attcagcgag gccggtagct cattgggaca 3360
3361 acagcccagg aaccccgcaag tatgggtacg atcacgccat tgccgccgaa ctctcccgta gatttccggt gttccagcta 3440
3441 gctgggaagg gcacacaact tgatttgcag acggggagaa ccagagttat tctctgcacag cataacctgg tcccggtgaa 3520
3521 ccgcaatctt cctcacgcct tagtccccga gtacaaggag aagcaacccg gcccggtcaa aaaattcttg aaccagttca 3600
3601 aacaccactc agtacttgtg gtatcagagg aaaaaattga agctccccgt aagagaatcg aatggatcgc ccgattggc 3680
3681 atagccggtg cagataagaa ctacaacctg gctttcgggt tccgccgca ggcacggtac gacctggtgt tcatcaacat 3760
3761 tggaactaaa tacagaaacc accactttca gcagtgcgaa gaccatgcgg cgaccttaaa aacccttcg cgttcggccc 3840
3841 tgaattgcct taacccagga ggcacctcg tggtgaagtc ctatggctac gccgaccgca acagtgagga cgtagtcacc 3920
3921 gctcttgcca gaaagtttgt cagggtgtct gcagcgagac cagattgtgt ctcaagcaat acagaaatgt acctgatttt 4000
4001 ccgacaacta gacaacagcc gtacacggca attcaccccg caccatctga attgcgtgat tcgtccgtg tatgagggta 4080
4081 caagagatgg agttggagcc gcgccgtcat accgcaccaa agggagaat attgctgact gtcaagagga agcagttgtc 4160
4161 aacgcagcca atccgctggg tagaccaggc gaaggagtct gccgtgccat ctataaacgt tggccgacca gttttaccga 4240
4241 ttcagccacg gagacaggca ccgcaagaat gactgtgtgc ctaggaaaga aagtgatcca cgcggtcggc cctgatttcc 4320
4321 ggaagcaccc agaagcagaa gccttgaaat tgctacaaaa cgcctaccat gcagtggcag acttagtaaa tgaacataac 4400
```

-continued

```
4401 atcaagtctg tcgccattcc actgctatct acaggcattt acgcagccgc cttgaagtat cacttaactg 4480
4481 cttgacaacc gcgctagaca gaactgacgc ggacgtaacc atctattgcc tggataagaa gtggaaggaa agaatcgacg 4560
4561 cggcactcca acttaaggag tctgtaacag agctgaagga tgaagatatg gagatcgacg atgagttagt atggattcat 4640
4641 ccagacagtt gcttgaaggg aagaaaggga ttcagtacta caaaaggaaa attgtattcg tacttcgaag gcaccaaatt 4720
4721 ccatcaagca gcaaaagaca tggcggagat aaaggtcctg ttccctaatg accaggaaag taatgaacaa ctgtgtgcct 4800
4801 acatattggg tgagaccatg gaagcaatcc gcgaaaagtg cccggtcgac cataacccgt cgtctagccc gcccaaaacg 4880
4881 ttgccgtgcc tttgcatgta tgccatgacg ccagaaaggg tccacagact tagaagcaat aacgtcaaag aagttacagt 4960
4961 atgctcctcc acccccttc ctaagcacaa aattaagaat gttcagaagg ttcagtgcac gaagtagtc ctgtttaatc 5040
5041 cgcacactcc cgcattcgtt cccgcccgta agtacataga agtgccagaa cagcctaccg ctcctcctgc acaggccgag 5120
5121 gaggcccccg aagttgtagc gacaccgtca ccatctacag ctgataacac ctcgcttgat gtcacagaca tctcactgga 5200
5201 tatggatgac agtagcgaag gctcactttt ttcgagcttt agcggatcgg acaactctat tactagtatg gacagttggt 5280
5281 cgtcaggacc tagttcacta gagatagtag accgaaggca ggtggtggtg gctgacgttc atgccgtcca agagcctgcc 5360
5361 cctattccac cgccaaggct aaagaagatg gcccgcctgg cagcggcaag aaaagagccc actccaccgg caagcaatag 5440
5441 ctctgagtcc ctccacctct cttttggtgg ggtatccatg tccctcggat caattttcga cggagagacg gcccgccagg 5520
5521 cagcggtaca accctggca acaggcccca cggatgtgcc tatgtctttc ggatcgtttt ccgacggaga gattgatgag 5600
5601 ctgagccgca gagtaactga gtccgaaccc gtcctgtttg gatcatttga accgggcgaa gtgaactcaa ttatatcgtc 5680
5681 ccgatcagcc gtatcttttc cactacgcaa gcagagacgt agacgcagga gcaggaggac tgaatactga ctaaccgggg 5760
5761 taggtgggta catattttcg acggacacag gccctgggca cttgcaaaag aagtccgttc tgcagaacca gcttacagaa 5840
5841 ccgaccttgg agcgcaatgt cctggaaaga attcatgccc cggtgctcga cacgtcgaaa gaggaacaac tcaaaactcag 5920
5921 gtaccagatg atgcccaccg aagccaacaa agtaggtac cagtctcgta agtagaaaa tcagaaagcc ataaccactg 6000
6001 agcgactact gtcaggacta cgactgtata actctgccac agatcagcca gaatgctata agatcaccta tccgaaacca 6080
6081 ttgtactcca gtagcgtacc ggcgaactac tccgatccac agttcgctgt agctgtctgt aacaactatc tgcatgagaa 6160
6161 ctatccgaca gtagcatctt atcagattac tgacgagtac gatgcttact tggatatggt agacgggaca gtcgcctgcc 6240
6241 tggatactgc aaccttctgc cccgctaagc ttagaagtta cccgaaaaaa catgagtata gagccccgaa tatccgcagt 6320
6321 gcggttccat cagcgatgca gaacacgcta caaatgtgc tcattgccgc aactaaaaga aattgcaacg tcacgcagat 6400
6401 gcgtgaactg ccaacactgg actcagcgac attcaatgtc gaatgctttc gaaaatatgc atgtaatgac gagtattggg 6480
6481 aggagttcgc tcggaagcca attaggatta ccactgagtt tgtcaccgca tatgtagcta gactgaaagg ccctaaggcc 6560
6561 gccgcactat ttgcaaagac gtataatttg gtcccattgc aagaagtgcc tatggataga ttcgtcatgg acatgaaaag 6640
6641 agacgtgaaa gttacaccag gcacgaaaca cacagaagaa agaccgaaag tacaagtgat acaagccgca gaaccccctgg 6720
6721 cgactgctta cttatgcggg attcaccggg aattagtgcg taggcttacg gccgtcttgc ttccaaacat tcacacgctt 6800
6801 tttgacatgt cggcggagga ttttgatgca atcatagcag aacacttcaa gcaaggcgac ccggtactgg agacggatat 6880
6881 cgcatcattc gacaaaagcc aagacgacgc tatggcgtta accggtctga tgatcttgga ggacctgggt gtggatcaac 6960
6961 cactactcga cttgatcgag tgcgcctttg gagaaaatatc atccacccat ctacctacgg gtactcgttt taaattcggg 7040
7041 gcgatgatga atccggaat gttcctcaca cttttttgtca acacagtttt gaatgtcgtt atcgccagca gagtactaga 7120
7121 agagcggctt aaaacgtcca gatgtgcagc gttcattggc gacgacaaca tcatacatgg agtagtatct gacaaagaaa 7200
7201 tggctgagag gtgcgccacc tggctcaaca tggaggttaa gatcatcgac gcagtcatcg gtgagagacc accttacttc 7280
7281 tgcggcggat ttatcttgca agattcggtt acttccacag cgtgccgcgt ggcggatccc ctgaaaaggc tgtttaagtt 7360
7361 gggtaaaccg ctcccagccg acgacgagca agacgaagac agaagacgcg ctctgctaga tgaaacaaag gcgtggttta 7440
7441 gagtaggtat aacaggcact ttagcagtgg ccgtgacgac ccggtatgag gtagacaata ttacacctgt cctactggca 7520
7521 ttgagaactt tgcccagag caaaagagca ttccaagcca tcagagggga aataaagcat ctctacggtg gtcctaaata 7600
```

```
7601 gtcagcatag tacatttcat ctgactaata ctacaacacc accacctcta gactcgagcg gccgccactg tgctggatat 7680

7681 ctgcagaatt ccaccacact ggactagtgg atccATGCAT GGAGATACAC CTACATTGCA TGAATATATG TTAGATTTGC 7760

7761 AACCAGAGAC AACTGATCTC TACTGTTATG AGCAATTAAA TGACAGCTCA GAGGAGGAGG ATGAAATAGA TGGTCCAGCT 7840

7841 GGACAAGCAG AACCGGACAG AGCCCATTAC AATATTGTAA CCTTTTGTTG CAAGTGTGAC TCTACGCTTC GGTTGTGCGT 7920

7921 ACAAAGCACA CACGTAGACA TTCGTACTTT GGAAGACCTG TTAATGGGCA CACTAGGAAT TGTGTGCCCC ATCTGTTCTC 8000

8001 AAGGATCCAT GGCTCGTGCG GTCGGGATCG ACCTCGGGAC CACCAACTCC GTCGTCTCGG TTCTGGAAGG TGGCGACCCG 8080

8081 GTCGTCGTCG CCAACTCCGA GGGCTCCAGG ACCACCCCGT CAATTGTCGC GTTCGCCCGC AACGGTGAGG TGCTGGTCGG 8160

8161 CCAGCCCGCC AAGAACCAGG CAGTGACCAA CGTCGATCGC ACCGTGCGCT CGGTCAAGCG ACACATGGGC AGCGACTGGT 8240

8241 CCATAGAGAT TGACGGCAAG AAATACACCG CGCCGGAGAT CAGCGCCCGC ATTCTGATGA AGCTGAAGCG CGACGCCGAG 8320

8321 GCCTACCTCG GTGAGGACAT TACCGACGCG GTTATCACGA CGCCCGCCTA CTTCAATGAC GCCCAGCGTC AGGCCACCAA 8400

8401 GGACGCCGGC CAGATCGCCG GCCTCAACGT GCTGCGGATC GTCAACGAGC CGACCGCGGC CGCGCTGGCC TACGGCCTCG 8480

8481 ACAAGGGCGA GAAGGAGCAG CGAATCCTGG TCTTCGACTT GGGTGGTGGC ACTTTCGACG TTTCCCTGCT GGAGATCGGC 8560

8561 GAGGGTGTGG TTGAGGTCCG TGCCACTTCG GGTGACAACC ACCTCGGCGG CGACGACTGG GACCAGCGGG TCGTCGATTG 8640

8641 GCTGGTGGAC AAGTTCAAGG GCACCAGCGG CATCGATCTG ACCAAGGACA GATGGCGAT GCAGCGGCTG CGGGAAGCCG 8720

8721 CCGAGAAGGC AAAGATCGAG CTGAGTTCGA GTCAGTCCAC CTCGATCAAC CTGCCCTACA TCACCGTCGA CGCCGACAAG 8800

8801 AACCCGTTGT TCTTAGACGA GCAGCTGACC CGCGCGGAGT TCCAACGGAT CACTCAGGAC CTGCTGGACC GCACTCGCAA 8880

8881 GCCGTTCCAG TCGGTGATCG CTGACACCGG CATTTCGGTG TCGGAGATCG ATCACGTTGT GCTCGTGGGT GGTTCGACCC 8960

8961 GGATGCCCGC GGTGACCGAT CTGGTCAAGG AACTCACCGG CGGCAAGGAA CCCAACAAGG GCGTCAACCC CGATGAGGTT 9040

9041 GTCGCGGTGG GAGCCGCTCT GCAGGCCGGC GTCCTCAAGG GCGAGGTGAA AGACGTTCTG CTGCTTGATG TTACCCCGCT 9120

9121 GAGCCTGGGT ATCGAGACCA AGGGCGGGGT GATGACCAGG CTCATCGAGC GCAACACCAC GATCCCCACC AAGCGGTCGG 9200

9201 AGACTTTCAC CACCGCCGAC GACAACCAAC CGTCGGTGCA GATCCAGGTC TATCAGGGGG AGCGTGAGAT CGCCGCGCAC 9280

9281 AACAAGTTGC TCGGGTCCTT CGAGCTGACC GGCATCCCGC CGGCGCCGCG GGGGATTCCG CAGATCGAGG TCACTTTCGA 9360

9361 CATCGACGCC AACGGCATTG TGCACGTCAC CGCCAAGGAC AAGGGCACCG GCAAGGAGAA CACGATCCGA ATCCAGGAAG 9440

9441 GCTCGGGCCT GTCCAAGGAA GACATTGACC GCATGATCAA GGACGCCGAA GCGCACGCCG AGGAGGATCG CAAGCGTCGC 9520

9521 GAGGAGGCCG ATGTTCGTAA TCAAGCCGAG ACATTGGTCT ACCAGACGGA GAAGTTCGTC AAAGAACAGC GTGAGGCCGA 9600

9601 GGGTGGTTCG AAGGTACCTG AAGACACGCT GAACAAGGTT GATGCCGCGG TGGCGGAAGC GAAGGCGGCA CTTGGCGGAT 9680

9681 CGGATATTTC GGCCATCAAG TCGGCGATGG AGAAGCTGGG CCAGGAGTCG CAGGCTCTGG GGCAAGCGAT CTACGAAGCA 9760

9761 GCTCAGGCTG CGTCACAGGC CACTGGCGCT GCCCACCCCG GCTCGGCTGA TGAAAGCTTa agtttgtgag catgcaggcc 9840

9841 ttgggcccaa tgatccgacc agcaaaactc gatgtacttc cgaggaactg atgtgcataa tgcatcaggc tggtacatta 9920

9921 gatcccgct taccgcgggc aatatagcaa cactaaaaac tcgatgtact tccgaggaag cgcagtgcat aatgctgcgc 10000

10001 agtgttgcca cataaccact atattaacca tttatctagc ggacgccaaa aactcaatgt atttctgagg aagcgtggtg 10080

10081 cataatgcca cgcagcgtct gcataacttt tattatttct tttattaatc aacaaaattt tgttttttaac atttcaaaaa 10160

10161 aaaaaaaaaa aaaaaaaaa aaaaaaaaaa aagggaattc ctcgattaat taagcggccg ctcgagggga ttaattcttt 10240

10241 gaagacgaaa gggccaggtg gcacttttcg gggaaatgtg cgcggaaccc ctatttgttt atttttctaa atacattcaa 10320

10321 atatgtatcc gctcatgaga caataaccct gataaatgct tcaataatat tgaaaaagga agagtatgag tattcaacat 10400

10401 ttccgtgtcg cccttattcc cttttttgcg gcattttgcc ttcctgtttt tgctcaccca gaaacgctgg tgaaagtaaa 10480

10481 agatgctgaa gatcagttgg gtgcacgagt gggttacatc gaactggatc tcaacagcgg taagatcctt gagagttttc 10560

10561 gccccgaaga acgttttcca atgatgagca cttttaaagt tctgctatgt ggcgcggtat tatcccgtgt tgacgccggg 10640

10641 caagagcaac tcggtcgccg catacactat tctcagaatg acttggttga gtactcacca gtcacagaaa agcatcttac 10720

10721 ggatggcatg acagtaagag aattatgcag tgctgccata accatgagtg ataacactgc ggccaactta cttctgacaa 10800
```

-continued

```
10801 cgatcggagg accgaaggag ctaaccgctt tttttgcacaa catgggggat catgtaactc gccttgatcg ttgggaaccg 10880
10881 gagctgaatg aagccatacc aaacgacgag cgtgacacca cgatgcctgt agcaatggca acaacgttgc gcaaactatt 10960
10961 aactggcgaa ctacttactc tagcttcccg gcaacaatta atagactgga tggaggcgga taaagttgca ggaccacttc 11040
11041 tgcgctcggc ccttccggct ggctggttta ttgctgataa atctggagcc ggtgagcgtg gtctcgcgg tatcattgca 11120
11121 gcactggggc cagatggtaa gccctcccgt atcgtagtta tctacacgac ggggagtcag gcaactatgg atgaacgaaa 11200
11201 tagacagatc gctgagatag gtgcctcact gattaagcat tggtaactgt cagaccaagt ttactcatat atactttaga 11280
11281 ttgatttaaa acttcatttt taatttaaaa ggatctaggt gaagatcctt tttgataatc tcatgaccaa atcccttaa 11360
11361 cgtgagtttt cgttccactg agcgtcagac cccgtagaaa agatcaaagg atcttcttga tccttttt ttctgcgcgt 11440
11441 aatctgctgc ttgcaaacaa aaaaaccacc gctaccagcg gtggtttgtt tgccggatca agagctacca actctttttc 11520
11521 cgaaggtaac tggcttcagc agagcgcaga taccaaatac tgtccttcta gtgtagccgt agttaggcca ccacttcaag 11600
11601 aactctgtag caccgcctac atacctcgct ctgctaatcc tgttaccagt ggctgctgcc agtggcgata agtcgtgtct 11680
11681 taccggttg gactcaagac gatagttacc ggataaggcg cagcggtcgg gctgaacggg gggttcgtgc acacagccca 11760
11761 gcttggagcg aacgacctac accgaactga gatacctaca gcgtgagcat tgagaaagcg ccacgcttcc cgaagggaga 11840
11841 aaggcggaca ggtatccggt aagcggcagg gtcggaacag gagagcgcac gagggagctt ccagggggaa acgcctggta 11920
11921 tctttatagt cctgtcgggt ttcgccacct ctgacttgag cgtcgatttt tgtgatgctc gtcaggggg cggagcctat 12000
12001 ggaaaaacgc cagcaacgcg agctcgtatg gacatattgt cgttagaacg cggctacaat taatacataa ccttatgtat 12080
12081 catacacata cgatttaggg gacactatag                                                        12110
             |    10   |    20   |    30   |    40   |    50   |    60   |    70   |    80   |
``` pSCA1-E7-Hsp70 SEQ ID NO:20 The E7-Hsp70 fusion sequence is shown in bold, caps

```
      |    10   |    20   |    30   |    40   |    50   |    60   |    70   |    80   |
   1 atggcggatg tgtgacatac acgacgccaa aagatttgt tccagctcct gccacctccg ctacgcgaga gattaaccac   80
  81 ccacgatggc cgccaaagtg catgttgata ttgaggctga cagcccattc atcaagtctt tgcagaaggc atttccgtcg  160
 161 ttcgaggtgg agtcattgca ggtcacacca aatgaccatg caaatgccaa agcattttcg cacctggcta ccaaattgat  240
 241 cgagcaggag actgacaaag acacactcat cttggatatc ggcagtgcgc cttccaggag aatgatgtct acgcacaaat  320
 321 accactgcgt atgccctatg cgcagcgcag aagaccccga aaggctcgat agctacgcaa agaaactggc agcggcctcc  400
 401 gggaaggtgc tggatagaga gatcgcagga aaaatcaccg acctgcagac cgtcatggct acgccagacg ctgaatctcc  480
 481 taccttttgc ctgcatacag acgtcacgtg tcgtacggca gccgaagtgg ccgtatacca ggacgtgtat gctgtacatg  560
 561 caccaacatc gctgtaccat caggcgatga aggtgtcag aacggcgtat ggattgggt ttgacaccac cccgtttatg  640
 641 tttgacgcgc tagcaggcgc gtatccaacc tacgccacaa actgggccga cgagcaggtg ttacaggcca ggaacatagg  720
 721 actgtgtgca gcatccttga ctgagggaag actcggcaaa ctgtccattc tccgcaagaa gcaattgaaa ccttgcgaca  800
 801 cagtcatgtt ctcggtagga tctacattgt acactgagag cagaaagcta ctgaggagct ggcacttacc ctccgtattc  880
 881 cacctgaaag gtaaacaatc ctttacctgt aggtgcgata ccatcgtatc atgtgaaggg tacgtagtta agaaaatcac  960
 961 tatgtgcccc ggcctgtacg gtaaaacggt agggtacgcc gtgacgtatc acgcggaggg attcctagtg tgcaagacca 1040
1041 cagacactgt caaggagaa agagtctcat tccctgtatg cacctacgtc cctcaaccat ctgtgatca aatgactggc 1120
1121 atactagcga ccgacgtcac accggaggac gcacagaagt tgttagtggg attgaatcag aggatagttg gaacgaaag 1200
1201 aacacagcga aacactaaca cgatgaagaa ctatctgctt ccgattgtgg ccgtcgcatt tagcaagtgg gcgagggaat 1280
1281 acaaggcaga ccttgatgat gaaaaacctc tgggtgtccg agagaggtca cttacttgct gctgcttgtg ggcatttaaa 1360
1361 acgaggaaga tgcacaccat gtacaagaaa ccagacaccc agacaatagt gaaggtgcct tcagagttta actcgttcgt 1440
1441 catcccgagc ctatggtcta caggcctcgc aatcccagtc agatcacgca ttaagatgct tttggccaag aagaccaagc 1520
```

-continued

```
1521 gagagttaat acctgttctc gacgcgtcgt cagccaggga tgctgaacaa gaggagaagg agaggttgga ggccgagctg 1600
1601 actagagaag ccttaccacc cctcgtcccc atcgcgccgg cggagacggg agtcgtcgac gtcgacgttg aagaactaga 1680
1681 gtatcacgca ggtgcagggg tcgtggaaac acctcgcagc gcgttgaaag tcaccgcaca gccgaacgac gtactactag 1760
1761 gaaattacgt agttctgtcc ccgcagaccg tgctcaagag ctccaagttg gcccccgtgc accctctagc agagcaggtg 1840
1841 aaaataataa cacataacgg gagggccggc ggttaccagg tcgacggata tgacggcagg gtcctactac catgtggatc 1920
1921 ggccattccg gtccctgagt ttcaagcttt gagcgagagc gccactatgg tgtacaacga aagggagttc gtcaacagga 2000
2001 aactatacca tattgccgtt cacggaccgt cgctgaacac cgacgaggag aactacgaga agtcagagc tgaaagaact 2080
2081 gacgccgagt acgtgttcga cgtagataaa aaatgctgcg tcaagagaga ggaagcgtcg ggtttggtgt tggtgggaga 2160
2161 gctaaccaac cccccgttcc atgaattcgc ctacgaaggg ctgaagatca ggccgtcggc accatataag actacagtag 2240
2241 taggagtctt tggggttccg ggatcaggca agtctgctat tattaagagc ctcgtgacca acacgatct ggtcaccagc 2320
2321 ggcaagaagg agaactgcca ggaaatagtt aacgacgtga agaagcaccg cgggaagggg acaagtaggg aaaacagtga 2400
2401 ctccatcctg ctaaacgggg tcgtcgtgc cgtggacatc ctatatgtgg acgaggcttt cgctagccat tccggtactc 2480
2481 tgctggccct aattgctctt gttaaacctc ggagcaaagt ggtgttatgc ggagacccca gcaatgcgg attcttcaat 2560
2561 atgatgcagc ttaaggtgaa cttcaaccac aacatctgca ctgaagtatg tcataaaagt atatccgac gttgcacgcg 2640
2641 tccagtcacg gccatcgtgt ctacgttgca ctacggaggc aagatgcgca cgaccaaccc gtgcaacaaa cccataatca 2720
2721 tagacaccac aggacagacc aagcccaagc caggagacat cgtgttaaca tgcttccgag ctgggcaaa gcagctgcag 2800
2801 ttggactacc gtggacacga agtcatgaca gcagcagcat ctcagggcct cacccgcaaa ggggtatacg ccgtaaggca 2880
2881 gaaggtgaat gaaaatccct tgtatgcccc tgtcgcggag cacgtgaatg tactgctgac gcgcactgag ataggctgg 2960
2961 tgtggaaaac gctggccggc gatccctgga ttaaggtcct atcaaacatt ccacagggta actttacggc acattggaa 3040
3041 gaatggcaag aagaacacga caaaataatg aaggtgattg aaggaccggg tgcgcctgtg gacgcgttcc agaacaaagc 3120
3121 gaacgtgtgt tgggcgaaaa gcctggtgcc tgtcctggac actgccggaa tcagattgac agcagaggag tggagcacca 3200
3201 taattacagc atttaaggag gacagagctt actctccagt ggtggccttg aatgaaattt gcaccaagta ctatggagtt 3280
3281 gacctggaca gtggcctgtt ttctgccccg aaggtgtccc tgtattacga gaacaaccac tgggataaca gacctggtgg 3360
3361 aaggatgtat ggattcaatg ccgcaacagc tgccaggctg gaagctagac ataccttcct gaaggggcag tggcatacgg 3440
3441 gcaagcaggc agttatcgca gaaagaaaaa tccaaccgct ttctgtgctg gacaatgtaa ttcctatcaa ccgcaggctg 3520
3521 ccgcacgccc tggtggctga gtacaagacg gttaaggca gtagggttga gtggctggtc aataaagtaa gagggtacca 3600
3601 cgtcctgctg gtgagtgagt acaacctggc tttgcctcga cgcagggtca cttggttgtc accgctgaat gtcacaggcg 3680
3681 ccgataggtg ctacgaccta agtttaggac tgccggctga cgccggcagg ttcgacttgg tctttgtgaa cattcacacg 3760
3761 gaattcagaa tccaccacta ccagcagtgt gtcgaccacg ccatgaagct gcagatgctt gggggagatg cgctacgact 3840
3841 gctaaaaccc ggcggcatct tgatgagagc ttacggatac gccgataaaa tcagcgaagc cgttgtttcc tccttaagca 3920
3921 gaaagttctc gtctgcaaga gtgttgcgcc cggattgtgt caccagcaat acagaagtgt tcttgctgtt ctccaacttt 4000
4001 gacaacgaaa agagaccctc tacgctacac cagatgaata ccaagctgag tgccgtgtat gccggagaag ccatgcacac 4080
4081 ggccgggtgt gcaccatcct acagagttaa gagagcagac atagccacgt gcacagaagc ggctgtggtt aacgcagcta 4160
4161 acgcccgtgg aactgtaggg gatggcgtat gcagggccgt ggcgaagaaa tggccgtcag cctttaaggg agcagcaaca 4240
4241 ccagtgggca caattaaaac agtcatgtgc ggctcgtacc ccgtcatcca cgctgtagcg cctaatttct ctgccacgac 4320
4321 tgaagcggaa ggggaccgcg aattggccgc tgtctaccgg gcagtggccg ccgaagtaaa cagactgtca ctgagcagcg 4400
4401 tagccatccc gctgctgtcc acaggagtgt tcagcggcgg aagagatagg ctgcagcaat ccctcaacca tctattcaca 4480
4481 gcaatggacg ccacggacgc tgacgtgacc atctactgca gagacaaaag ttgggagaag aaaatccagg aagccattga 4560
4561 catgaggacg gctgtggagt tgctcaatga tgacgtggag ctgaccacag acttggtgag agtgcacccg gacagcagcc 4640
4641 tggtgggtcg taagggctac agtaccactg acgggtcgct gtactcgtac tttgaaggta cgaaattcaa ccaggctgct 4720
```

```
4721 attgatatgg cagagatact gacgttgtgg cccagactgc aagaggcaaa cgaacagata tgcctatacg cgctgggcga 4800
4801 aacaatggac aacatcagat ccaaatgtcc ggtgaacgat tccgattcat caacacctcc caggacagtg ccctgcctgt 4880
4881 gccgctacgc aatgacagca gaacggatcg cccgccttag gtcacaccaa gttaaaagca tggtggtttg ctcatctttt 4960
4961 cccctcccga ataccatgt agatggggtg cagaaggtaa agtgcgagaa ggttctcctg ttcgacccga cggtaccttc 5040
5041 agtggttagt ccgcggaagt atgccgcatc tacgacggac cactcagatc ggtcgttacg agggtttgac ttggactgga 5120
5121 ccaccgactc gtcttccact gccagcgata ccatgtcgct acccagtttg cagtcgtgtg acatcgactc gatctacgag 5200
5201 ccaatggctc ccatagtagt gacggctgac gtacaccctg aacccgcagg catcgcggac ctggcggcag atgtgcaccc 5280
5281 tgaacccgca gaccatgtgg acctcgagaa cccgattcct ccaccgcgcc cgaagagagc tgcataccTT gcctcccgc 5360
5361 cggcggagcg accggtgccg cgccgagaa agccgacgcc tgccccaagg actgcgttta ggaacaagct gcctttgacg 5440
5441 ttcggcgact ttgacgagca cgaggtcgat gcgttggcct ccgggattac tttcggagac ttcgacacg tcctgcgact 5520
5521 aggccgcgcg ggtgcatata ttttctcctc ggacactggc agcggacatt tacaacaaaa atccgttagg cagcacaatc 5600
5601 tccagtgcgc acaactggat gcggtccagg aggagaaaat gtacccgcca aaattggata ctgagaggga gaagctgttg 5680
5681 ctgctgaaaa tgcagatgca cccatcggag gctaataaga gtcgatacca gtctcgcaaa gtggagaaca tgaaagccac 5760
5761 ggtggtggac aggctcacat cggggggccag attgtacacg ggagcggacg taggccgcat accaacatac gcggttcggt 5840
5841 accccgccc cgtgtactcc cctaccgtga tcgaaagatt ctcaagcccc gatgtagcaa tcgcagcgtg caacgaatac 5920
5921 ctatccagaa attacccaac agtggcgtcg taccagataa cagatgaata cgacgcatac ttggacatgg ttgacgggtc 6000
6001 ggatagttgc ttggacagag cgacattctg cccggcgaag ctccggtgct acccgaaaca tcatgcgtac caccagccga 6080
6081 ctgtacgcag tgccgtcccg tcacccttc agaacacact acagaacgtg ctagcggccg ccaccaagag aaactgcaac 6160
6161 gtcacgcaaa tgcgagaact acccaccatg gactcggcag tgttcaacgt ggagtgcttc aagcgctatg cctgctccgg 6240
6241 agaatattgg gaagaatatg ctaaacaacc tatccggata accactgaga acatcactac ctatgtgacc aaattgaaag 6320
6321 gcccgaaagc tgctgccttg ttcgctaaga cccacaactt ggttccgctg caggaggttc ccatggacag attcacggtc 6400
6401 gacatgaaac gagatgtcaa agtcactcca gggacgaaac acacagagga aagacccaaa gtccaggtaa ttcaagcagc 6480
6481 ggagccattg gcgaccgctt acctgtgcgg catccacagg gaattagtaa ggagactaaa tgctgtgtta cgccctaacg 6560
6561 tgcacacatt gtttgatatg tcggccgaag actttgacgc gatcatcgcc tctcacttcc acccaggaga cccggttcta 6640
6641 gagacggaca ttgcatcatt cgacaaaagc caggacgact ccttggctct tacaggttta atgatcctcg aagatctagg 6720
6721 ggtggatcag tacctgctgg acttgatcga ggcagccttt gggaaaatat ccagctgtca cctaccaact ggcacgcgct 6800
6801 tcaagttcgg agctatgatg aaatcgggca tgtttctgac tttgtttatt aacactgttt tgaacatcac catagcaagc 6880
6881 agggtactgg agcagagact cactgactcc gcctgtgcgg ccttcatcgg cgacgacaac atcgttcacg gagtgatctc 6960
6961 cgacaagctg atggcggaga ggtgcgcgtc gtgggtcaac atggaggtga agatcattga cgctgtcatg gcgaaaaac 7040
7041 ccccatattt ttgtgggga ttcatagttt ttgacagcgt cacacagacc gcctgccgtg tttcagaccc acttaagcgc 7120
7121 ctgttcaagt tgggtaagcc gctaacagct gaagacaagc aggacgaaga caggcgacga gcactgagtg acgaggttag 7200
7201 caagtggttc cggacaggct gggggccga actggaggtg gcactaacat ctaggtatga ggtagagggc tgcaaaagta 7280
7281 tcctcatagc catggccacc ttggcgaggg acattaaggc gtttaagaaa ttgagaggac ctgttataca cctctacgcg 7360
7361 ggtcctagat tggtgcgtta atacacagaa ttctgattgg atccATGCAT GGAGATACAC CTACATTGCA TGAATATATG 7440
7441 TTAGATTTGC AACCAGAGAC AACTGATCTC TACTGTTATG AGCAATTAAA TGACAGCTCA GAGGAGGAGG ATGAAATAGA 7520
7521 TGGTCCAGCT GGACAAGCAG AACCGGACAG AGCCCATTAC AATATTGTAA CCTTTTGTTG CAAGTGTGAC TCTACGCTTC 7600
7601 GGTTGTGCGT ACAAAGCACA CACGTAGACA TTCGTACTTT GGAAGACCTG TTAATGGGCA CACTAGGAAT TGTGTGCCCC 7680
7681 ATCTGTTCTC AAGGATCCAT GGCTCGTGCG GTCGGGATCG ACCTCGGGAC CACCAACTCC GTCGTCTCGG TTCTGGAAGG 7760
7761 TGGCGACCCG GTCGTCGTCC CAACTCCGA GGGCTCCAGG ACCACCCCGT CAATTGTCGC GTTCGCCCGC AACGGTGAGG 7840
7841 TGCTGGTCGG CCAGCCCGCC AAGAACCAGG CAGTGACCAA CGTCGATCGC ACCGTGCGCT CGGTCAAGCG ACACATGGGC 7920
```

-continued

```
7921  AGCGACTGGT CCATAGAGAT TGACGGCAAG AAATACACCG CGCCGGAGAT CAGCGCCCGC ATTCTGATGA AGCTGAAGCG  8000
8001  CGACGCCGAG GCCTACCTCG GTGAGGACAT TACCGACGCG GTTATCACGA CGCCCGCCTA CTTCAATGAC GCCCAGCGTC  8080
8081  AGGCCACCAA GGACGCCGGC CAGATCGCCG GCCTCAACGT GCTGCGGATC GTCAACGAGC CGACCGCGGC CGCGCTGGCC  8160
8161  TACGGCCTCG ACAAGGGCGA GAAGGAGCAG CGAATCCTGG TCTTCGACTT GGGTGGTGGC ACTTTCGACG TTTCCCTGCT  8240
8241  GGAGATCGGC GAGGGTGTGG TTGAGGTCCG TGCCACTTCG GGTGACAACC ACCTCGGCGG CGACGACTGG GACCAGCGGG  8320
8321  TCGTCGATTG GCTGGTGGAC AAGTTCAAGG GCACCAGCGG CATCGATCTG ACCAAGGACA GATGGCGAT GCAGCGGCTG  8400
8401  CGGGAAGCCG CCGAGAAGGC AAAGATCGAG CTGAGTTCGA GTCAGTCCAC CTCGATCAAC CTGCCCTACA TCACCGTCGA  8480
8481  CGCCGACAAG AACCCGTTGT TCTTAGACGA GCAGCTGACC CGCGCGGAGT TCCAACGGAT CACTCAGGAC CTGCTGGACC  8560
8561  GCACTCGCAA GCCGTTCCAG TCGGTGATCG CTGACACCGG CATTTCGGTG TCGGAGATCG ATCACGTTGT GCTCGTGGGT  8640
8641  GGTTCGACCC GGATGCCCGC GGTGACCGAT CTGGTCAAGG AACTCACCGG CGGCAAGGAA CCCAACAAGG GCGTCAACCC  8720
8721  CGATGAGGTT GTCGCGGTGG GAGCCGCTCT GCAGGCCGGC GTCCTCAAGG GCGAGGTGAA AGACGTTCTG CTGCTTGATG  8800
8801  TTACCCCGCT GAGCCTGGGT ATCGAGACCA AGGGCGGGGT GATGACCAGG CTCATCGAGC GCAACACCAC GATCCCCACC  8880
8881  AAGCGGTCGG AGACTTTCAC CACCGCCGAC GACAACCAAC CGTCGGTGCA GATCCAGGTC TATCAGGGGG AGCGTGAGAT  8960
8961  CGCCGCGCAC AACAAGTTGC TCGGGTCCTT CGAGCTGACC GGCATCCCGC CGGCGCCGCG GGGGATTCCG CAGATCGAGG  9040
9041  TCACTTTCGA CATCGACGCC AACGGCATTG TGCACGTCAC CGCCAAGGAC AAGGGCACCG GCAAGGAGAA CACGATCCGA  9120
9121  ATCCAGGAAG GCTCGGGCCT GTCCAAGGAA GACATTGACC GCATGATCAA GGACGCCGAA GCGCACGCCG AGGAGGATCG  9200
9201  CAAGCGTCGC GAGGAGGCCG ATGTTCGTAA TCAAGCCGAG ACATTGGTCT ACCAGACGGA GAAGTTCGTC AAAGAACAGC  9280
9281  GTGAGGCCGA GGGTGGTTCG AAGGTACCTG AAGACACGCT GAACAAGGTT GATGCCGCGG TGGCGGAAGC GAAGGCGGCA  9360
9361  CTTGGCGGAT CGGATATTTC GGCCATCAAG TCGGCGATGG AGAAGCTGGG CCAGGAGTCG CAGGCTCTGG GGCAAGCGAT  9440
9441  CTACGAAGCA GCTCAGGCTG CGTCACAGGC CACTGGCGCT GCCCACCCCG GCTCGGCTGA TGAAAGCTTa agtttgggta  9520
9521  attaattgaa ttacatccct acgcaaacgt tttacggccg ccggtggcgc ccgcgcccgg cggcccgtcc ttggccgttg  9600
9601  caggccactc cggtggctcc cgtcgtcccc gacttccagg cccagcagat gcagcaactc atcagcgccg taaatgcgct  9680
9681  gacaatgaga cagaacgcaa ttgctcctgc taggcctccc aaaccaaaga agaagaagac aaccaaacca agccgaaaa  9760
9761  cgcagcccaa gaagatcaac ggaaaaacgc agcagcaaaa gaagaaagac aagcaagccg acaagaagaa gaagaaaccc  9840
9841  ggaaaaagag aaagaatgtg catgaagatt gaaaatgact gtatcttcgt atgcggctag ccacagtaac gtagtgtttc  9920
9921  cagacatgtc gggcaccgca ctatcatggg tgcagaaaat ctcgggtggt ctgggggcct tcgcaatcgg cgctatcctg  10000
10001 gtgctggttg tggtcacttg cattgggctc cgcagataag ttagggtagg caatggcatt gatatagcaa gaaaattgaa  10080
10081 aacagaaaaa gttagggtaa gcaatggcat ataaccataa ctgtataact tgtaacaaag cgcaacaaga cctgcgcaat  10160
10161 tggccccgtg gtccgcctca cggaaactcg gggcaactca tattgacaca ttaattggca ataattgaa gcttacataa  10240
10241 gcttaattcg acgaataatt ggatttttat tttattttgc aattggtttt taatatttcc aaaaaaaaa aaaaaaaaa  10320
10321 aaaaaaaaa aaaaaaaaa aaaaaaaaa aaaaaaaaa aaaaaaaaa ctagtgatca taatcagcca taccacattt  10400
10401 gtagaggttt tacttgcttt aaaaaacctc ccacacctcc ccctgaacct gaaacataaa atgaatgcaa ttgttgttgt  10480
10481 taacttgttt attgcagctt ataatggtta caaataaagc aatagcatca caaatttcac aaataaagca tttttttcac  10560
10561 tgcattctag ttgtggtttg tccaaactca tcaatgtatc ttatcatgtc tggatctagt ctgcattaat gaatcggcca  10640
10641 acgcgcgggg agaggcggtt tgcgtattgg gcgctcttcc gcttcctcgc tcactgactc gctgcgctcg gtcgttcggc  10720
10721 tgcggcgagc ggtatcagct cactcaaagg cggtaatacg gttatccaca gaatcagggg ataacgcagg aaagaacatg  10800
10801 tgagcaaaag gccagcaaaa ggccaggaac cgtaaaaagg ccgcgttgct ggcgtttttc cataggctcc gcccccctga  10880
10881 cgagcatcac aaaaatcgac gctcaagtca gaggtggcga aacccgacag gactataaag ataccaggcg tttccccctg  10960
10961 gaagctccct cgtgcgctct cctgttccga ccctgccgct taccggatac ctgtccgcct ttctcccttc gggaagcgtg  11040
11041 gcgctttctc aatgctcgcg ctgtaggtat ctcagttcgg tgtaggtcgt tcgctccaag ctgggctgtg tgcacgaacc  11120
```

-continued

```
11121 ccccgttcag cccgaccgct gcgccttatc cggtaactat cgtcttgagt ccaacccggt aagacacgac ttatcgccac 11200
11201 tggcagcagc cactggtaac aggattagca gagcgaggta tgtaggcggt gctacagagt tcttgaagtg gtggcctaac 11280
11281 tacggctaca ctagaaggac agtatttggt atctgcgctc tgctgaagcc agttaccttc ggaaaaagag ttggtagctc 11360
11361 ttgatccggc aaacaaacca ccgctggtag cggtggtttt tttgtttgca agcagcagat tacgcgcaga aaaaaaggat 11440
11441 ctcaagaaga tcctttgatc ttttctacgg ggcattctga cgctcagtgg aacgaaaact cacgttaagg gattttggtc 11520
11521 atgagattat caaaaaggat cttcacctag atcctttaa attaaaaatg aagttttaaa tcaatctaaa gtatatatga 11600
11601 gtaaacttgg tctgacagtt accaatgctt aatcagtgag gcacctatct cagcgatctg tctatttcgt tcatccatag 11680
11681 ttgcctgact ccccgtcgtg tagataacta cgatacggga gggcttacca tctggcccca gtgctgcaat gataccgcga 11760
11761 gacccacgct caccggctcc agatttatca gcaataaacc agccagccgg aagggccgag cgcagaagtg gtcctgcaac 11840
11841 tttatccgcc tccatccagt ctattaattg ttgccgggaa gctagagtaa gtagttcgcc agttaatagt ttgcgcaacg 11920
11921 ttgttgccat tgctacaggc atcgtggtgt cacgctcgtc gtttggtatg gcttcattca gctccggttc ccaacgatca 12000
12001 aggcgagtta catgatcccc catgttgtgc aaaaaagcgg ttagctcctt cggtcctccg atcgttgtca gaagtaagtt 12080
12081 ggccgcagtg ttatcactca tggttatggc agcactgcat aattctctta ctgtcatgcc atccgtaaga tgcttttctg 12160
12161 tgactggtga gtactcaacc aagtcattct gagaatagtg tatgcggcga ccgagttgct cttgcccggc gtcaatacgg 12240
12241 gataataccg cgccacatag cagaacttta aaagtgctca tcattggaaa acgttcttcg gggcgaaaac tctcaaggat 12320
12321 cttaccgctg ttgagatcca gttcgatgta acccactcgt gcacccaact gatcttcagc atcttttact ttcaccagcg 12400
12401 tttctgggtg agcaaaaaca ggaaggcaaa atgccgcaaa aaagggaata agggcgacac ggaaatgttg aatactcata 12480
12481 ctcttccttt ttcaatatta ttgaagcatt tatcagggtt attgtctcat gagcggatac atatttgaat gtatttagaa 12560
12561 aaataaacaa ataggggttc cgcgcacatt tccccgaaaa gtgccacctg acgtctaaga aaccattatt atcatgacat 12640
12641 taacctataa aaataggcgt atcacgaggc cctttcgtct cgcgcgtttc ggtgatgacg gtgaaaacct ctgacacatg 12720
12721 cagctcccgg agacggtcac agcttctgtc taagcggatg ccgggagcag acaagcccgt cagggcgcgt cagcgggtgt 12800
12801 tggcgggtgt cggggctggc ttaactatgc ggcatcagag cagattgtac tgagagtgca ccatatcgac gctctccctt 12880
12881 atgcgactcc tgcattagga agcagcccag tactaggttg aggccgttga gcaccgccgc cgcaaggaat ggtgcatgcg 12960
12961 taatcaatta cggggtcatt agttcatagc ccatatatgg agttccgcgt tacataactt acggtaaatg gcccgcctgg 13040
13041 ctgaccgccc aacgaccccc gcccattgac gtcaataatg acgtatgttc ccatagtaac gccaatagggg actttccatt 13120
13121 gacgtcaatg ggtggagtat ttacggtaaa ctgcccactt ggcagtacat caagtgtatc atatgccaag tacgccccct 13200
13201 attgacgtca atgacggtaa atggcccgcc tggcattatg cccagtacat gaccttatgg gactttccta cttggcagta 13280
13281 catctacgta ttagtcatcg ctattaccat ggtgatgcgg ttttggcagt acatcaatgg gcgtggatag cggtttgact 13360
13361 cacggggatt tccaagtctc cacccccattg acgtcaatgg gagtttgttt tggcaccaaa atcaacggga ctttccaaaa 13440
13441 tgtcgtaaca actccgcccc attgacgcaa atgggcggta ggcgtgtacg gtgggaggtc tatataagca gagctctctg 13520
13521 gctaactaga acccactg cttaactggc ttatcgaaat taatacgact cactataggg agaccggaag cttgaattc 13599
              |    10    |    20    |    30    |    40    |    50    |    60    |    70    |    80    |
``` pcDNA3-FL-E7 SEQ ID NO:21 FL-E7 fusion sequence is
shown in bold, caps

```
              |    10    |    20    |    30    |    40    |    50    |    60    |    70    |    80    |
   1 gacggatcgg gagatctccc gatccctat ggtcgactct cagtacaatc tgctctgatg ccgcatagtt aagccagtat    80
  81 ctgctccctg cttgtgtgtt ggaggtcgct gagtagtgcg cgagcaaaat ttaagctaca acaaggcaag gcttgaccga  160
 161 caattgcatg aagaatctgc ttaggggtag gcgttttgcg ctgcttcgcg atgtacgggc cagatatacg cgttgacatt  240
 241 gattattgac tagttattaa tagtaatcaa ttacggggtc attagttcat agcccatata tggagttccg cgttacataa  320
```

```
 321 cttacggtaa atggcccgcc tggctgaccg cccaacgacc cccgcccatt gacgtcaata atgacgtatg ttcccatagt  400

401 aacgccaata gggactttcc attgacgtca atgggtggac tatttacggt aaactgccca cttggcagta catcaagtgt  480

481 atcatatgcc aagtacgccc cctattgacg tcaatgacgg taaatggccc gcctggcatt atgcccagta catgacctta  560

561 tgggactttc ctacttggca gtacatctac gtattagtca tcgctattac catggtgatg cggttttggc agtacatcaa  640

641 tgggcgtgga tagcggtttg actcacgggg atttccaagt ctccacccca ttgacgtcaa tgggagtttg ttttggcacc  720

721 aaaatcaacg ggactttcca aaatgtcgta acaactccgc cccattgacg caaatgggcg gtaggcgtgt acggtgggag  800

801 gtctatataa gcagagctct ctggctaact agagaaccca ctgcttactg gcttatcgaa attaatacga ctcactatag  880

881 ggagacccaa gctggctagc gtttaaacgg gccctctaga ATGACAGTGC TGGCGCCAGC CTGGAGCCCA AATTCCTCCC  960

961 TGTTGCTGCT GTTGCTGCTG CTGAGTCCTT GCCTGCGGGG GACACCTGAC TGTTACTTCA GCCACAGTCC CATCTCCTCC 1040

1041 AACTTCAAAG TGAAGTTTAG AGAGTTGACT GACCACCTGC TTAAAGATTA CCCAGTCACT GTGGCCGTCA ATCTTCAGGA 1120

1121 CGAGAAGCAC TGCAAGGCCT TGTGGAGCCT CTTCCTAGCC CAGCGCTGGA TAGAGCAACT GAAGACTGTG GCAGGGTCTA 1200

1201 AGATGCAAAC GCTTCTGGAG GACGTCAACA CCGAGATACA TTTTGTCACC TCATGTACCT TCCAGCCCCT ACCAGAATGT 1280

1281 CTGCGATTCG TCCAGACCAA CATCTCCCAC CTCCTGAAGG ACACCTGCAC ACAGCTGCTT GCTCTGAAGC CCTGTATCGG 1360

1361 GAAGGCCTGC CAGAATTTCT CTCGGTGCCT GGAGGTGCAG TGCCAGCCGG ACTCCTCCAC CCTGCTGCCC CCAAGGAGTC 1440

1441 CCATAGCCCT AGAAGCCACG GAGCTCCCAG AGCCTCGGCC CAGGCAGGGA TCCATGCATG GAGATACACC TACATTGCAT 1520

1521 GAATATATGT TAGATTTGCA ACCAGAGACA ACTGATCTCT ACTGTTATGA GCAATTAAAT GACAGCTCAG AGGAGGAGGA 1600

1601 TGAAATAGAT GGTCCAGCTG GACAAGCAGA ACCGGACAGA GCCCATTACA ATATTGTAAC CTTTTGTTGC AAGTGTGACT 1680

1681 CTACGCTTCG GTTGTGCGTA CAAAGCACAC ACGTAGACAT TCGTACTTTG GAAGACCTGT TAATGGGCAC ACTAGGAATT 1760

1761 GTGTGCCCCA TCTGTTCTCA GGATAAGCTT aagtttaaac cgctgatcag cctcgactgt gccttctagt tgccagccat 1840

1841 ctgttgtttg cccctccccc gtgccttcct gaccctgga aggtgccact cccactgtcc tttcctaata aaatgaggaa 1920

1921 attgcatcgc attgtctgag taggtgtcat tctattctgg ggggtgggt ggggcaggac agcaagggg aggattggga 2000

2001 agacaatagc aggcatgctg gggatgcggt gggctctatg gcttctgagg cggaaagaac cagctggggc tctaggggt 2080

2081 atccccacgc gccctgtagc ggcgcattaa gcgcggcggg tgtggtggtt acgcgcagcg tgaccgctac acttgccagc 2160

2161 gccctagcgc ccgctccttt cgctttcttc ccttcctttc tcgccacgtt cgccggcttt ccccgtcaag ctctaaatcg 2240

2241 gggcatccct ttagggttcc gatttagtgc tttacggcac ctcgacccca aaaaacttga ttagggtgat ggttcacgta 2320

2321 gtgggccatc gccctgatag acggtttttc gccctttgac gttggagtcc acgttcttta atagtggact cttgttccaa 2400

2401 actggaacaa cactcaaccc tatctcggtc tattcttttg atttataagg attttgggg atttcggcct attggttaaa 2480

2481 aaatgagctg atttaacaaa aatttaacgc gaattaattc tgtggaatgt gtgtcagtta gggtgtggaa agtccccagg 2560

2561 ctccccaggc aggcagaagt atgcaaagca tgcatctcaa ttagtcagca accaggtgtg gaaagtcccc aggctcccca 2640

2641 gcaggcagaa gtatgcaaag catgcatctc aattagtcag caaccatagt cccgccccta actccgccca tcccgcccct 2720

2721 aactccgccc agttccgccc attctccgcc ccatggctga ctaatttttt ttatttatgc agaggccgag gccgcctctg 2800

2801 cctctgagct attccagaag tagtgaggag gcttttttgg aggcctaggc ttttgcaaaa agctcccggg agcttgtata 2880

2881 tccattttcg gatctgatca agagacagga tgaggatcgt ttcgcatgat tgaacaagat ggattgcacg caggttctcc 2960

2961 ggccgcttgg gtggagaggc tattcggcta tgactgggca acagacaa tcggctgctc tgatgccgcc gtgttccggc 3040

3041 tgtcagcgca ggggcgcccg gttcttttt caagaccga cctgtccggt gccctgaatg aactgcagga cgaggcagcg 3120

3121 cggctatcgt ggctggccac gacgggcgtt ccttgcgcag ctgtgctcga cgttgtcact gaagcgggaa gggactggct 3200

3201 gctattgggc gaagtgccgg ggcaggatct cctgtcatct caccttgctc ctgccgagaa agtatccatc atggctgatg 3280

3281 caatgcggcg gctgcatacg cttgatccgg ctacctgccc attcgaccac caagcgaaac atcgcatcga gcgagcacgt 3360

3361 actcggatgg aagccggtct tgtcgatcag gatgatctgg acgaagagca tcagggctc gcgccagccg aactgttcgc 3440

3441 caggctcaag gcgcgcatgc ccgacggcga ggatctcgtc gtgacccatg gcgatgcctg cttgccgaat atcatggtgg 3520
```

-continued

```
3521 aaaatggccg cttttctgga ttcatcgact gtggccggct gggtgtggcg gaccgctatc aggacatagc gttggctacc 3600

3601 cgtgatattg ctgaagagct tggcggcgaa tgggctgacc gcttcctcgt gctttacggt atcgccgctc ccgattcgca 3680

3681 gcgcatcgcc ttctatcgcc ttcttgacga gttcttctga gcgggactct ggggttcgaa atgaccgacc aagcgacgcc 3760

3761 caacctgcca tcacgagatt tcgattccac cgccgccttc tatgaaaggt tgggcttcgg aatcgttttc cgggacgccg 3840

3841 gctggatgat cctccagcgc ggggatctca tgctggagtt cttcgcccac cccaacttgt ttattgcagc ttataatggt 3920

3921 tacaaataaa gcaatagcat cacaaatttc acaaataaag catttttttc actgcattct agttgtggtt tgtccaaact 4000

4001 catcaatgta tcttatcatg tctgtatacc gtcgacctct agctagagct tggcgtaatc atggtcatag ctgtttcctg 4080

4081 tgtgaaattg ttatccgctc acaattccac acaacatacg agccgaagc ataaagtgta aagcctgggg tgcctaatga 4160

4161 gtgagctaac tcacattaat tgcgttgcgc tcactgcccg ctttccagtc gggaaacctg tcgtgccagc tgcattaatg 4240

4241 aatcggccaa cgcgcgggga gaggcggttt gcgtattggg cgctcttccg cttcctcgct cactgactcg ctgcgctcgg 4320

4321 tcgttcggct gcggcgagcg gtatcagctc actcaaaggc ggtaatacgg ttatccacag aatcagggga taacgcagga 4400

4401 aagaacatgt gagcaaaagg ccagcaaaag gccaggaacc gtaaaaaggc cgcgttgctg gcgtttttcc ataggctccg 4480

4481 ccccctgac gagcatcaca aaaatcgacg ctcaagtcag aggtggcgaa acccgacagg actataaaga taccaggcgt 4560

4561 ttccccctgg aagctccctc gtgcgctctc ctgttccgac cctgccgctt accggatacc tgtccgcctt tctcccttcg 4640

4641 ggaagcgtgg cgctttctca atgctcacgc tgtaggtatc tcagttcggt gtaggtcgtt cgctccaagc tgggctgtgt 4720

4721 gcacgaaccc cccgttcagc ccgaccgctg cgccttatcc ggtaactatc gtcttgagtc caaccggta agacacgact 4800

4801 tatcgccact ggcagcagcc actggtaaca ggattagcag agcgaggtat gtaggcggtg ctacagagtt cttgaagtgg 4880

4881 tggcctaact acggctacac tagaaggaca gtatttggta tctgcgctct gctgaagcca gttaccttcg gaaaaagagt 4960

4961 tggtagctct tgatccggca aacaaaccac cgctggtagc ggtggttttt ttgtttgcaa gcagcagatt acgcgcagaa 5040

5041 aaaaaggatc tcaagaagat cctttgatct tttctacggg gtctgacgct cagtggaacg aaaactcacg ttaagggatt 5120

5121 ttggtcatga gattatcaaa aaggatcttc acctagatcc ttttaaatta aaaatgaagt tttaaatcaa tctaaagtat 5200

5201 atatgagtaa acttggtctg acagttacca atgcttaatc agtgaggcac ctatctcagc gatctgtcta tttcgttcat 5280

5281 ccatagttgc ctgactcccc gtcgtgtaga taactacgat acgggagggc ttaccatctg gccccagtgc tgcaatgata 5360

5361 ccgcgagacc cacgctcacc ggctccagat ttatcagcaa taaaccagcc agccggaagg gccgagcgca gaagtggtcc 5440

5441 tgcaacttta tccgcctcca tccagtctat taattgttgc cgggaagcta gagtaagtag ttcgccagtt aatagtttgc 5520

5521 gcaacgttgt tgccattgct acaggcatcg tggtgtcacg ctcgtcgttt ggtatggctt cattcagctc cggttcccaa 5600

5601 cgatcaaggc gagttacatg atcccccatg ttgtgcaaaa aagcggttag ctccttcggt cctccgatcg ttgtcagaag 5680

5681 taagttggcc gcagtgttat cactcatggt tatggcagca ctgcataatt ctcttactgt catgccatcc gtaagatgct 5760

5761 tttctgtgac tggtgagtac tcaaccaagt cattctgaga atagtgtatg cggcgaccga gttgctcttg cccggcgtca 5840

5841 atacgggata ataccgcgcc acatagcaga actttaaaag tgctcatcat tggaaaacgt tcttcggggc gaaaactctc 5920

5921 aaggatctta ccgctgttga gatccagttc gatgtaaccc actcgtgcac ccaactgatc ttcagcatct tttactttca 6000

6001 ccagcgtttc tgggtgagca aaaacaggaa ggcaaaatgc cgcaaaaaag ggaataaggg cgacacggaa atgttgaata 6080

6081 ctcatactct tcctttttca atattattga agcatttatc agggttattg tctcatgagc ggatacatat ttgaatgtat 6160

6161 ttagaaaaat aaacaaatag gggttccgcg cacatttccc cgaaaagtgc cacctgacgt c        6221
         |        10 |        20 |        30 |        40 |        50 |        60 |        70 |        80 |
```

General Recombinant DNA Methods

Basic texts disclosing general methods of molecular biology, all of which are incorporated by reference, include: Sambrook, J et al., *Molecular Cloning: A Laboratory Manual*, 2$^{nd}$ Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, 2$^{nd}$ Ed., Garland Publishing, Inc., New York, N.Y. (1989); Watson, J D et al., *Recombinant DNA*, 2$^{nd}$ Ed., Scientific American Books, New York, 1992; and Old, R W et al., *Principles of Gene Manipulation: An Introduction to Genetic Engineering*, 2$^{nd}$ Ed., University of California Press, Berkeley, Calif. (1981).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to the fusion polypeptide of the present invention or fragments or derivatives thereof can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

This invention includes isolated nucleic acids having a nucleotide sequence encoding the novel fusion polypeptides that comprise a MHC-I-PP or a DC-PP and an antigen, fragments thereof or equivalents thereof. The term nucleic acid as used herein is intended to include such fragments or equivalents. The nucleic acid sequences of this invention can be DNA or RNA.

A cDNA nucleotide sequence the fusion polypeptide can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins. For example, a natural polymorphism Hsp70 or FL nucleotide sequence (especially at the third base of a codon) may be manifest as "silent" mutations which do not change the amino acid sequence. Furthermore, there may be one or more naturally occurring isoforms or related, immunologically cross-reactive family members of these proteins. Such isoforms or family members are defined as proteins that share function amino acid sequence similarity to, for example, Hsp70 or FL.

Fragment of Nucleic Acid

A fragment of the nucleic acid sequence is defined as a nucleotide sequence having fewer nucleotides than the nucleotide sequence encoding the full length MHC-I-PP or DC-PP protein, antigenic polypeptide or the fusion thereof. This invention includes such nucleic acid fragments that encode polypeptides which retain (1) the ability of the fusion polypeptide to induce increases in frequency or reactivity of T cells, preferably CD8+ T cells, that are specific for the antigen part of the fusion polypeptide.

For example, a nucleic acid fragment as intended herein encodes a FL polypeptide that retains the ability to improve the immunogenicity of an antigen when administered as a fusion polypeptide with an antigenic polypeptide or peptide.

Generally, the nucleic acid sequence encoding a fragment of a FL or Hsp70 polypeptide comprises of nucleotides from the sequence encoding the mature protein (or an active fragment thereof such as the FL ECD or the C-terminal domain of Hsp70.

Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

The techniques for assembling and expressing DNA coding sequences for MHC-I-PP or DC-pp types of proteins, and DNA coding sequences for antigenic polypeptides, include synthesis of oligonucleotides, PCR, transforming cells, constructing vectors, expression systems, and the like; these are well-established in the art such that those of ordinary skill are familiar with standard resource materials, specific conditions and procedures.

Expression Vectors and Host Cells

This invention includes an expression vector comprising a nucleic acid sequence encoding a MHC-I-PP/antigen fusion polypeptide or a DC-PP/antigen fusion polypeptide operably linked to at least one regulatory sequence.

The term "expression vector" or "expression cassette" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons (see Example 1, below), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant microorganism or cell culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of the fusion polypeptide and its functional derivatives (defined herein) including polypeptide fragments, variants, etc.

Such expression vectors are used to transfect host cells (in vitro, ex vivo or in vivo) for expression of the DNA and production of the encoded proteins which include fusion proteins or peptides. It will be understood that a genetically modified cell expressing the fusion polypeptide may transiently express the exogenous DNA for a time sufficient for the cell to be useful for its stated purpose.

The present in invention provides methods for producing the fusion polypeptides, fragments and derivatives. For example, a host cell transfected with a nucleic acid vector that encodes the fusion polypeptide is cultured under appropriate conditions to allow expression of the polypeptide.

Host cells may also be transfected with one or more expression vectors that singly or in combination comprise DNA encoding at least a portion of the fusion polypeptide and DNA encoding at least a portion of a second protein, so that the host cells produce yet further fusion polypeptides that include both the portions.

A culture typically includes host cells, appropriate growth media and other byproducts. Suitable culture media are well known in the art. The fusion polypeptide can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Methods in Enzymology*, 22:233-577 (1971)). Once purified, partially or to homogeneity, the recombinant polypeptides of the invention can be utilized in pharmaceutical compositions as described in more detail herein.

The term "isolated" as used herein, when referring to a molecule or composition, such as a MHC-I-PP or nucleic acid coding therefor, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). Even where a protein has been isolated so as to appear as a homogenous or dominant band in a gel pattern, there are trace contamninants which co-purify with it.

Prokaryotic or eukaryotic host cells transformed or transfected to express the fusion polypeptide or a homologue or functional derivative thereof are within the scope of the invention. For example, the fusion polypeptide may be expressed in bacterial cells such as *E. coli*, insect cells (baculovirus), yeast, or mammalian cells such as Chinese hamster ovary cells (CHO) or human cells. Other suitable host cells may be found in Goeddel, (1990) supra or are otherwise known to those skilled in the art.

Expression in eukaryotic cells leads to partial or complete glycosylation and/or formation of relevant inter- or intrachain disulfide bonds of the recombinant protein.

Although preferred vectors are described in the Examples, other examples of expression vectors are provided here. Examples of vectors for expression in yeast *S. cerevisiae* include pYepSec1 (Baldari et al., (1987) *EMBO J.* 6:229-234), pMFa (Kurjan et al. (1982) *Cell* 30:933-943), pJRY88 (Schultz et al., (1987) *Gene* 54:113-123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156-2165,) and the pVL series (Lucklow, V. A., and Summers, M. D., (1989) *Virology* 170:31-39). Generally, COS cells (Gluzman, Y., (1981) *Cell* 23:175-182) are used in conjunction with such vectors as pCDM 8 (Aruffo A. and Seed, B., supra, for transparent amplification/expression in mammalian cells, while CHO (dhfr-negative CHO) cells are used with vectors such as pMT2PC (Kaufman et al. (1987), *EMBO J.* 6:187-195) for stable amplification/expression in mammalian cells. The NS0 myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn 10-lacO fusion promoter mediated by coexpressed viral RNA polymerase (T7gn1). Th is viral polymerase is supplied by host strains BL21(DE3) or HMS174(DE3) from a resident λ prophage harboring a T7gn 1 under the transcriptional control of the lacUV 5 promoter.

One embodiment of this invention is a transfected cell which expresses novel fusion polypeptide.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivative. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Synthetic oligonucleotides are prepared by either the phosphotriester method as described by references cited above or the phosphoramidite method as described by Beaucage, S. L., and Caruthers, M. H., *Tet Left* (1981) 22:1859; and Matteucci, M. D., and Caruthers, M. H., *J Am Chem Soc* (1981) 103:3185 and can be prepared using commercially available automated oligonucleotide synthesizers. Kinase treatment of single strands prior to annealing or for labeling is achieved using an excess, e.g., about 10 units of polynucleotide kinase to 1 nmole substrate in the presence of 50 mM Tris, pH 7.6, 10 mM MgCl$_2$, 5 mM dithiothreitol, 1-2 mM ATP, 1.7 pmoles γ-$^{32}$P-ATP (2.9 mCi/mmole), 0.1 mM spermidine, 0.1 mM EDTA.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are typically performed in 15-50 ml volumes under the following standard conditions and temperatures: for example, 20 mM Tris-HCl pH 7.5, 10 mM MgCl$_2$, 10 mM DTT, 33 µg/ml BSA, 10-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 nM total end concentration). Intermolecular blunt end ligations are performed at 1 mM total ends concentration.

In vector construction employing "vector fragments", the fragment is commonly treated with bacterial alkaline phosphatase (BAP) or calf intestinal alkaline phosphatase (CIAP) in order to remove the 5' phosphate and prevent self-ligation. Digestions are conducted at pH 8 in approximately 10 mM Tris-HCl, 1 mM EDTA using BAP or CIAP at about 1 unit/mg vector at 60° for about one hour. The preparation is extracted with phenol/chloroform and ethanol precipitated. Alternatively, re-ligation can be prevented in vectors which have been double digested by additional restriction enzyme and separation of the unwanted fragments.

Any of a number of methods are used to introduce mutations into the coding sequence to generate the variants of the invention. These mutations include simple deletions or insertions, systematic deletions, insertions or substitutions of clusters of bases or substitutions of single bases.

For example, modifications of the MHC-I-PP or DC-pp or the antigenic polypeptide DNA sequence are created by site-directed mutagenesis, a well-known technique for which protocols and reagents are commercially available (Zoller, M J et al., *Nucleic Acids Res* (1982) 10:6487-6500 and Adelman, J P et al., *DNA* (1983) 2:183-193)). Correct ligations for plasmid construction are confirmed, for example, by first transforming *E. coli* strain MC1061 (Casadaban, M., et al., *J Mol Biol* (1980) 138:179-207) or other suitable host with the ligation mixture. Using conventional methods, transformants are selected based on the presence of the ampicillin-, tetracycline- or other antibiotic resistance gene (or other selectable marker) depending on the mode of plasmid construction. Plasmids are then prepared from the transformants with optional chloramphenicol amplification optionally following chloramphenicol amplification ((Clewell, D B et al., *Proc Natl Acad Sci USA* (1969) 62:1159; Clewell, D. B., *J Bacteriol* (1972) 110:667). Several mini DNA preps are commonly used. See, e.g., Holmes, D S, et al, *Anal Biochem* (1981) 114:193-197; Birnboim, H C et al., *Nucleic Acids Res* (1979) 7:1513-1523. The isolated DNA is analyzed by restriction and/or sequenced by the dideoxy nucleotide method of Sanger (*Proc Natl Acad Sci USA* (1977) 74:5463) as further described by Messing, et al, *Nucleic Acids Res* (1981) 9:309, or by the method of Maxam et al. *Methods in Enzymology* (1980) 65:499.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Known fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn 10-lacO fusion promoter mediated by coexpressed viral RNA polymerase (T7gn 1). This viral polymerase is supplied by host strains BL21(DE3) or HMS174(DE3) from a resident λ prophage harboring a T7gn 1 under the transcriptional control of the lacUV 5 promoter.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence.

Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., Cell 41:521 (1985)) or in the RSV-LTR (from Rous sarcoma virus) (Gorman, C. M., Proc. Natl. Acad. Sci. USA 79:6777 (1982). Also useful are the promoter of the mouse metallothionein 1 gene (Hamer, D., et al., J. Mol. Appl. Gen. 1:273-288 (1982)); the TK promoter of Herpes virus (McKnight, S., Cell 31:355-365 (1982)); the SV40 early promoter (Benoist, C., et al., Nature 290:304-310 (1981)); and the yeast gal4 gene promoter (Johnston, S. A., et al., Proc. Natl. Acad. Sci. (USA) 79:6971-6975 (1982); Silver, P. A., et al., Proc. Natl. Acad. Sci. (USA) 81:5951-5955 (1984)). Other illustrative descriptions of transcriptional factor association with promoter regions and the separate activation and DNA binding of transcription factors include: Keegan et al., Nature (1986) 231:699; Fields et al., Nature (1989) 340:245; Jones, Cell (1990) 61:9; Lewin, Cell (1990)-61:1161; Ptashne et al., Nature (1990) 346:329; Adams et al., Cell (1993) 72:306. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B. M., Genes IV, Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

The nucleic acid sequences of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al., U.S. Pat. No. 4,598,049; Caruthers et al. U.S. Pat. No. 4,458,066; and Itakura U.S. Pat. Nos. 4,401,796 and 4,373,071, incorporated by reference herein).

Proteins and Polypeptides

The terms "polypeptide," "protein," and "peptide" when reeferring to compositions of the invention are meant to include variants, analogues, and mimetics with structures and/or activity that substantially correspond to the polypeptide or peptide from which the variant,e tc. was derived.

The present invention includes an "isolated" fusion polypeptide comprising a MHC-I-PP and/or a DC-PP linked to an antigenic polypeptide. A preferred MHC-I-PP is Hsp70. A preferred DC-PP if FL or the ECD or FL. Preferred fusion polyhpeptides are Hsp70/E7 (SEQ ID NO:8) and FL-E7 (SEQ ID NO:12). While the present disclosure exemplifies the full length Hsp70 and the ECD of FL, it is to be understood that homologues of Hsp70 from other bacteria or from eukaryotic origin, homlogues of FL or its ECD, and mutants thereof that possess the characteristics disclosed herein are intended within the scope of this invention.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises an MHC-I-PP or a DC-PP e.g., Hsp60 or FL, and the second domain comprising an antigenic epitope, e.g., an MHC class I-binding peptide epitope. Additional domains can comprise a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means. The chimeric molecules of the invention (e.g., MHC-I-PP-fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

Also included is a "functional derivative" of Hsp70 or FL, which refers to an amino acid substitution variant, a "fragment," or a "chemical derivative" of the protein, which terms are defined below. A functional derivative retains measurable (a) Hsp70-like or (b) FL-like activity, preferably that of promoting immunogenicity of one or more antigenic epitopes fused thereto by either (a) promoting presentation by class I pathways or (b) promoting maturation or activation of APCs, which permits the "functional derivative's" utility in accordance with the present invention. "Functional derivatives" encompass "variants" and "fragments" regardless of whether the terms are used in the conjunctive or the alternative herein.

A functional homologue must possess the above biochemical and biological activity. In view of this functional characterization, use of homologous Hsp70 or FL proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence (e.g., Hsp70, SEQ ID NO:4 and FL-ECD, SEQ ID NO:10). The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to Hsp70 or FL nucleic acid molecules. BLAST protein searches can be performed with the XBLAST program, score=50, wordlength=3 to obtain amino acid sequences homologous to. HVP22 protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Thus, a homologue of Hsp70 or of FL described above is characterized as having (a) functional activity of native Hsp70 or FL and (b) sequence similarity to a native Hsp70 protein (such as SEQ ID NO:4) or native FL (SEQ ID NO:10) when determined as above, of at least about 20% (at the amino acid level), preferably at least about 40%, more preferably at least about 70%, even more preferably at least about 90%.

It is within the skill in the art to obtain and express such a protein using DNA probes based on the disclosed sequences of Hsp70 or FL. Then, the fusion protein's biochemical and biological activity can be tested readily using art-recognized methods such as those described herein, for example, a T cell proliferation, cytokine secretion or a cytolytic assay, or an in vivo assay of tumor protection or tumor therapy. A biological assay of the stimulation of antigen-specific T cell reactivity will indicate whether the homologue has the requisite activity to qualify as a "functional" homologue.

A "variant" refers to a molecule substantially identical to either the full protein or to a fragment thereof in which one or more amino acid residues have been replaced (substitution variant) or which has one or several residues deleted (deletion variant) or added (addition variant). A "fragment" of Hsp70 or FL refers to any subset of the molecule, that is, a shorter polypeptide of the full-length protein.

A number of processes can be used to generate fragments, mutants and variants of the isolated DNA sequence. Small subregions or fragments of the nucleic acid encoding the spreading protein, for example 1-30 bases in length, can be prepared by standard, chemical synthesis. Antisense oligonucleotides and primers for use in the generation of larger synthetic fragment.

A preferred group of variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g.,, Leu, Ile, Phe, Val or Ala; (iii) substitution of a Cys residue for (or by) any other residue; (iv) substitution of a residue having an electropositive side chain, e.g.,, Lys, Arg or His, for (or by) a residue having an electronegative charge, e.g.,, Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the wild-type or native protein in terms of its intercellular spreading activity and its ability to stimulate antigen specific T cell reactivity to an antigenic epitope or epitopes that are fused to the spreading protein. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

The term "chemically linked" refers to any chemical bonding of two moieties, e.g., as in one embodiment of the invention, where an MHC-I-PP or DC-PP is chemically linked to an antigenic peptide. Such chemical linking includes the peptide bonds of a recombinantly or in vivo generated fusion protein.

Chemical Derivatives

"Chemical derivatives" of the polypeptide or fusion polypeptide of the invention contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington's Pharmaceutical Sciences*, $16^{th}$ ed., Mack Publishing Co., Easton, Pa. (1980).

Such modifications may be introduced into the molecule by reacting targeted amino acid residues of the polypeptide with an organic derivatizing agent that is capable of reacting with selected side chains or terminal residues. Another modification is cyclization of the protein. Examples of chemical derivatives of the polypeptide follow.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86.), acetylation of the N-terminal amine, and amidation of the C-terminal carboxyl groups.

Also included are peptides wherein one or more D-amino acids are substituted for one or more L-amino acids.

Multimeric Peptides

The present invention also includes longer polypeptides in which a basic peptidic sequence obtained from the sequence of either the MHC-I-PP or the DC-PP, or the antigenic polypeptide or peptide unit, is repeated from about two to about 100 times, with or without intervening spacers or linkers. It is understood that such multimers may be built from any of the peptide variants defined herein. Moreover, a peptide multimer may comprise different combinations of peptide monomers and the disclosed substitution variants thereof. Such oligomeric or multimeric peptides can be made by chemical synthesis or by recombinant DNA techniques as discussed herein. When produced chemically, the oligomers preferably have from 2-12repeats of the basic peptide sequence. When produced recombinantly, the multimers may have as many repeats as the expression system permits, for example from two to about 100 repeats.

In tandem multimers, preferably dimers and trimers, of the fusion polypeptide, the chains bonded by interchain disulfide bonds or other "artificial" covalent bonds between the chains such that the chains are "side-by-side" rather than "end to end."

Therapeutic Compositions and Their Administration

A vaccine composition comprising the nucleic acid encoding the fusion polypeptide, or a cell expressing this nucleic acid is administered to a mammalian subject, preferably a human. The vaccine composition is administered in a pharmaceutically acceptable carrier in a biologically effective or a therapeutically effective amount. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of a nucleic acid encoding the fusion polypeptide may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount is between about 1 nanogram and about 10 milligram per kilogram of body weight of the recipient, more preferably between about 0.1 µg and 1 g/kg. Dosage forms suitable for internal administration preferably contain (for the latter dose range) from about 0.01 µg to 100 µg of active ingredient per unit. The active ingredient may vary from 0.5 to 95% by weight based on the total weight of the composition. Alternatively, an effective dose of cells expressing the nucleic acid is between about $10^4$ and $10^8$ cells. Those skilled in the art of immunotherapy will be able to adjust these doses without undue experimentation.

The active compound may be administered in a convenient manner, e.g., injection by a convenient and effective route. Preferred routes include subcutaneous, intradermal, intravenous and intramuscular routes. Other possible routes include oral administration, intrathecal, inhalation, transdermal application, or rectal administration. For the treatment of existing tumors which have not been completely resected or which have recurred, direct intratumoral injection is also intended.

Depending on the route of administration, the active compound may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol).or in an appropriate carrier such as liposomes (including water-in-oil-in-water emulsions as well as conventional liposomes (Strejan et al., (1984) *J. Neuroimmunol* 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like.

Compositions are preferably formulated in dosage unit form for ease of administration and uniformity of dosage. Dosage unit form refers to physically discrete units suited as unitary dosages for a mammalian subject; each unit contains a predetermined quantity of active material (e.g., the nucleic acid vaccine) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, ndividual subjects For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Other pharmaceutically acceptable carriers for the nucleic acid vaccine compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Antigens Associated with Pathogens

A major use for the present invention is the use of the present nucleic acid compositions in therapeutic vaccine for cancer and for major chronic viral infections that cause morbidity and mortality worldwide. Such vaccines are designed to eliminate infected cells—this requires T cell responses as antibodies are often ineffective. The vaccines of the present invention are designed to meet these needs.

Preferred antigens are epitopes of pathogenic microorganisms against which the host is defended by effector T cells responses, including cytotoxic T lymphocyte (CTL) and delayed type hypersensitivity. These typically include viruses, intracellular parasites such as malaria, and bacteria that grow intracellularly such as Mycobacteria and Listeria species. Thus, the types of antigens included in the vaccine compositions of this invention are any of those associated with such pathogens (in addition, of course, to tumor-specific antigens). It is noteworthy that some viral antigens are also tumor antigens in the case where the virus is a causative factor in cancer.

In fact, the two most common cancers worldwide, hepatoma and cervical cancer, are associated with viral infection. Hepatitis B virus(HBV) (Beasley, R. P. et al., *Lancet* 2, 1129-1133 (1981) has been implicated as etiologic agent of hepatomas. 80-90% of cervical cancers express the E6 and E7 antigens (exemplified herein) from one of four "high risk" human papillomavirus types: HPV-16, HPV-18, HPV-31 and HPV-45 (Gissmann, L. et al., *Ciba Found Symp.* 120, 190-207 (1986); Beaudenon, S., et al. *Nature* 321, 246-249 (1986). The HPV E6 and E7 antigens are the most promising targets for virus associated cancers in immunocompetent individuals because of their ubiquitous expression in cervical cancer. In addition to their importance as targets for therapeutic cancer vaccines, virus associated tumor antigens are also ideal candidates for prophylactic vaccines. Indeed, introduction of prophylactic HBV vaccines in Asia have decreased the incidence of hepatoma (Chang, M. H., et al. *New Engl. J. Med.* 336, 1855-1859 (1997), representing a great impact on cancer prevention.

Among the most important viruses in chronic human viral infections are HPV, HBV, hepatitis C Virus (HCV), human immunodeficiency virus (HIV-1 and HIV-2), herpesviruses such as Epstein Barr Virus (EBV), cytomegalovirus (CMV) and HSV-1 and HSV-2 and influenza virus. Useful antigens include HBV surface antigen or HBV core antigen; ppUL83 or pp89 of CMV; antigens of gp120, gp41 or p24 proteins of HIV-1; ICP27, gD2, gB of HSV; or influenze nucleoprotein (Anthony, L S et al., *Vaccine* 1999; 17:373-83). Other antigens associated with pathogens that can be utilized as described herein are antigens of various parasites, includes malaria, preferably malaria peptide (NANP)40.

In addition to its applicability to human cancer and infectious diseases,, the present invention is also intended for use in treating animal diseases in the veterinary medicine context. Thus, the approaches described herein may be readily applied by one skilled in the art to treatment of veterinary herpesvirus infections including equine herpesviruses, bovine viruses such as bovine viral diarrhea virus (for example, the E2 antigen), bovine herpesviruses, Marek's disease virus in chickens and other fowl; animal retroviral and lentiviral diseases (e.g., feline leukemia, feline immunodeficiency, simian immunodeficiency viruses, etc.); pseudorabies and rabies; and the like.

As for tumor antigens, any tumor-associated or tumor-specific antigen that can be recognized by T cells, preferably by CTL, can be used. In addition to the HPV-E7 antigen exemplified herein is mutant p53 or HER2/neu or a peptide thereof. Any of a number of melanoma-associated antigens may be used, such as MAGE-1, MAGE-3, MART-1/Melan-A, tyrosinase, gp75, gp100, BAGE, GAGE-1, GAGE-2, GnT-V, and p 15 (see, U.S. Pat. No. 6,187,306).

The following references set forth principles and current information in the field of basic, medical and veterinary virology and are incorporated by reference: *Fields Virology*, Fields, B N et al., eds., Lippincott Williams & Wilkins, NY, 1996; *Principles of Virology: Molecular Biology, Pathogenesis, and Control. Flint*, S. J. et al., eds., Amer Society for Microbiology, Washington, 1999; *Principles and Practice of Clinical Virology*, 4th Edition, Zuckerman. A. J. et al., eds, John Wiley & Sons, NY, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds., World Scientific Pub Co, 1998; *Veterinary Virology*, Murphy, F. A. et al., eds., Academic Press, NY, 1999; *Avian Viruses: Function and Control*, Ritchie, B. W., Iowa State University Press, Ames, 2000; *Virus Taxonomy: Classification and Nomenclature of Viruses: Seventh Report of the International Committee on Taxonomy of Viruses*, by M. H. V. Van Regenmortel, MHV et al., eds., Academic Press; NY, 2000.

Delivery of Vaccine Nucleic Acid to Cells and Animals

Examples I-III describe certain preferred approaches to delivery of the vaccines of the present invention: naked DNA, self-replicating RNA and virally-based suicide DNA. A broader description of other approaches including viral and nonviral vectors and delivery mechanisms follow.

DNA delivery involves introduction of a "foreign" DNA into a cell ex vivo and ultimately, into a live animal or directly into the animal. Several general strategies for gene delivery (=delivery of nucleic acid vectors) for purposes that include "gene therapy" have been studied and reviewed extensively (Yang, N-S., *Crit. Rev. Biotechnol.* 12:335-356 (1992); Anderson, W. F., *Science* 256:808-813 (1992); Miller, A. S., *Nature* 357:455460 (1992); Crystal, R. G., *Amer. J. Med.* 92(suppl 6A):44S-52S (1992); Zwiebel, J. A. et al., *Ann. N. Y. Acad. Sci.* 618:394404 (1991); McLachlin, J. R. et al., *Prog. Nucl. Acid Res. Molec. Biol.* 38:91-135 (1990); Kohn, D. B. et al., *Cancer Invest.* 7:179-192 (1989), which references are herein incorporated by reference in their entirety).

One approach comprises nucleic acid transfer into primary cells in culture followed by autologous transplantation of the ex vivo transformed cells into the host, either systemically or into a particular organ or tissue.

The term "systemic administration" refers to administration of a composition or agent such as a molecular vaccine as described herein, in a manner that results in the introduction of the composition into the subject's circulatory system or otherwise permits its spread throughout the body. "Regional" administration refers to administration into a specific, and somewhat more limited, anatomical space, such as intraperitoneal, intrathecal, subdural, or to a specific organ. The term "local administration" refers to administration of a composition or drug into a limited, or circumscribed, anatomic space, such as intratumoral injection into a tumor mass, subcutaneous injections, intramuscular injections. One of skill in the art would understand that local administration or regional administration may also result in entry of a composition into the circulatory system.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J. A. et al., *Science* 247:1465 (1990); Acsadi, G. et al., *The New Biologist* 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues was effective for in vivo transfer and prolonged expression of foreign genes in lung respiratory epithelium (Rosenfeld, M. A. et al., *Science* 252: 431 (1991); (e) Herpes simplex virus vectors achieved in vivo gene transfer into brain tissue (Ahmad, F. et al., eds, *Miami Short Reports—Advances in Gene Technology. The Molecular Biology of Human Genetic Disease*, Vol 1, Boehringer Manneheim 1 Biochemicals, USA, 1991).

Retroviral-mediated human therapy utilizes amphotrophic, replication-deficient retrovirus systems (Temin, H. M., Human Gene Therapy 1:111 (1990); Temin et al., U.S. Pat. No. 4,980,289; Temin et al., U.S. Pat. No. 4,650, 764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., *Mol. Cell. Biol.* 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the fusion polypeptides of the present invention may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R. F. et al., *Cell* 33:153-159 (1983); Miller, A. D. et al., *Molec. Cell. Biol.* 5:431-437 (1985),; Sorge, J., et al., *Molec. Cell. Biol.* 4:1730-1737 (1984); Hock, R. A. et al., *Nature* 320:257 25 (1986); Miller, A. D. et al., *Molec. Cell. Biol.* 6:2895-2902 (1986). Newer packaging cell lines which are efficient an safe for gene transfer have also been described (Bank et al., U.S. Pat. No. 5,278,056.

This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: *Virology*, Fields, B N et al., eds, Raven Press, New York, 1990, p. 1679; Berkner, K. L., *Biotechniques* 6:616 9191988), Strauss, S. E., In: *The Adenoviruses*, Ginsberg, H S, ed., Plenum Press, New York, 1984, chapter 11), herpes simplex virus (HSV) for neuron-specific delivery and persistence. Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R. J. et al., *EMBO J.* 10:3941 (1991) according to the present invention.

Another vector which can express the DNA molecule of the present invention, and is useful in the present therapeutic setting, particularly in humans, is vaccinia virus, which can be rendered non-replicating (U.S. Pat. Nos. 5,225,336; 5,204, 243; 5,155,020; 4,769,330; Sutter, G et al., *Proc. Natl. Acad. Sci. USA* (1992) 89:10847-1085 1; Fuerst, T. R. et al., *Proc. Natl. Acad. Sci. USA* (1989) 86:2549-2553; Falkner F. G. et al.; *Nucl. Acids Res* (1 987) 15:7192; Chakrabarti, S et al., *Molec. Cell. Biol.* (1985) 5:3403-3409). Descriptions of recombinant vaccinia viruses and other viruses containing heterologous DNA and their uses in immunization and DNA therapy are reviewed in: Moss, B., *Curr. Opin. Genet. Dev.* (1993) 3:86-90; Moss, B. *Biotechnology* (1992) 20:345-362; Moss, B., *Curr Top Microbiol Immunol* (1992) 158:25-38; Moss, B., *Science* (1991) 252:1662-1667; Piccini, A et al., *Adv. Virus Res.* (1988) 34:43-64; Moss, B. et al., *Gene Amplif Anal* (1983) 3:201-213.

In addition to naked DNA or RNA, or viral vectors, engineered bacteria may be used as vectors. A number of bacterial strains including *Salmonella*, BCG and *Listeria monocytogenes*(LM) (Hoiseth & Stocker, *Nature* 291, 238-239 (1981); Poirier, T P et al. *J. Exp. Med.* 168, 25-32 (1988); (Sadoff, J. C., et al., *Science* 240, 336-338 (1988); Stover, C. K., et al., *Nature* 351, 456-460 (1991); Aldovini, A. et al., *Nature* 351, 479-482 (1991); Schafer, R., et al., *J. Immunol.* 149, 53-59 (1992); Ikonomidis, G. et al., *J. Exp. Med.* 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al., *FEBS Lett.* 280:94 (1991); Zelenin, A. V. et al., *FEBS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al., *Biochim. Biophys. Acta* 1088:131 ((1991)).

"Carrier mediated gene transfer" has also been described (Wu, C. H. et al., *J. Biol. Chem.* 264:16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)). Preferred carriers are targeted liposomes (Nicolau, C. et al., *Proc. Natl. Acad. Sci. USA* 80:1068 (1983); Soriano et al., supra) such as immuno-liposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Quiagen procedure (Quiagen), followed by DNA purification using known methods, such as the methods exemplified herein.

Having now generally described the invention, the same will be more readily understood through reference to the following examples which are provided by way of illustration, and are not intended to be limiting of the present invention, unless specified.

EXAMPLE I

Enhancement of Sindbis Virus Self-Replicating RNA Vaccine Potency by Linkage of Nucleic Acid encoding *Mycobacterium Tuberculosis*

Heat Shock Protein 70 and an Antigen

The present study investigated whether DNA linking full-length E7 to Hsp70 can enhance the potency of self-replicating Sindbis RNA vaccines. We showed that a Sindbis RNA vaccine linking E7 with Hsp70 significantly increased expansion and activation of E7-specific $CD8^+$ T cells and NK cells, bypassing the requirement for CD4+ T cell-mediated help and resulting in potent anti-tumor immunity against E7-expressing tumors. Mechanistic studies confirmed that the Sindbis E7/Hsp70 RNA vaccine induced apoptotic death of host cells and promoted processing of this apoptotic material by dendritic cells (DCs), leading to significantly increased expansion and activation of E7-specific $CD8^+$ T cells. This enhanced CD8 response resulted in a state of potent anti-tumor immunity against an E7-expressing tumor cell line.

Materials and Methods

Plasmid DNA Constructs and Preparation

The generation of pcDNA3-Hsp70, pcDNA3-E7, and pcDNA3-E7/Hsp70 has been described previously (Chen et al., supra). The Sindbis virus RNA replicon vector, SINrep5 has also been described previously (Bredenbeek, P J et al., 1993. *J Virol* 67:6439-46). For the generation of SINrep5-Hsp70, SINrep5-E7, and SINrep5-E7/Hsp70, DNA fragments encoding Mtb Hsp70, HPV-16 E7, and chimeric E7/Hsp70 were isolated by cutting pcDNA3-Hsp70, pcDNA3-E7, and pcDNA3-E7/Hsp70 respectively with Xba I and Pme I restriction enzymes, followed by gel recovery from the digested products. These isolated DNA fragments were further cloned into the corresponding Xba I and Pme I sites of the SINrep5 vector to generate SINrep5-Hsp70, SINrep5-E7, and SINrep5-E7/Hsp70 constructs. SINrep5-E7/GFP constructs were generated to evaluate the effect of linkage of E7 to an irrelevant protein. For the generation of SINrep5-E7/GFP, we first constructed pcDNA3-GFP. For the generation of pcDNA3-GFP, a DNA fragment encoding the green fluorescent protein (GFP) was first amplified with PCR using pEGFPN 1 DNA (Clontech, Palo Alto, Calif.) and a set of primers: 5'-atcggatccatggtgagcaagggcgaggag-3' (SEQ ID NO:24) and 5'-gggaagctttacttgtacagctcgtccatg-3' (SEQ ID NO:25). The amplified product was digested with BamHI/HindIII and further cloned into the BamHI/HindIII cloning sites of pcDNA3 vector. For the generation of pDNA3-E7/GFP, a DNA fragment encoding HPV-16 E7 first amplified with PCR using pcDNA3-E7 as a template and a set of primers: 5'-ggggaattcatgcatggagatacaccta-3' (SEQ ID NO:26) and 5'-ggtggatccttgagaacagatgg-3' (SEQ ID NO:27). The amplified product was then digested with EcoRI/BamHI and further cloned into the EcoRI/BamHI cloning sites of pcDNA3-GFP. E7/GFP was cut with XbaI/PmeI from pcDNA3-E7/GFP and cloned into XbaI/PmeI sites of SIN5rep. The accuracy of these constructs was confirmed by DNA sequencing.

In Vitro RNA Preparation

The generation of RNA transcripts from SINrep5-Hsp70, SINrep5-E7, SINrep5-E7/GFP, SINrep5-E7/Hsp70 and SINrep5 was performed using the protocol described by Mandl et al., (Mandl, C W et al., 1998. *Nat Med* 4:1438-40). SpeI was used to linearize DNA templates for the synthesis of RNA replicons from SINrep5-Hsp70, SINrep5-E7, SINrep5-E7/Hsp70 and SINrep5. RNA vaccines were transcribed in vitro and capped using SP6 RNA polymerase and capping analog from the in vitro transcription kit (Life Technologies, Rockville, Md.) according to vendor's manual. After synthesis, DNA was removed by digestion with DNase I. Synthesized RNA was quantified and analyzed using denaturing formaldehyde agarose gels (Mandl et al., supra). The purified RNA was divided into aliquots to be used for vaccination in animals and for transfection of a baby hamster kidney (BHK21) cell line. The protein expression of the transcripts was assessed by transfection of the RNA into BHK21 cells using electroporation.

Cell Lines

BHK21 cells were obtained from the ATCC (Rockville, Md.) and grown in Glasgow MEM supplemented with 5% FBS, 10% tryptose phosphate broth, 2 mM glutamine, and antibiotics. Cells were kept at 37° C. in a humidified 5% $CO_2$ atmosphere and were passaged every 2 days. The production and maintenance of TC-1 cells has been described previously (Lin, KY et al., 1996. *Cancer Research* 56:21-26). On the day of tumor challenge, TC-1 cells were harvested by trypsinization, washed twice with 1× Hanks buffered salt solution (HBSS), and finally resuspended in 1×HBSS to the designated concentration for injection.

ELISA to Detect E7 Protein Expression of SINrep5 RNA Vaccines

The expression of E7 protein from SINrep5-E7 and SINrep5-E7/Hsp70 RNA was determined by indirect ELISA. The quantity of E7 protein was determined using cell lysates from SIN5rep-E7 or -E7/Hsp70 transfected BHK21 cells. Briefly, $10^7$ BHK21 cells were transfected with the 4 μg SINrep5, SINrep5-E7, SINrep5-Hsp70, SINrep5-E7/GFP or SINrep5-E7/Hsp70 RNA transcripts respectively via electroporation as described by Liljestrom et al., (Liljestrom, P S et al., 1991. *J Virol* 65:4107-13). We used SINrep5-vector containing the β-gal gene and determined the transfection efficiency. The transfected cells were fixed and stained for lacZ expression using X-Gal (Sanes, J R et al., 1986. *Embo J* 5:3133-42). In general, the transfection efficiency in our electroporation was consistent and measured around 30%. The transfected BHK21 cells were collected 16-20 hrs after electroporation. A 96-microwell plate was coated BHK 21 cell lysates that were transfected with various SINrep5 RNA constructs in a final volume of 100 μl, and were incubated at 4° C. overnight. The bacteria-derived HPV-16 E7 proteins were used as a positive control. The wells were then blocked with PBS containing 20% fetal bovine serum. Diluted anti-E7 Ab (Zymed, San Francisco, Calif.) were added to the ELISA wells, and incubated on 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at room temperature for one hour. The plate was washed, developed with 1-Step™ Turbo TMB-ELISA (Pierce, Rockford, Ill.), and stopped with 1M $H_2SO_4$. The ELISA plate was read with a standard ELISA reader at 450 nm. The quantity of E7.protein of the cell lysates was then calculated and determined by comparing with the standardized E7 protein.

Mice 6 to 8-week-old female C57BL/6 mice from the National Cancer Institute (Frederick, Md.) were purchased and kept in the oncology animal facility of the Johns Hopkins Hospital (Baltimore, Md.). All animal procedures were performed according to approved protocols and in accordance with recommendations for the proper use and care of laboratory animals.

RNA Vaccination

All SINrep5 RNA vaccines were generated using in vitro transcription as described earlier. RNA concentration was determined by optical density measured at 260 nm. The integrity and quantity of RNA transcripts were further checked using denaturing gel electrophoresis. Mice were vaccinated intramuscularly with 10 μg of SINrep5-Hsp70, SINrep5-E7, SINrep5-E7 mixed with SINrep5-Hsp70, SINrep5-E7/GFP or SINrep5 RNA vaccines in the right hind leg while SINrep5-E7/Hsp70 was administered in 0.1, 1, and 10 μg quantities.

ELISA to Measure Anti-E7 Antibodies

Anti-HPV 16 E7 antibodies in the sera were determined by direct ELISA as described previously (Wu, T C 1995. *Proc Natl Acad. Sci. USA* 92:11671-5). A 96-microwell plate was coated with 100 μl bacteria-derived HPV-16 E7 proteins (5 μg/ml) and incubated at 4° C. overnight. The wells were then blocked with PBS containing 20% fetal bovine serum. Sera obtained from mice on day 14 post-immunization were serially diluted in PBS, added to the ELISA wells, and incubated at 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at room temperature for one hour. The plate was washed, developed with 1-Step™ Turbo TMB-ELISA (Pierce, Rockford, Ill.), and stopped with 1M $H_2SO_4$. The ELISA plate was read with a standard ELISA reader at 450 nm.

ELISA to Measure IFNγ

Splenocytes were harvested 2 weeks after vaccination and cultured with the E7 peptide (aa 49-57) containing the MHC class I epitope (RAHYNIVTF, SEQ ID NO:22) (Feltkamp, M C et al., 1993. *Eur J Immunol* 23:2242-9) or the E7 peptide (aa 30-67) containing the class II epitope (DSSEEEDEIDG-PAGQAEPDRAHYNIVTFCCKCDSTLRL; SEQ ID NO:23) (Tindle, R W 1991. *Proc Natl Acad Sci USA* 88:5887-91) in a total volume of 2 ml of RPMI 1640, supplemented with 10% (vol/vol) fetal bovine serum, 50 units/ml penicillin and streptomycin, 2 mM L-glutamine, 1 mM sodium pyruvate, 2 mM nonessential amino acids in a 24-well tissue culture plate for 6 days. The supernatants were harvested and assayed for the presence of IFNγ using a Commercial ELISA kit (Endogen, Woburn, Mass.) according to the manufacturer's protocol.

Cytotoxic T Lymphocyte (CTL) Assays

Cytolysis was determined by quantitative measurements of lactate dehydrogenase (LDH) released from cells using Cyto-Tox96®, a non-radioactive cytotoxicity assay kit (Promega, Madison, Wis.) according to the manufacturer's protocol. Briefly, splenocytes were harvested and pooled 2 weeks after RNA vaccination. Five mice were used for each vaccinated group. Splenocytes were cultured with the E7 peptide (aa 49-57) in a total volume of 2 ml of RPMI 1640, supplemented with 10% (vol/vol) fetal bovine serum, 50 units/ml penicillin/streptomycin, 2 mM L-glutamine, 1 mM sodium pyruvate, 2 mM nonessential amino acids in a 24-well tissue culture plate for 6 days as effector cells. TC-1 tumor cells were used as target cells. The TC-1 cells mixed with splenocytes at various effector/target (E/T) ratios. After 5 hr incubation at 37° C., 50 µl of the culture medium was collected to assess the amount of LDH present. The percentage of lysis was calculated from the formula: $100 \times \{(A-B)/(C-D)\}$, where A is the reading of experimental-effector signal value, B is the effector spontaneous background signal value, C is maximum signal value from target cells, D is the target spontaneous background signal value.

In Vivo Tumor Protection Experiments

For the tumor protection study, mice (5 per group) were immunized i.m. with 10 µg/mouse of SINrep5-Hsp70, SINrep5-E7, SINrep5-E7 mixed with SINrep5-Hsp70, SINrep5-E7/GFP or SINrep5 RNA, or 0.1 µg/mouse, 1 µg/mouse, or 10 µg/mouse of SINrep5-E7/Hsp70 RNA. 14 days after immunization, mice were injected intravenously with $1 \times 10^4$ cells/mouse TC-1 tumor cells in the tail vein. Three weeks after tumor challenge, mice were euthanized. The number of tumor nodules on the lung surface in each mouse was evaluated and counted by experimenters in a blinded fashion.

In Vivo Depletion of Cells Using Monclonal Antibodies

The procedure was described previously (Lin, KY et al., 1996. *Cancer Research* 56:21-26; Wu, T C et al., 1995. *J. Exp. Med* 182:1415-1421). In brief, each mouse was vaccinated with 1 µg self-replicating SINrep5-E7/Hsp70 RNA i.m. and challenged with $10^4$ TC-1 tumor cells i.v. (via tail vein). Depletions were initiated one week prior to tumor challenge. $IgG_{2a}$ antibody (PharMingen, San Diego, Calif.) was used as a non-specific isotype control. MAb GK1.5 (Dialynas, D P 1983. *J Immunol.* 131:2445) was used for depletion of CD4+ cells; mAb 2.43 (Sarmiento, M A et al., 1980. *J. Immunol.* 125:2665) was used for depletion of CD8+ cells; and mAb PK136 (Koo, G C et al., *J Immunol.* 137:3742) was used for depletion of NK1.1+ cells. Flow cytometry analysis revealed that >95% of the cells of the appropriate lymphocyte subset were depleted while numbers of cells of other subsets were unchanged. Depletion treatment was discontinued on day 21 after tumor challenge.

Cell Surface Marker Staining and Flow Cytometric Analysis

Splenocytes from naïve or vaccinated mice were immediately stained for cell surface markers according to Ji, H et al., 1999, *Human Gene Therapy* 10:2727-2740. Cells were then washed once in FACScan® buffer and stained with PE-conjugated monoclonal rat anti-mouse NK1.1 antibody or FITC-conjugated monoclonal rat anti-mouse CD3 antibody (PharMingen, San Diego, Calif.). NK cells are NK1.1+ and CD3-negative. Flow cytometry was used to determine the percent of splenocytes that were NK cells.

In Vitro Analysis of Cell Death $10^7$ BHK21 cells were transfected with 4 µg SINrep5, SINrep5-E7, SINrep5-Hsp70 or SINrep5-E7/Hsp70 RNA transcripts as mentioned above. The transfection efficiency was around 20-30%. Native BHK21 cells or BHK21 cells that were electroporated without SINrep5 RNA served as controls. BHK21 cells were collected and assessed every 24 hr, until hour 72. The percentages of apoptotic and necrotic BHK21 cells were determined using annexin V apoptosis detection kits (PharMingen, San Diego, Calif.) according to the manufacturer's protocol, followed by flow cytometry.

Generation and Culture of Dendritic Cells (DCs) from Bone Marrow

DCs were generated by culturing bone marrow cells in the presence of GM-CSF as described previously (Lu, Z et al., 2000. *J Exp Med* 191:541-550). Briefly, bone marrow was collected from the tibias of mice. Erythrocytes were lysed, and the remaining cells were passed through a nylon mesh to remove small pieces of bone and debris. The cells were collected and $10^6$ cells/ml were placed in 24-well plates in RPMI 1640, supplemented with 5% FCS, 2 mM β-mercaptoethanol, 1% nonessential amino acids, 100 U/ml penicillin and 100 µg/ml streptomycin (Life Technologies, Rockville, Md.), and 100 U/ml GM-CSF (PharMingen, San Diego, Calif.). Two-thirds of the medium was replaced every 2 days, and nonadherent cells were harvested on day 7. The collected cells were characterized by flow cytometry for DC markers as previously described (Wang, T L et al., 2000. *J Exp Med* 191:541-550).

CTL Assay Using DCs Pulsed with BHK21 Cells that had been Transfected with Various RNA Transcripts as Target Cells CTL assays using DCs pulsed with BHK21 cells that had been transfected with various RNA transcripts as target cells were performed using a protocol similar to that described by Albert, M L et al., 1998. *Nature* 392:86-9 and Albert M L, et al., 1998. *J Exp Med* 188:1359-68). Briefly, $10^7$ BHK21 cells were transfected with 4pig of various self-replicating SINrep5 RNA constructs via electroporation. The cells were collected 16-20 hr later. The levels of E7 protein expression in BHK21 cells transfected with SINrep5-E7, or SINrep5-E7/Hsp70 RNA transcripts were similar, as determined by ELISA. $3 \times 10^5$ transfected BHK21 cells were co-incubated with $10^5$ of bone marrow-derived DCs at 37° C. for 48 hr. These "prepared" DCs were then used as target cells (T) and the $H-2D^b$-restricted E7-specific CD8+ T cells were used as effector cells (E) (Wang, et al., supra). CTL assays were performed with $10^4$ target cells and effector cells numbers yielding E/T ratios of 1, 3 and 9, incubated in a final volume of 200 µl. After 5 hrs at 37° C., 50 µl of culture supernatant were collected to assess the amount of LDH as described above. Negative controls included DCs co-incubated with untransfected BHK21 cells, transfected BHK21 cells incubated alone, untreated DCs incubated alone, and cells of the CD8+ T cell line incubated alone.

Results

Construction and Characterization of Self-Replicating RNA Constructs

Generation of plasmid DNA constructs and subsequent preparation of self-replicating SINrep5 RNA constructs was performed as described above. The SINrep5 vector includes DNA encoding Sindbis virus RNA replicase and the SP6 promoter ((Bredenbeek, P J et al., 1993. *J Virol* 67:6439-46)). A schematic diagram of SINrep5, SINrep5-Hsp70, SINrep5-E7, SINrep5-E7/GFP and SINrep5-E7/Hsp70 RNA transcripts using SP6 RNA polymerase is shown in Figure 1. An ELISA to test expression of E7 protein by BHK21 cells transfected with the various self-replicating RNA constructs showed that SINrep5-E7 and SINrep5-E7/Hsp70 expressed similar amounts of E7 protein.

Figure 2:
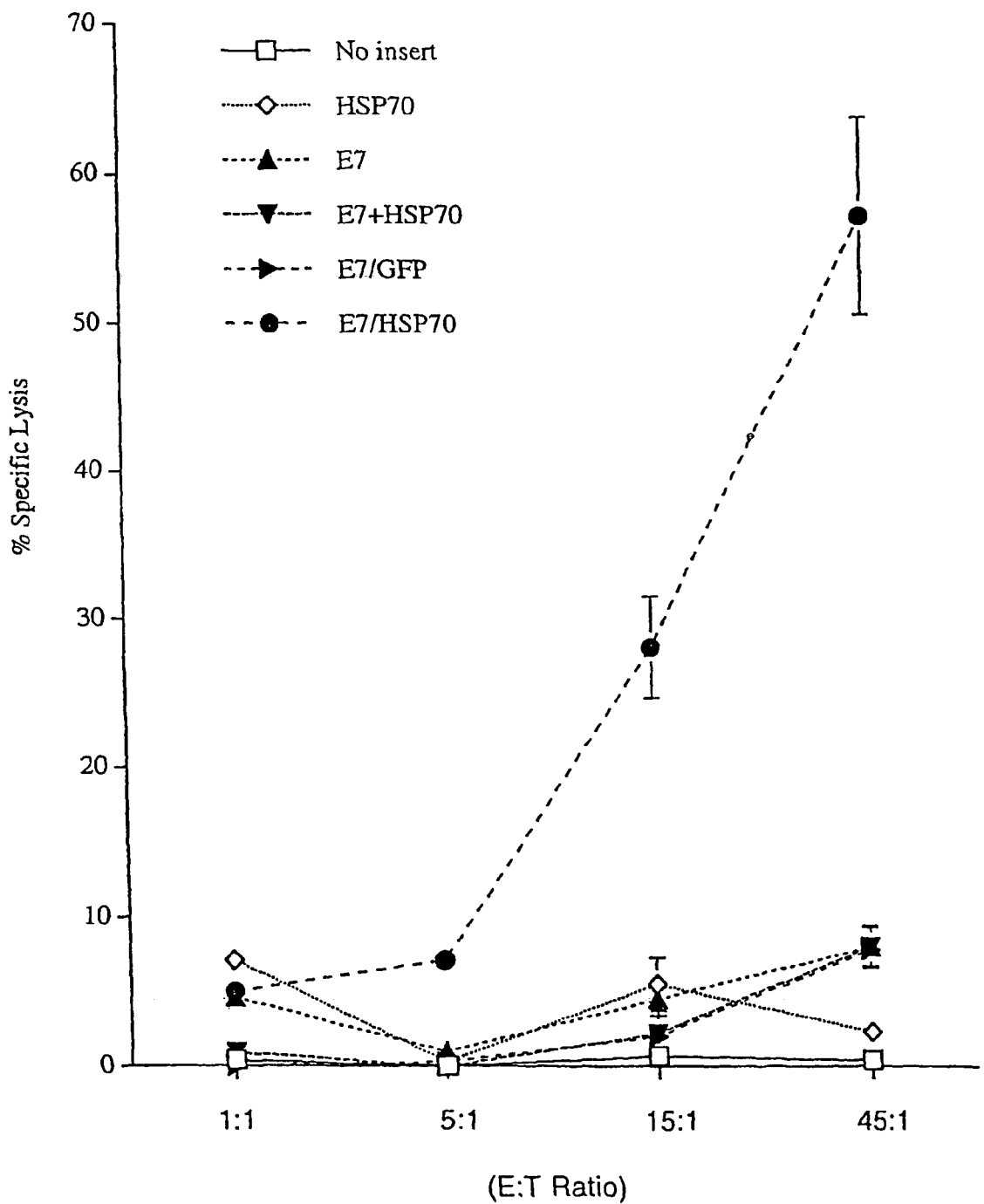
FIG. 2. Antigen ppecific $CD8^+$ T cell cytotoxic activity. Mice (5 per group) were immunized with various RNA vaccines via intramuscular (i.m.) injection. Splenocytes from each group (5 mice per group) were pooled 14 days after vaccination. To perform the cytotoxicity assay, pooled splenocytes from the various self-replicating RNA vaccines were cultured with E7 peptide (aa 49-57, RAHYNIVTF, SEQ ID NO:22, which includes a MHC class I epitope) for 6 days and used as effector cells. TC-1 tumor target cells were mixed with splenocytes at various effector/target (E/T) ratios. Cytolysis was determined by quantitative measurement of LDH release. The self-replicating RNA E7/Hsp70 vaccine generated significantly higher lysis than the other RNA vaccines ($p<0.001$). Error bars reflect 3 samples for each group. CTL assays shown are from one representative experiment of three performed.

Vaccination with Self-Replicating SINrep5-E7/Hsp70 RNA Enhances an E7-Specific Cytotoxic T cell Response $CD8^+$ T lymphocytes are important effectors of anti-tumor immunity. Generation of E7-specific $CD8^+$ CTLs following vaccination was assessed. FIG. 2 shows results of a study wherein splenocytes from the various self-replicating SINrep5 RNA vaccines were cultured with the E7 peptide (aa 49-57) for 6 days and were examined as effector cells against TC-1 tumor cell targets The self-replicating SINrep5-E7/Hsp70 generated a significantly greater lytic activity in the lymphocyte population compared to cells from mice vaccinated with the other SINrep5 RNA vaccines ($p < 0.001$, one-way ANOVA). The capacity of SINrep5-E7/Hsp70 RNA to generate lytic activity was approximately 7 times that induced by self-replicating SINrep5-E7 RNA (57.2±6.8% versus 8.0±1.3%, E/T ratio 45, p<0.001).

Figure 3:
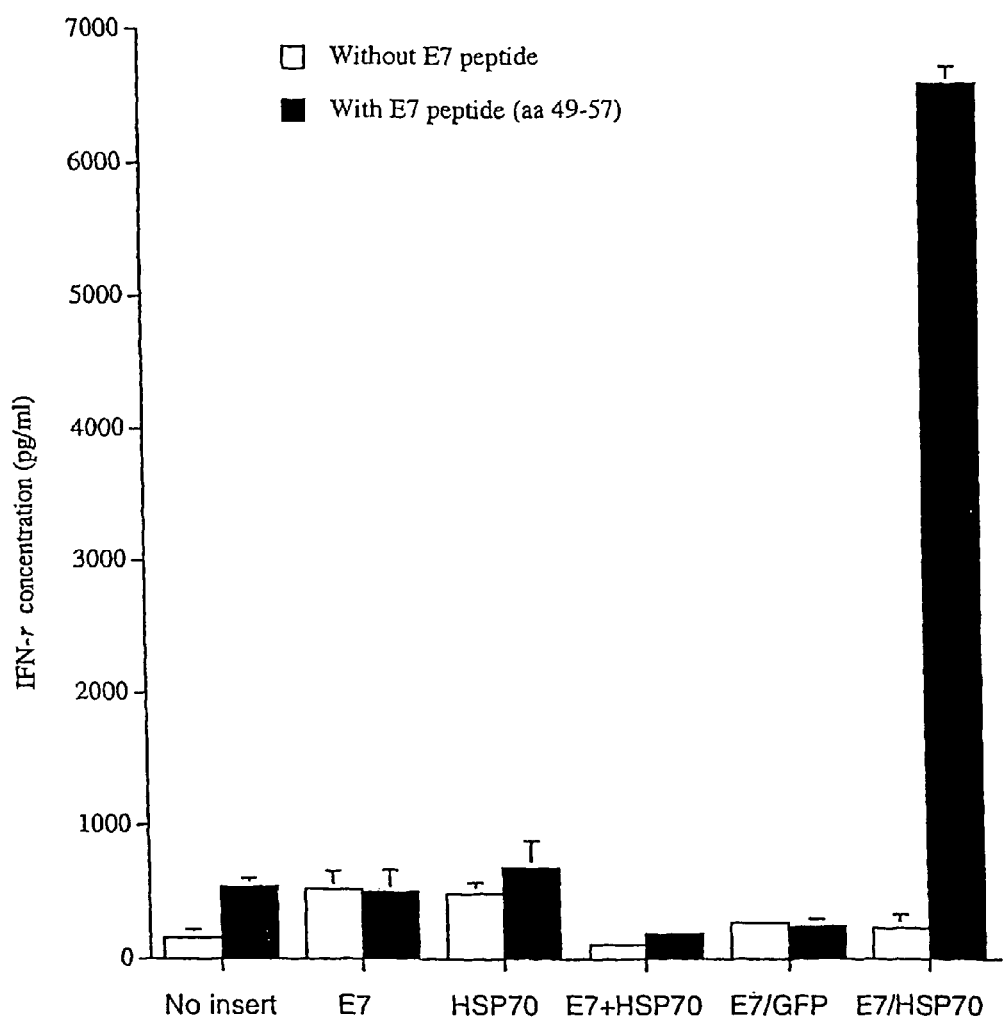
FIG. 3. IFN-γ secretion by E7-specific $CD8^+$ T cells. Mice were immunized i.m. with various self-replicating RNA vaccines. Splenocytes were collected 14 days after vaccination. Splenocytes from various self-replicating RNA vaccines were cultured in vitro with E7 peptide RAHYNIVTF, with or without peptide for 6 days. The culture supernatants were collected for measurement of IFN-γ concentration by ELISA. The $CD8^+$ T cells were induced by the MHC class I epitope of E7. Splenocytes from the self-replicating E7/Hsp70 RNA group stimulated with the E7 RAHYNIVTF secreted the most IFN-γ compared to the other RNA vaccines ($p<0.001$, one-way ANOVA). Results from the ELISA are from one representative experiment of three performed.

The concentration of IFN-γ in the supernatant of stimulated splenocytes was assessed by ELISA. Splenocytes from mice given the various self-replicating RNA vaccines were cultured in vitro with E7 peptide (aa 49-57) (MHC class I epitope (Feltkamp et al., supra)) for 6 days. As a negative control, the stimulatory peptide was omitted. Culture supernatants were collected for measurement of IFN-γ concentration. As shown in FIG. 3, peptide-stimulated splenocytes from mice vaccinated with self-replicating E7/Hsp70 RNA secreted the highest concentration of IFN-γ compared to cells from mice given the other RNA vaccines (p<0.001, one-way ANOVA). Fusion of Hsp70 to E7 significantly enhanced IFN-γ-secreting E7-specific CD8+ T cell activity.

Figure 4:
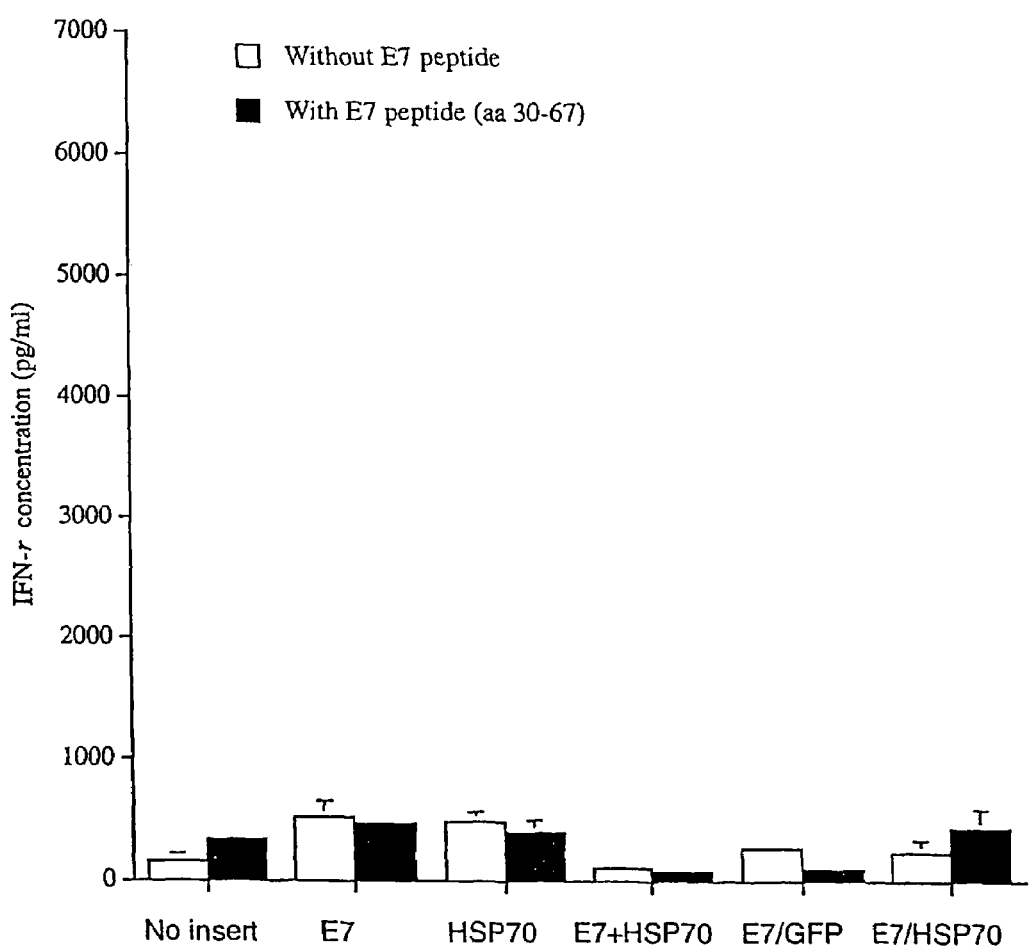
FIG. 4. IFN-γ secretion by E7-specific $CD4^+$ T cells. Splenocytes from mice vaccinated with various self-replicating RNA vaccines were cultured in vitro with E7 peptide containing the MHC class II epitope (aa 30-67, DSSEEEDEIDG-PAGQAEPDRAHYNIVTFCCKCDSTLRL, (SEQ ID NO:23), or no peptide (control). The culture supernatants were collected for measurement of IFN-γ concentrations by ELISA. There was no significant increase in secretion of WFN-γ by splenocytes from the self-replicating E7/Hsp70 RNA group stimulated with the above peptide compared to the other RNA vaccines (one-way ANOVA). Results from the ELISA are from one representative experiment of three performed.

Vaccination with Self-Replicating SINrep5-E7/Hsp70 RNA Did Not Enhance IFN-γ-secreting E7-Specific CD4+ T cells or Anti-E7 Antibodies ELISA was used to assess the E7-specific CD4+ T cell responses generated by the vaccines by measuring concentration of IFN-γ in the supernatant of cultured splenocytes. Splenocytes were cultured in the presence of with E7 peptide (aa 30-67) (that includes an MHC class II epitope (Tindle et al., supra) for 6 days. The peptide was omitted in the negative control. As shown in FIG. 4, there was no significant increase in the concentration of IFN-γ from splenocytes obtained from mice vaccinated with self-replicating E7/Hsp70 RNA compared to the other RNA vaccines. Therefore, a vaccine in which Hsp70 is fused to E7 does appear to enhance IFN-γ-secreting E7-specific CD4+ T cell activity.

The quantity of anti- E7 antibodies in the sera of the vaccinated mice was determined y direct ELISA two weeks after vaccination. Sera of mice vaccinated with SINrep5-E7/Hsp70 did have higher titers of E7-specific antibodies compared to mice vaccinated with other RNA vaccine constructs.

Figure 5:
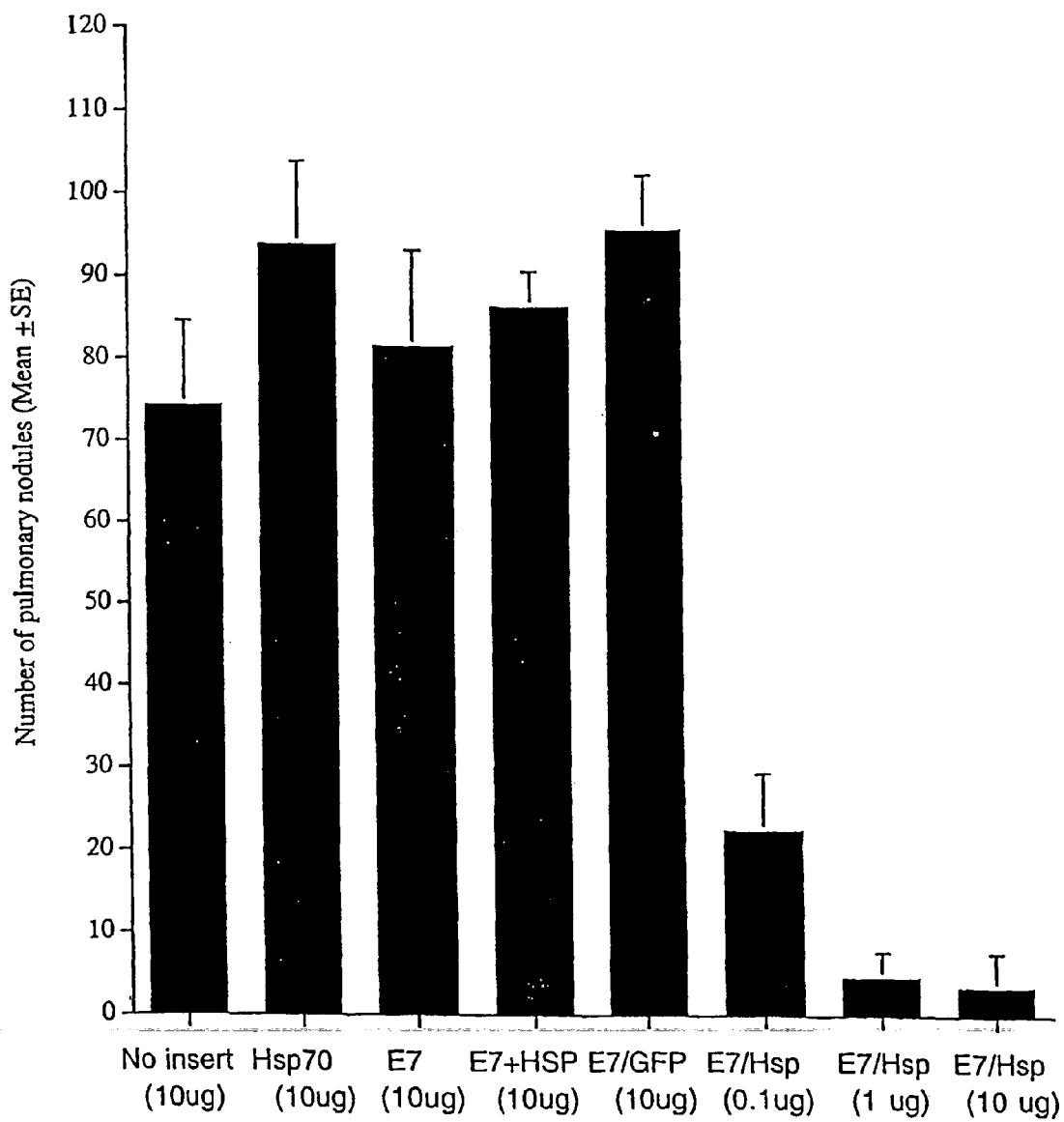
FIG. 5. Various SINrep5 self-replicating RNA vaccines induce tumor protection. Mice (5 per group) were immunized i.m. with the RNA vaccines. Two weeks later, mice were challenged with TC-1 tumor cells i.v. (tail vein) at $10^4$ cells/mouse. Mice were monitored twice weekly and sacrificed on day 21 after challenge. Lungs were dissected from the mice 35 days after vaccination with SINrep5, SINrep5-Hsp70, SINrep5-E7, SINrep5-E7 mixed with SINrep5-Hsp70, SINrep5-E7/GFP or SINrep5-E7/Hsp70 RNA. The mean number of tumor nodules on the lung surface of the vaccinated mice were counted, wher a decrease was an indication of vaccine effectiveness at controlling growth of a tumor expressin HPV-16 E7. There were fewer mean pulmonary nodules in mice vaccinated with self-replicating E7/Hsp70 RNA vaccines (0.1 μg, 1 μg, and 10 μg) compred to mice vaccinated with the other RNA vaccines (10 μg) ($p<0.001$, one-way ANOVA). Self-replicating SINrep5-E7/Hsp70 RNA vaccines protect mice from intravenous tumor challenge even at the low dose of 0.1 μg whereas mice vaccinated with 10 μg of all the other vaccines developed numerous lung nodules. These tumor protection experiments were repeated three times with similar results.
Figure 6:
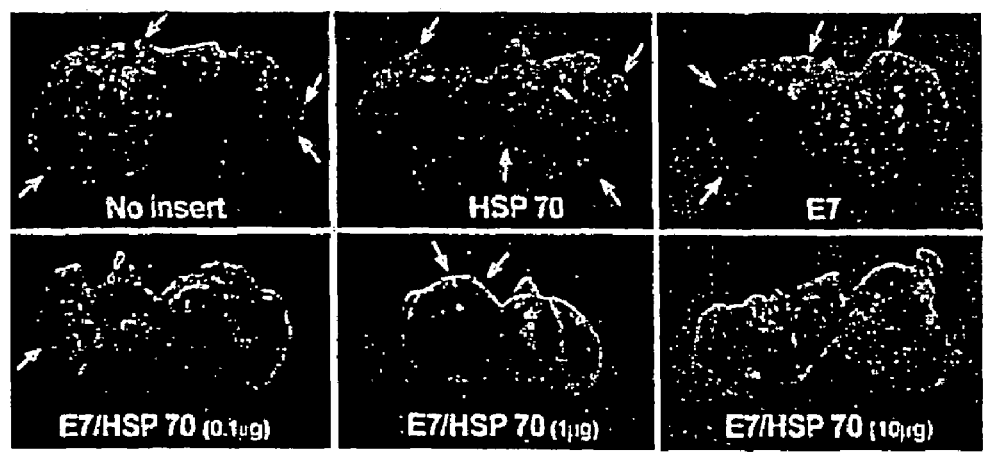
FIG. 6 shows representative photographs of lung tumors in each group. C57BL/6 mice were vaccinated i.m. with various RNA replicon-based vaccines (10 μg/mouse) and challenged with TC-1 tumor i.v., as above. Mice were sacrificed 35 days after vaccination. There are multiple grossly visible lung tumors in unvaccinated control mice and mice vaccinated with SINrep5 or SINrep5-E7 RNA vaccines. Lung tumors in SINrep5-E7/Hsp70 RNA vaccinated group are not evident at the magnification used.

Vaccination with Self-Replicating SINrep5-E7/Hsp70 RNA Protects Mice Better Against the Growth of E7-Expressing TC-1 Tumors An in vivo tumor protection experiment was performed using different doses of SINrep5-E7/Hsp70 RNA administered intramuscularly in the right hind leg. Each mouse was vaccinated with 10 μg of one of the following constructs: self-replicating SINrep5, SINrep5-E7, SINrep5-Hsp70, SINrep5-E7 mixed with SINrep5-Hsp70, SINrep5-E7/GFP or SINrep5-E7/Hsp70 RNA. Self-replicating E7/Hsp70 RNA was also tested at doses of 0.1 and 1 μg/mouse. E7-expressing TC-1 cells were injected i.v. 14 days later. Such tumor challenge simulates hematogenous spread of the tumor cells, allowing evaluation of vaccine effects on metastasis to the lungs via he bloodstream. Pulmonary nodules were assessed 21 days after tumor challenge. FIG. 5 shows a lower mean number of pulmonary nodules in mice vaccinated with the self-replicating E7/Hsp70 RNA vaccines (0.1 μg, 1 μg, and 10 μg) compared to mice given the other RNA vaccines (p<0.001, one-way ANOVA). Representative photographs of the lung tumors (unmagnified) are shown in FIG. 6. The results demonstrated that self-replicating RNA SINrep5-E7/Hsp70 vaccines protected mice from i.v. tumor challenge even at the lower dose of 0.1 μg whereas vaccination with 10 μg of SINrep5 without insert, SINrep5-E7, SINrep5-Hsp70, SINrep5-E7 mixed with SINrep5-Hsp70, or SINrep5-E7/GFP RNA showed no or little protection, developing numerous tumor nodules. These results also showed that linkage of RNA encoding E7 to RNA encoding. an irrelevant protein such as GFP did not result in an antitumor effect, but rather that and that antitumor protection offered by Hsp70 required physical linkage of E7 to Hsp70 at the nucleic acid level.

CD8+ T Cells and NK Cells are Important for the Anti-Tumor Effect

Figure 7:
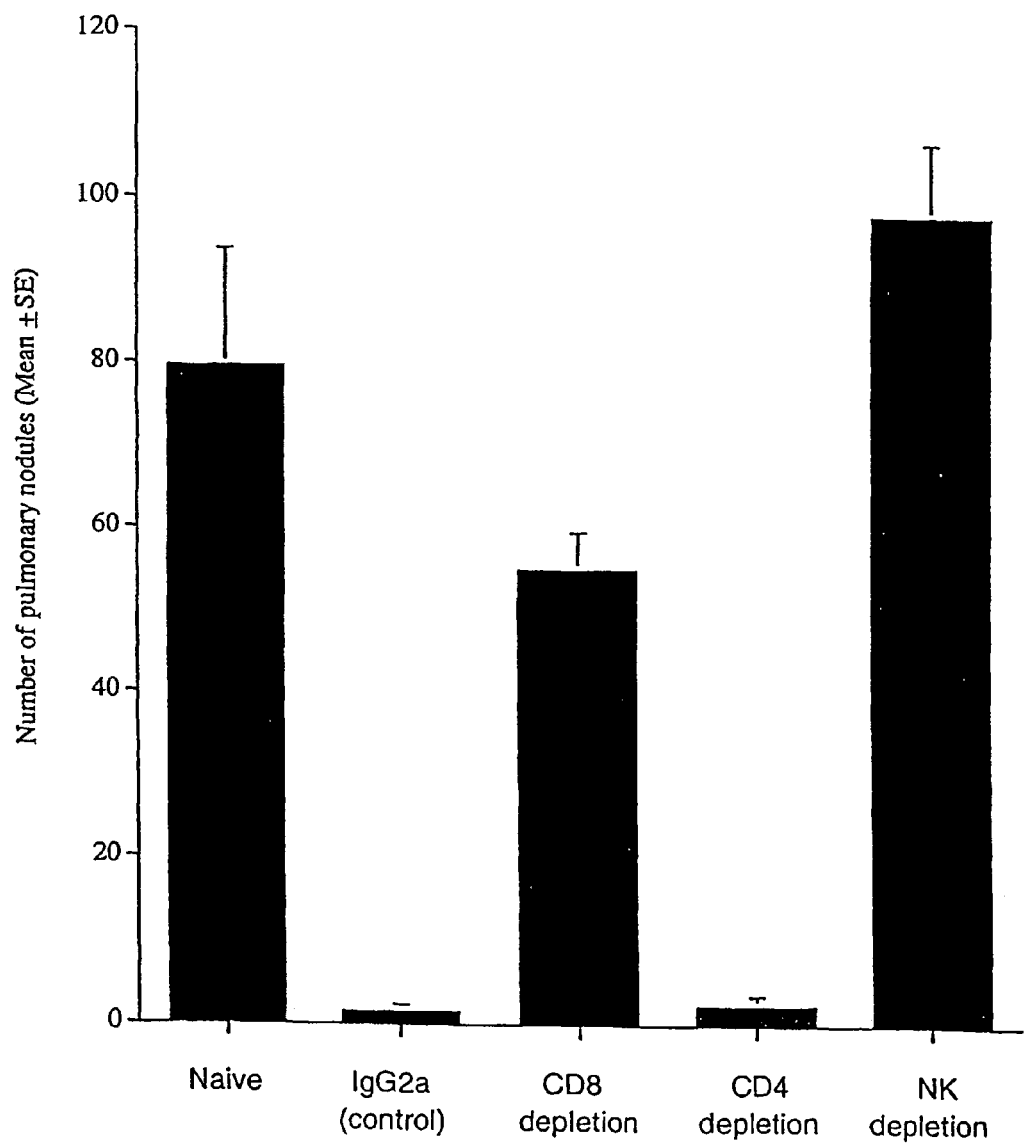
FIG. 7 shows the effect of lymphocyte subset depletion on the potency of self-replicating SINrep5-E7/Hsp70 RNA vaccine. Mice were immunized with 1 μg of thils vaccine i.m. Two weeks after vaccination, mice were challenged with $1\times10^4$ TC-1 cells/mouse i.v. Depletions were initiated one week prior to tumor challenge and were carried out for 28 days. Three weeks after tumor challenge, mice were sacrificed. The mean number of pulmonary nodules in vaccinated mice was determined as above. Depletion of $CD8^+$ T cells or of NK1.1 cells resulted in a higher number of pulmonary nodules vs. animals receiving control $IgG_{2a}$ isotype antibody. The mean number of lung nodules in mice depleted of $CD4^+$ T cells were similar to those in mice receiving control antibody, indicating that $CD4^+$ T cells were not critical for the antitumor effect. Depletion of NK1.1+ cells had a greater impact on antitumor activity than did loss of $CD8^+$ T cells.

To determine the types of lymphocytes required for protection against E7-expressing tumors, in vivo antibody depletion experiments were done in which depletion was initiated one week before tumor challenge and terminated on day 21 after tumor challenge. As shown in FIG. 7, the mean number of pulmonary nodules from mice depleted of CD8+ T cells or of NK1.1+ cells was significantly higher than that observed in mice treated with control IgG2a isotype antibody (which was similar to no antibody depletion). Furthermore, depletion of NK1.1+ cells resulted in a higher number of tumor lung nodules than depletion of CD8+ cells. In contrast, the mean number of pulmonary nodules from mice depleted of CD4+ T cells resembled the isotype controls, indicating that CD4+ T cells were not critical for this effect. Therefore, it was concluded that (Hariharan et al., supra). CD8+ T cells are essential for generation of antigen-specific anti-tumor immunity by SINrep5-E7/Hsp70 RNA vaccine and (Berglund, PM et al., 1997. *AIDS Res Hum Retroviruses* 13:1487-95) NK cells play an important role as well.

Figure 8:
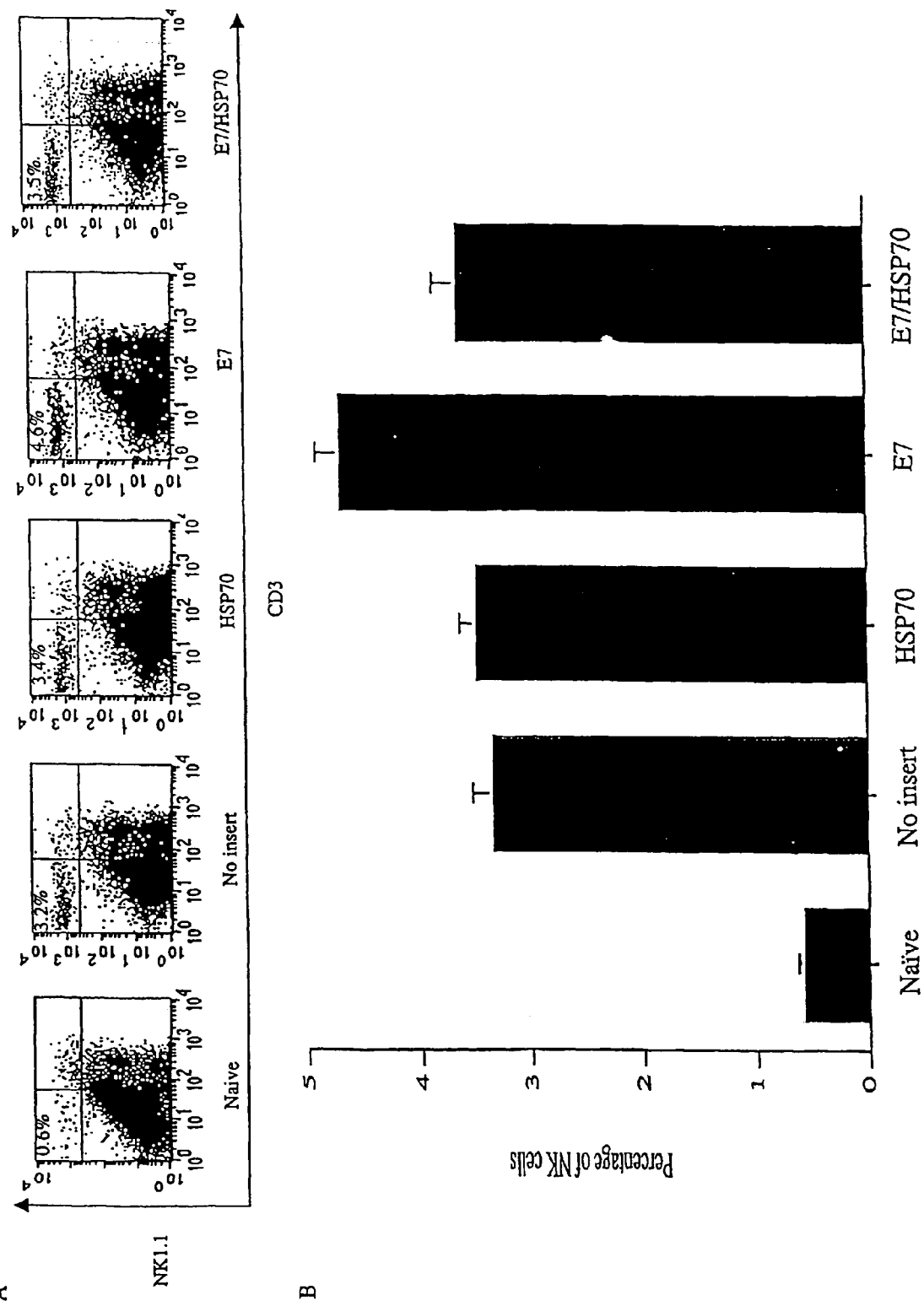
FIG. 8 shows flow cytometric analysis of NK cells in mice immunized with various self-replicating SINrep5 RNA vaccines. Splenocytes were stained for CD3 and NK1.1 immediately, without stimulation.

To investigate whether NK cells were significantly expanded in mice vaccinated with various RNA constructs, flow cytometry analysis was performed, evaluating CD3(-), NK1.1+ cells. The proportion of NK cells was markedly increased in mice vaccinated with each of the all constructs (E7/Hsp70, E7, Hsp70, and control plasmid) relative to nave mice, indicating that the expansion of NK cells is not a response limited to the E7/Hsp70 vaccine (FIG. 8).

Self-Replicating RNA Vaccines Induce Apoptosis

Figure 9:
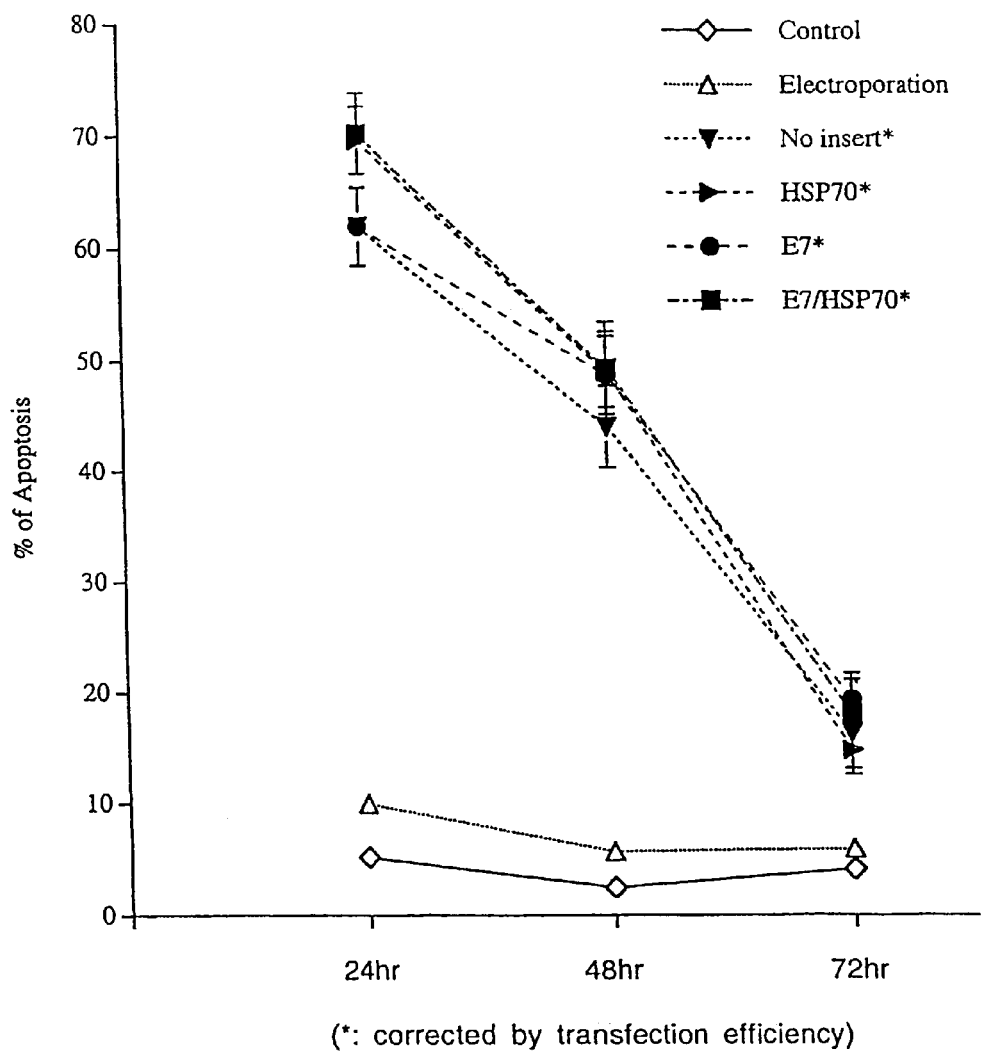
FIG. 9 shows apoptotic death of host cells induced by self-replicating RNA vaccines. To, determine if self-replicating RNA vaccines killed host cells, RNA transcribed in vitro from various SINrep5 plasmids was transfected into BHK21 cells. BHK 21 cells that were electroporated in the absence of RNA or unhandled BHK21 cells served as controls. The percentages of apoptotic and necrotic BHK21 cells were determined by staining with annexin V-FITC and propidium iodide (PI) and flow cytometric analysis. Transfection with SINrep5 RNA vaccines caused a decline in the percentages of apoptotic cells 24 hr to 72 hr after electroporation (representative with SIN5-E7/Hsp70 70.3±3.6% for 24 hr, 49.3±4.2% for 48 hr, 18.0±3.1% for 72 hr, p<0.001, one-way ANOVA). Thus no statistically significant difference were observed whe comparing the percentage of apoptotic cells transfected with various SINrep5 RNA vaccines. This experiment was repeated twice with similar results.

Self-replicating RNA vaccines have been shown to induce apoptotic changes following uptake by cells (Ying et al., supra). We evaluated apoptosis in BHK21 cells transfected with various RNA vaccines. Percentages of apoptotic BHK21 cells were normalized for transfection efficiency. As shown in FIG. 9, apoptosis was induced in all groups of BHK21 cells transfected with various of the RNA vaccines compared to two negative control groups (untransfected or electroporated without RNA). There were no significant difference between the different RNA vaccines. there A steady decline in apoptosis occurred from 24 hr to 72 hr after transfection (with SIN5-E7/Hsp70: 70.3±3.6% at 24 hr, 49.3±4.2% at 48 hr, 18.0±3.1% at 72 hr, p<0.001, one-way ANOVA). These results confirm that cells transfected with each of these self-replicating RNA vaccines undergo apoptotic changes.

Figure 10:
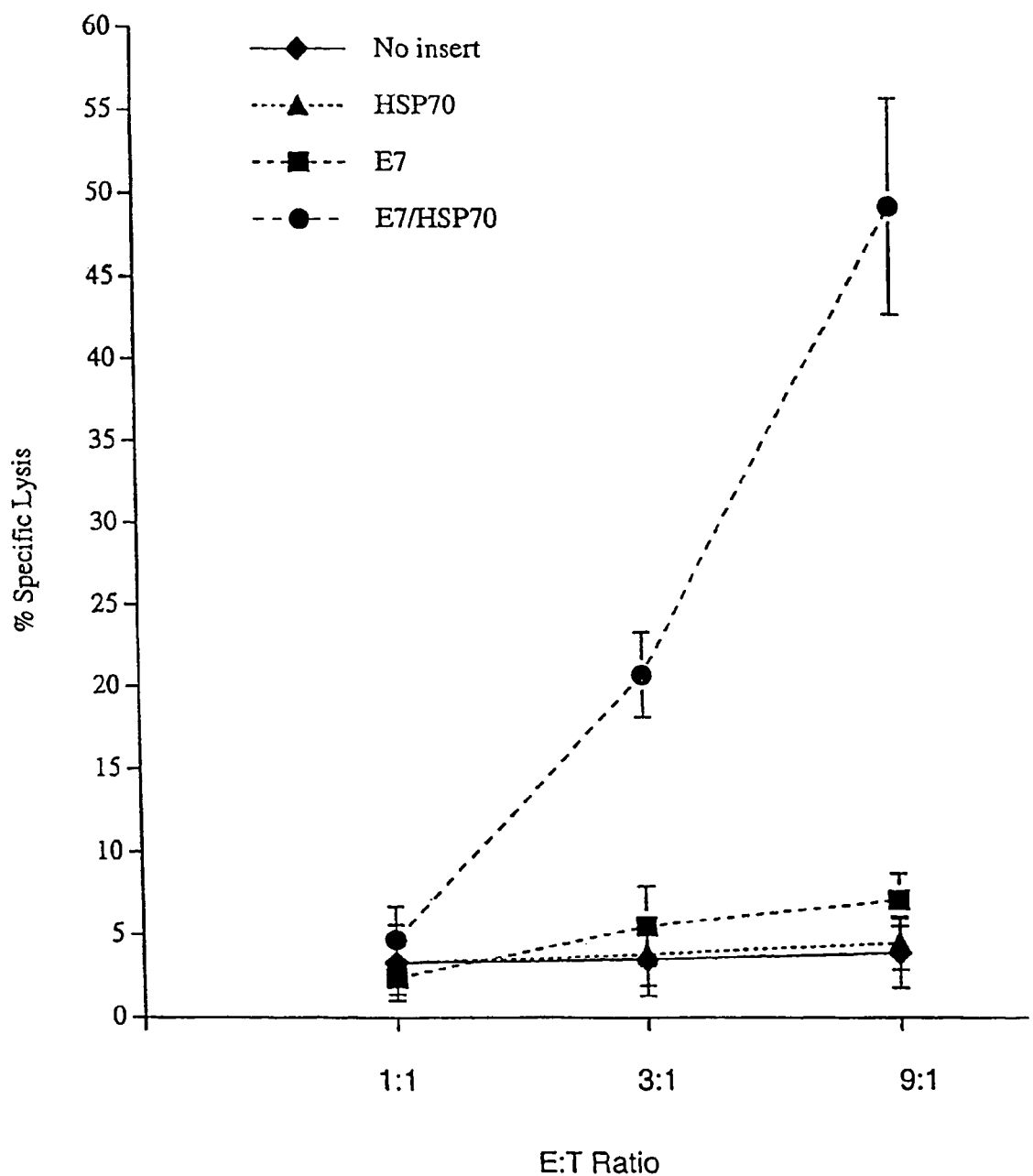
FIG. 10. Enhanced MHC class I presentation of E7 to in bone marrow derived DCs pulsed with BHK21 cells transfected by SINrep5-E7/Hsp70 RNA as measured in CTL assays. BHK21 cells were electroporated with various self-replicating RNA constructs and co-cultured with BM-derived DCs. The DCs were then used as target cells for E7-specific CD8$^+$ T effector cells (28). Cytolysis was determined by quantitative measurements of LDH as described herein. Self-replicating E7/Hsp70 RNA vaccines generated significantly higher lysis (at 3:1 and 9:1 E/T ratios) compared to the other RNA vaccines (p<0.001). CTL assays shown here are from one representative experiment of two performed.

Enhanced Presentation of E7 through the MHC Class I Pathway in Dendritic Cells Pulsed With Cells Transfected with SINrep5-E7/Hsp70 RNA Enhanced E7-specific CD8+ T cell responses in vivo may occur as a result of presentation of E7 via the MHC class I pathway resulting from uptake of apoptotic cellular material expressing various E7 constructs by host APCs. An experiment was performed to characterize the MHC class I presentation of E7 in DCs "pulsed" with BHK21 cells that had been transfected with various self-replicating RNA constructs. As noted above, the transfection efficiency and E7 expression is similar in BHK21 cells transfected with the various E7-containing self-replicating RNAs. Here, transfected BHK21 cells were incubated with bone marrow-derived DCs to allow antigen uptake and processing by the DCs. These DCs were then used as target cells for killing by E7-specific CD8+ CTL. As shown in FIG. 10, DCs incubated with BHK21 cells that had been transfected with SINrep5-E7/Hsp70 RNA were lysed to a higher degree than DCs incubated with BHK21cells transfected with SINrep5-E7 RNA (p<0.001). These results suggested that the presence of Hsp70 in a fusion protein with E7 (that was "fed" to DCs in the form of RNA-transfected BHK21 cells) resulted in more effective presentation of E7 by DCs (via the MHC class I pathway) to CD8+ T cells as compared to E7 protein alone.

Discussion

A vaccine designated SINrep5-E7/Hsp70, administered in vivo significantly enhanced E7-specific $CD8^+$ T cell responses compared to the SINrep5-E7 RNA vaccine lacking Hsp70. It is unlikely that this effect results from occurs improved direct MHC class I presentation of E7 to CTLs by the cells that actually express E7/Hsp70—a process known as "direct priming". Intramuscular delivery of RNA replicons is believed to deliver RNA into muscle cells, which are not "professional" APCs because they do not express co-stimulatory molecules that are important for efficient activation of T cells. Even if the various SINrep5 constructs are delivered to other cell types after i.m. administration, the self-replicating RNA eventually causes apoptosis of the cells it transfects (Frolov et al., supra). The cell initially transfected are therefore unlikely to be efficient direct presenters of antigen.

Rather, the enhanced $CD8^+$ T cell responses are likely a result of a process whereby apoptotic cells (and subcellular material) are endocytosed and processed by professional APCs via MHC class I pathways for more effective presentation to $CD8^+$ T cells (Albert et al., supra) Alternatively, apoptotic cells may release the chimeric E7/Hsp70 protein which is then taken up and processed by APCs via the MHC class I-restricted pathway (Srivastava, P K et al., *Immunogenetics* 39:93-8; Arnold, D et al., 1995. *J Exp Med* 182:885-9; Suto, R et al., 1995. *Science* 269:1585-8). Hsp70 complexes are known to enter professional APCs by binding specifically to the cell surface followed by receptor-mediated endocytosis (Arnold-Schild, D et al., 1999. *J Immunol* 162:3757-60). In recent investigations of receptors for heat shock proteins, CD91 was identified as the receptor for gp96, one member of the HSP family on APCs (Binder, R J et al., 2000 *Nat. Immunol* 2:151-155).

Another important factor for enhanced activation of antigen specific $CD8^+$ T cells by chimeric Hsp70/E7 may be the biology of professional APCs, primarily DCs. Cho et al., recently reported that a mycobacterial HSP fused to an antigen stimulates DCs to upregulate expression of MHC class I, class II and co-stimulatory molecules (Cho, B K 2000. *Immunity* 12:263-272). Thus, induction of DC "maturation" by Hsp70 linked to antigen may augment T cell activity, explaining the results described herein with the chimeric E7/Hsp70 RNA vaccine.

The present study demonstrated that depletion of NK cells reduced the antitumor effect induced by the E7/Hsp70 RNA replicon-based vaccine (FIG. 7), indicating that these cells are a necessary component. However, NK cell activity alone cannot account for the observed antitumor effect because other of the RNA replicon-based compositions produced a similar change in NK cell number (FIG. 8). The in vivo antibody depletion study suggested that $CD8^+$ CTLs were important for this antitumor effect (FIG. 7). Thus, it was concluded that both NK cells and $CD8^+$ T cells are important contributors to the antitumor effect of the E7/Hsp70 RNA vaccine. Interactions among these two cell populations might also be of interest in understanding the outcome of such vaccination.

A comparison of the study described above with previous studies of the present inventors and their colleagues reveals that different forms of nucleic acid vaccines may activate different subsets of effector cells in the vaccinated host and act via different mechanisms.

Even though NK cells appeared to play a role in the antitumor effects induced by E7/Hsp70 RNA replicons, NKs were not essential when the vaccine was a naked E7/Hsp70 DNA vaccine. Thus, depletion of $NK1.1^+$ cells in mice vaccinated with naked E7/Hsp70 DNA did not decrease the anti-tumor immunity (Chen et al., supra).

In contrast, $CD8^+$ T cells were important for antitumor effects induced by both E7/Hsp70 DNA and E7/Hsp70 RNA replicon-based vaccines.

The apoptotic changes promoted by the self-replicating RNA vaccine raise potential safety concerns. With RNA replicon-based vaccines, increased apoptotic changes and inflammatory responses are localized to the injection sites. However, microscopic examination of the vital organs of E7/Hsp70-vaccinated mice did not show any significant histopathological changes. Potential risks attend the presence of HPV-16 E7 protein in host cells as E7 happens to be a viral oncoprotein that disrupts cell cycle regulation by binding to tumor suppressor pRB protein in nuclei (Lukas, J H et al., 1994. *J Cell Biol* 125:625-38), leading to potential incidence and accumulation of genetic aberrations and eventual malignant transformation. Use of a self-replicating RNA vector eases the concern about oncogenicity of E7 protein since the transfected cells eventually undergo apoptosis.

In summary, the results reveal that fusion of DNA encoding Mtb Hsp70 to DNA encoding HPV-16 E7 in an RNA replicon results in a vaccine composition that induces a marked antigen (E7)-specific $CD8^+$ T cell-mediated immune response that produces a state of anti-tumor immunity against tumors expressing the antigen. Fusion of Hsp70 DNA to DNA encoding an antigen further enhances the potency of the RNA replicon-based vaccine. These findings are applicable to other tumors and types of cancer where tumor-specific antigens can be identified. Further, these findings are directly applicable to vaccines against organisms responsible for infectious diseases such as viruses, protozoa, fungi and bacteria.

EXAMPLE II

Enhancement of Suicidal DNA Vaccine Potency by Linking *Mycobacterium Tuberculosis* Heat Shock Protein 70 to an Antigen Recently, RNA replicon vaccines have emerged as an important strategy to alleviate the concerns for potential chromosomal integration and cell transformation noted above (Ying et al., supra). These vaccines are self-replicating, self-limiting and may be administered either as RNA or as DNA which is then transcribed into RNA replicons in transfected cells in vitro or in vivo. DNA-based self-replicating RNA replicons, also known as "suicidal DNA," eventually cause lysis of transfected cells(Berglund et al., supra; Leitner et al., supra).

The present vaccine was developed using the Semliki Forest virus suicidal DNA vector, pSCA1 (DiCiommo, D P et al., *J Biol Chem* 1998; 273:18060-6). Such vectors alleviate some concern about naked DNA because they eventually cause apoptosis of transfected cells. This feature is particularly desirable for vaccines that encode potentially oncogenic proteins, such as the HPV E7 protein (Wu, T C. *Curr Opin Immunol* 1994; 6:746-754). Because suicidal DNA vectors eventually kill transfected cells, any expression of DNA from these vectors is necessarily transient, conceivably compromising their potency. Therefore, the present inventors have conceived of strategies to enhance the potency of suicidal DNA vaccines.

Disclosed herein are the findings of an investigation of the impact of linking full-length Hsp70 to E7 on the potency of suicidal DNA vaccines. The suicidal DNA vaccine, pSCA1-E7/Hsp70, significantly increased expansion and activation of E7-specific $CD8^+$ T cells compared to a vaccine comprising only pSCA1-E7. This enhanced response resulted in potent anti-tumor immunity against E7-expressing tumor cells.

Materials and Methods

Plasmid DNA Constructs and Preparation pSCA1 vector (DiCiommo et al., supra) was a gift from Dr. Bremner at the University of Toronto. This vector contains the human CMV immediate early gene (HCMV IE) promoter upstream of the Semliki Forrest virus (SFV) replicon. The subgenomic promoter is located after the SFV replicon, upstream of a multiple cloning sites for insertion of DNA of interest. For the generation of pSCA1-E7, E7 was cut from pcDNA3-E7 by BamHI/PmeI (Chen et al., supra) and cloned into BamHI/SmaI sites of pSCA1. To construct pSCA1-Hsp70, Hsp70 was cut from pcDNA3-Hsp70[8] by BamHI/PmeI and cloned into BamHI/SmaI sites of pSCA1. For the generation of pSCA1-E7/Hsp70, E7/Hsp70 DNA was cut from pcDNA3-E7/Hsp70 (Chen et al., supra) by BamHI/PmeI and cloned into BamHI/SmaI sites of pSCA1. The accuracy of these constructs was confirmed by DNA sequencing. Plasmid DNA vectors encoding pSCA1-E7, pSCA1-Hsp70, pSCA1-E7/Hsp70 or pSCA1 with no insert were transfected into subcloning efficient DH5™ cells (Life Technologies, USA). The DNA was then amplified and purified (Chen et al., supra). The integrity of plasmid DNA and the absence of Escherichia coli DNA or RNA were checked in each preparation using 1% agarose gel electrophoresis. DNA concentration was determined by optical density measured at 260 nm. The presence of the inserted E7 fragment was confirmed by restriction enzyme digestion and gel electrophoresis.

Cell Lines

The production and maintenance of TC-1 cells has been described previously (Lin et al., supra). In brief, HPV-16 E6, E7 and ras oncogene DNA were used to transform primary lung epithelial cells from C57BL/6 mice. The cells were grown in RPMI 1640, supplemented with 10% (vol/vol) fetal bovine serum, antibiotics, L-glutamine, sodium pyruvate, nonessential amino acids at 37° C. with 5% $CO_2$. On the day of tumor challenge, TC-1 cells were harvested by trypsinization, washed twice with 1×Hanks buffered salt solution (HBSS) and finally resuspended in 1×HBSS to the designated concentration for injection.

Mice 6- to 8-week old female C57BL/6 mice from the National Cancer Institute (Frederick, Md.) were purchased and kept in the oncology animal facility of the Johns Hopkins Hospital (Baltimore, Md.). All animal procedures were performed according to approved protocols and in accordance with recommendations for the proper use and care of laboratory animals.

DNA Vaccination

Gene gun particle-mediated DNA vaccination was performed using a helium-driven gene gun (Bio-rad, Hercules, Calif.) according to the protocol provided by the manufacturer. Briefly, DNA coated gold particles were prepared by combining 25 mg of 1.6 μm gold microcarriers (Bio-rad, Hercules, Calif.) and 100 μl of 0.05 M spermidine (Sigma, St, Louis, Mo.). Plasmid DNA (50 μg) and 1.0 M $CaCl_2$ (100 μl) were added sequentially to the microcarriers while mixing by vortex. This mixture was allowed to precipitate at room temperature for 10 minutes. The microcarrier/DNA suspension was then centrifuged (10,000 rpm. for 5 sec) and washed 3 times in fresh absolute ethanol before resuspending in 3 ml of polyvinylpyrrolidone (0.1 mg/ml) (Bio-rad, Hercules, Calif.) in absolute ethanol. The solution was then loaded into tubing and allowed to settle for 4 min. The ethanol was gently removed and the microcarrier/DNA suspension was evenly attached to the inside surface of the tubing by rotating the tube. The tube was then dried using 0.4 liters per minute of flowing nitrogen gas. The dried tubing coated with microcarrier/DNA was then cut to 0.5-inch cartridges and stored in a capped dry bottle at 4° C. As a result, each cartridge contained 1 μg of plasmid DNA and 0.5 mg of gold. The DNA coated gold particles (1 μg DNA/bullet) were delivered to the shaved abdominal region of the mice using a helium-driven gene gun (Bio-rad, Hercules, Calif.) with a discharge pressure of 400 p.s.i.

Intracytoplasmic Cytokine Staining and Flow Cytometry Analysis

Splenocytes from groups naïve or vaccinated mice (5 mice per group) were collected and pooled one week after the last vaccination and incubated either with the E7 peptide (aa 49-57, RAHYNIVTF; SEQ ID NO:22) containing MHC class I epitope or the E7 peptide (aa 30-67) containing MHC class 11 peptide. The E7 peptide was added at a concentration of 2 μg/ml for 20 hours. To detect E7-specific $CD8^+$ T cell precursors and E7-specific $CD4^+$ T helper cell responses, $CD8^+$ CTL epitopes aa 49-57 or aa 30-67 of E7 were used, respectively. Golgistop (Pharmingen, San Diego, Calif.) was added 6 hr before harvesting the cells from the culture. Cells were then washed once in FACScan buffer and stained with phycoerythrin (PE)-conjugated monoclonal rat anti-mouse CD8 or CD4 antibody (Pharmingen, San Diego, Calif.). Cells were subjected to intracellular cytokine staining using the Cytofix/Cytoperm kit according to the manufacturer's instructions (Pharmingen). FITC-conjugated anti-IFN-γ or anti-IL-4 antibodies and the immunoglobulin isotype control antibody (rat IgG1) were all purchased from Pharmingen. Analysis was done on a Becton-Dickinson FACScan flow cytometer with CELLQuest software (Becton Dickinson Immunocytometry System, Mountain View, Calif.).

ELISA for anti-E7 antibody (see EXAMPLE I)

In vivo Tumor Protection

These studies were generally as Example I, except that different DNA preparations and deliver was used: gene gun with 2 μg of pSCA1-E7, pSCA1-Hsp70, pSCA1-E7/Hsp70 DNA, or pSCA1 without insert. One week later, mice were boosted with the same regimen and, on day 14, were challenged subcutaneously with $10^4$ TC-1 tumor cells in the right leg.

Tumor Therapy

The tumor cells and DNA vaccines were prepared as above. Each mouse (5 per group) was challenged i.v. with $10^4$ TC-1 tumor cells on day 0. Three days later, mice were given 2 μg of a vaccine preparation (pSCA1-E7, pSCA1-Hsp70, pSCA1-E7/Hsp70 DNA, or pSCA1 without insert) via gene gun. One week later, animals were boosted using the same regimen and were sacrificed on day 21. The number of tumor nodules on the surface of the lung of each mouse were evaluated and counted by experimenters blinded to sample identity. Statistical significance was tested using one-way ANOVA.

In vivo Antibody Depletion Experiments

The procedure was done as in Example I. Here, vaccination was with 2 μg DNA via gene gun, boosted one week later, and challenged with $5 \times 10^4$ TC-1 tumor cells. Depletion treatment was terminated 40 days after tumor challenge.

Results

Construction and Characterization of the PSCA1-7/Hsp70 Suicidal DNA Vaccine

Figure 11:
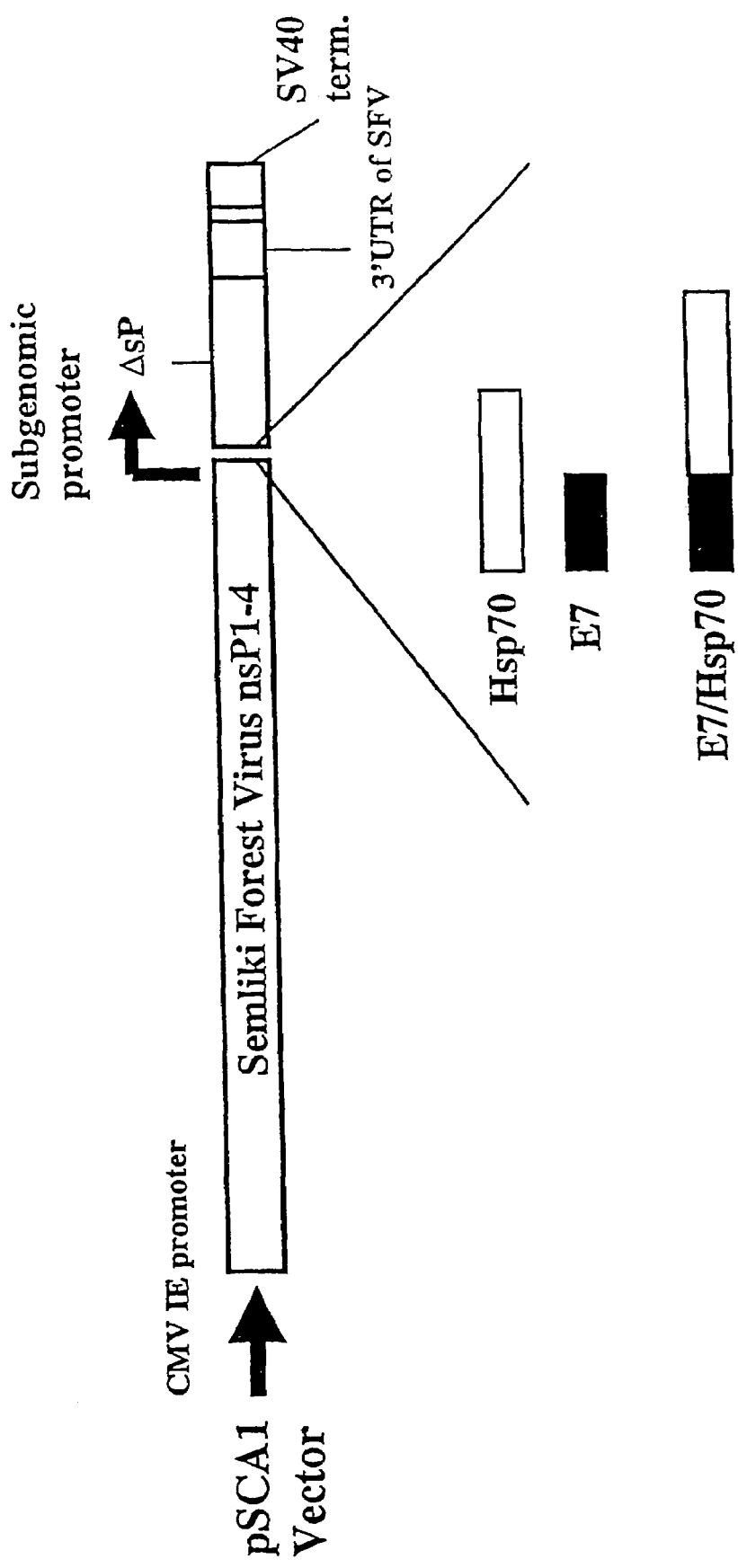
FIG. 11 is a schematic diagram of pSCA1-E7, pSCA1-Hsp70 and pSCA1-E7/Hsp70 constructs. The DNA-based SFV replicon vector, pSCA1, encodes the alphaviral replicon from Semliki Forest virus. E7, Hsp70, and E7/Hsp70 DNA were cloned into the BamHI/SmaI sites of pSCA1. The HCMV IE promoter with subgenomic promoter are indicated with arrows.

The generation of plasmid DNA constructs and subsequent preparation of DNA-based self-replicating pSCA1 vaccines was performed as described above. The pSCA1 vector includes the HCMV IE promoter and a replicon from the SFV (DiCiommo et al, supra). A schematic diagram depicting DNA-based self-replicating pSCA1-E7, pSCA1-Hsp70, and pSCA1-E7/Hsp70 constructs is shown in FIG. 11.

An ELISA to test expression of E7 protein by BHK21 cells transfected with the various DNA-based self-replicating E7-containing pSCA1 DNA constructs showed that similar amounts of E7 protein were expressed by each of these constructs.

Figure 12A:
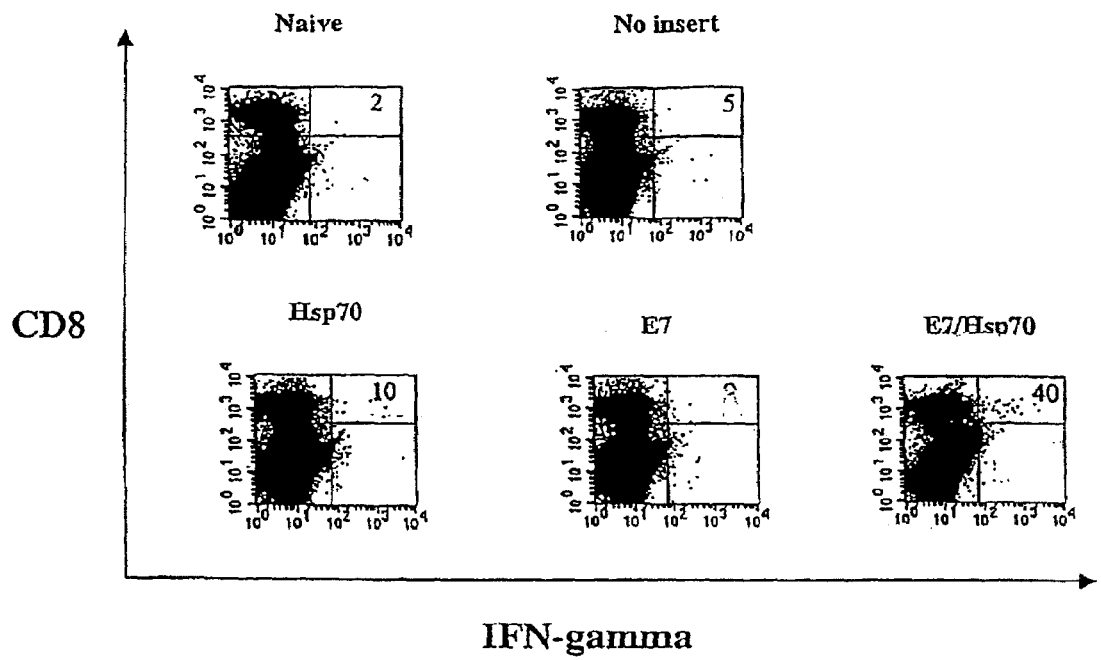
FIGS. 12A and 12B show measurement of E7-specific CD8$^+$ T cell precursors ("Tp") by intracellular cytokine staining and flow cytometric analysis. C57BL/6 mice were immunized with DNA-based self-replicating pSCA1-E7, pSCA1-Hsp70, pSCA1-E7/Hsp70, or pSCA1 without insert, using a gene gun and were boosted with the same regimen one week later.
Figure 12B:
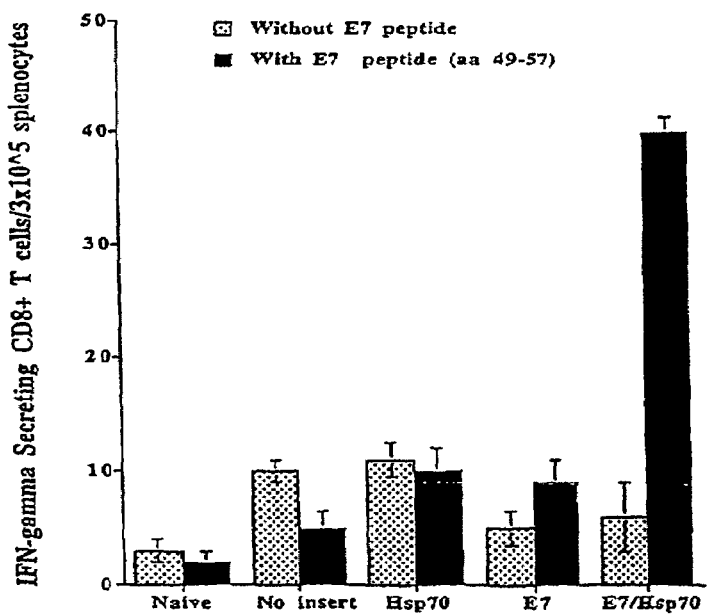

Vaccination with the pSCA1-E7/Hsp70 Suicidal DNA Vaccine Enhances E7-Specific $CD8^+$ T Cell-Mediated Immune Responses $CD8^+$ T lymphocytes are important effectors of anti-tumor immunity. As a measure of the E7-specific $CD8^+$ T cell response generated-by the DNA-based self-replicating pSCA1-E7/Hsp70 vaccine, intracellular cytokine staining was evaluated in splenocytes from mice vaccinated intradermally via gene gun. As shown in FIG. 12A, vaccination of mice with pSCA1-E7/Hsp70 suicidal DNA vaccine generated the highest number of E7-specific IFN-$\gamma^+$ $CD8^+$ T cell precursors (40 per $3\times10^5$ splenocytes) compared to vaccination with pSCA1-E7 DNA (12 per $3\times10^5$ splenocytes) ($p<0.01$). pSCA1-E7/Hsp70 DNA immunization led to a nearly 4-fold increase in the number of E7-specific $CD8^+$ T cell precursors. The mean number of IFN-$\gamma$-producing E7-specific $CD8^+$ T cells was determined in the presence (solid columns) and absence (open columns) of E7 peptide aa 49-57(SEQ ID NO:22) and shown in FIG. 12B. These results indicated that linkage of Hsp70 to E7 significantly enhanced the frequency of E7-specific $CD8^+$ T cell precursors in vaccinated mice.

Figure 13A:
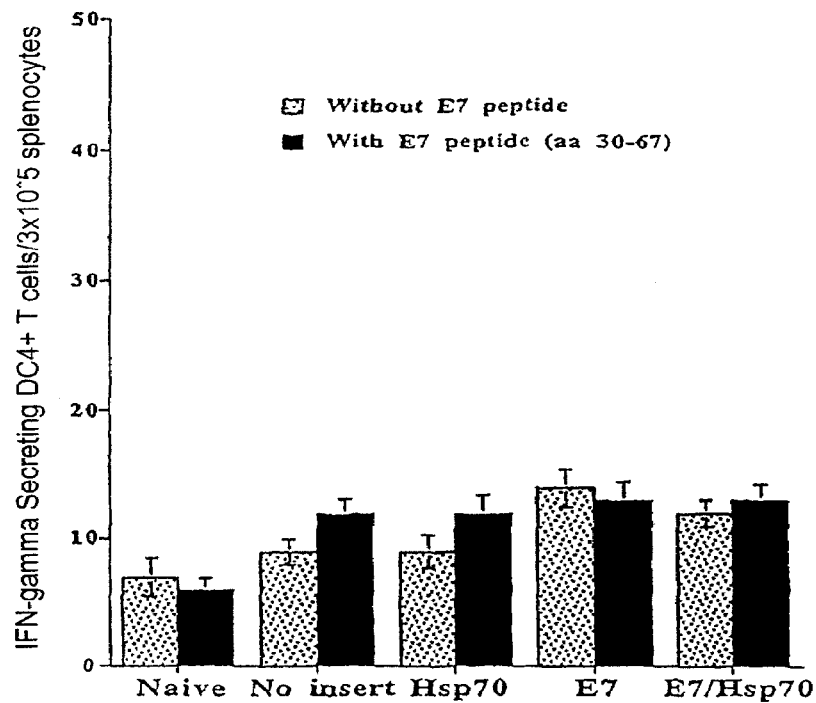
FIGS. 13A and 13B show flow cytometry analysis of IFN-γ secreting or inteleukin-4 (IL-4)-secreting E7-specific CD4$^+$ T cells in mice vaccinated with various suicidal DNA vaccines. Mice were immunized as described in the description of FIG. 12 (FIG. 13). Splenocytes from vaccinated mice were stimulated in vitro with the T-helper E7 peptide DSSEEEDEIDG-PAGQAEPDRAHYNIVTFCCKCDSTLRL (SEQ ID NO: 23, see above) overnight and were stained for both CD4 and intracellular IFN-γ subjected to flow cytometry. No significant differences in the frequency of E7-specific IFN-γ-secreting CD4$^+$ cells was observed in mice immunized with various recombinant DNA vaccines vs control.
Figure 13B:
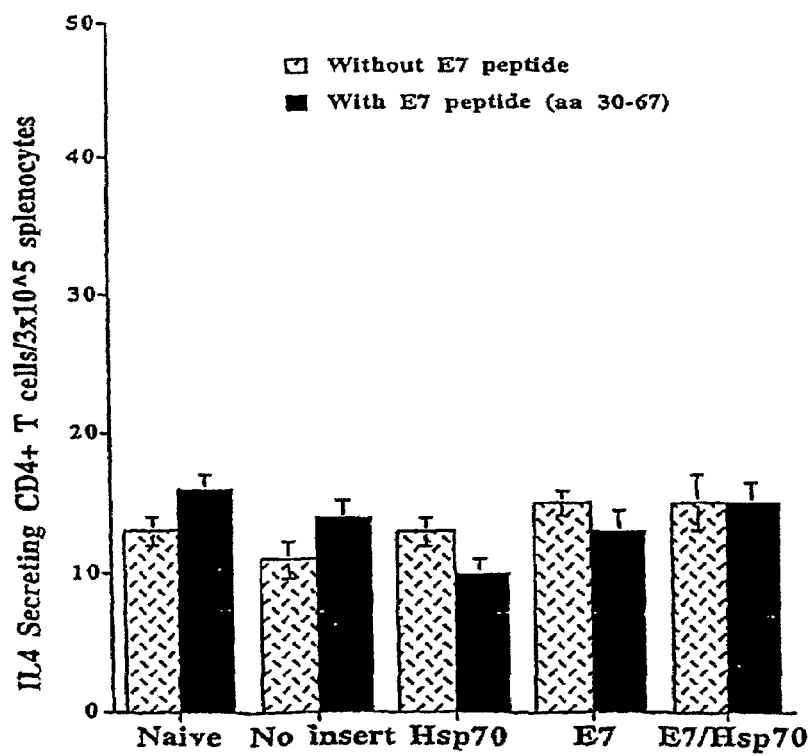

Vaccination with pSCA1-E7/Hsp70 Suicidal DNA Vaccine did not Induce Significant E7-Specific T Cell Responses Mediated by CD4+ Cells To examine if various pSCA1 suicidal DNA vaccines stimulated E7-specific $CD4^+$ T cell precursors to produce cytokines, double staining flow cytometry for surface CD4 and intracellular IFN-$\gamma$ or IL-4 was performed to enumerate CD4+ cytokine secreting cells in splenocytes from vaccinated mice. FIGS. 13A and 13B show no significant difference in the number of E7-specific IFN-$\gamma$-secreting (or IL-4-secreting) $CD4^+$ cells among the various groups. Thus, linkage of Hsp70 to E7 in a suicidal DNA vaccine did not lead to stimulation of E7-specific $CD4^+$ T cell precursors in vivo.

Figure 14:
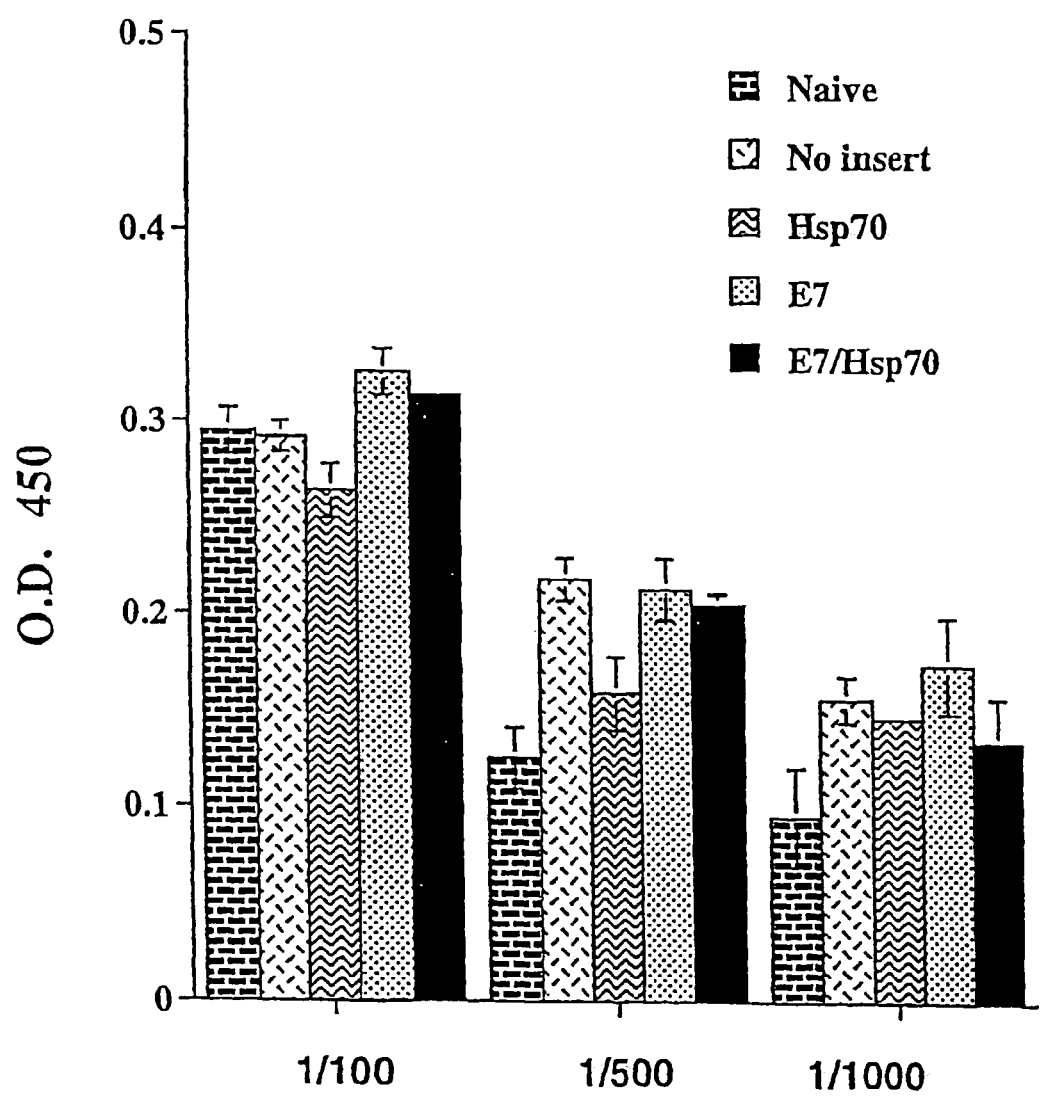
FIG. 14 shows E7-specific antibody responses in mice immunized with various pSCA1 suicide DNA vaccines. E7-specific antibodies were measured with ELISA using a serial dilution of serum. The results from the 1:100 dilution are presented, showing mean absorbance (OD$_{450}$) (±SEM). The results are from one representative experiment of two performed.

Vaccination with pSCA1-E7/Hsp70 Suicidal DNA Vaccine did not Induce Antti-E7 Antibodies The quantity of anti-E7 antibodies in the sera of the vaccinated mice was determined y direct ELISA two weeks after vaccination. Sera of the mice vaccinated with pSCA1-E7/Hsp70 did not have higher titers of E7-specific antibodies compared to those mice vaccinated with pSCA1-E7 vaccine (FIG. 14).

Figure 15:
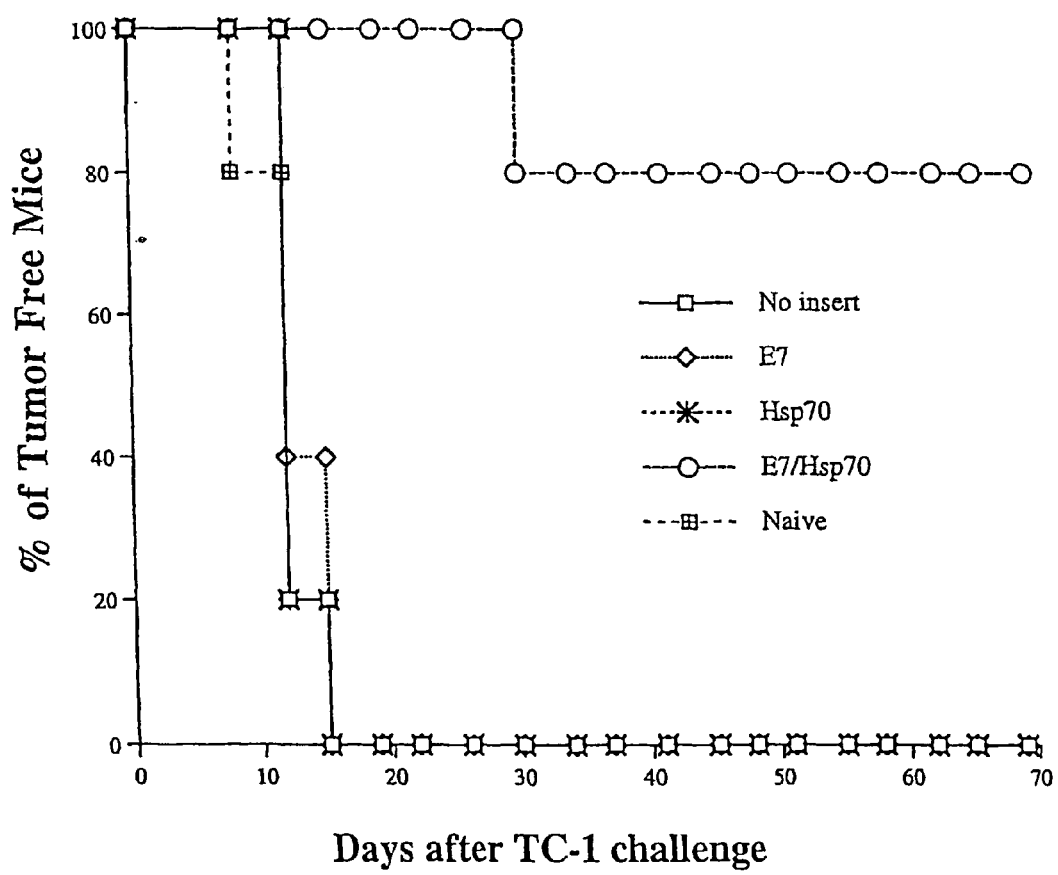
FIG. 15 shows in vivo tumor protection against the growth of TC-1 tumors. Mice were immunized with various suicidal DNA vaccines and inoculated with tumors as described below. 80% of mice vaccinated with the pSCA1-E7/Hsp70 suicidal DNA vaccine remained tumor-free 70 days after TC-1 challenge. The results shown here are from one representative experiment of two performed.

Vaccination with pSCA1-E7/Hsp70 Suicidal DNA Vaccine Protects Mice Better Against the Growth of E7-Expressing TC-1 Tumors An in vivo tumor protection experiments was performed using DNA-based self-replicating pSCA1-E7/Hsp70 DNA vaccine and an E7-expressing tumor, TC-1, in C57BL/6 mice. As shown in FIG. 15, 80% of mice receiving this vaccine remained tumor-free 70 days after TC-1 challenge. In contrast, all mice receiving wild-type pSCA1-E7 and pSCA1-Hsp70 constructs as well as all naïve mice developed tumors within 2 weeks. Therefore, the DNA-based self-replicating pSCA1-E7/Hsp70 vaccine significantly enhanced anti-tumor immunity.

Figure 16A:
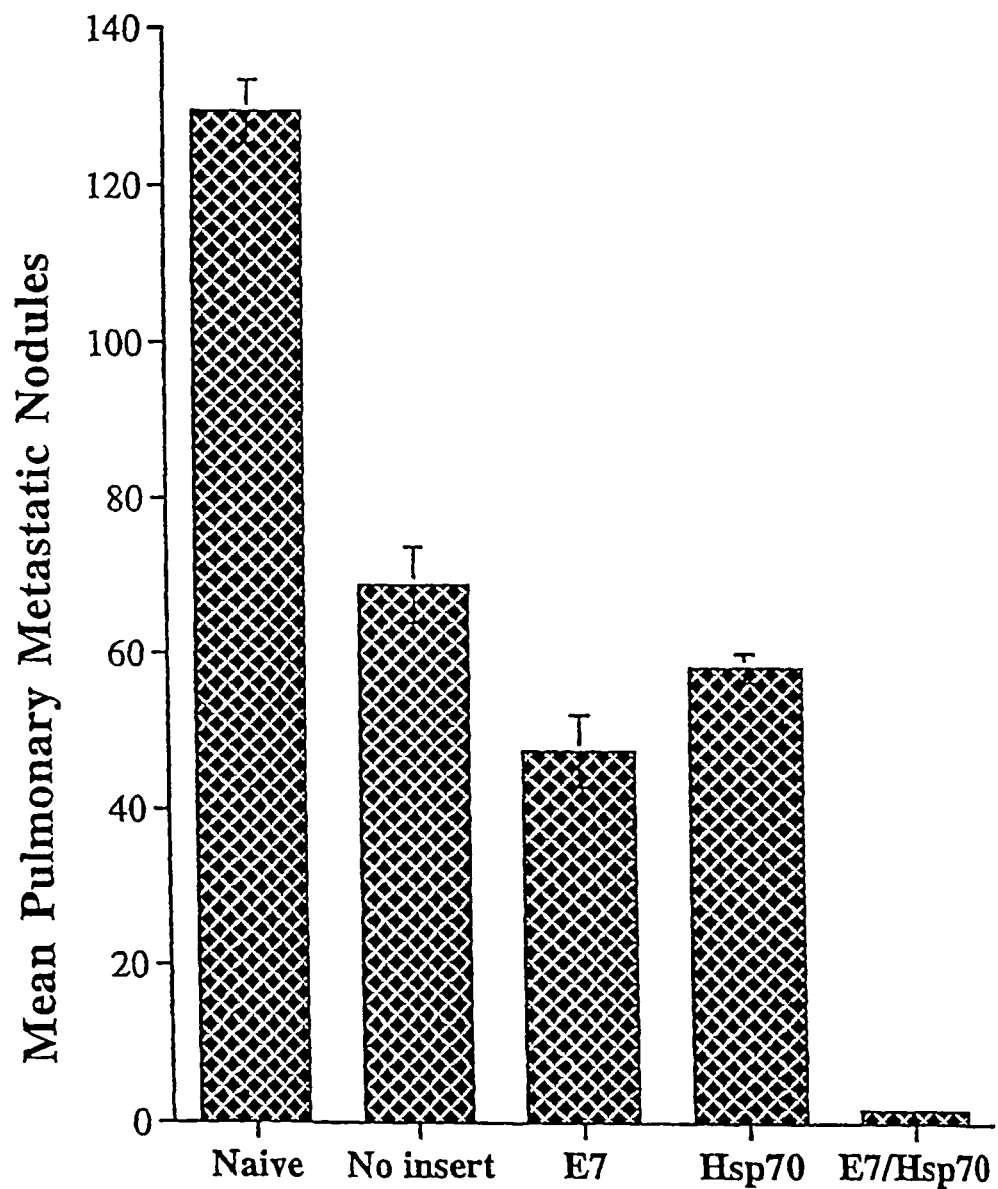
FIGS. 16A and 16B show results of in vivo tumor therapy against pre-existing metastatic TC-1 tumor cells. Mice were first inoculated i.v. with tumors and then treated with various suicidal DNA vaccines.
Figure 16B:
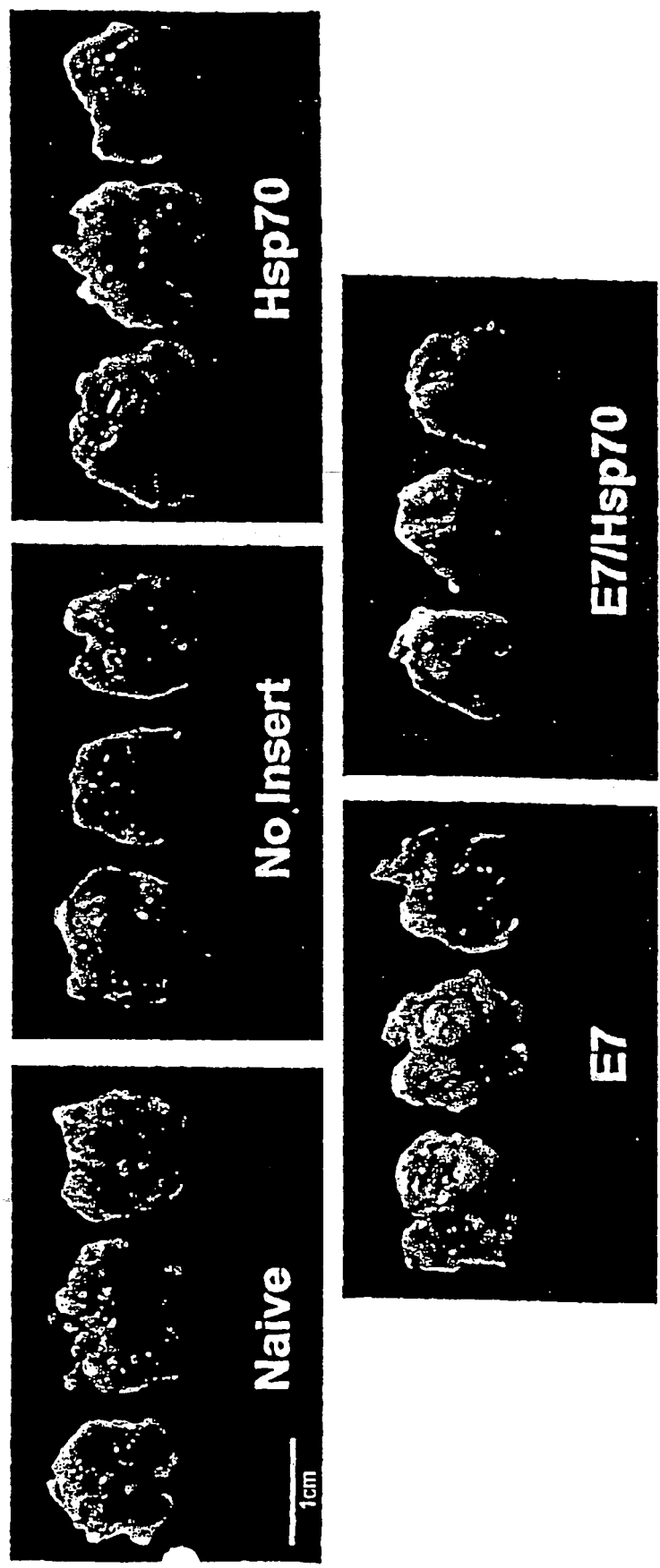

Treatment with pSCA1-E7/Hsp70 Suicidal DNA Vaccine Eradicates Established Tumors in the Lungs To determine the therapeutic potential of the DNA-based self-replicating pSCA1-E7/Hsp70 vaccine for lung metastases, each mouse was challenged with $10^4$ TC-1 tumor cells i.v. Results are shown in FIG. B/6A as the number of pulmonary metastatic tumor nodules ±SEM. Mice treated with the pSCA1-E7/Hsp70 suicidal DNA vaccine had the lowest number of pulmonary nodules (1.8±0.5) compared to mice vaccinated with wild-type pSCA1-E7 (47.7±4.6), pSCA1-Hsp70 (58.3±1.8), pSCA1 alone (69.0±4.9) or naïve mice (129.5±4.0) (ANOVA, p<0.001). Representative photographs of the lung tumors (unmagnified) are shown in FIG. 16. These results indicate that the linkage of Hsp70 to E7 in a suicidal DNA vaccine significantly enhanced the antitumor therapeutic effect.

$CD8^+$ T Cells are Essential for Antitumor Effects

Figure 17:
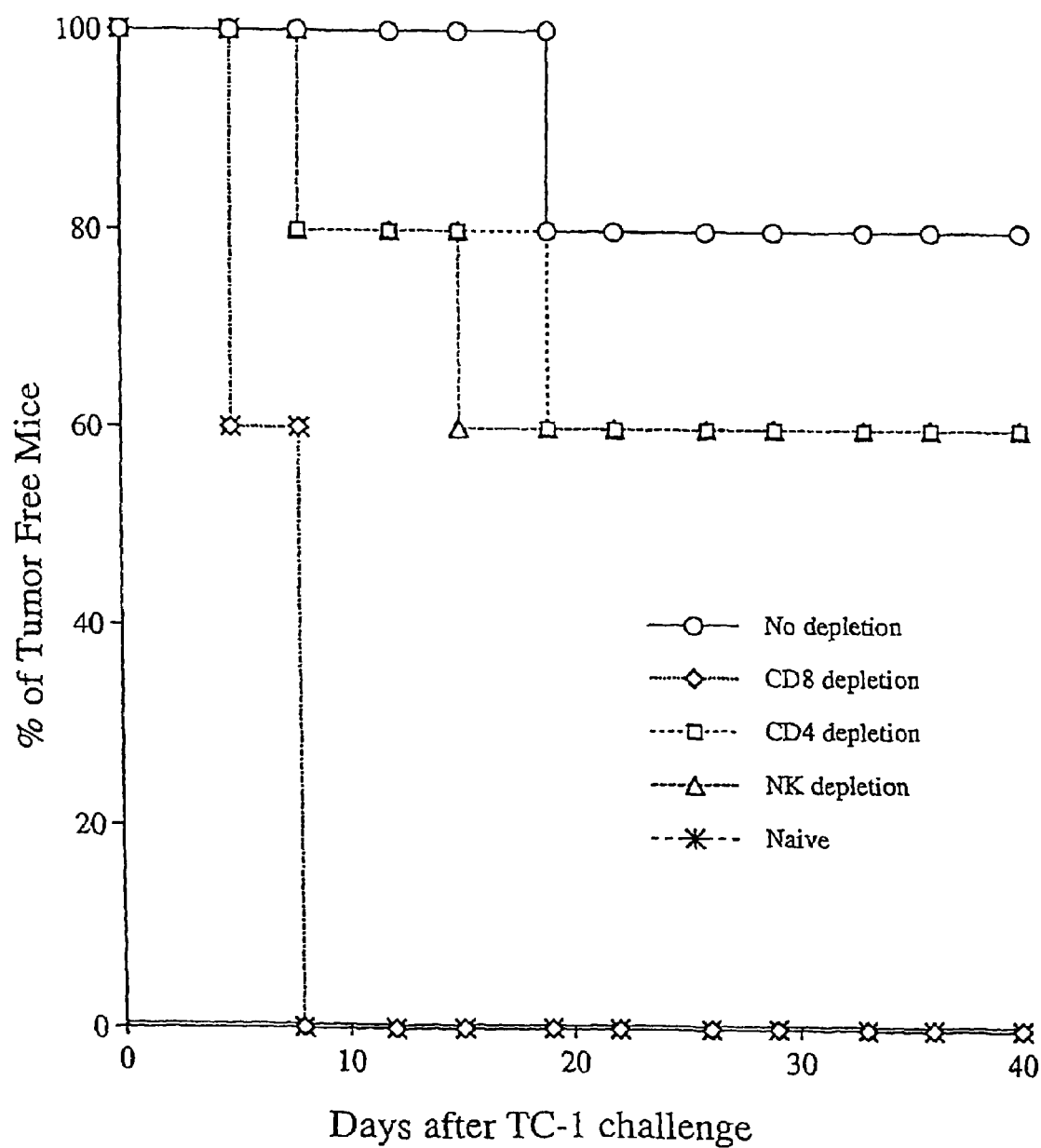
FIG. 17. In vivo antibody depletion experiments determined the requirement for cells of certain lymphocyte subsets on the potency of the pSCA1-E7/Hsp70 suicidal DNA vaccine. Mice were inoculated i.v. with tumors and treated with the pSCA1-E7/Hsp70 suicidal DNA vaccine as described herein. CD4, CD8 or NK1.1 depletion were initiated one week prior to tumor challenge and lasted 40 days after tumor challenge. All naïve mice and mice depleted of CD8$^+$ T cells grew tumors within 10 days

To determine the types of lymphocytes required for protection against E7-expressing tumors, in vivo antibody depletion experiments were done. As shown in FIG. 17, tumors grew out within 10 days of inoculation in all naïve mice and all mice depleted of $CD8^+$ T cells. In contrast, 80% of the non-depleted mice remained tumor free 40 days after tumor challenge. Tumor grew within two weeks in 40% of mice depleted of CD4+ or of NK1.1+ cells. These results suggest that $CD8^+$ T cells are essential for E7-specific anti-tumor immunity induced by the pSCA1-E7/Hsp70 suicidal DNA vaccine. CD4+ and NK1.1+ contributed to a lesser degree to the total antitumor effect.

Discussion

The inventors have demonstrated that linkage of Hsp70 to E7 significantly enhanced the potency of an E7-expressing DNA that was administered as a suicidal DNA vaccine based on a replicating RNA replicon. Such suicidal DNA incorporating Hsp70 fused to E7 generated potent E7-specific $CD8^+$ T cell-mediated immunity. Furthermore, this chimeric pSCA1-E7/Hsp70 suicidal DNA vaccine successfully prevented lethal pulmonary metastases in an experimental metastasis model.

Stimulation of $CD8^+$ T cell activity is important in antitumor immune responses. (For review, see Chen, CH et al., *J Biomed Sci* 1998, 5:231-52; Pardoll, D M *Nat Med* 1998, 4:525-3 1). Such immunity was augmented by administration of a pSCA1-E7/Hsp70 suicidal DNA vaccine and was manifest as protection against tumor growth and as therapy of a pre-existing tumor. The importance of this T cell subset is emphasized by the fact that depletion of $CD8^+$ CTLs abolished this effect. Activated CTL function as effector cells that kill tumor cells directly or through the release of cytokines that interfere with tumor cell growth or survival. Therefore, the enhanced antigen-specific antitumor $CD8^+$ T cell activity is critical to the potency of the pSCA1-E7/Hsp70 vaccine.

One mechanisms by which E7-specific $CD8^+$ T cell responses are stimulated in vivo is the direct MHC class I-restricted presentation of E7 to $CD8^+$ T cells by APCs that express E7/Hsp70. This is known as "direct priming". However, because the suicidal DNA vaccine eventually results in the apoptosis of the very cells it transfects, direct priming by directly transfected APCs is unlikely to be effective.

Rather the enhanced $CD8^+$ T cell responses observed in pSCA1-E7/Hsp70-vaccinated mice is likely a result of "cross priming," (Huang, A Y et al., *Science* 1994; 264:961-5) whereby cells expressing the E7/Hsp70 vaccine DNA release the antigen as an exogenous protein that is subsequently taken up and processed by other APCs via the MHC class I-restricted pathway. Cross-priming is the most likely mechanism for the enhanced $CD8^+$ T cell activity because the suicidal DNA composition lyses transfected cells (Frolov et al., *Proc Natl Acad Sci USA* 1996; 93:11371-7) leading to release of antigen which becomes available to other APCs. Previous studies reported that Hsp70 linked to malaria peptide (NANP) 40 (Barrios, C et al., *Clin Exp Immunol* 1994; 98:229-33), HIV-1 p24 (Suzue et al., supra), ovalbumin (Suzue, K et al., *Proc Natl Acad Sci USA* 1997; 94:13146-51), or influenza nucleoprotein (Anthony et al., supra) and administered as an exogenous protein enhanced MHC class I presentation of the linked antigens. Hsp70 fusion proteins are likely taken up by professional APCs which are known to be important in presenting exogenous Hsp70-associated antigens through the MHC class I pathway (Mitchell, D A et al., *Eur J Immunol* 1998; 28:1923-33; Suto, R et al., *Science* 1995; 269:1585-8). It was suggested that Hsp70 complexes can enter professional APCs via receptor-mediated endocytosis (Arnold-Schild et al., supra). Mtb HSP protein fused to antigen stimulated DCs in vitro and in vivo to upregulate the level of MHC class I, MHC class II and co-stimulatory molecules (Cho et al., supra). According to the present invention, the lytic effect of the pSCA1 vector, the enhancement of MHC class I processing, the maturation of DCs, all of which are induced by Hsp70 fused to the antigen, all contribute to augmentation of $CD8^+$ T cell activity resulting from be pSCA1-E7/Hsp70 vaccine via a cross-priming pathway.

Although use of suicidal DNA vectors and their induction of apoptosis alleviate some concerns about DNA vaccine integration into the host genome, the potency of such vaccines may be limited because of that same apoptotic outcome. The present inventors and their colleagues previously demonstrated that linkage of Mtb Hsp70 to E7 antigen enhanced the potency of a conventional naked DNA vaccine. (Chen et al., 2000, supra). Here, the inventors have successfully extended the chimeric Hsp70 strategy to a suicidal DNA vector. However, the DNA-based RNA replicon vector approach appeared to be less efficacious than the conventional DNA vector approach in generating E7-specific CD8+ T cells. For example, approximately 130 E7-specific CD8+ T cells were generated per $10^6$ splenocytes when vaccinating mice with the pSCA1-E7/Hsp70 composition. Meanwhile, the previous study of chimeric E7/Hsp70 in a conventional mammalian expression plasmid (pcDNA3) generated about 430 E7-specific CD8+ T cells per $10^6$ splenocytes in vaccinated mice. (Chen et al., supra). Although DNA-based replicons may be expected produce more E7 than do conventional DNA plasmids because of their self-replicating nature, Leitner et al. (supra) showed that replicon-based DNA plasmids did not produce more antigen. Furthermore, the apoptotic outcome of transfection with a DNA-based replicon may limit direct presentation of antigen by transfected APCs to CD8+ T cells, also contributing to lower vaccine potency.

This induction of apoptosis also raises concerns about potential tissue damage of the administration of such a vaccine. However, here, microscopic examination of the vital organs of E7/Hsp70-vaccinated mice did not reveal any significant histopathological changes.

Another risk is the presence of E7 protein in host cells (since E7 is a viral oncoprotein that disrupts cell cycle regulation by binding to tumor suppressor pRB protein in nuclei) leading to potential incidence and accumulation of genetic aberrations and eventual malignant transformation. Use of the suicidal DNA vector eases the concern about oncogenicity of E7 protein since the transfected cells eventually undergo apoptosis. Oncogenicity of E7 can be further reduced by introducing mutations into E7 DNA that eliminate binding of the E7 protein to pRB (Heck, D V et al., *Proc Natl Acad Sci USA* 1992; 89:4442-6) while the cells still maintain most of their antigenicity.

In summary, the results revealed that fusion of DNA encoding Mtb Hsp70 to DNA encoding HPV-16 E7 in a suicidal DNA vaccine resulted in a vaccine that induced marked antigen (E7)-specific $CD8^+$ T cell-responses manifest as a state of anti-tumor immunity against tumors expressing the antigen. Since a majority of cervical cancers express HPV E7, the present is useful for controlling of HPV-associated tumors. These findings are applicable to other tumors and types of cancer where tumor-specific antigens can be identified. Further, these findings are directly applicable to vaccines against organisms responsible for infectious diseases such as viruses, protozoa, fungi and bacteria. Because the DNA-based RNA replicon vaccines are stable and easy to prepare in mass quantities, such vaccines are particularly desirable in developing countries which have high prevalence of HPV-associated cervical malignancy while lacking facilities for storing biological agents

EXAMPLE III

Enhancement of DNA Vaccine Potency by Linking DNA Encoding Antigen to DNA Encoding the Extracellular Domain of Flt3-Ligand Prior to the present invention, To date, FL had not been used as part of a chimeric DNA vaccine. The present inventors and their colleagues investigated whether linking a full-length E7 DNA to DNA encoding the ECD of FL would enhance the potency of a DNA vaccine. They chose HPV-16 E7 as a model antigen for vaccine development (see above).

Studies were done to compare DNA vaccines containing wild-type E7 with DNA vaccines containing full-length E7 fused to FL for their stimulation of immune responses and their ability to protect animals against growth or metastasis of E7-expressing tumors (Lin et al., supra). The results presented below indicate that linking DNA encoding the ECD of FL to E7 dramatically increased the expansion and activation of E7-specific $CD8^+$ T cells, completely bypassing the CD4 arm. This strategy led not only to enhanced E7-specific $CD8^+$ T cell responses, but also to potent anti-tumor immunity against established metastatic tumors expressing E7.

Materials and Methods

Plasmid DNA Constructs and Preparation pcDNA3 was used as an expression vector (instead of a previously described pCMV-Neo-Bam vector (Chen et al., supra). The pcDNA3 expression vector was selected since it was used effectively to investigate the correlation between the E7-specifc T cell responses with the antitumor effects produced various DNA vaccines. The production of HPV-16 E7-expressing plasmid, pcDNA3-E7 has been described previously (Chen et al., supra).

For making the plasmid encoding the ECD of mouse FL, pcDNA3-FL, the DNA fragment encoding the signal peptide and ECD of mouse FL was first amplified with PCR using conditions described previously (Chen, CH et al., *Cancer Research.* 60:1035-1042., 2000) with a mouse FL DNA template, sfHAV-EO410 (ATCC, Manassas, Va.) and a set of primers: 5'-gggtctagaatgacagtgctggcgccagc-3' [SEQ ID NO:28] and 5'-gggggatccctgcctgggccgaggctctgg-3' [SEQ ID NO:29]. The amplified product was digested with XbaI and BamHI and further cloned into the XbaI and BamHI cloning sites of pcDNA3 vector (Invitrogen, Carlsbad, Calif.). For making pcDNA3-FL-E7, the E7 DNA fragment was isolated from pcDNA3-E7 by digestion with BamHI and HindIII and gel-recovered. The isolated fragment was cloned into the BamHI and HindIII cloning sites of pcDNA3-FL. For making pcDNA3-GFP, a DNA fragment encoding the green fluorescent protein (GFP) was first amplified in PCR using pEGFPN 1 DNA (Clontech, Palo Alto, Calif.) and a set of primers: 5'-atcggatccatggtgagcaagggcgaggag-3' [SEQ ID NO:30] and 5'gggaagctttacttgtacagctcgtccatg-3' [SEQ ID NO:31]. The amplified product was digested with BamHI and HindIII and cloned into the BamHI and HindIII cloning sites of pcDNA3 (Invitrogen). To make pDNA3-E7-GFP, the DNA fragment encoding E7 first amplified with PCR using pcDNA3-E7 as template and a set of primers: 5'-ggggaattcatgcatggagatacac-cta-3' [SEQ ID NO:32] and 5'-ggtggatccttgagaacagatgg-3' [SEQ ID NO:33]. The amplified product was digested with EcoRI and BamHI and cloned into the EcoRI and BamHI cloning sites of pcDNA3-GFP. For making pcDNA3-FL-E7-GFP, the DNA encoding the signal peptide and ECD of FL was amplified with PCR using pcDNA3-FL as a DNA template and a set of primers: 5'-gggtctagaatgacagtgctggcgccagc-3' [SEQ ID NO:34] and 5'-cgagaattcctgcctgggccgaggctctg-3' [SEQ ID NO:35]. The amplified product was digested with XbaI and EcoRI and cloned into the XbaI and EcoRI cloning sites of pcDNA3-E7-GFP vector. The accuracy of these constructs was confirmed by DNA sequencing. pcDNA3 DNA with FL, E7, FL-E7, E7-GFP or FL-E7-GFP inserts and the "empty" plasmid, pcDNA3 were transfected into subcloning-efficient DH5α™ cells (Life Technologies, USA). The DNA was then amplified and purified (Chen et al., supra). The integrity of plasmid DNA and the absence of E. coli DNA or RNA was checked in each preparation using 1% agarose gel electrophoresis. DNA concentration was determined by the optical density measured at 260 nm. The presence of inserted E7 fragment was confirmed by restriction enzyme digestion and gel electrophoresis.

The schematic domain structure of the Flt3-ligand protein and FL-E7 fusion peptide are shown in FIG. 18A. The sequence of the FL-E7 construct, comprising the ECD of FL is shown in FIG. 18B (SEQ IDNO:11 and 12). Residues 1-189 are FL-derived, residues 191-287 are E7-derived. The remaining residues (e.g.,, 288-302) are from the vector DNA.

Cell Lines

For description of TC-1 cells and their use, see above (and Lin et al., supra). A human embryonic kidney cell line, 293, expressing MHC genes H-2D$^b$ and H-2K$^b$ (293 D$^b$K$^b$) (Bloom, M B et al., J Exp Med. 185: 453-9, 1997) was a gift from Dr. J C Yang (National Cancer Institute, NIH, Bethesda). These cells were grown in DMEM containing 10% heat-inactivated fetal calf serum, 0.3% glutamine, 0.01 M HEPES, 100 U/ml penicillin, 100 μg/ml streptomycin and 400 μg/ml G418.

The production and maintenance of TC-1 cells has been described previously (20). On the day of tumor challenge, TC-1 cells were harvested by trypsinization, washed twice with 1× Hanks buffered salt solution (HBSS) and resuspended in 1×HBSS to the designated concentration for injection. A human embryonic kidney cell line, 293, expressing the MHC genes H-2D$^b$ and H-2K$^b$ (293 D$^b$K$^b$) (24) was a gift from Dr. J C Yang (National Cancer Institute, NIH, Bethesda, Md.). These cells were grown in DMEM containing 10% heat-inactivated fetal calf serum, 0.3% glutamine, 0.01 M HEPES, 100 U/ml penicillin, 100 μg/ml streptomycin and 400 μg/ml G418.

Confocal Fluorescence Microscopy

293 D$^b$K$^b$ cells transfected with pcDNA E7-GFP and pcDNA FL-E7-GFP DNA were cultured for 24-36 hr, then cytocentrifuged onto glass slides. Cells were fixed with 4% paraformaldehyde in 1×PBS for 30 min at room temperature, permeabilized with 1×PBS containing 0.05% saponin and 1% BSA, and then incubated with mouse anti-calnexin mAb (Stressgen Biotechnologies, Victoria, Canada) at a concentration of 1 μg/ml for 30 min at room temperature. Unbound antibodies were removed by washing three times in 1×PBS. The cells were then incubated with Cy3-conjugated F(ab')$_2$ fragment of goat anti-mouse IgG (Jackson ImmunoReseach Laboratories) at a concentration of 10 μg/ml for 30 min. The slides were washed with 1×PBS containing and 1% BSA. The glass slides were mounted with anti-fading medium, Mowiol 4-88 (Calbiochem Inc. La Jolla, Calif.) and covered with coverslips. Slides in which primary antibody was omitted were used as negative controls. Samples were examined on a confocal laser scanning microscope.

Mice 6- to 8-week-old female C57BL/6 mice from the National Cancer Institute (Frederick, Md.) were purchased and kept in the oncology animal facility of the Johns Hopkins Hospital (Baltimore, Md.). All animal procedures were performed according to approved protocols and in accordance with recommendations for the proper use and care of laboratory animals.

DNA Vaccination

Preparation of DNA-coated gold particles and gene gun particle-mediated DNA vaccination was performed using a helium-driven gene gun (Bio-rad, Hercules, Calif.) (see Chen et al., supra).

Intracytoplasmic Cytokine Staining and Flow Cytometry Analysis

Pooled splenocytes from groups of naïve or vaccinated mice (5 mice per group) were incubated either with (a) the E7 peptide (aa 49-57) including an MHC class I epitope (Fetlkamp et al., supra) for detecting E7-specific CD8$^+$ T cell precursors, or (b) the E7 peptide (aa 30-67) containing the MHC class II peptide (Tindle et al., supra) for detecting E7-specific CD4$^+$ T helper cell precursors.

E7 peptide was added at 2 μg/ml for 20 hours. Golgistop (Pharmingen, San Diego, Calif.) was added 6 hours before harvesting cells from the culture. Cells were washed once in FACScan buffer and stained with phycoerythrin (PE)-conjugated monoclonal rat anti-mouse CD8 or CD4 antibody (PharMingen, San Diego, Calif.). Cells were subjected to intracellular cytokine staining using the Cytofix/Cytoperm kit according to the manufacturer's instructions (PharMingen). FITC-conjugated anti-IFN-γ antibody and the immunoglobulin isotype control antibody (rat IgG1) were all purchased from PharMingen. Analysis was done on a Becton Dickinson FACScan with CELLQuest software (Becton Dickinson Immunocytometry System, Mountain View, Calif.).

ELISA for anti-E7 Antibody (see EXAMPLE I)

In Vivo Tumor Protection

These studies were generally as Example I and II: gene gun with 2 μg of FL DNA, E7 DNA, FL-E7 DNA, FL mixed with E7 (FL+E7), or unvaccinated. One week later, mice were boosted with the same regimen and challenged subcutaneously on day 14 with 10$^4$ TC-1 tumor cells in the right leg. Statistical analysis was performed using SAS version 6.12 (SAS Institute Inc., Cary, N.C., USA). Percent of tumor free mice was analyzed using the Kaplan-Meier analysis. Statistical significance was tested using log-rank statistics.

Tumor Therapy

The tumor cells and DNA vaccines were prepared as above. See Example H for description of tumor challenge. Three days later, mice were given 2 μg of a vaccine preparation ((FL DNA, E7 DNA, FL-E7 DNA via gene gun or were left unvaccinated)). One week later, animals were boosted using the same regimen and were sacrificed on day 25. Lung tumor nodules were evaluated as in Example II. Statistical significance was tested using one-way ANOVA.

In Vivo Antibody Depletion Experiments

The procedure was done as in Example II

Generation of DCs DCs were generated by culturing bone marrow cells in the presence of GM-CSF as described previously (Fernanadez, N C et al., Nat Med. 5: 405-11, 1999). Briefly, bone marrow was collected from mouse femurs and tibias. Erythrocytes were lysed, and the remaining cells were passed through a nylon mesh to remove small pieces of bone and debris. The cells were collected and 10$^6$ cells /ml were placed in 24-well plates in RPMI 1640 medium supplemented with 5% FCS, 2 mM β-mercaptoethanol, 1% nonessential amino acids, 100 U/ml penicillin and 100 μg/ml streptomycin (Life Technologies, Rockville, Md.) and 100 U/ml GM-CSF (PharMingen, San Diego, Calif.). Two-thirds of the medium was replaced every 2 days. Non-adherent cells were harvested on day 7 and characterized by flow cytometry for DC markers as previously described (Wang, T L et al., *Gene Therapy.* 7: 726-733., 2000).

Generation of E7-Specific CD8+ T Cell Lines

See Wang et al., supra. Briefly, female C57BL/6 (H-2$^b$) mice were immunized intraperitoneally with vaccinia-Sig/E7/LAMP-1. Splenocytes were harvested on day 8. The cells were incubated with IL-2 (20 U/ml) and E7 peptide (aa 49-57) (1 μM) for 6 days. Cells of the E7 specific CTL cell line were propagated in 24-well plates by mixing, in a final volume of 2 ml, (a) $10^6$ splenocytes that included the E7-specific CTLs (b) $3 \times 10^6$ irradiated splenocytes (c) IL-2 (20 U/ml) and (d) E7 peptide (aa 49-57) at 1 μM. This procedure was repeated every 6 days. The target-cell specificity of the E7 CTL line was characterized in a CTL assay. Flow cytometry was used demonstrate CD8 expression.

CTL Assay Using Transfected 293 $D^bK^b$ Cells as Target Cells

CTL assays were performed in 96-well round-bottom plates as described by Corr et al., (Corr, M et al., *J Immunol.* 163: 4721-7, 1999) and in Examples I and II. Transfected 293 $D^bK^b$ cells were used as target cells while E7-specific CD8+ T cells served as effectors. $5 \times 10^6$ 293 $D^bK^b$ cells were transfected with 20 μg of pcDNA3 (empty plasmid), E7, FL, or FL-E7 DNA vaccines with lipofectamine 2000 (Life Technologies, Rockville, Md.) according to manufacturer's instructions. Cells were collected 40-44 hr after transfection. Levels of E7 protein expression, determined by ELISA, were similar in E7 and FL-E7-transfected cells. Cells were incubated and lysis measured as above.

CTL Assay Using DCs Pulsed with Lysates of Transfected 293 $D^bK^b$ Cells as Target Cells CTL assays using as targets DCs pulsed with cell lysates were generally in accordance with Uger, R A et al., *J Immunol.* 160: 1598-605, 1998. Briefly, 293 $D^bK^b$ cells were transfected as above and subjected to three freeze-thaw cycles. Protein concentrations were determined using the BioRad protein assay (Bio-Rad, Hercules, Calif.) using the vendor's protocol. The quantity of E7 protein was determined by ELISA. Cell lysates from E7 or FL-E7 DNA transfected 293 $D^bK^b$ cells were standardized for E7 protein concentration.

DCs were prepared for use as target cells by pulsing $10^6$ DCs with different concentrations of cell lysates (50, 10, 2 and 0.4 μg/ml) in a final volume of 2 ml for 16-20 hrs. E7-specific CD8+ T cells were effector cells. CTL assays were performed at a fixed E/T ratio of 9 using $9 \times 10^4$ T cells and $10^4$ prepared DC targets in a final volume of 200 μl. Results were determined by measurements of LDH as above.

Results

Linkage of the Extracellular Domain of FL to E7 Protein Re-routes E7 into the Endoplasmic Reticulum To determine the expression and localization of wild-type E7 and E7 fusion proteins, DNA encoding the green fluorescent protein (GFP) was linked to the 3' end of E7 DNA and chimeric FL-E7 DNA as a tag. Transfection and subsequent examination by fluorescence microscopy was used to determine the expression and localization of wild-type and modified E7 protein. Levels of protein expression was quite similar between cells transfected with E7-GFP or FL-E7-GFP. As expected, cells transfected with the E7-GFP showed cytoplasmic/nuclear distribution. In comparison, cells transfected with the chimeric FL-E7-GFP displayed a network pattern consistent with endoplasmic reticulum (ER) localization. To test whether the FL-E7-GFP chimera had in fact been distributed to the ER, cells were further stained with an antibody to calnexin and examined by immunofluorescence. Calnexin is a well-characterized marker for the ER. Co-localization of E7-GFP and calnexin was only observed in cells transfected with FL-E7-GFP but not E7-GFP, indicating that at least some of the FL-E7 fusion product but not E7-GFP was targeted to ER compartments. These results indicated that the addition of the ECD of FL to E7 facilitates the entry into ER compartments.

Vaccination with FL-E7 Fusion DNA Significantly Enhanced E7-Specific CD8+ T Cell Responses CD8+ T lymphocytes are important effectors of anti-tumor immunity. As a measure of the E7-specific CD8+ T cell response generated by the FL-E7 DNA vaccine, intracellular IFNγ cytokine staining was evaluated in splenocytes from vaccinated mice. This is a sensitive functional assay for measuring IFN-γ production at the single-cell level (Murali-Kristna, K et al., *Immunity.* 8: 177-87).

Figure 19A:
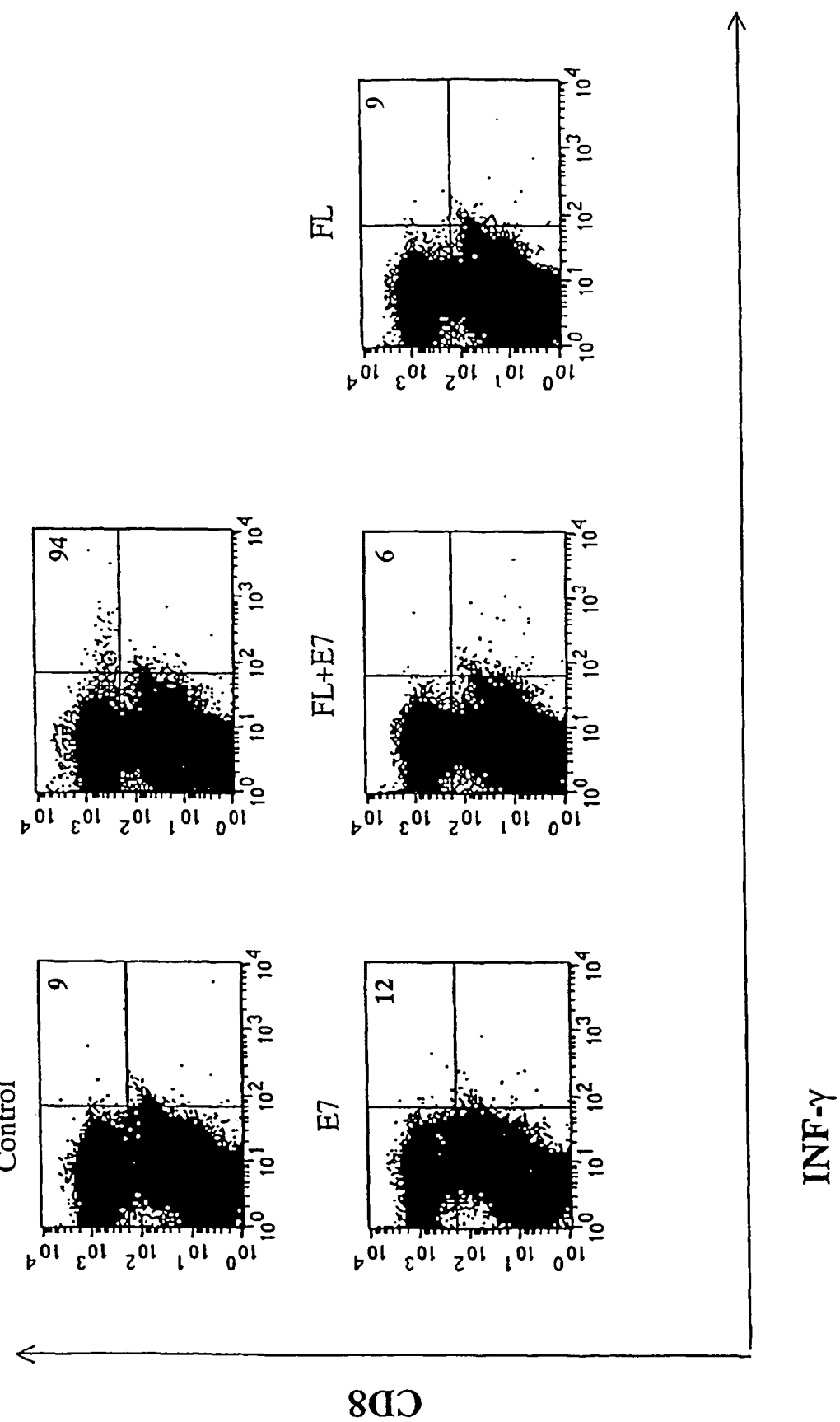
FIGS. 19A and 19B. Intracellular cytokine staining with flow cytometry analysis to determine E7-specific CD8$^+$ T cell precursors in C57BL/6 mice. Mice were immunized with FL DNA, E7 DNA (E7), FL-E7 DNA or FL mixed with E7 DNA (FL+E7) via gene gun, or received no vaccination. For vaccinated mice, 2 µg DNA /mouse was administered twice. Splenocytes were harvested 7 days after the last DNA vaccination. E7-specific CD8$^+$ T cells.
Figure 19B:
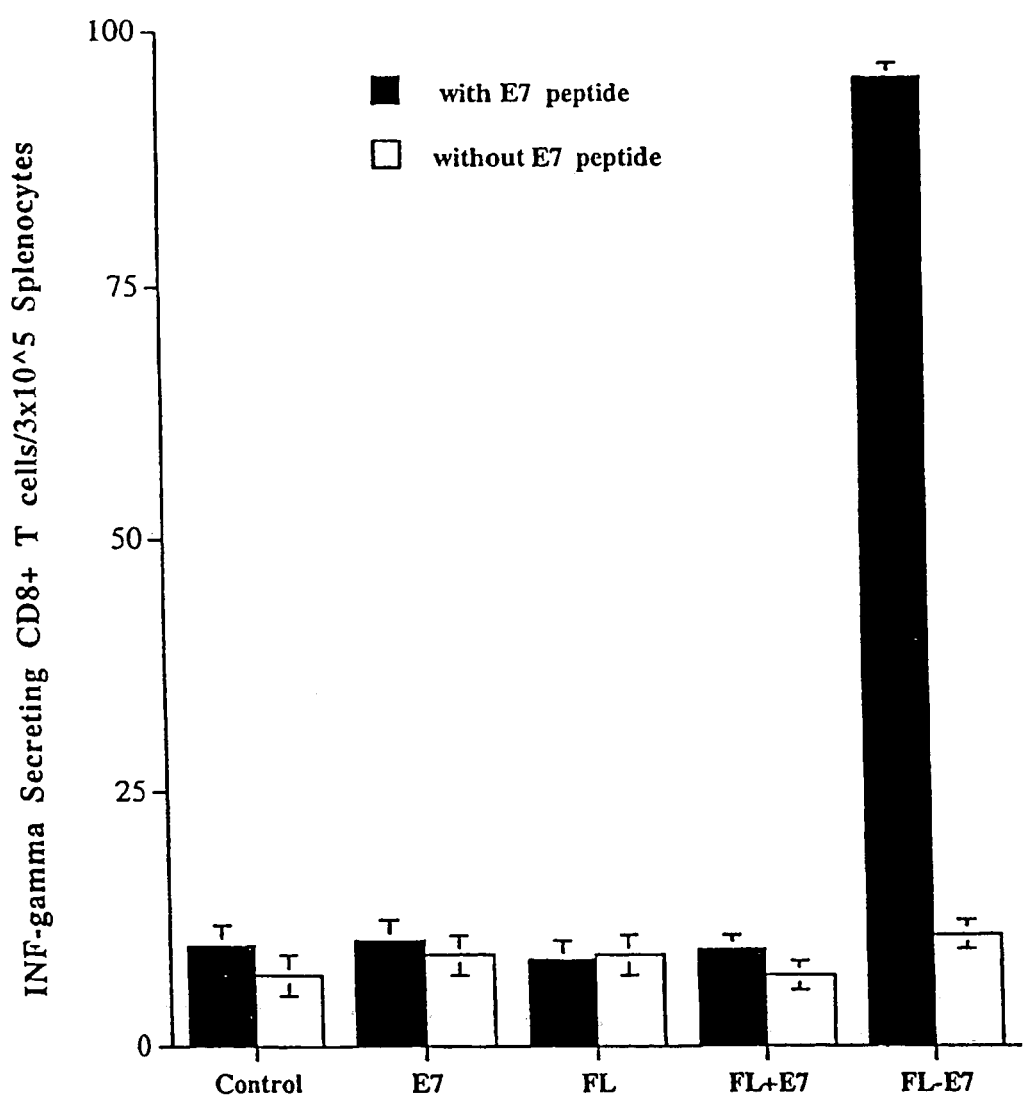

As shown in FIG. 19A and B, vaccination of mice with FL-E7 DNA generated the highest number of E7-specific IFN-γ+ CD8+ T cell precursors (940 per $3 \times 10^5$ splenocytes) compared to vaccination with E7 DNA (12 per $3 \times 10^5$ splenocytes) (p<0.01). Thus, FL-E7 DNA immunization led to a nearly 8-fold increase in the number of E7-specific CD8+ T cell precursors. These results also indicated that fusion of E7 to FL was required for this enhancement because vaccination with a mixture of FL-DNA and E7-DNA did not generate such enhanced CD8+ T cell activity.

Figures 20A, 20B:
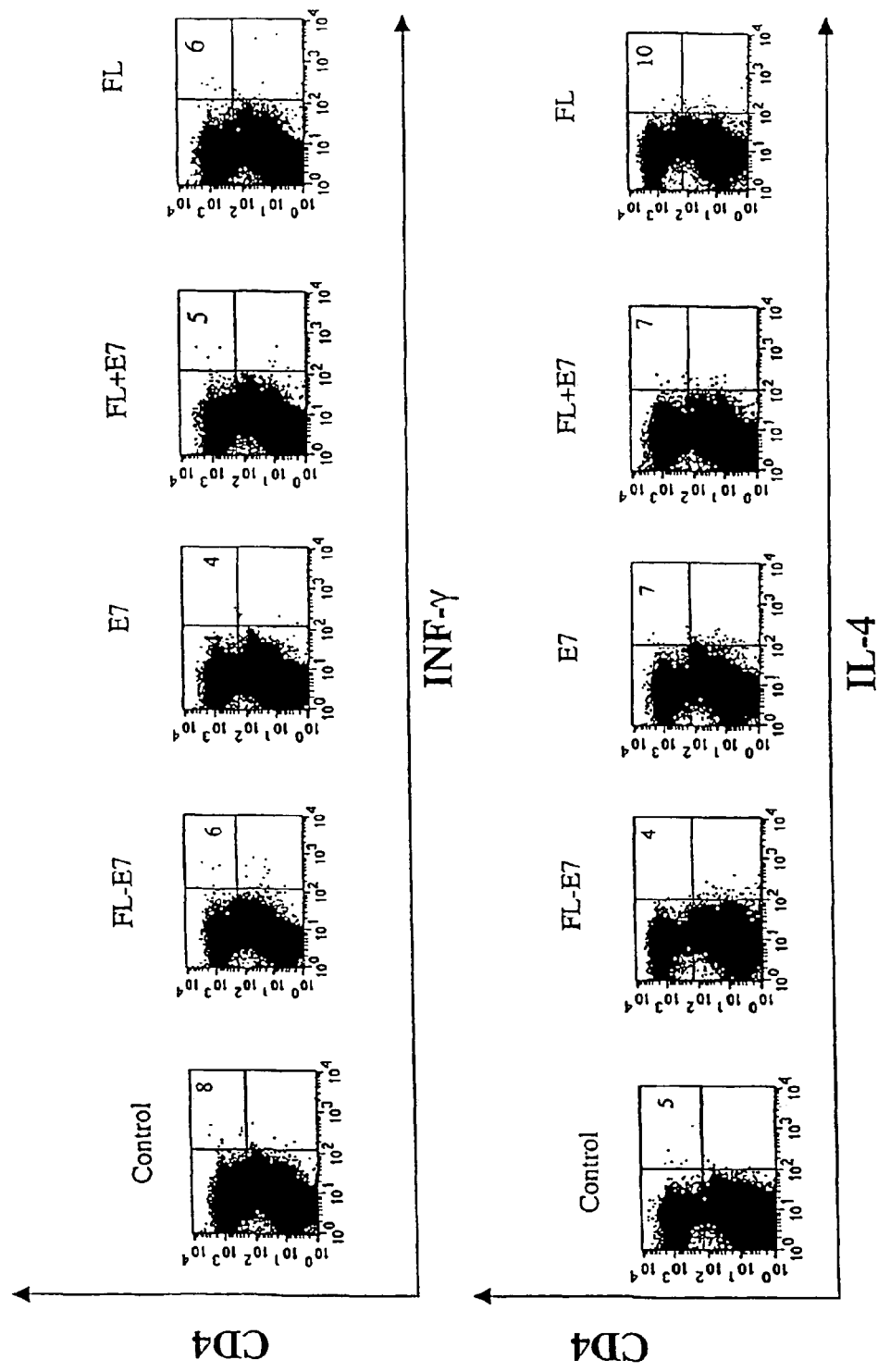
FIGS. 20A and 20B. Flow cytometry analysis of IFN-γ secreting and IL-4-secreting E7-specific CD4$^+$ cells in mice vaccinated with various recombinant DNA vaccines. Mice were immunized as described in FIG. Legend 2.

Vaccination with FL-E7 Fusion DNA did not Induce Significant E7-Specific CD4+ T Cell Responses or Anti-E7 Antibodies E7-specific CD4+ T precursor cells secreting the cytokine IFN-γ or IL-4) were assessed by double staining for surface CD4 and intracellular IFN-γ or IL-4 using flow cytometry Splenocytes were from immunized mice. FIG. 20A shows that mice vaccinated with FL-E7 DNA developed no significant increase in CD4+ IFN-γ+ double positive cells compared to mice vaccinated with FL DNA, wild-type E7 DNA, plasmid DNA or unvaccinated naïve mice. Positive control splenocytes were from Sig/E7/LAMP-1 DNA vaccinated mice (Ji et al., supra). Similarly, no significant increases in CD4+ IL-4+ double-positive cells were observed (FL-E7 vaccinated compared with FL DNA, wild-type E7 DNA, plasmid DNA or unvaccinated naïve mice (FIG. 20B). IL-4-secreting activated mouse splenocytes (MiCK-2, PharMingen) were positive controls to assure successful intracellular IL-4 staining.

To determine the levels of E7-specific antibodies in the sera of the vaccinated mice, ELISA was performed 2 weeks after the last vaccination. No significant E7-specific antibody responses were detected in mice. Sera of the mice vaccinated with chimeric FL-E7 DNA did not have higher titers of E7-specific antibodies compared to mice vaccinated with FL, empty plasmids, or unvaccinated naïve mice.

Figure 21:
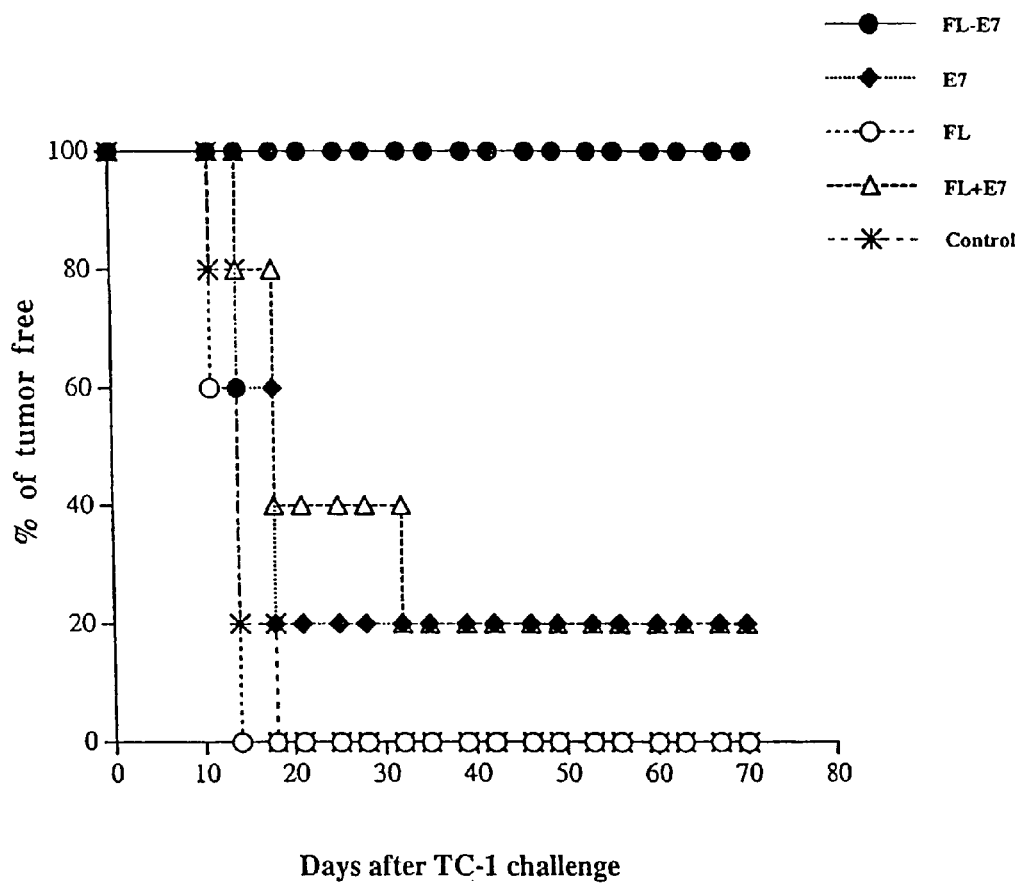
FIG. 21. In vivo tumor protection experiments against the growth of TC-1 tumors. Mice were immunized with FL DNA, E7 DNA, FL-E7 DNA or FL mixed with E7 DNA (FL+E7) via gene gun and boosted with the same regimen one week later. One week after the last vaccination, mice were challenged with $1\times10^4$ TC-1 cells/mouse subcutaneously. Mice were monitored for evidence of tumor growth by palpation and inspection twice a week. 100% of mice receiving FL-E7 DNA vaccination remained tumor-free 60 days after TC-1 challenge. The data collected from the in vivo tumor protection experiments shown here are from one representative experiment of two performed.

Vaccination with Chimeric FL-E7 DNA Vaccine Protects Mice Better Against the Growth of E7-Expressing TC-1 Tumors Results of an in vivo tumor protection study is shown in FIG. 21. 100% of mice vaccinated with FL-E7 DNA remained tumor-free 70 days after challenge (log-rank, p<0.001). In contrast, only 20% of mice receiving wild-type E7 remained tumor free after day 32 and all unvaccinated mice, or mice given FL DNA developed tumors within 20 days of challenge. Fusion of E7 to FL was required for generating protective immunity, since only 20% of mice vaccinated with a mixture E7 DNA and FL DNA) remained tumor free after 32 days. Therefore, FL-E7 fusion DNA significantly enhanced anti-tumor immunity.

Figure 23:
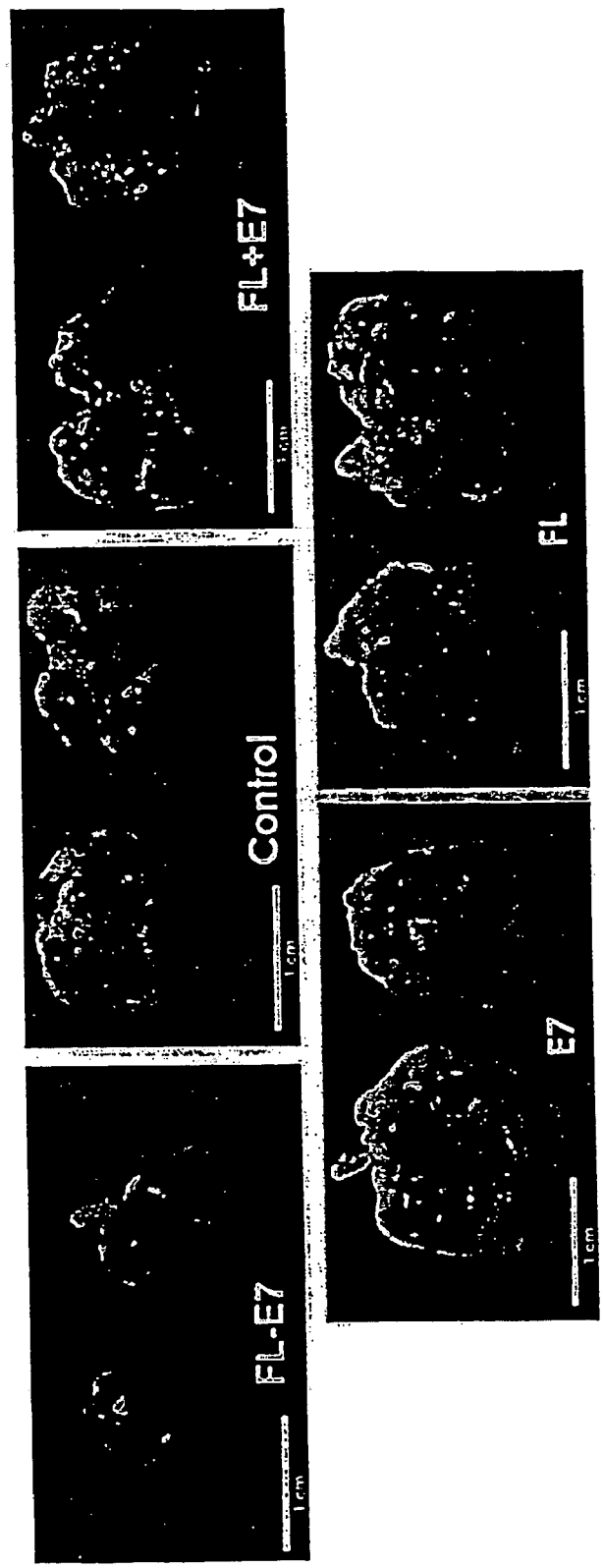
FIG. 23. Representative gross pictures of the lung tumors in each vaccinated group. Following in vivo tumor treatment experiments against pre-existing metastatic TC-1 tumor cells, there are multiple grossly visible lung tumors in unvaccinated control mice and mice vaccinated with FL, wild-type E7 DNA or FL mixed with E7 DNA. The lung tumors in FL-E7 vaccinated group cannot be seen at the magnification provided in this figure.

Treatment with FL-E7 Fusion DNA Eradicates Established E7-expressing Tumors in the Lungs To determine the therapeutic potential of a chimeric FL-E7 DNA construct in treating TC-1 lung metastases, each mouse was challenged with tumor cells i.v. Results are shown in FIG. 22A as the mean number of pulmonary metastatic tumor nodules ±SEM. Mice vaccinated with FL-E7 DNA had the lowest mean number of pulmonary nodules (5.8±3.6) compared to mice vaccinated with wild-type E7 DNA (67.5±3.5), FL DNA mixed with E7 DNA (68±15), FL DNA (65.0±5.0) or unvaccinated mice (50.7±7.3) (one-way ANOVA, p<0.001). FIG. 22B shows lung weights (mean ±SEM in grams). Mice vaccinated with FL-E7 DNA had the lowest lung weight (0.158±0.025) compared to mice vaccinated with wild-type E7 DNA (0.462±0.02), FL DNA plus E7 DNA (0.469±0.08), or FL DNA (0.6±0.03), or unvaccinated mice (0.645±0.08) (one-way ANOVA, p<0.001). Representative photographs of the lung tumors are shown in FIG. 23.

CD8+ T Cells but not CD4+ T Cells are Essential for Anti-Tumor Effects

Figure 24:
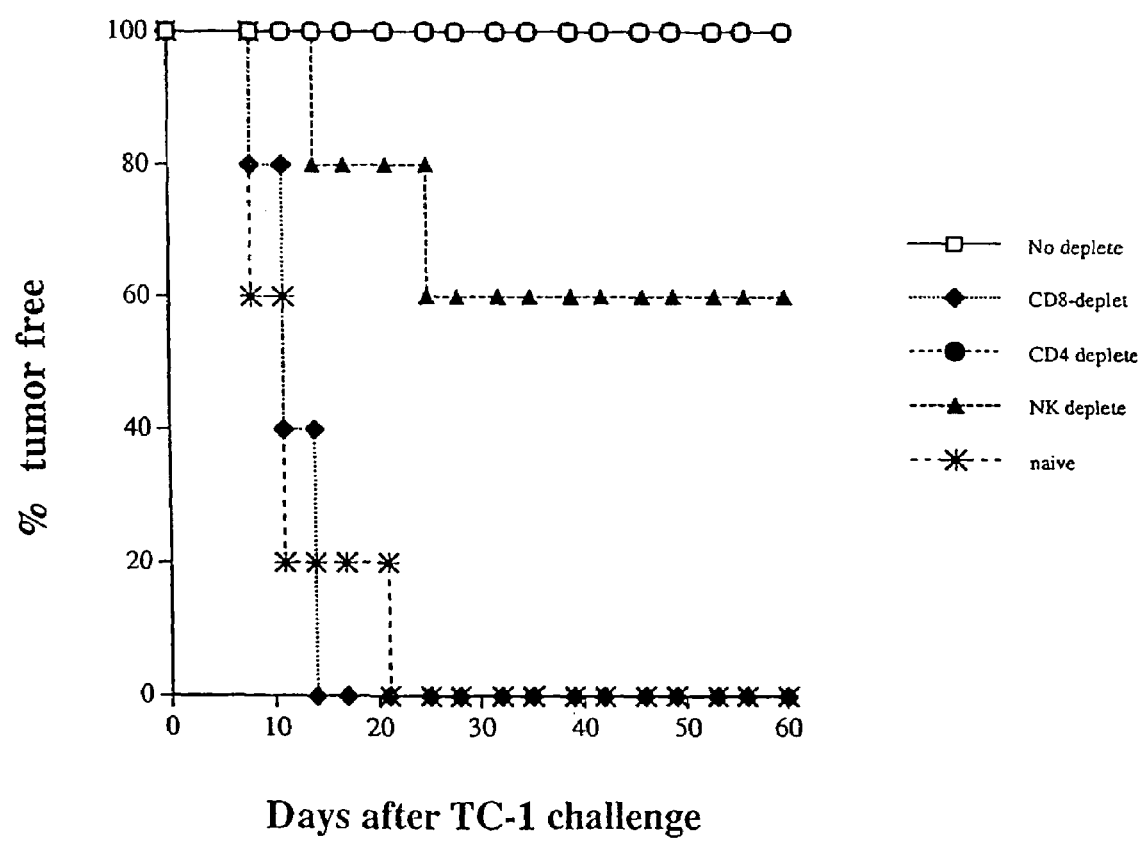
FIG. 24. In vivo antibody depletion experiments to determine the effect of lymphocyte subset on the potency of FL-E7 DNA vaccine. Mice were immunized with 2 μg FL-E7 DNA via gene gun and boosted with 2 μg FL-E7 DNA one week later. One week after the last vaccination, mice were challenged with $1\times10^4$ TC-1 cells/mouse subcutaneously. CD4, CD8 and NK1.1 depletions were initiated one week prior to tumor challenge and lasted 40 days after tumor challenge. Note: all of the unvaccinated mice and all of the mice depleted of CD8+ T cells grew tumors within 14 days after tumor challenge. The data of antibody depletion experiments shown here are from one representative experiment of two performed.

To determine the types of lymphocytes required for protection against E7-expressing tumors, in vivo antibody depletion experiments (Lin et al., supra; Wu et al., 1995, supra) were done. Depletion of lymphocyte subsets was assessed on the day of tumor injection, and weekly thereafter by flow cytometric analysis of spleen cells. More than 99% of cells of the appropriate subset were depleted in all cases without effect on the other subsets. As shown in FIG. 24, 100% of unvaccinated mice and mice depleted of CD8+ T cells grew tumors within 14 days after challenge. In contrast, all non-depleted mice and all mice depleted of CD4+ T cells remained tumor-free 60 days after challenge. 40% of mice in which NK1.1+ cells were depleted grew tumors 6 weeks after challenge. Even though there appeared to have been an effect of NK cell depletion, the difference from controls is result was not statistically significant (log-rank, p=.13). It was concluded that CD8+ T cells are essential for E7-specific antitumor immunity-induced by the-FL-E7 DNA vaccine.

Enhanced Presentation of E7 via the MHC Class I Pathway in Cells Transfected with FL-E7 DNA As noted earlier, mice vaccinated with FL-E7 generated the highest number of E7-specific CD8+ T cell precursors. To understand the mechanism underlying this effect, the inventors tested whether enhanced MHC class I presentation of E7 occurred in cells expressing FL-E7 (in this case, human embryonic kidney 293 cells $D^bK^b$ transfected with FL-E7). CTL assays employing $D^b$-restricted E7-specific CD8+ effector T cells were used to determine if target 293 $D^bK^b$ cells transfected with FL-E7 were killed more efficiently than 293 $D^bK^b$ cells transfected with wild-type E7. 293 $D^bK^b$ cells were selected because of their stable and high transfection efficiency (Bloom et al., supra). In addition, levels of E7 expression in 293 $D^bK^b$ cells transfected with FL-E7 DNA or E7 DNA were similar.

Figure 25:
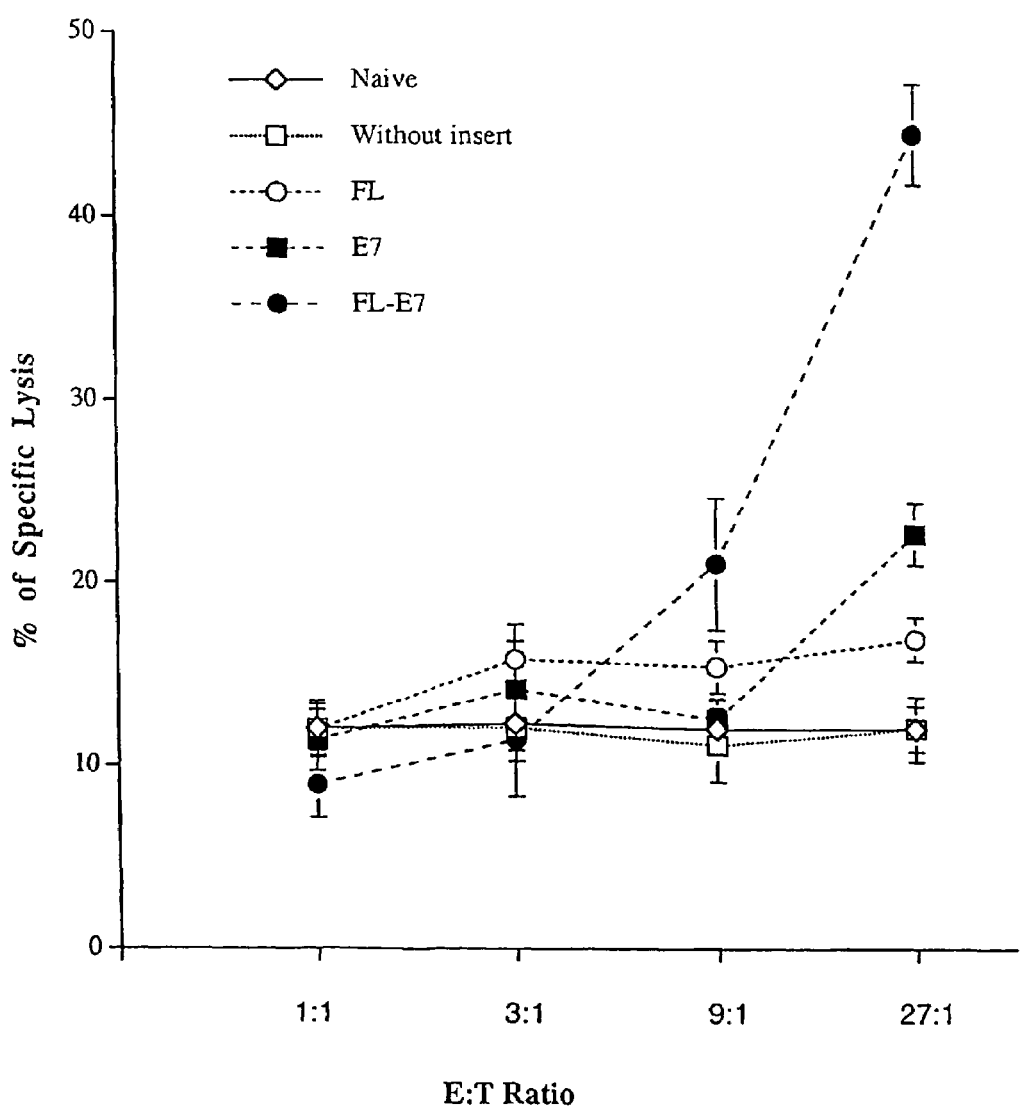
FIG. 25. CTL assays to demonstrate enhanced presentation of E7 through the MHC class I pathway in cells transfected with FL-E7 DNA. 293 $D^bK^b$ cells were transfected with various DNA vaccines with lipofectamine and collected 40-44 hr after transfection. Transfected 293 $D^bK^b$ cells were used as target cells while $D^b$-restricted E7-specific CD8+ T cells were used as effector cells. CTL assays with various E/T ratios were performed. Note: The 293 $D^bKb$ cells transfected with FL-E7 DNA generated significantly higher percentages of specific lysis as compared to 293 $D^bKb$ cells transfected with other DNA vaccines. CTL assays shown here are from one representative experiment of two performed.

In the CTL assays, targets were 293 $D^bK^b$ cells that had been transfected with either empty plasmid, FL DNA, E7 DNA, or FL-E7 DNA, or that were not transfected. Effector cells were added to achieve various E/T ratios (1, 3, 9, 27). As shown in FIG. 25, 293 $D^bK^b$ cells transfected with FL-E7 DNA were lysed at a higher level than targets cells transfected with wild-type E7 DNA. Transfection with FL-E7 DNA thus resulted in more efficient presentation of E7 antigen via the MHC class I pathway.

Enhanced Presentation of E7 Through the MHC Class I Pathway in DCs Pulsed With Chimeric FL-E7 Protein Enhanced E7-specific CD8+ T cell responses in vivo may occur as a result of presentation of E7 via the MHC class I pathway resulting from uptake of lysed cellular material expressing various E7 constructs by host APCs ("cross-priming").

A cross priming experiment was performed to characterize the MHC class I presentation of E7 of DCs pulsed with cell lysates of 293 $D^bK^b$ cells transfected with empty plasmid, FL, E7, or FL-E7 DNA.

Figure 26:
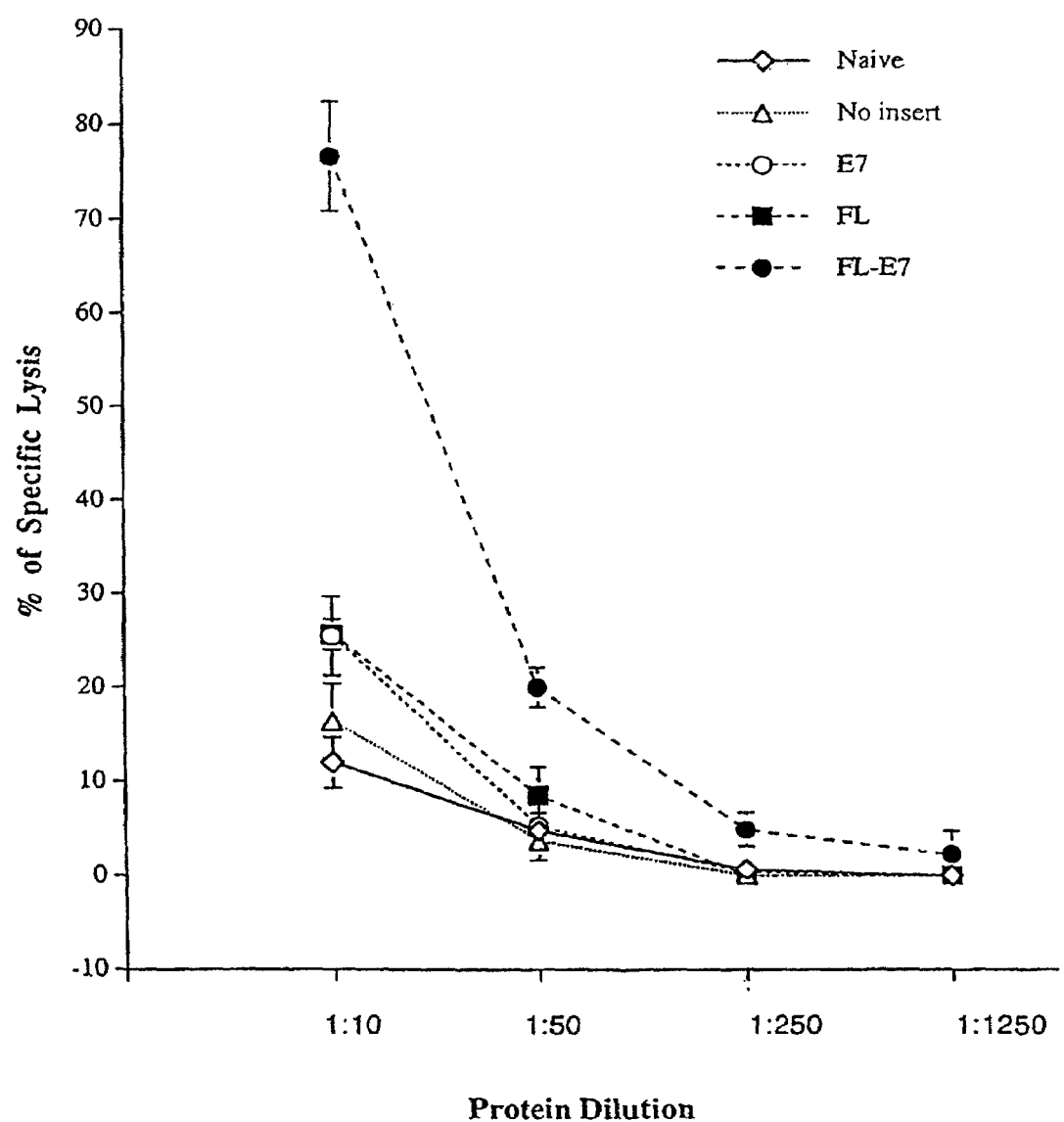
FIG. 26. CTL assays to demonstrate enhanced MHC class I presentation of E7 in bone marrow derived dendritic cells pulsed with cell lysates containing chimeric FL-E7 protein. Bone marrow-derived DCs were pulsed with cell lysates from 293 $D^bKb$ cells transfected with various DNA vaccines in different concentration (50 μg/ml, 10 μg/ml, 2 μg/ml, and 0.4 μg/ml) for 16-24 hrs. $D^b$-restricted E7-specific CD8+ T cells were used as effector cells. CTL assays was performed at fixed E/T (9/1) ratio with $9\times10^4$ of E7-specific T cells mixed with $1\times10^4$ of prepared DCs in a final volume of 200 μl. Results of CTL assays were assessed using by quantitative measurements of LDH as described in the Materials and Methods. Note: DCs pulsed with lysates from cells transfected with FL-E7 DNA generated significantly higher percentages of specific lysis compared to DCs pulsed with lysates from cells transfected with other DNA vaccines. CTL assays shown here are from one representative experiment of two performed.

Lysates of transfected 293 $D^bK^b$ cells were obtained by repeated cycles of freeze-thaw. $10^6$ bone marrow-derived DCs were pulsed with serial dilutions (50, 10, 2 or 0.4 μg) of lysate derived from 293 $D^bK^b$ cells transfected with different constructs. These DCs were used as target cells for lysis by $D^b$-restricted E7-specific CD8+ CTL. CTL assays were performed at a fixed E/T ratio of 9. As shown in FIG. 26, DCs pulsed with lysates from 293 $D^bK^b$ cells transfected with FL-E7 DNA were lysed at a higher percentage compared to DCs pulsed with lysates from 293 $D^bK^b$ cells transfected with the other DNA constructs and non-transfected DCs. It was concluded that DCs pulsed with FL-E7 fusion protein presented E7 antigen through the MHC class I pathway more efficiently than DCs pulsed with wild-type E7 protein. Thus, the fusion of FL to E7 enhanced E7-specific CD8+ T cell immune responses via cross priming effects.

Discussion

The foregoing study demonstrated that linking the ECD of FL to E7 significantly enhanced the potency of E7-expressing DNA vaccines to induce potent CD8+ T cell-immune responses that were protective and therapeutic against E7-expressing tumors, such that mice were protected from both primary tumor growth and development of lethal pulmonary metastases.

The incorporation of FL into the vaccine preferentially enhanced CD8+ T cell responses vs. E7-specific CD4+ T cell responses that were not significantly changed. Linking FL to E7 in the vaccine directly enhanced MHC class I presentation of E7 (compared to a wild-type E7 vaccine) in transfected cells in vitro. Since biolistic DNA delivery introduces DNA directly into dermal professional APCs, FL-E7 DNA-transfected APCs may act by directly presenting E7 via the MHC class I pathway to CD8+ T cells in vivo.

Although it is not clear how this linkage directly enhances MHC class I presentation, one mechanism involves a chaperone effect of FL. When expressed in cells, FL may be distributed to the ER (Chklovoskaia, E et al., *Blood.* 93: 2595-604, 1999). Fluorescence microscopic examination revealed that in cells transfected with FL-E7-GFP, most of the FL-E7-GFP fusion protein co-localized with calnexin in the ER, suggesting that this linkage facilitates entry of E7 into the ER. Several studies demonstrated that ER targeting can enhance antigen-specific MHC class I-restricted CTL activity (Shiver, J W et al., *J Pharm Sci* 85: 1317-24, 1996; Hsu, S C et al., *Int Immunol.* 10: 1441-7, 1998).

Another mechanism that may contribute to the present observations is "cross-priming," whereby lysis of cells expressing FL-E7 releases protein that is taken up and processed by other APCs via the MHC class I-restricted pathway. The present results show that DCs pulsed with FL-E7 fusion protein are capable of presenting E7 antigen through the MHC class I pathway in a more efficient manner than DCs pulsed with wild-type E7 protein. (FIG. 26). However, the "cross-priming" of chimeric FL-E7 probably does not play a major role in gene gun-mediated FL-E7 DNA vaccination. Direct priming, but not cross-priming, of CD8+ T cells by DNA-transfected DCs is the key event in gene gun-mediated DNA immunization (Porgador, A et al., *J Exp Med.* 188: 1075-82, 1998; Akbari, O et al., *J Exp Med.* 189: 169-78, 1999). However, the possibility of cross-priming cannot be ruled out, because FL-E7 might be released from other cell types, such as keratinocytes (which are also transfected by gene gun vaccination), and then enter DCs via a cross-priming mechanism.

No significant increases in the numbers of DCs or NK cells were detected in the spleens of mice vaccinated with FL-E7 DNA vaccines even though FL is known to expand these cell-populations-(Peron et al., supra; Williams, N S et al., *J Exp Med*. 186: 1609-14, 1997, Shaw, S G et al., *J Immunol*. 161: 2817-24, 1998). This may be related to small amounts of FL-E7 present in the circulation after DNA vaccination. FL-E7 protein could not be detected in sera of mice vaccinated with FL-E7 DNA, which also raises a question about the source of FL-E7 protein for cross-priming. FL-E7 protein from the lysis of transfected keratinocytes may be taken up by Langerhans' cells and further processed in the draining lymph nodes without entering the circulation in detectable quantities.

The E7 DNA vaccine described above had weaker antitumor effects compared to an E7 DNA vaccine using a different mammalian expression vector (Chen et al., 1999, supra Ji et al., supra). In these previous studies, a pCMV-Neo-Bam expression vector that includes the HCMV promoter was used E7 DNA vaccine using that vector generated a very impressive antitumor effect in the relative absence of E7-specific CD8$^+$ T cell responses. In the current study, a relatively weak E7-specific CD8$^+$ T cell response and a relatively weak anti-tumor response were observed in mice vaccinated with E7 DNA in the form of the pcDNA3 vector. The discrepancy in the anti-tumor response evoked by the same DNA in a different vector may be explained simply by different levels of expression. Furthermore, bacterial DNA can contain immunostimulatory elements such as CpG islands (Sato, Y et al., *Science*. 273: 352-4, 1996; Klinman, D M et al., *J Immunol*. 158: 3635-9, 1997), which can cause simultaneous maturation and activation of DCs (Sparwasser, T et al., *Eur J Immunol*. 28: 2045-54, 1998) thereby acting as an adjuvant for tumor immunization (Weiner, G J et al., *Proc Natl Acad Sci USA*. 94: 10833-7, 1997).

The FL-E7 DNA vaccine may raise certain safety concerns because DNA could integrate into the host genome, though it is estimated that the frequency of integration is much lower than that of spontaneous mutation and should not pose any real risk (Nichols, W W et al., *Annals of NY Academy of Science*. 772: 30-39., 1995). The risks of HPV-16 E7 protein was discussed above. There is a concern about possible autoimmune effects resulting from excessive expansion of DCs in vivo. However, here, no significant increase in the numbers of DCs was observed in the spleen and lymph nodes of mice vaccinated with FL or FL-E7 DNA vaccines. Examination of vital organs in all of the FL-E7-vaccinated mice did not reveal any significant gross or microscopic pathology. Therefore, FL-E7 can be used as a potent DNA vaccine without observable-detrimental side effects.

In summary, fusion of DNA encoding the ECD of the FL protein to E7 DNA generated potent E7-specific CD8$^+$ T cell responses and anti-tumor effects against E7-expressing tumors. Linkage of DNA encoding FL to DNA encoding an antigen enhances the potency of DNA vaccines and are applicable to other tumors and types of cancer where tumor-specific antigens can be identified. Further, these findings are directly applicable to vaccines against organisms responsible for infectious diseases such as viruses, protozoa, fungi and bacteria.

The references cited above are all incorporated by reference herein, whether specifically incorporated or not. All publications, patents, patent applications, GenBank sequences and ATCC deposits, cited herein are hereby expressly incorporated by reference for all purposes.

Citation of the documents herein is not intended as an admission that any of them is pertinent prior art. All statements as to the date or representation as to the contents of these documents is based on the information available to the applicant and does not constitute any admission as to the correctness of the dates or contents of these documents.

What is claimed is:

1. A eukaryotic expression vector comprising a nucleic acid molecule encoding a fission polypeptide consisting of:
   (a) a first polypeptide consisting of an amino acid sequence selected from the group consisting of SEQ ID NO:4, amino acids 312 to the C-terminal amino acid of SEQ ID NO: 4, amino acids 517 to the C-terminal amino acid of SEQ ID NO: 4, and a fragment of SEQ ID NO:4 comprising amino acids 517 to the C-terminal amino acid of SEQ ID NO: 4 ; and
   (b) a second polypeptide comprising an antigenic polypeptide or peptide.

2. The eukaryotic expression vector of claim 1, wherein the antigenic peptide comprises an epitope that binds to a MHC class I protein.

3. The eukaryotic expression vector of claim 2, wherein said epitope is between about 8 amino acid residues and about 11 amino acid residues in length.

4. The eukaryotic expression vector of claim 1, which comprises a promoter that is active in a mammalian cell.

5. The eukaryotic expression vector of claim 4, wherein the promoter is one which is expressed in an APC.

6. The eukaryotic expression vector of claim 1, wherein the first polypeptide consists of the amino acid sequence from amino acid 517 to the C-terminal amino acid of SEQ ID NO:4.

7. The eukaryotic expression vector of claim 1, wherein the first polypeptide consists of a fragment of SEQ ID NO:4 comprising amino acids 517 to the C-terminal amino acid of SEQ ID NO: 4.

8. The eukaryotic expression vector of claim 1, wherein the second polypeptide is located N-terminal to the first polypeptide.

9. The eukaryotic expression vector of claim 1, wherein the antigen is one which is present on or cross-reactive with an epitope of a pathogenic organism, cell, or virus.

10. The eulkaryotic expression vector of claim 9, wherein the virus is a human papilloma virus.

11. The eukaryotic expression vector of claim 10, wherein the antigen is the E7 polypeptide of HPV-16 or an antigenic fragment thereof, or the E6 polypeptide of HPV-16 or an antigenic fragment thereof.

12. The eukaryotic expression vector of claim 9, wherein the pathogenic cell is a tumor cell, and wherein the antigen is a tumor-specific or tumor-associated antigen, or any antigenic epitope thereof.

13. The eukaryotic expression vector of claim 1, wherein the first polypeptide consists of the amino acid sequence from amino acid 312 to the C-terminal amino acid of SEQ ID NO:4.

14. The expression vector of claim 1 which is a viral vector or a plasmid.

15. The expression vector of claim 14, wherein said plasmid is pcDNA3.

16. The expression vector of claim 1 which is a self-replicating RNA replicon.

17. The expression vector of claim 16, wherein the self-replicating RNA replicon is a Sindbis virus self-replicating RNA replicon.

18. The expression vector of claim 17, wherein the replicon consists of the sequence of SEQ ID NO: 16.

19. A pharmaceutical composition for inducing or enhancing an antigen-specific immune response, comprising:
   a pharmaceutically and immunologically acceptable excipient in combination with;
   the expression vector of claim 17.

20. The expression vector of claim 1 which is a suicidal DNA vector.

21. The expression vector of claim 20 wherein said suicidal DNA vector is an alphavirus DNA vector.

22. The expression vector of claim 21 wherein said alphavirus is Semliki Forest virus (SFV).

23. The expression vector of claim 22 wherein said SFV vector is pSCA1.

24. The expression vector of claim 20 wherein the suicidal DNA is derived from the sequence of SEQ ID NO: 17 into which is inserted the nucleic acid sequences encoding said first or said second polypeptides.

25. An isolated cell comprising the expression vector of claim 1.

26. A pharmaceutical composition for inducing or enhancing an antigen-specific immune response, comprising:
- a pharmaceutically and immunologically acceptable excipient in combination with;
- the isolated cell of claim 25.

27. The isolated cell of claim 25 which is an APC.

28. The isolated cell of claim 27 wherein the APC is a dendritic cell, a keratinocyte, a macrophage, a monocyte, a B lymphocyte, a microglial cell, an astrocyte, or an activated endothelial cell.

29. A particle comprising the expression vector of claim 1.

30. The particle of claim 29 which comprises a material that is suitable for introduction into a cell or an animal by particle bombardment.

31. The particle of claim 30, wherein the material is gold.

32. A pharmaceutical composition for inducing or enhancing an antigen-specific immune response, comprising:
- a pharmaceutically and immunologically acceptable excipient in combination with;
- the particle of claim 29.

33. A pharmaceutical composition for inducing or enhancing an antigen-specific immune response, comprising:
- a pharmaceutically and immunologically acceptable excipient in combination with;
- the eukaryotic expression vector of claim 1.

34. The eukaryotic expression vector of claim 1, wherein the fusion polypeptide consists of SEQ ID NO: 8.

35. A eukaryotic expression vector comprising a nucleic acid molecule encoding a fusion polypeptide consisting of:
- (a) a first polypeptide consisting of an amino acid sequence selected from the group consisting of SEQ ID NO:4, amino acids 312 to the C-terminal amino acid of SEQ ID NO: 4, amino acids 517 to the C-terminal amino acid of SEQ ID NO: 4, and a fragment of SEQ ID NO:4 comprising amino acids 517 to the C-terminal amino acid of SEQ ID NO: 4;
- (b) a second polypeptide comprising an antigenic polypeptide or peptide; and
- (c) a third polypeptide comprising a linker peptide.

36. The eukaryotic expression vector of claim 35, wherein the first polypeptide is encoded by a first nucleic acid sequence, the second polypeptide is encoded by a second nucleic acid sequence, and the third polypeptide is encoded by a third nucleic acid sequence, wherein the first and second nucleic acid sequences are independently linked in frame to the third nucleic acid sequence.

* * * * *

SEQUENCE LISTING

<160> NUMBER OF SEQ ID NOS: 35

<210> SEQ ID NO 1
<211> LENGTH: 297
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(297)

<400> SEQUENCE: 1

```
atg cat gga gat aca cct aca ttg cat gaa tat atg tta gat ttg caa      48
Met His Gly Asp Thr Pro Thr Leu His Glu Tyr Met Leu Asp Leu Gln
1               5                   10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
    50                  55                  60
```

```
ctt cgg ttg tgc gta caa agc aca cac gta gac att cgt act ttg gaa      240
Leu Arg Leu Cys Val Gln Ser Thr His Val Asp Ile Arg Thr Leu Glu
 65                  70                  75                  80 gac ctg tta atg ggc aca cta gga att gtg tgc ccc atc tgt tct cag      288
Asp Leu Leu Met Gly Thr Leu Gly Ile Val Cys Pro Ile Cys Ser Gln
                 85                  90                  95 gat aag ctt                                                          297
Asp Lys Leu <210> SEQ ID NO 2
<211> LENGTH: 99
<212> TYPE: PRT
<213> ORGANISM: Artificial Sequence
<220> FEATURE:
<223> OTHER INFORMATION: Synthetic Construct

<400> SEQUENCE: 2

Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Asp Lys Leu

<210> SEQ ID NO 3
<211> LENGTH: 1809
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(1809)

<400> SEQUENCE: 3 atg gct cgt gcg gtc ggg atc gac ctc ggg acc acc aac tcc gtc gtc       48
Met Ala Arg Ala Val Gly Ile Asp Leu Gly Thr Thr Asn Ser Val Val
 1               5                  10                  15 tcg gtt ctg gaa ggt ggc gac ccg gtc gtc gtc gcc aac tcc gag ggc       96
Ser Val Leu Glu Gly Gly Asp Pro Val Val Val Ala Asn Ser Glu Gly
                20                  25                  30 tcc agg acc acc ccg tca att gtc gcg ttc gcc cgc aac ggt gag gtg      144
Ser Arg Thr Thr Pro Ser Ile Val Ala Phe Ala Arg Asn Gly Glu Val
            35                  40                  45 ctg gtc ggc cag ccc gcc aag aac cag gca gtg acc aac gtc gat cgc      192
Leu Val Gly Gln Pro Ala Lys Asn Gln Ala Val Thr Asn Val Asp Arg
        50                  55                  60 acc gtg cgc tcg gtc aag cga cac atg ggc agc gac tgg tcc ata gag      240
Thr Val Arg Ser Val Lys Arg His Met Gly Ser Asp Trp Ser Ile Glu
 65                  70                  75                  80 att gac ggc aag aaa tac acc gcg ccg gag atc agc gcc cgc att ctg      288
Ile Asp Gly Lys Lys Tyr Thr Ala Pro Glu Ile Ser Ala Arg Ile Leu
                 85                  90                  95 atg aag ctg aag cgc gac gcc gag gcc tac ctc ggt gag gac att acc      336
```

```
            Met Lys Leu Lys Arg Asp Ala Glu Ala Tyr Leu Gly Glu Asp Ile Thr
                        100                 105                 110 gac gcg gtt atc acg acg ccc gcc tac ttc aat gac gcc cag cgt cag       384
Asp Ala Val Ile Thr Thr Pro Ala Tyr Phe Asn Asp Ala Gln Arg Gln
            115                 120                 125 gcc acc aag gac gcc ggc cag atc gcc ggc ctc aac gtg ctg cgg atc       432
Ala Thr Lys Asp Ala Gly Gln Ile Ala Gly Leu Asn Val Leu Arg Ile
            130                 135                 140 gtc aac gag ccg acc gcg gcc gcg ctg gcc tac ggc ctc gac aag ggc       480
Val Asn Glu Pro Thr Ala Ala Ala Leu Ala Tyr Gly Leu Asp Lys Gly
145                 150                 155                 160 gag aag gag cag cga atc ctg gtc ttc gac ttg ggt ggt ggc act ttc       528
Glu Lys Glu Gln Arg Ile Leu Val Phe Asp Leu Gly Gly Gly Thr Phe
                165                 170                 175 gac gtt tcc ctg ctg gag atc ggc gag ggt gtg gtt gag gtc cgt gcc       576
Asp Val Ser Leu Leu Glu Ile Gly Glu Gly Val Val Glu Val Arg Ala
            180                 185                 190 act tcg ggt gac aac cac ctc ggc ggc gac gac tgg gac cag cgg gtc       624
Thr Ser Gly Asp Asn His Leu Gly Gly Asp Asp Trp Asp Gln Arg Val
            195                 200                 205 gtc gat tgg ctg gtg gac aag ttc aag ggc acc agc ggc atc gat ctg       672
Val Asp Trp Leu Val Asp Lys Phe Lys Gly Thr Ser Gly Ile Asp Leu
            210                 215                 220 acc aag gac aag atg gcg atg cag cgg ctg cgg gaa gcc gcc gag aag       720
Thr Lys Asp Lys Met Ala Met Gln Arg Leu Arg Glu Ala Ala Glu Lys
225                 230                 235                 240 gca aag atc gag ctg agt tcg agt cag tcc acc tcg atc aac ctg ccc       768
Ala Lys Ile Glu Leu Ser Ser Ser Gln Ser Thr Ser Ile Asn Leu Pro
                245                 250                 255 tac atc acc gtc gac gcc gac aag aac ccg ttg ttc tta gac gag cag       816
Tyr Ile Thr Val Asp Ala Asp Lys Asn Pro Leu Phe Leu Asp Glu Gln
            260                 265                 270 ctg acc cgc gcg gag ttc caa cgg atc act cag gac ctg ctg gac cgc       864
Leu Thr Arg Ala Glu Phe Gln Arg Ile Thr Gln Asp Leu Leu Asp Arg
            275                 280                 285 act cgc aag ccg ttc cag tcg gtg atc gct gac acc ggc att tcg gtg       912
Thr Arg Lys Pro Phe Gln Ser Val Ile Ala Asp Thr Gly Ile Ser Val
            290                 295                 300 tcg gag atc gat cac gtt gtg ctc gtg ggt ggt tcg acc cgg atg ccc       960
Ser Glu Ile Asp His Val Val Leu Val Gly Gly Ser Thr Arg Met Pro
305                 310                 315                 320 gcg gtg acc gat ctg gtc aag gaa ctc acc ggc ggc aag gaa ccc aac      1008
Ala Val Thr Asp Leu Val Lys Glu Leu Thr Gly Gly Lys Glu Pro Asn
                325                 330                 335 aag ggc gtc aac ccc gat gag gtt gtc gcg gtg gga gcc gct ctg cag      1056
Lys Gly Val Asn Pro Asp Glu Val Val Ala Val Gly Ala Ala Leu Gln
            340                 345                 350 gcc ggc gtc ctc aag ggc gag gtg aaa gac gtt ctg ctg ctt gat gtt      1104
Ala Gly Val Leu Lys Gly Glu Val Lys Asp Val Leu Leu Leu Asp Val
            355                 360                 365 acc ccg ctg agc ctg ggt atc gag acc aag ggc ggg gtg atg acc agg      1152
Thr Pro Leu Ser Leu Gly Ile Glu Thr Lys Gly Gly Val Met Thr Arg
            370                 375                 380 ctc atc gag cgc aac acc acg atc ccc acc aag cgg tcg gag act ttc      1200
Leu Ile Glu Arg Asn Thr Thr Ile Pro Thr Lys Arg Ser Glu Thr Phe
385                 390                 395                 400 acc acc gcc gac gac aac caa ccg tcg gtg cag atc cag gtc tat cag      1248
Thr Thr Ala Asp Asp Asn Gln Pro Ser Val Gln Ile Gln Val Tyr Gln
            405                 410                 415
```

```
ggg gag cgt gag atc gcc gcg cac aac aag ttg ctc ggg tcc ttc gag      1296
Gly Glu Arg Glu Ile Ala Ala His Asn Lys Leu Leu Gly Ser Phe Glu
            420                 425                 430 ctg acc ggc atc ccg ccg gcg ccg cgg ggg att ccg cag atc gag gtc      1344
Leu Thr Gly Ile Pro Pro Ala Pro Arg Gly Ile Pro Gln Ile Glu Val
        435                 440                 445 act ttc gac atc gac gcc aac ggc att gtg cac gtc acc gcc aag gac      1392
Thr Phe Asp Ile Asp Ala Asn Gly Ile Val His Val Thr Ala Lys Asp
450                 455                 460 aag ggc acc ggc aag gag aac acg atc cga atc cag gaa ggc tcg ggc      1440
Lys Gly Thr Gly Lys Glu Asn Thr Ile Arg Ile Gln Glu Gly Ser Gly
465                 470                 475                 480 ctg tcc aag gaa gac att gac cgc atg atc aag gac gcc gaa gcg cac      1488
Leu Ser Lys Glu Asp Ile Asp Arg Met Ile Lys Asp Ala Glu Ala His
                485                 490                 495 gcc gag gag gat cgc aag cgt cgc gag gag gcc gat gtt cgt aat caa      1536
Ala Glu Glu Asp Arg Lys Arg Arg Glu Glu Ala Asp Val Arg Asn Gln
            500                 505                 510 gcc gag aca ttg gtc tac cag acg gag aag ttc gtc aaa gaa cag cgt      1584
Ala Glu Thr Leu Val Tyr Gln Thr Glu Lys Phe Val Lys Glu Gln Arg
        515                 520                 525 gag gcc gag ggt ggt tcg aag gta cct gaa gac acg ctg aac aag gtt      1632
Glu Ala Glu Gly Gly Ser Lys Val Pro Glu Asp Thr Leu Asn Lys Val
530                 535                 540 gat gcc gcg gtg gcg gaa gcg aag gcg gca ctt ggc gga tcg gat att      1680
Asp Ala Ala Val Ala Glu Ala Lys Ala Ala Leu Gly Gly Ser Asp Ile
545                 550                 555                 560 tcg gcc atc aag tcg gcg atg gag aag ctg ggc cag gag tcg cag gct      1728
Ser Ala Ile Lys Ser Ala Met Glu Lys Leu Gly Gln Glu Ser Gln Ala
                565                 570                 575 ctg ggg caa gcg atc tac gaa gca gct cag gct gcg tca cag gcc act      1776
Leu Gly Gln Ala Ile Tyr Glu Ala Ala Gln Ala Ala Ser Gln Ala Thr
            580                 585                 590 ggc gct gcc cac ccc ggc tcg gct gat gaa agc                          1809
Gly Ala Ala His Pro Gly Ser Ala Asp Glu Ser
        595                 600

<210> SEQ ID NO 4
<211> LENGTH: 603
<212> TYPE: PRT
<213> ORGANISM: Artificial Sequence
<220> FEATURE:
<223> OTHER INFORMATION: Synthetic Construct

<400> SEQUENCE: 4

Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110
```

-continued

```
Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
        355                 360                 365

Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
            420                 425                 430

Leu Thr Gly Ile Pro Pro Ala Pro Arg Gly Ile Pro Gln Ile Glu Val
        435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Glu Ala Asp Val Arg Asn Gln
            500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
```

```
                530                 535                 540
Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
                580                 585                 590

Gly Ala Ala His Pro Gly Ser Ala Asp Glu Ser
            595                 600

<210> SEQ ID NO 5
<211> LENGTH: 81
<212> TYPE: DNA
<213> ORGANISM: Mycobacterium tuberculosis

<400> SEQUENCE: 5
ggcgagccgg gcggtgccca ccccggctcg gctgatgacg ttgtggacgc ggaggtggtc        60
gacgacggcc gggaggccaa g                                                  81

<210> SEQ ID NO 6
<211> LENGTH: 15
<212> TYPE: DNA
<213> ORGANISM: Artificial Sequence
<220> FEATURE:
<223> OTHER INFORMATION: synthetic construct

<400> SEQUENCE: 6
tcggctgatg aaagc                                                         15

<210> SEQ ID NO 7
<211> LENGTH: 2104
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(2103)

<400> SEQUENCE: 7 atg cat gga gat aca cct aca ttg cat gaa tat atg tta gat ttg caa         48
Met His Gly Asp Thr Pro Thr Leu His Glu Tyr Met Leu Asp Leu Gln
1               5                  10                  15 cca gag aca act gat ctc tac tgt tat gag caa tta aat gac agc tca         96
Pro Glu Thr Thr Asp Leu Tyr Cys Tyr Glu Gln Leu Asn Asp Ser Ser
                20                  25                  30 gag gag gag gat gaa ata gat ggt cca gct gga caa gca gaa ccg gac        144
Glu Glu Glu Asp Glu Ile Asp Gly Pro Ala Gly Gln Ala Glu Pro Asp
            35                  40                  45 aga gcc cat tac aat att gta acc ttt tgt tgc aag tgt gac tct acg        192
Arg Ala His Tyr Asn Ile Val Thr Phe Cys Cys Lys Cys Asp Ser Thr
        50                  55                  60 ctt cgg ttg tgc gta caa agc aca cac gta gac att cgt act ttg gaa        240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct caa        288
Asp Leu Leu Met Gly Thr Leu Gly Ile Val Cys Pro Ile Cys Ser Gln
                85                  90                  95 gga tcc atg gct cgt gcg gtc ggg atc gac ctc ggg acc acc aac tcc        336
Gly Ser Met Ala Arg Ala Val Gly Ile Asp Leu Gly Thr Thr Asn Ser
                100                 105                 110
```

```
gtc gtc tcg gtt ctg gaa ggt ggc gac ccg gtc gtc gtc gcc aac tcc      384
Val Val Ser Val Leu Glu Gly Gly Asp Pro Val Val Val Ala Asn Ser
        115                 120                 125 gag ggc tcc agg acc acc ccg tca att gtc gcg ttc gcc cgc aac ggt      432
Glu Gly Ser Arg Thr Thr Pro Ser Ile Val Ala Phe Ala Arg Asn Gly
130                 135                 140 gag gtg ctg gtc ggc cag ccc gcc aag aac cag gca gtg acc aac gtc      480
Glu Val Leu Val Gly Gln Pro Ala Lys Asn Gln Ala Val Thr Asn Val
145                 150                 155                 160 gat cgc acc gtg cgc tcg gtc aag cga cac atg ggc agc gac tgg tcc      528
Asp Arg Thr Val Arg Ser Val Lys Arg His Met Gly Ser Asp Trp Ser
            165                 170                 175 ata gag att gac ggc aag aaa tac acc gcg ccg gag atc agc gcc cgc      576
Ile Glu Ile Asp Gly Lys Lys Tyr Thr Ala Pro Glu Ile Ser Ala Arg
            180                 185                 190 att ctg atg aag ctg aag cgc gac gcc gag gcc tac ctc ggt gag gac      624
Ile Leu Met Lys Leu Lys Arg Asp Ala Glu Ala Tyr Leu Gly Glu Asp
        195                 200                 205 att acc gac gcg gtt atc acg acg ccc gcc tac ttc aat gac gcc cag      672
Ile Thr Asp Ala Val Ile Thr Thr Pro Ala Tyr Phe Asn Asp Ala Gln
        210                 215                 220 cgt cag gcc acc aag gac gcc ggc cag atc gcc ggc ctc aac gtg ctg      720
Arg Gln Ala Thr Lys Asp Ala Gly Gln Ile Ala Gly Leu Asn Val Leu
225                 230                 235                 240 cgg atc gtc aac gag ccg acc gcg gcc gcg ctg gcc tac ggc ctc gac      768
Arg Ile Val Asn Glu Pro Thr Ala Ala Ala Leu Ala Tyr Gly Leu Asp
                245                 250                 255 aag ggc gag aag gag cag cga atc ctg gtc ttc gac ttg ggt ggt ggc      816
Lys Gly Glu Lys Glu Gln Arg Ile Leu Val Phe Asp Leu Gly Gly Gly
            260                 265                 270 act ttc gac gtt tcc ctg ctg gag atc ggc gag ggt gtg gtt gag gtc      864
Thr Phe Asp Val Ser Leu Leu Glu Ile Gly Glu Gly Val Val Glu Val
        275                 280                 285 cgt gcc act tcg ggt gac aac cac ctc ggc ggc gac gac tgg gac cag      912
Arg Ala Thr Ser Gly Asp Asn His Leu Gly Gly Asp Asp Trp Asp Gln
        290                 295                 300 cgg gtc gtc gat tgg ctg gtg gac aag ttc aag ggc acc agc ggc atc      960
Arg Val Val Asp Trp Leu Val Asp Lys Phe Lys Gly Thr Ser Gly Ile
305                 310                 315                 320 gat ctg acc aag gac aag atg gcg atg cag cgg ctg cgg gaa gcc gcc     1008
Asp Leu Thr Lys Asp Lys Met Ala Met Gln Arg Leu Arg Glu Ala Ala
                325                 330                 335 gag aag gca aag atc gag ctg agt tcg agt cag tcc acc tcg atc aac     1056
Glu Lys Ala Lys Ile Glu Leu Ser Ser Ser Gln Ser Thr Ser Ile Asn
            340                 345                 350 ctg ccc tac atc acc gtc gac gcc gac aag aac ccg ttg ttc tta gac     1104
Leu Pro Tyr Ile Thr Val Asp Ala Asp Lys Asn Pro Leu Phe Leu Asp
        355                 360                 365 gag cag ctg acc cgc gcg gag ttc caa cgg atc act cag gac ctg ctg     1152
Glu Gln Leu Thr Arg Ala Glu Phe Gln Arg Ile Thr Gln Asp Leu Leu
    370                 375                 380 gac cgc act cgc aag ccg ttc cag tcg gtg atc gct gac acc ggc att     1200
Asp Arg Thr Arg Lys Pro Phe Gln Ser Val Ile Ala Asp Thr Gly Ile
385                 390                 395                 400 tcg gtg tcg gag atc gat cac gtt gtg ctc gtg ggt ggt tcg acc cgg     1248
Ser Val Ser Glu Ile Asp His Val Val Leu Val Gly Gly Ser Thr Arg
                405                 410                 415 atg ccc gcg gtg acc gat ctg gtc aag gaa ctc acc ggc ggc aag gaa     1296
Met Pro Ala Val Thr Asp Leu Val Lys Glu Leu Thr Gly Gly Lys Glu
            420                 425                 430
```

```
ccc aac aag ggc gtc aac ccc gat gag gtt gtc gcg gtg gga gcc gct         1344
Pro Asn Lys Gly Val Asn Pro Asp Glu Val Val Ala Val Gly Ala Ala
            435                 440                 445 ctg cag gcc ggc gtc ctc aag ggc gag gtg aaa gac gtt ctg ctg ctt         1392
Leu Gln Ala Gly Val Leu Lys Gly Glu Val Lys Asp Val Leu Leu Leu
450                 455                 460 gat gtt acc ccg ctg agc ctg ggt atc gag acc aag ggc ggg gtg atg         1440
Asp Val Thr Pro Leu Ser Leu Gly Ile Glu Thr Lys Gly Gly Val Met
465                 470                 475                 480 acc agg ctc atc gag cgc aac acg atc ccc acc aag cgg tcg gag              1488
Thr Arg Leu Ile Glu Arg Asn Thr Thr Ile Pro Thr Lys Arg Ser Glu
                485                 490                 495 act ttc acc acc gcc gac gac aac caa ccg tcg gtg cag atc cag gtc         1536
Thr Phe Thr Thr Ala Asp Asp Asn Gln Pro Ser Val Gln Ile Gln Val
            500                 505                 510 tat cag ggg gag cgt gag atc gcc gcg cac aac aag ttg ctc ggg tcc         1584
Tyr Gln Gly Glu Arg Glu Ile Ala Ala His Asn Lys Leu Leu Gly Ser
            515                 520                 525 ttc gag ctg acc ggc atc ccg ccg gcg ccg cgg ggg att ccg cag atc         1632
Phe Glu Leu Thr Gly Ile Pro Pro Ala Pro Arg Gly Ile Pro Gln Ile
530                 535                 540 gag gtc act ttc gac atc gac gcc aac ggc att gtg cac gtc acc gcc         1680
Glu Val Thr Phe Asp Ile Asp Ala Asn Gly Ile Val His Val Thr Ala
545                 550                 555                 560 aag gac aag ggc acc ggc aag gag aac acg atc cga atc cag gaa ggc         1728
Lys Asp Lys Gly Thr Gly Lys Glu Asn Thr Ile Arg Ile Gln Glu Gly
                565                 570                 575 tcg ggc ctg tcc aag gaa gac att gac cgc atg atc aag gac gcc gaa         1776
Ser Gly Leu Ser Lys Glu Asp Ile Asp Arg Met Ile Lys Asp Ala Glu
            580                 585                 590 gcg cac gcc gag gag gat cgc aag cgt cgc gag gag gcc gat gtt cgt         1824
Ala His Ala Glu Glu Asp Arg Lys Arg Arg Glu Glu Ala Asp Val Arg
            595                 600                 605 aat caa gcc gag aca ttg gtc tac cag acg gag aag ttc gtc aaa gaa         1872
Asn Gln Ala Glu Thr Leu Val Tyr Gln Thr Glu Lys Phe Val Lys Glu
            610                 615                 620 cag cgt gag gcc gag ggt ggt tcg aag gta cct gaa gac acg ctg aac         1920
Gln Arg Glu Ala Glu Gly Gly Ser Lys Val Pro Glu Asp Thr Leu Asn
625                 630                 635                 640 aag gtt gat gcc gcg gtg gcg gaa gcg aag gcg gca ctt ggc gga tcg         1968
Lys Val Asp Ala Ala Val Ala Glu Ala Lys Ala Ala Leu Gly Gly Ser
                645                 650                 655 gat att tcg gcc atc aag tcg gcg atg gag aag ctg ggc cag gag tcg         2016
Asp Ile Ser Ala Ile Lys Ser Ala Met Glu Lys Leu Gly Gln Glu Ser
            660                 665                 670 cag gct ctg ggg caa gcg atc tac gaa gca gct cag gct gcg tca cag         2064
Gln Ala Leu Gly Gln Ala Ile Tyr Glu Ala Ala Gln Ala Ala Ser Gln
            675                 680                 685 gcc act ggc gct gcc cac ccc ggc tcg gct gat gaa agc a                    2104
Ala Thr Gly Ala Ala His Pro Gly Ser Ala Asp Glu Ser
690                 695                 700
```

<210> SEQ ID NO 8
<211> LENGTH: 701
<212> TYPE: PRT
<213> ORGANISM: Artificial Sequence
<220> FEATURE:
<223> OTHER INFORMATION: Synthetic Construct

<400> SEQUENCE: 8

-continued

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Gly Ser Met Ala Arg Ala Val Gly Ile Asp Leu Gly Thr Thr Asn Ser
            100                 105                 110

Val Val Ser Val Leu Glu Gly Gly Asp Pro Val Val Val Ala Asn Ser
        115                 120                 125

Glu Gly Ser Arg Thr Thr Pro Ser Ile Val Ala Phe Ala Arg Asn Gly
    130                 135                 140

Glu Val Leu Val Gly Gln Pro Ala Lys Asn Gln Ala Val Thr Asn Val
145                 150                 155                 160

Asp Arg Thr Val Arg Ser Val Lys Arg His Met Gly Ser Asp Trp Ser
                165                 170                 175

Ile Glu Ile Asp Gly Lys Lys Tyr Thr Ala Pro Glu Ile Ser Ala Arg
            180                 185                 190

Ile Leu Met Lys Leu Lys Arg Asp Ala Glu Ala Tyr Leu Gly Glu Asp
        195                 200                 205

Ile Thr Asp Ala Val Ile Thr Thr Pro Ala Tyr Phe Asn Asp Ala Gln
    210                 215                 220

Arg Gln Ala Thr Lys Asp Ala Gly Gln Ile Ala Gly Leu Asn Val Leu
225                 230                 235                 240

Arg Ile Val Asn Glu Pro Thr Ala Ala Ala Leu Ala Tyr Gly Leu Asp
                245                 250                 255

Lys Gly Glu Lys Glu Gln Arg Ile Leu Val Phe Asp Leu Gly Gly Gly
            260                 265                 270

Thr Phe Asp Val Ser Leu Leu Glu Ile Gly Glu Gly Val Val Glu Val
        275                 280                 285

Arg Ala Thr Ser Gly Asp Asn His Leu Gly Gly Asp Trp Asp Gln
290                 295                 300

Arg Val Val Asp Trp Leu Val Asp Lys Phe Lys Gly Thr Ser Gly Ile
305                 310                 315                 320

Asp Leu Thr Lys Asp Lys Met Ala Met Gln Arg Leu Arg Glu Ala Ala
                325                 330                 335

Glu Lys Ala Lys Ile Glu Leu Ser Ser Ser Gln Ser Thr Ser Ile Asn
            340                 345                 350

Leu Pro Tyr Ile Thr Val Asp Ala Asp Lys Asn Pro Leu Phe Leu Asp
        355                 360                 365

Glu Gln Leu Thr Arg Ala Glu Phe Gln Arg Ile Thr Gln Asp Leu Leu
    370                 375                 380

Asp Arg Thr Arg Lys Pro Phe Gln Ser Val Ile Ala Asp Thr Gly Ile
385                 390                 395                 400

Ser Val Ser Glu Ile Asp His Val Val Leu Val Gly Gly Ser Thr Arg
                405                 410                 415

Met Pro Ala Val Thr Asp Leu Val Lys Glu Leu Thr Gly Gly Lys Glu
```

-continued

```
                420             425             430
Pro Asn Lys Gly Val Asn Pro Asp Glu Val Ala Val Gly Ala Ala
        435                 440                 445

Leu Gln Ala Gly Val Leu Lys Gly Glu Val Lys Asp Val Leu Leu Leu
    450                 455                 460

Asp Val Thr Pro Leu Ser Leu Gly Ile Glu Thr Lys Gly Gly Val Met
465                 470                 475                 480

Thr Arg Leu Ile Glu Arg Asn Thr Thr Ile Pro Thr Lys Arg Ser Glu
                485                 490                 495

Thr Phe Thr Thr Ala Asp Asp Asn Gln Pro Ser Val Gln Ile Gln Val
                500                 505                 510

Tyr Gln Gly Glu Arg Glu Ile Ala Ala His Asn Lys Leu Leu Gly Ser
                515                 520                 525

Phe Glu Leu Thr Gly Ile Pro Pro Ala Pro Arg Gly Ile Pro Gln Ile
            530                 535                 540

Glu Val Thr Phe Asp Ile Asp Ala Asn Gly Ile Val His Val Thr Ala
545                 550                 555                 560

Lys Asp Lys Gly Thr Gly Lys Glu Asn Thr Ile Arg Ile Gln Glu Gly
                565                 570                 575

Ser Gly Leu Ser Lys Glu Asp Ile Asp Arg Met Ile Lys Asp Ala Glu
            580                 585                 590

Ala His Ala Glu Glu Asp Arg Lys Arg Arg Glu Ala Asp Val Arg
        595                 600                 605

Asn Gln Ala Glu Thr Leu Val Tyr Gln Thr Glu Lys Phe Val Lys Glu
610                 615                 620

Gln Arg Glu Ala Glu Gly Gly Ser Lys Val Pro Glu Asp Thr Leu Asn
625                 630                 635                 640

Lys Val Asp Ala Ala Val Ala Glu Ala Lys Ala Ala Leu Gly Gly Ser
                645                 650                 655

Asp Ile Ser Ala Ile Lys Ser Ala Met Glu Lys Leu Gly Gln Glu Ser
                660                 665                 670

Gln Ala Leu Gly Gln Ala Ile Tyr Glu Ala Ala Gln Ala Ala Ser Gln
            675                 680                 685

Ala Thr Gly Ala Ala His Pro Gly Ser Ala Asp Glu Ser
        690                 695                 700

<210> SEQ ID NO 9
<211> LENGTH: 567
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(567)

<400> SEQUENCE: 9 atg aca gtg ctg gcg cca gcc tgg agc cca aat tcc tcc ctg ttg ctg      48
Met Thr Val Leu Ala Pro Ala Trp Ser Pro Asn Ser Ser Leu Leu Leu
1               5                   10                  15 ctg ttg ctg ctg ctg agt cct tgc ctg cgg ggg aca cct gac tgt tac      96
Leu Leu Leu Leu Leu Ser Pro Cys Leu Arg Gly Thr Pro Asp Cys Tyr
            20                  25                  30 ttc agc cac agt ccc atc tcc tcc aac ttc aaa gtg aag ttt aga gag     144
Phe Ser His Ser Pro Ile Ser Ser Asn Phe Lys Val Lys Phe Arg Glu
        35                  40                  45 ttg act gac cac ctg ctt aaa gat tac cca gtc act gtg gcc gtc aat     192
Leu Thr Asp His Leu Leu Lys Asp Tyr Pro Val Thr Val Ala Val Asn
```

```
Leu Thr Asp His Leu Leu Lys Asp Tyr Pro Val Thr Val Ala Val Asn
 50                  55                  60 ctt cag gac gag aag cac tgc aag gcc ttg tgg agc ctc ttc cta gcc      240
Leu Gln Asp Glu Lys His Cys Lys Ala Leu Trp Ser Leu Phe Leu Ala
 65                  70                  75                  80 cag cgc tgg ata gag caa ctg aag act gtg gca ggg tct aag atg caa      288
Gln Arg Trp Ile Glu Gln Leu Lys Thr Val Ala Gly Ser Lys Met Gln
                 85                  90                  95 acg ctt ctg gag gac gtc aac acc gag ata cat ttt gtc acc tca tgt      336
Thr Leu Leu Glu Asp Val Asn Thr Glu Ile His Phe Val Thr Ser Cys
            100                 105                 110 acc ttc cag ccc cta cca gaa tgt ctg cga ttc gtc cag acc aac atc      384
Thr Phe Gln Pro Leu Pro Glu Cys Leu Arg Phe Val Gln Thr Asn Ile
        115                 120                 125 tcc cac ctc ctg aag gac acc tgc aca cag ctg ctt gct ctg aag ccc      432
Ser His Leu Leu Lys Asp Thr Cys Thr Gln Leu Leu Ala Leu Lys Pro
    130                 135                 140 tgt atc ggg aag gcc tgc cag aat ttc tct cgg tgc ctg gag gtg cag      480
Cys Ile Gly Lys Ala Cys Gln Asn Phe Ser Arg Cys Leu Glu Val Gln
145                 150                 155                 160 tgc cag ccg gac tcc tcc acc ctg ctg ccc cca agg agt ccc ata gcc      528
Cys Gln Pro Asp Ser Ser Thr Leu Leu Pro Pro Arg Ser Pro Ile Ala
                165                 170                 175 cta gaa gcc acg gag ctc cca gag cct cgg ccc agg cag                  567
Leu Glu Ala Thr Glu Leu Pro Glu Pro Arg Pro Arg Gln
            180                 185

<210> SEQ ID NO 10
<211> LENGTH: 189
<212> TYPE: PRT
<213> ORGANISM: Artificial Sequence
<220> FEATURE:
<223> OTHER INFORMATION: Synthetic Construct

<400> SEQUENCE: 10

Met Thr Val Leu Ala Pro Ala Trp Ser Pro Asn Ser Ser Leu Leu Leu
 1                5                  10                  15

Leu Leu Leu Leu Leu Ser Pro Cys Leu Arg Gly Thr Pro Asp Cys Tyr
                 20                  25                  30

Phe Ser His Ser Pro Ile Ser Ser Asn Phe Lys Val Lys Phe Arg Glu
             35                  40                  45

Leu Thr Asp His Leu Leu Lys Asp Tyr Pro Val Thr Val Ala Val Asn
 50                  55                  60

Leu Gln Asp Glu Lys His Cys Lys Ala Leu Trp Ser Leu Phe Leu Ala
 65                  70                  75                  80

Gln Arg Trp Ile Glu Gln Leu Lys Thr Val Ala Gly Ser Lys Met Gln
                 85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln
            180                 185
```

<210> SEQ ID NO 11
<211> LENGTH: 867
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(867)

<400> SEQUENCE: 11

```
atg aca gtg ctg gcg cca gcc tgg agc cca aat tcc tcc ctg ttg ctg      48
Met Thr Val Leu Ala Pro Ala Trp Ser Pro Asn Ser Ser Leu Leu Leu
1               5                   10                  15 ctg ttg ctg ctg ctg agt cct tgc ctg cgg ggg aca cct gac tgt tac      96
Leu Leu Leu Leu Leu Ser Pro Cys Leu Arg Gly Thr Pro Asp Cys Tyr
                20                  25                  30 ttc agc cac agt ccc atc tcc tcc aac ttc aaa gtg aag ttt aga gag     144
Phe Ser His Ser Pro Ile Ser Ser Asn Phe Lys Val Lys Phe Arg Glu
            35                  40                  45 ttg act gac cac ctg ctt aaa gat tac cca gtc act gtg gcc gtc aat     192
Leu Thr Asp His Leu Leu Lys Asp Tyr Pro Val Thr Val Ala Val Asn
        50                  55                  60 ctt cag gac gag aag cac tgc aag gcc ttg tgg agc ctc ttc cta gcc     240
Leu Gln Asp Glu Lys His Cys Lys Ala Leu Trp Ser Leu Phe Leu Ala
65                  70                  75                  80 cag cgc tgg ata gag caa ctg aag act gtg gca ggg tct aag atg caa     288
Gln Arg Trp Ile Glu Gln Leu Lys Thr Val Ala Gly Ser Lys Met Gln
                85                  90                  95 acg ctt ctg gag gac gtc aac acc gag ata cat ttt gtc acc tca tgt     336
Thr Leu Leu Glu Asp Val Asn Thr Glu Ile His Phe Val Thr Ser Cys
            100                 105                 110 acc ttc cag ccc cta cca gaa tgt ctg cga ttc gtc cag acc aac atc     384
Thr Phe Gln Pro Leu Pro Glu Cys Leu Arg Phe Val Gln Thr Asn Ile
        115                 120                 125 tcc cac ctc ctg aag gac acc tgc aca cag ctg ctt gct ctg aag ccc     432
Ser His Leu Leu Lys Asp Thr Cys Thr Gln Leu Leu Ala Leu Lys Pro
    130                 135                 140 tgt atc ggg aag gcc tgc cag aat ttc tct cgg tgc ctg gag gtg cag     480
Cys Ile Gly Lys Ala Cys Gln Asn Phe Ser Arg Cys Leu Glu Val Gln
145                 150                 155                 160 tgc cag ccg gac tcc tcc acc ctg ctg ccc cca agg agt ccc ata gcc     528
Cys Gln Pro Asp Ser Ser Thr Leu Leu Pro Pro Arg Ser Pro Ile Ala
                165                 170                 175 cta gaa gcc acg gag ctc cca gag cct cgg ccc agg cag gaa ttc atg     576
Leu Glu Ala Thr Glu Leu Pro Glu Pro Arg Pro Arg Gln Glu Phe Met
            180                 185                 190 cat gga gat aca cct aca ttg cat gaa tat atg tta gat ttg caa cca     624
His Gly Asp Thr Pro Thr Leu His Glu Tyr Met Leu Asp Leu Gln Pro
        195                 200                 205 gag aca act gat ctc tac tgt tat gag caa tta aat gac agc tca gag     672
Glu Thr Thr Asp Leu Tyr Cys Tyr Glu Gln Leu Asn Asp Ser Ser Glu
    210                 215                 220 gag gag gat gaa ata gat ggt cca gct gga caa gca gaa ccg gac aga     720
Glu Glu Asp Glu Ile Asp Gly Pro Ala Gly Gln Ala Glu Pro Asp Arg
225                 230                 235                 240 gcc cat tac aat att gta acc ttt tgt tgc aag tgt gac tct acg ctt     768
Ala His Tyr Asn Ile Val Thr Phe Cys Cys Lys Cys Asp Ser Thr Leu
                245                 250                 255
```

```
cgg ttg tgc gta caa agc aca cac gta gac att cgt act ttg gaa gac    816
Arg Leu Cys Val Gln Ser Thr His Val Asp Ile Arg Thr Leu Glu Asp
        260                 265                 270 ctg tta atg ggc aca cta gga att gtg tgc ccc atc tgt tct caa gga    864
Leu Leu Met Gly Thr Leu Gly Ile Val Cys Pro Ile Cys Ser Gln Gly
            275                 280                 285 tcc                                                                867
Ser
```

<210> SEQ ID NO 12
<211> LENGTH: 289
<212> TYPE: PRT
<213> ORGANISM: Artificial Sequence
<220> FEATURE:
<223> OTHER INFORMATION: Synthetic Construct

<400> SEQUENCE: 12

```
Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
                20                  25                  30

Phe Ser His Ser Pro Ile Ser Ser Asn Phe Lys Val Lys Phe Arg Glu
            35                  40                  45

Leu Thr Asp His Leu Leu Lys Asp Tyr Pro Val Thr Val Ala Val Asn
        50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Glu Phe Met
            180                 185                 190

His Gly Asp Thr Pro Thr Leu His Glu Tyr Met Leu Asp Leu Gln Pro
        195                 200                 205

Glu Thr Thr Asp Leu Tyr Cys Tyr Glu Gln Leu Asn Asp Ser Ser Glu
    210                 215                 220

Glu Glu Asp Glu Ile Asp Gly Pro Ala Gly Gln Ala Glu Pro Asp Arg
225                 230                 235                 240

Ala His Tyr Asn Ile Val Thr Phe Cys Cys Lys Cys Asp Ser Thr Leu
                245                 250                 255

Arg Leu Cys Val Gln Ser Thr His Val Asp Ile Arg Thr Leu Glu Asp
            260                 265                 270

Leu Leu Met Gly Thr Leu Gly Ile Val Cys Pro Ile Cys Ser Gln Gly
        275                 280                 285

Ser
```

<210> SEQ ID NO 13

<211> LENGTH: 1584
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(1584)

<400> SEQUENCE: 13

```
atg aca gtg ctg gcg cca gcc tgg agc cca aat tcc tcc ctg ttg ctg        48
Met Thr Val Leu Ala Pro Ala Trp Ser Pro Asn Ser Ser Leu Leu Leu
1               5                  10                  15 ctg ttg ctg ctg ctg agt cct tgc ctg cgg ggg aca cct gac tgt tac        96
Leu Leu Leu Leu Leu Ser Pro Cys Leu Arg Gly Thr Pro Asp Cys Tyr
            20                  25                  30 ttc agc cac agt ccc atc tcc tcc aac ttc aaa gtg aag ttt aga gag       144
Phe Ser His Ser Pro Ile Ser Ser Asn Phe Lys Val Lys Phe Arg Glu
        35                  40                  45 ttg act gac cac ctg ctt aaa gat tac cca gtc act gtg gcc gtc aat       192
Leu Thr Asp His Leu Leu Lys Asp Tyr Pro Val Thr Val Ala Val Asn
    50                  55                  60 ctt cag gac gag aag cac tgc aag gcc ttg tgg agc ctc ttc cta gcc       240
Leu Gln Asp Glu Lys His Cys Lys Ala Leu Trp Ser Leu Phe Leu Ala
65                  70                  75                  80 cag cgc tgg ata gag caa ctg aag act gtg gca ggg tct aag atg caa       288
Gln Arg Trp Ile Glu Gln Leu Lys Thr Val Ala Gly Ser Lys Met Gln
                85                  90                  95 acg ctt ctg gag gac gtc aac acc gag ata cat ttt gtc acc tca tgt       336
Thr Leu Leu Glu Asp Val Asn Thr Glu Ile His Phe Val Thr Ser Cys
            100                 105                 110 acc ttc cag ccc cta cca gaa tgt ctg cga ttc gtc cag acc aac atc       384
Thr Phe Gln Pro Leu Pro Glu Cys Leu Arg Phe Val Gln Thr Asn Ile
        115                 120                 125 tcc cac ctc ctg aag gac acc tgc aca cag ctg ctt gct ctg aag ccc       432
Ser His Leu Leu Lys Asp Thr Cys Thr Gln Leu Leu Ala Leu Lys Pro
    130                 135                 140 tgt atc ggg aag gcc tgc cag aat ttc tct cgg tgc ctg gag gtg cag       480
Cys Ile Gly Lys Ala Cys Gln Asn Phe Ser Arg Cys Leu Glu Val Gln
145                 150                 155                 160 tgc cag ccg gac tcc tcc acc ctg ctg ccc cca agg agt ccc ata gcc       528
Cys Gln Pro Asp Ser Ser Thr Leu Leu Pro Pro Arg Ser Pro Ile Ala
                165                 170                 175 cta gaa gcc acg gag ctc cca gag cct cgg ccc agg cag gaa ttc atg       576
Leu Glu Ala Thr Glu Leu Pro Glu Pro Arg Pro Arg Gln Glu Phe Met
            180                 185                 190 cat gga gat aca cct aca ttg cat gaa tat atg tta gat ttg caa cca       624
His Gly Asp Thr Pro Thr Leu His Glu Tyr Met Leu Asp Leu Gln Pro
        195                 200                 205 gag aca act gat ctc tac tgt tat gag caa tta aat gac agc tca gag       672
Glu Thr Thr Asp Leu Tyr Cys Tyr Glu Gln Leu Asn Asp Ser Ser Glu
    210                 215                 220 gag gag gat gaa ata gat ggt cca gct gga caa gca gaa ccg gac aga       720
Glu Glu Asp Glu Ile Asp Gly Pro Ala Gly Gln Ala Glu Pro Asp Arg
225                 230                 235                 240 gcc cat tac aat att gta acc ttt tgt tgc aag tgt gac tct acg ctt       768
Ala His Tyr Asn Ile Val Thr Phe Cys Cys Lys Cys Asp Ser Thr Leu
                245                 250                 255 cgg ttg tgc gta caa agc aca cac gta gac att cgt act ttg gaa gac       816
Arg Leu Cys Val Gln Ser Thr His Val Asp Ile Arg Thr Leu Glu Asp
            260                 265                 270
```

-continued

| | | |
|---|---|---|
| ctg tta atg ggc aca cta gga att gtg tgc ccc atc tgt tct caa gga<br>Leu Leu Met Gly Thr Leu Gly Ile Val Cys Pro Ile Cys Ser Gln Gly<br>               275                       280                        285 | 864 |

```
ctg tta atg ggc aca cta gga att gtg tgc ccc atc tgt tct caa gga      864
Leu Leu Met Gly Thr Leu Gly Ile Val Cys Pro Ile Cys Ser Gln Gly
            275                 280                 285 tcc atg gtg agc aag ggc gag gag ctg ttc acc ggg gtg gtg ccc atc      912
Ser Met Val Ser Lys Gly Glu Glu Leu Phe Thr Gly Val Val Pro Ile
        290                 295                 300 ctg gtc gag ctg gac ggc gac gta aac ggc cac aag ttc agc gtg tcc      960
Leu Val Glu Leu Asp Gly Asp Val Asn Gly His Lys Phe Ser Val Ser
305                 310                 315                 320 ggc gag ggc gag ggc gat gcc acc tac ggc aag ctg acc ctg aag ttc     1008
Gly Glu Gly Glu Gly Asp Ala Thr Tyr Gly Lys Leu Thr Leu Lys Phe
                325                 330                 335 atc tgc acc acc ggc aag ctg ccc gtg ccc tgg ccc acc ctc gtg acc     1056
Ile Cys Thr Thr Gly Lys Leu Pro Val Pro Trp Pro Thr Leu Val Thr
            340                 345                 350 acc ttc acc tac ggc gtg cag tgc ttc agc cgc tac ccc gac cac atg     1104
Thr Phe Thr Tyr Gly Val Gln Cys Phe Ser Arg Tyr Pro Asp His Met
        355                 360                 365 aag cag cac gac ttc ttc aag tcc gcc atg ccc gaa ggc tac gtc cag     1152
Lys Gln His Asp Phe Phe Lys Ser Ala Met Pro Glu Gly Tyr Val Gln
370                 375                 380 gag cgc acc atc ttc ttc aag gac gac ggc aac tac aag acc cgc gcc     1200
Glu Arg Thr Ile Phe Phe Lys Asp Asp Gly Asn Tyr Lys Thr Arg Ala
385                 390                 395                 400 gag gtg aag ttc gag ggc gac acc ctg gtg aac cgc atc gag ctg aag     1248
Glu Val Lys Phe Glu Gly Asp Thr Leu Val Asn Arg Ile Glu Leu Lys
                405                 410                 415 ggc atc gac ttc aag gag gac ggc aac atc ctg ggg cac aag ctg gag     1296
Gly Ile Asp Phe Lys Glu Asp Gly Asn Ile Leu Gly His Lys Leu Glu
            420                 425                 430 tac aac tac aac agc cac aac gtc tat atc atg gcc gac aag cag aag     1344
Tyr Asn Tyr Asn Ser His Asn Val Tyr Ile Met Ala Asp Lys Gln Lys
        435                 440                 445 aac ggc atc aag gtg aac ttc aag atc cgc cac aac atc gag gac ggc     1392
Asn Gly Ile Lys Val Asn Phe Lys Ile Arg His Asn Ile Glu Asp Gly
450                 455                 460 agc gtg cag ctc gcc gac cac tac cag cag aac acc ccc atc ggc gac     1440
Ser Val Gln Leu Ala Asp His Tyr Gln Gln Asn Thr Pro Ile Gly Asp
465                 470                 475                 480 ggc ccc gtg ctg ctg ccc gac aac cac tac ctg agc acc cag tcc gcc     1488
Gly Pro Val Leu Leu Pro Asp Asn His Tyr Leu Ser Thr Gln Ser Ala
                485                 490                 495 ctg agc aaa gac ccc aac gag aag cgc gat cac atg gtc ctg ctg gag     1536
Leu Ser Lys Asp Pro Asn Glu Lys Arg Asp His Met Val Leu Leu Glu
            500                 505                 510 ttc gtg acc gcc gcc ggg atc act ctc ggc atg gac gag ctg tac aag     1584
Phe Val Thr Ala Ala Gly Ile Thr Leu Gly Met Asp Glu Leu Tyr Lys
        515                 520                 525

<210> SEQ ID NO 14
<211> LENGTH: 528
<212> TYPE: PRT
<213> ORGANISM: Artificial Sequence
<220> FEATURE:
<223> OTHER INFORMATION: Synthetic Construct

<400> SEQUENCE: 14

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30
```

```
Phe Ser His Ser Pro Ile Ser Ser Asn Phe Lys Val Lys Phe Arg Glu
         35                  40                  45

Leu Thr Asp His Leu Leu Lys Asp Tyr Pro Val Thr Val Ala Val Asn
 50                  55                  60

Leu Gln Asp Glu Lys His Cys Lys Ala Leu Trp Ser Leu Phe Leu Ala
 65                  70                  75                  80

Gln Arg Trp Ile Glu Gln Leu Lys Thr Val Ala Gly Ser Lys Met Gln
                 85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Glu Phe Met
            180                 185                 190

His Gly Asp Thr Pro Thr Leu His Glu Tyr Met Leu Asp Leu Gln Pro
        195                 200                 205

Glu Thr Thr Asp Leu Tyr Cys Tyr Glu Gln Leu Asn Asp Ser Ser Glu
    210                 215                 220

Glu Glu Asp Glu Ile Asp Gly Pro Ala Gly Gln Ala Glu Pro Asp Arg
225                 230                 235                 240

Ala His Tyr Asn Ile Val Thr Phe Cys Cys Lys Cys Asp Ser Thr Leu
                245                 250                 255

Arg Leu Cys Val Gln Ser Thr His Val Asp Ile Arg Thr Leu Glu Asp
            260                 265                 270

Leu Leu Met Gly Thr Leu Gly Ile Val Cys Pro Ile Cys Ser Gln Gly
        275                 280                 285

Ser Met Val Ser Lys Gly Glu Glu Leu Phe Thr Gly Val Val Pro Ile
    290                 295                 300

Leu Val Glu Leu Asp Gly Asp Val Asn Gly His Lys Phe Ser Val Ser
305                 310                 315                 320

Gly Glu Gly Glu Gly Asp Ala Thr Tyr Gly Lys Leu Thr Leu Lys Phe
                325                 330                 335

Ile Cys Thr Thr Gly Lys Leu Pro Val Pro Trp Pro Thr Leu Val Thr
            340                 345                 350

Thr Phe Thr Tyr Gly Val Gln Cys Phe Ser Arg Tyr Pro Asp His Met
        355                 360                 365

Lys Gln His Asp Phe Phe Lys Ser Ala Met Pro Glu Gly Tyr Val Gln
    370                 375                 380

Glu Arg Thr Ile Phe Phe Lys Asp Asp Gly Asn Tyr Lys Thr Arg Ala
385                 390                 395                 400

Glu Val Lys Phe Glu Gly Asp Thr Leu Val Asn Arg Ile Glu Leu Lys
                405                 410                 415

Gly Ile Asp Phe Lys Glu Asp Gly Asn Ile Leu Gly His Lys Leu Glu
            420                 425                 430

Tyr Asn Tyr Asn Ser His Asn Val Tyr Ile Met Ala Asp Lys Gln Lys
        435                 440                 445
```

```
Asn Gly Ile Lys Val Asn Phe Lys Ile Arg His Asn Ile Glu Asp Gly
            450                 455                 460

Ser Val Gln Leu Ala Asp His Tyr Gln Gln Asn Thr Pro Ile Gly Asp
465                 470                 475                 480

Gly Pro Val Leu Leu Pro Asp Asn His Tyr Leu Ser Thr Gln Ser Ala
                485                 490                 495

Leu Ser Lys Asp Pro Asn Glu Lys Arg Asp His Met Val Leu Leu Glu
            500                 505                 510

Phe Val Thr Ala Ala Gly Ile Thr Leu Gly Met Asp Glu Leu Tyr Lys
            515                 520                 525

<210> SEQ ID NO 15
<211> LENGTH: 5431
<212> TYPE: DNA
<213> ORGANISM: Artificial Sequence
<220> FEATURE:
<223> OTHER INFORMATION: synthetic construct

<400> SEQUENCE: 15
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960
accacactgg actagtggat ccgagctcgg taccaagctt aagtttaaac cgctgatcag   1020
cctcgactgt gccttctagt tgccagccat ctgttgtttg cccctccccc gtgccttcct   1080
tgaccctgga aggtgccact cccactgtcc tttcctaata aaatgaggaa attgcatcgc   1140
attgtctgag taggtgtcat tctattctgg ggggtggggt ggggcaggac agcaagggg    1200
aggattggga agacaatagc aggcatgctg gggatgcggt gggctctatg gcttctgagg   1260
cggaaagaac cagctggggc tctagggggt atccccacgc gccctgtagc ggcgcattaa   1320
gcgcggcggg tgtggtggtt acgcgcagcg tgaccgctac acttgccagc gccctagcgc   1380
ccgctccttt cgctttcttc ccttcctttc tcgccacgtt cgccggcttt ccccgtcaag   1440
ctctaaatcg ggcatccct ttagggttcc gatttagtgc tttacggcac ctcgacccca   1500
aaaaacttga ttagggtgat ggttcacgta gtgggccatc gccctgatag acggtttttc   1560
gccctttgac gttggagtcc acgttcttta atagtggact cttgttccaa actggaacaa   1620
```

```
cactcaaccc tatctcggtc tattcttttg atttataagg gattttgggg atttcggcct   1680
attggttaaa aaatgagctg atttaacaaa aatttaacgc gaattaattc tgtggaatgt   1740
gtgtcagtta gggtgtggaa agtccccagg ctccccaggc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca acagacaa    2220 tcggctgctc tgatgccgcc gtgttccggc tgtcagcgca ggggcgcccg gttcttttg    2280 tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacggcga ggatctcgtc gtgacccatg   2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tgggctgacc gcttcctcgt gctttacggt atcgccgctc   2880
ccgattcgca gcgcatcgcc ttctatcgcc ttcttgacga gttcttctga gcgggactct   2940
ggggttcgaa atgaccgacc aagcgacgcc caacctgcca tcacgagatt tcgattccac   3000
cgccgccttc tatgaaaggt tgggcttcgg aatcgttttc cgggacgccg gctggatgat   3060
cctccagcgc ggggatctca tgctggagtt cttcgcccac cccaacttgt ttattgcagc   3120
ttataatggt tacaaataaa gcaatagcat cacaaatttc acaaataaag cattttttc    3180 actgcattct agttgtggtt tgtccaaact catcaatgta tcttatcatg tctgtatacc   3240
gtcgacctct agctagagct tggcgtaatc atggtcatag ctgtttcctg tgtgaaattg   3300
ttatccgctc acaattccac acaacatacg agccggaagc ataaagtgta aagcctgggg   3360
tgcctaatga gtgagctaac tcacattaat tgcgttgcgc tcactgcccg ctttccagtc   3420
gggaaacctg tcgtgccagc tgcattaatg aatcggccaa cgcgcgggga gaggcggttt   3480
gcgtattggg cgctcttccg cttcctcgct cactgactcg ctgcgctcgg tcgttcggct   3540
gcggcgagcg gtatcagctc actcaaaggc ggtaatacgg ttatccacag aatcagggga   3600
taacgcagga aagaacatgt gagcaaaagg ccagcaaaag gccaggaacc gtaaaaaggc   3660
cgcgttgctg gcgttttcc ataggctccg ccccctgac gagcatcaca aaaatcgacg     3720
ctcaagtcag aggtggcgaa acccgacagg actataaaga taccaggcgt ttccccctgg   3780
aagctccctc gtgcgctctc ctgttccgac cctgccgctt accggatacc tgtccgcctt   3840
tctcccttcg ggaagcgtgg cgctttctca atgctcacgc tgtaggtatc tcagttcggt   3900
gtaggtcgtt cgctccaagc tgggctgtgt gcacgaaccc cccgttcagc ccgaccgctg   3960
cgccttatcc ggtaactatc gtcttgagtc caacccggta agacacgact tatcgccact   4020
```

-continued

```
ggcagcagcc actggtaaca ggattagcag agcgaggtat gtaggcggtg ctacagagtt      4080
cttgaagtgg tggcctaact acggctacac tagaaggaca gtatttggta tctgcgctct      4140
gctgaagcca gttaccttcg gaaaaagagt tggtagctct tgatccggca aacaaaccac      4200
cgctggtagc ggtggttttt tgtttgcaa gcagcagatt acgcgcagaa aaaaggatc       4260
tcaagaagat cctttgatct tttctacggg gtctgacgct cagtggaacg aaaactcacg      4320
ttaagggatt ttggtcatga gattatcaaa aaggatcttc acctagatcc ttttaaatta     4380
aaaatgaagt tttaaatcaa tctaaagtat atatgagtaa acttggtctg acagttacca     4440
atgcttaatc agtgaggcac ctatctcagc gatctgtcta tttcgttcat ccatagttgc     4500
ctgactcccc gtcgtgtaga taactacgat acgggagggc ttaccatctg gccccagtgc     4560
tgcaatgata ccgcgagacc cacgctcacc ggctccagat ttatcagcaa taaaccagcc     4620
agccggaagg gccgagcgca gaagtggtcc tgcaacttta tccgcctcca tccagtctat     4680
taattgttgc cgggaagcta gagtaagtag ttcgccagtt aatagtttgc gcaacgttgt     4740
tgccattgct acaggcatcg tggtgtcacg ctcgtcgttt ggtatggctt cattcagctc     4800
cggttcccaa cgatcaaggc gagttacatg atcccccatg ttgtgcaaaa aagcggttag     4860
ctccttcggt cctccgatcg ttgtcagaag taagttggcc gcagtgttat cactcatggt     4920
tatggcagca ctgcataatt ctcttactgt catgccatcc gtaagatgct tttctgtgac     4980
tggtgagtac tcaaccaagt cattctgaga atagtgtatg cggcgaccga gttgctcttg     5040
cccggcgtca atacgggata ataccgcgcc acatagcaga actttaaaag tgctcatcat     5100
tggaaaacgt tcttcgggc gaaaactctc aaggatctta ccgctgttga tccagttc       5160
gatgtaaccc actcgtgcac ccaactgatc ttcagcatct tttactttca ccagcgtttc     5220
tgggtgagca aaaacaggaa ggcaaaatgc cgcaaaaaag gaataagggc gacacggaa      5280
atgttgaata ctcatactct ccttttttca atattattga agcatttatc agggttattg     5340
tctcatgagc ggatacatat ttgaatgtat ttagaaaaat aaacaaatag gggttccgcg     5400
cacatttccc cgaaaagtgc cacctgacgt c                                    5431
```

<210> SEQ ID NO 16
<211> LENGTH: 9951
<212> TYPE: DNA
<213> ORGANISM: Artificial Sequence
<220> FEATURE:
<223> OTHER INFORMATION: synthetic construct

<400> SEQUENCE: 16

```
attgacggcg tagtacacac tattgaatca aacagccgac caattgcact accatcacaa       60
tggagaagcc agtagtaaac gtagacgtag accccccagag tccgtttgtc gtgcaactgc     120
aaaaaagctt cccgcaattt gaggtagtag cacagcaggt cactccaaat gaccatgcta     180
atgccagagc attttcgcat ctggccagta aactaatcga gctggaggtt cctaccacag     240
cgacgatctt ggacataggc agcgcaccgg ctcgtagaat gttttccgag caccagtatc     300
attgtgtctg ccccatgcgt agtccagaag acccggaccg catgatgaaa tacgccagta     360
aactggcgga aaaagcgtgc aagattacaa acaagaactt gcatgagaag attaaggatc     420
tccggaccgt acttgatacg ccggatgctg aaacaccatc gctctgcttt cacaacgatg     480
ttacctgcaa catgcgtgcc gaatattccg tcatgcagga cgtgtatatc aacgctcccg     540
gaactatcta tcatcaggct atgaaaggcg tgcggaccct gtactggatt ggcttcgaca     600
```

```
ccacccagtt catgttctcg gctatggcag gttcgtaccc tgcgtacaac accaactggg    660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggt gttccacttg aatggaaagc agtcgtacac ttgccgctgt gatacagtgg    900
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacct   1380
gcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggagggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga agaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat cacccctgaaa   2580 aagacatatg caccaagaca ttctacaagt atatctcccg gcgttgcaca cagccagtta   2640
cagctattgt atcgacactg cattacgatg aaaagatgaa aaccacgaac ccgtgcaaga   2700
agaacattga aatcgatatt acaggggcca caaagccgaa gcagggggat atcatcctga   2760
catgtttccg cggtgggtt aagcaattgc aaatcgacta tccgcgacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag cccactaaca   3000
```

```
tacctaaagg aaactttcag gctactatag aggactggga agctgaacac aagggaataa    3060
ttgctgcaat aaacagcccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttttcggca tggacttgac aagcggactg ttttctaaac   3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat ctctgcacag cataacctgg tcccggtgaa ccgcaatctt cctcacgcct    3540
tagtccccga gtacaaggag aagcaacccg gcccggtcaa aaaattcttg aaccagttca    3600
aacaccactc agtacttgtg gtatcagagg aaaaaattga agctcccgt aagagaatcg     3660 aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aacccttcg cgttcggccc     3840 tgaattgcct taacccagga ggcacccctcg tggtgaagtc ctatggctac gccgaccgca   3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga attgcgtgat ttcgtccgtg tatgagggta    4080
caagagatgg agttggagcc gcgccgtcat accgcaccaa aagggagaat attgctgact    4140
gtcaagagga agcagttgtc aacgcagcca atccgctggg tagaccaggc gaaggagtct    4200
gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
cggcactcca acttaaggag tctgtaacag agctgaagga tgaagatatg gagatcgacg    4620
atgagttagt atggattcat ccagacagtt gcttgaaggg aagaaaggga ttcagtacta    4680
caaaaggaaa attgtattcg tacttcgaag gcaccaaatt ccatcaagca gcaaagaca    4740 tggcggagat aaaggtcctg ttccctaatg accaggaaag taatgaacaa ctgtgtgcct    4800
acatattggg tgagaccatg aagcaatcc gcgaaaagtg cccggtcgac cataacccgt     4860
cgtctagccc gcccaaaacg ttgccgtgcc tttgcatgta tgccatgacg ccagaaaggg    4920
tccacagact tagaagcaat aacgtcaaag aagttacagt atgctcctcc accccccttc    4980
ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
```

```
atgccgtcca agagcctgcc cctattccac cgccaaggct aaagaagatg gcccgcctgg      5400
cagcggcaag aaaagagccc actccaccgg caagcaatag ctctgagtcc ctccacctcc      5460
cttttggtgg ggtatccatg tccctcggat caattttcga cggagagacg gcccgccagg      5520
cagcggtaca accccctggca acaggcccca cggatgtgcc tatgtctttc ggatcgtttt      5580
ccgacggaga gattgatgag ctgagccgca gagtaactga gtccgaaccc gtcctgtttg      5640
gatcatttga accgggcgaa gtgaactcaa ttatatcgtc ccgatcagcc gtatcttttc      5700
cactacgcaa gcagagacgt agacgcagga gcaggaggac tgaatactga ctaaccgggg      5760
taggtgggta catattttcg acggacacag gccctgggca cttgcaaaag aagtccgttc      5820
tgcagaacca gcttacagaa ccgaccttgg agcgcaatgt cctggaaaga attcatgccc      5880
cggtgctcga cacgtcgaaa gaggaacaac tcaaactcag gtaccagatg atgcccaccg      5940
aagccaacaa agtaggtac cagtctcgta agtagaaaa tcagaaagcc ataaccactg       6000
agcgactact gtcaggacta cgactgtata actctgccac agatcagcca gaatgctata      6060
agatcaccta tccgaaacca ttgtactcca gtagcgtacc ggcgaactac tccgatccac      6120
agttcgctgt agctgtctgt aacaactatc tgcatgagaa ctatccgaca gtagcatctt      6180
atcagattac tgacgagtac gatgcttact ggatatggt agacgggaca gtcgcctgcc       6240
tggatactga aaccttctgc cccgctaagc ttagaagtta cccgaaaaaa catgagtata      6300
gagccccgaa tatccgcagt gcggttccat cagcgatgca gaacacgcta caaaatgtgc      6360
tcattgccgc aactaaaaga aattgcaacg tcacgcagat gcgtgaactg ccaacactgg      6420
actcagcgac attcaatgtc gaatgctttc gaaaatatgc atgtaatgac gagtattggg      6480
aggagttcgc tcggaagcca attaggatta ccactgagtt tgtcaccgca tatgtagcta      6540
gactgaaagg ccctaaggcc gccgcactat ttgcaaagac gtataatttg gtcccattgc      6600
aagaagtgcc tatggataga ttcgtcatgg acatgaaaag agacgtgaaa gttacaccag      6660
gcacgaaaca cacagaagaa agaccgaaag tacaagtgat acaagccgca gaaccctgg       6720 cgactgctta cttatgcggg attcaccggg aattagtgcg taggcttacg gccgtcttgc      6780
ttccaaacat tcacacgctt tttgacatgt cggcggagga ttttgatgca atcatagcag      6840
aacacttcaa gcaaggcgac ccggtactgg agacggatat cgcatcattc gacaaaagcc      6900
aagacgacgc tatggcgtta accggtctga tgatcttgga ggacctgggt gtggatcaac      6960
cactactcga cttgatcgag tgcgcctttg gagaaatatc atccacccat ctacctacgg      7020
gtactcgttt taaattcggg gcgatgatga atccggaat gttcctcaca cttttttgtca     7080 acacagtttt gaatgtcgtt atcgccagca gagtactaga agagcggctt aaaacgtcca      7140
gatgtgcagc gttcattggc gacgacaaca tcatacatgg agtagtatct gacaaagaaa      7200
tggctgagag gtgcgccacc tggctcaaca tggaggttaa gatcatcgac gcagtcatcg      7260
gtgagagacc accttacttc tgcggcggat ttatcttgca agattcggtt acttccacag      7320
cgtgccgcgt ggcggatccc ctgaaaaggc tgtttaagtt gggtaaaccg ctcccagccg      7380
acgacgagca agacgaagac agaagacgcg ctctgctaga tgaaacaaag gcgtggttta      7440
gagtaggtat aacaggcact ttagcagtgg ccgtgacgac ccggtatgag gtagacaata      7500
ttacacctgt cctactggca ttgagaactt ttgcccagag caaaagagca ttccaagcca      7560
tcagagggga aataaagcat ctctacggtg gtcctaaata gtcagcatag tacatttcat      7620
ctgactaata ctacaacacc accacctcta gacgcgtaga tctcacgtga gcatgcaggc      7680
cttgggccca atgatccgac cagcaaaact cgatgtactt ccgaggaact gatgtgcata      7740
```

```
atgcatcagg ctggtacatt agatccccgc ttaccgcggg caatatagca acactaaaaa    7800
ctcgatgtac ttccgaggaa gcgcagtgca taatgctgcg cagtgttgcc acataaccac    7860
tatattaacc atttatctag cggacgccaa aaactcaatg tatttctgag gaagcgtggt    7920
gcataatgcc acgcagcgtc tgcataactt ttattatttc ttttattaat caacaaaatt    7980
ttgttttaa catttcaaaa aaaaaaaaaa aaaaaaaaaa aaaaaaaaaa aaagggaatt     8040
cctcgattaa ttaagcggcc gctcgagggg aattaattct tgaagacgaa agggccaggt    8100
ggcacttttc ggggaaatgt gcgcggaacc cctatttgtt tattttcta aatacattca    8160
aatatgtatc cgctcatgag acaataaccc tgataaatgc ttcaataata ttgaaaaagg    8220
aagagtatga gtattcaaca tttccgtgtc gcccttattc ccttttttgc ggcattttgc    8280
cttcctgttt ttgctcaccc agaaacgctg gtgaaagtaa aagatgctga agatcagttg    8340
ggtgcacgag tgggttacat cgaactggat ctcaacagcg gtaagatcct tgagagtttt    8400
cgccccgaag aacgttttcc aatgatgagc acttttaaag ttctgctatg tggcgcggta    8460
ttatcccgtg ttgacgccgg gcaagagcaa ctcggtcgcc gcatacacta ttctcagaat    8520
gacttggttg agtactcacc agtcacagaa aagcatctta cggatggcat gacagtaaga    8580
gaattatgca gtgctgccat aaccatgagt gataacactg cggccaactt acttctgaca    8640
acgatcggag gaccgaagga gctaaccgct tttttgcaca acatggggga tcatgtaact    8700
cgccttgatc gttgggaacc ggagctgaat gaagccatac caaacgacga gcgtgacacc    8760
acgatgcctg tagcaatggc aacaacgttg cgcaaactat taactggcga actacttact    8820
ctagcttccc ggcaacaatt aatagactgg atggaggcgg ataaagttgc aggaccactt    8880
ctgcgctcgg cccttccggc tggctggttt attgctgata atctggagc cggtgagcgt     8940
gggtctcgcg gtatcattgc agcactgggg ccagatggta agccctcccg tatcgtagtt    9000
atctacacga cggggagtca ggcaactatg gatgaacgaa atagacagat cgctgagata    9060
ggtgcctcac tgattaagca ttggtaactg tcagaccaag tttactcata tactttag     9120
attgatttaa aacttcattt ttaatttaaa aggatctagg tgaagatcct ttttgataat    9180
ctcatgacca aaatccctta acgtgagttt tcgttccact gagcgtcaga ccccgtagaa    9240
aagatcaaag gatcttcttg agatcctttt tttctgcgcg taatctgctg cttgcaaaca    9300
aaaaaaccac cgctaccagc ggtggtttgt ttgccggatc aagagctacc aactcttttt    9360
ccgaaggtaa ctggcttcag cagagcgcag ataccaaata ctgtccttct agtgtagccg    9420
tagttaggcc accacttcaa gaactctgta gcaccgccta catcctcgc tctgctaatc     9480
ctgttaccag tggctgctgc cagtggcgat aagtcgtgtc ttaccgggtt ggactcaaga    9540
cgatagttac cggataaggc gcagcggtcg ggctgaacgg ggggttcgtg cacacagccc    9600
agcttggagc gaacgaccta caccgaactg agatacctac agcgtgagca ttgagaaagc    9660
gccacgcttc ccgaagggag aaaggcggac aggtatccgg taagcggcag gtcggaaca    9720
ggagagcgca cgagggagct tccagggga aacgcctggt atctttatag tcctgtcggg     9780
tttcgccacc tctgacttga gcgtcgattt ttgtgatgct cgtcagggg gcggagccta     9840
tggaaaacg ccagcaacgc gagctcgtat ggacatattg tcgttagaac gcggctacaa     9900
ttaatacata accttatgta tcatacacat acgatttagg ggacactata g             9951
```

<210> SEQ ID NO 17
<211> LENGTH: 11489
<212> TYPE: DNA

<213> ORGANISM: Artificial Sequence
<220> FEATURE:
<223> OTHER INFORMATION: synthetic construct

<400> SEQUENCE: 17

```
atggcggatg tgtgacatac acgacgccaa aagattttgt tccagctcct gccacctccg      60
ctacgcgaga gattaaccac ccacgatggc cgccaaagtg catgttgata ttgaggctga     120
cagcccattc atcaagtctt tgcagaaggc atttccgtcg ttcgaggtgg agtcattgca     180
ggtcacacca aatgaccatg caaatgccag agcattttcg cacctggcta ccaaattgat     240
cgagcaggag actgacaaag acacactcat cttggatatc ggcagtgcgc cttccaggag     300
aatgatgtct acgcacaaat accactgcgt atgccctatg cgcagcgcag aagaccccga     360
aaggctcgat agctacgcaa agaaactggc agcggcctcc gggaaggtgc tggatagaga     420
gatcgcagga aaaatcaccg acctgcagac cgtcatggct acgccagacg ctgaatctcc     480
tacctttgc ctgcatacag acgtcacgtg tcgtacggca gccgaagtgg ccgtatacca      540
ggacgtgtat gctgtacatg caccaacatc gctgtaccat caggcgatga aggtgtcag      600
aacgcgtat tggattgggt ttgacaccac cccgtttatg tttgacgcgc tagcaggcgc      660
gtatccaacc tacgccacaa actgggccga cgagcaggtg ttacaggcca ggaacatagg     720
actgtgtgca gcatccttga ctgagggaag actcggcaaa ctgtccattc ccgcaagaa      780
gcaattgaaa ccttgcgaca cagtcatgtt ctcggtagga tctacattgt acactgagag     840
cagaaagcta ctgaggagct ggcacttacc ctccgtattc cacctgaaag gtaaacaatc     900
ctttacctgt aggtgcgata ccatcgtatc atgtgaaggg tacgtagtta agaaaatcac     960
tatgtgcccc ggcctgtacg gtaaaacggt agggtacgcc gtgacgtatc acgcggaggg    1020
attcctagtg tgcaagacca cagacactgt caaaggagaa agagtctcat tccctgtatg    1080
cacctacgtc ccctcaacca tctgtgatca aatgactggc atactagcga ccgacgtcac    1140
accggaggac gcacagaagt tgttagtggg attgaatcag aggatagttg tgaacggaag    1200
aacacagcga acactaaca cgatgaagaa ctatctgctt ccgattgtgg ccgtcgcatt     1260
tagcaagtgg gcgagggaat acaaggcaga ccttgatgat gaaaaacctc tgggtgtccg    1320
agagaggtca cttacttgct gctgcttgtg ggcatttaaa acgaggaaga tgcacaccat    1380
gtacaagaaa ccagacaccc agacaatagt gaaggtgcct tcagagttta actcgttcgt    1440
catcccgagc ctatggtcta caggcctcgc aatcccagtc agatcacgca ttaagatgct    1500
tttggccaag aagaccaagc gagagttaat acctgttctc gacgcgtcgt cagccaggga    1560
tgctgaacaa gaggagaagg agaggttgga ggccgagctg actagagaag ccttaccacc    1620
cctcgtcccc atcgcgccgg cggagacggg agtcgtcgac gtcgacgttg aagaactaga    1680
gtatcacgca ggtgcagggg tcgtggaaac acctcgcagc gcgttgaaag tcaccgcaca    1740
gccgaacgac gtactactag gaaattacgt agttctgtcc ccgcagaccg tgctcaagag    1800
ctccaagttg gcccccgtgc accctctagc agagcaggtg aaaataataa cacataacgg    1860
gagggccggc ggttaccagg tcgacggata tgacggcagg gtcctactac catgtggatc    1920
ggccattccg gtccctgagt ttcaagcttt gagcgagagc gccactatgg tgtacaacga    1980
aagggagttc gtcaacagga aactatacca tattgccgtt cacggaccgt cgctgaacac    2040
cgacgaggag aactacgaga aagtcagagc tgaaagaact gacgccgagt acgtgttcga    2100
cgtagataaa aaatgctgcg tcaagagaga ggaagcgtcg ggtttggtgt tggtgggaga    2160
gctaaccaac ccccgttcc atgaattcgc ctacgaaggg ctgaagatca ggccgtcggc    2220
```

```
accatataag actacagtag taggagtctt tggggttccg ggatcaggca agtctgctat    2280
tattaagagc ctcgtgacca aacacgatct ggtcaccagc ggcaagaagg agaactgcca    2340
ggaaatagtt aacgacgtga agaagcaccg cgggaagggg acaagtaggg aaaacagtga    2400
ctccatcctg ctaaacgggt gtcgtcgtgc cgtggacatc ctatatgtgg acgaggcttt    2460
cgctagccat tccggtactc tgctggccct aattgctctt gttaaacctc ggagcaaagt    2520
ggtgttatgc ggagacccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag gctgggcaaa gcagctgcag ttggactacc gtggacacga    2820
agtcatgaca gcagcagcat ctcagggcct caccccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag acagagctt actctccagt    3240 ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420 gaagggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttgggagaag aaaatccagg aagccattga    4560
```

```
catgaggacg gctgtggagt tgctcaatga tgacgtggag ctgaccacag acttggtgag    4620
agtgcacccg gacagcagcc tggtgggtcg taagggctac agtaccactg acgggtcgct    4680
gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
aacaatggac aacatcagat ccaaatgtcc ggtgaacgat tccgattcat caacacctcc    4860
caggacagtg ccctgcctgt gccgctacgc aatgacagca gaacggatcg cccgccttag    4920
gtcacaccaa gttaaaagca tggtggtttg ctcatctttt cccctcccga ataccatgt     4980 agatggggtg cagaaggtaa agtgcgagaa ggttctcctg ttcgacccga cggtaccttc    5040
agtggttagt ccgcggaagt atgccgcatc tacgacggac cactcagatc ggtcgttacg    5100
agggtttgac ttggactgga ccaccgactc gtcttccact gccagcgata ccatgtcgct    5160
acccagtttg cagtcgtgtg acatcgactc gatctacgag ccaatggctc ccatagtagt    5220
gacggctgac gtacaccctg aacccgcagg catcgcggac ctggcggcag atgtgcaccc    5280
tgaacccgca gaccatgtgg acctcgagaa cccgattcct ccaccgcgcc cgaagagagc    5340
tgcataccct gcctcccgcg cggcggagcg accggtgccg gcgccgagaa agccgacgcc    5400
tgccccaagg actgcgttta ggaacaagct gcctttgacg ttcggcgact ttgacgagca    5460
cgaggtcgat gcgttggcct ccgggattac tttcggagac ttcgacgacg tcctgcgact    5520
aggccgcgcg ggtgcatata ttttctcctc ggacactggc agcggacatt tacaacaaaa    5580
atccgttagg cagcacaatc tccagtgcgc acaactggat gcggtccagg aggagaaaat    5640
gtacccgcca aaattggata ctgagaggga gaagctgttg ctgctgaaaa tgcagatgca    5700
cccatcggag gctaataaga gtcgatacca gtctcgcaaa gtggagaaca tgaaagccac    5760
ggtggtggac aggctcacat cgggggccag attgtacacg ggagcggacg taggccgcat    5820
accaacatac gcggttcggt accccgcccc cgtgtactcc cctaccgtga tcgaaagatt    5880
ctcaagcccc gatgtagcaa tcgcagcgtg caacgaatac ctatccagaa attacccaac    5940
agtggcgtcg taccagataa cagatgaata cgacgcatac ttggacatgg ttgacgggtc    6000
ggatagttgc ttggacagag cgacattctg cccggcgaag ctccggtgct acccgaaaca    6060
tcatgcgtac caccagccga ctgtacgcag tgccgtcccg tcacccttc agaacacact     6120 acagaacgtg ctagcggccg ccaccaagag aaactgcaac gtcacgcaaa tgcgagaact    6180
acccaccatg gactcggcag tgttcaacgt ggagtgcttc aagcgctatg cctgctccgg    6240
agaatattgg gaagaatatg ctaaacaacc tatccggata accactgaga acatcactac    6300
ctatgtgacc aaattgaaag gcccgaaagc tgctgccttg ttcgctaaga cccacaactt    6360
ggttccgctg caggaggttc ccatggacag attcacggtc gacatgaaac gagatgtcaa    6420
agtcactcca gggacgaaac acacagagga aagacccaaa gtccaggtaa ttcaagcagc    6480
ggagccattg cgaccgcttt acctgtgcgg catccacagg gaattagtaa ggagactaaa    6540
tgctgtgtta cgccctaacg tgcacacatt gtttgatatg tcggccgaag actttgacgc    6600
gatcatcgcc tctcacttcc acccaggaga cccggttcta gagacggaca ttgcatcatt    6660
cgacaaaagc caggacgact ccttggctct tacaggttta atgatcctcg aagatctagg    6720 ggtgatcag tacctgctgg acttgatcga ggcagccttt gggaaatat ccagctgtca      6780 cctaccaact ggcacgcgct tcaagttcgg agctatgatg aaatcgggca tgtttctgac    6840
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
```

```
cgacaagctg atggcggaga ggtgcgcgtc gtgggtcaac atggaggtga agatcattga    7020
cgctgtcatg ggcgaaaaac ccccatattt ttgtggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acgaggttag    7200
caagtggttc cggacaggct gggggccga actggaggtg gcactaacat ctaggtatga     7260
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atcccgggta attaattgaa ttacatccct acgcaaacgt    7440
tttacgcccg ccggtggcgc ccgcgcccgg cggcccgtcc ttggccgttg caggccactc    7500
cggtggctcc cgtcgtcccc gacttccagg cccagcagat gcagcaactc atcagcgccg    7560
taaatgcgct gacaatgaga cagaacgcaa ttgctcctgc taggcctccc aaaccaaaga    7620
agaagaagac aaccaaacca aagccgaaaa cgcagcccaa gaagatcaac ggaaaaacgc    7680
agcagcaaaa gaagaagac aagcaagccg acaagaagaa gaagaaaccc ggaaaaagag     7740
aaagaatgtg catgaagatt gaaaatgact gtatcttcgt atgcggctag ccacagtaac    7800
gtagtgtttc cagacatgtc gggcaccgca ctatcatggg tgcagaaaat ctcgggtggt    7860
ctgggggcct tcgcaatcgg cgctatcctg gtgctggttg tggtcacttg cattgggctc    7920
cgcagataag ttagggtagg caatggcatt gatatagcaa gaaaattgaa aacagaaaaa    7980
gttagggtaa gcaatggcat ataaccataa ctgtataact tgtaacaaag cgcaacaaga    8040
cctgcgcaat tggccccgtg gtccgcctca cggaaactcg gggcaactca tattgacaca    8100
ttaattggca ataattggaa gcttacataa gcttaattcg acgaataatt ggatttttat    8160
tttatttgc aattggtttt taatatttcc aaaaaaaaaa aaaaaaaaaa aaaaaaaaaa     8220
aaaaaaaaaa aaaaaaaaaa aaaaaaaaaa aaaaaaaaaa ctagtgatca taatcagcca    8280
taccacattt gtagaggttt tacttgcttt aaaaaacctc ccacacctcc ccctgaacct    8340
gaaacataaa atgaatgcaa ttgttgttgt taacttgttt attgcagctt ataatggtta    8400
caaataaagc aatagcatca caaatttcac aaataaagca ttttttttcac tgcattctag   8460
ttgtggtttg tccaaactca tcaatgtatc ttatcatgtc tggatctagt ctgcattaat    8520
gaatcggcca acgcgcgggg agaggcggtt tgcgtattgg gcgctcttcc gcttcctcgc    8580
tcactgactc gctgcgctcg gtcgttcggc tgcggcgagc ggtatcagct cactcaaagg    8640
cggtaatacg gttatccaca gaatcagggg ataacgcagg aaagaacatg tgagcaaaag    8700
gccagcaaaa ggccaggaac cgtaaaaagg ccgcgttgct ggcgtttttc cataggctcc    8760
gcccccctga cgagcatcac aaaaatcgac gctcaagtca gaggtggcga aacccgacag    8820
gactataaag ataccaggcg tttccccctg gaagctccct cgtgcgctct cctgttccga    8880
ccctgccgct taccggatac ctgtccgcct ttctcccttc gggaagcgtg gcgctttctc    8940
aatgctcgcg ctgtaggtat ctcagttcgg tgtaggtcgt tcgctccaag ctgggctgtg    9000
tgcacgaacc cccgttcag cccgaccgct gcgccttatc cggtaactat cgtcttgagt     9060
ccaacccggt aagacacgac ttatcgccac tggcagcagc cactggtaac aggattagca    9120
gagcgaggta tgtaggcggt gctacagagt tcttgaagtg gtggcctaac tacggctaca    9180
ctagaaggac agtatttggt atctgcgctc tgctgaagcc agttaccttc ggaaaaagag    9240
ttggtagctc ttgatccggc aaacaaacca ccgctggtag cggtggtttt tttgtttgca    9300
```

-continued

```
agcagcagat tacgcgcaga aaaaaaggat ctcaagaaga tcctttgatc ttttctacgg    9360
ggcattctga cgctcagtgg aacgaaaact cacgttaagg gattttggtc atgagattat    9420
caaaaaggat cttcacctag atccttttaa attaaaaatg aagttttaaa tcaatctaaa    9480
gtatatatga gtaaacttgg tctgacagtt accaatgctt aatcagtgag gcacctatct    9540
cagcgatctg tctatttcgt tcatccatag ttgcctgact ccccgtcgtg tagataacta    9600
cgatacggga gggcttacca tctggcccca gtgctgcaat gataccgcga gacccacgct    9660
caccggctcc agatttatca gcaataaacc agccagccgg aagggccgag cgcagaagtg    9720
gtcctgcaac tttatccgcc tccatccagt ctattaattg ttgccgggaa gctagagtaa    9780
gtagttcgcc agttaatagt ttgcgcaacg ttgttgccat tgctacaggc atcgtggtgt    9840
cacgctcgtc gtttggtatg gcttcattca gctccggttc ccaacgatca aggcgagtta    9900
catgatcccc catgttgtgc aaaaaagcgg ttagctcctt cggtcctccg atcgttgtca    9960
gaagtaagtt ggccgcagtg ttatcactca tggttatggc agcactgcat aattctctta   10020
ctgtcatgcc atccgtaaga tgcttttctg tgactggtga gtactcaacc aagtcattct   10080
gagaatagtg tatgcggcga ccgagttgct cttgcccggc gtcaatacgg gataataccg   10140
cgccacatag cagaacttta aaagtgctca tcattggaaa acgttcttcg ggcgaaaac    10200
tctcaaggat cttaccgctg ttgagatcca gttcgatgta acccactcgt gcacccaact   10260
gatcttcagc atcttttact ttcaccagcg tttctgggtg agcaaaaaca ggaaggcaaa   10320
atgccgcaaa aaagggaata agggcgacac ggaaatgttg aatactcata ctcttccttt   10380
ttcaatatta ttgaagcatt tatcagggtt attgtctcat gagcggatac atatttgaat   10440
gtatttagaa aaataaacaa ataggggttc cgcgcacatt tccccgaaaa gtgccacctg   10500
acgtctaaga aaccattatt atcatgacat taacctataa aaataggcgt atcacgaggc   10560
cctttcgtct cgcgcgtttc ggtgatgacg gtgaaaacct ctgacacatg cagctcccgg   10620
agacggtcac agcttctgtc taagcggatg ccggagcag acaagcccgt cagggcgcgt    10680
cagcgggtgt tggcgggtgt cggggctggc ttaactatgc ggcatcagag cagattgtac   10740
tgagagtgca ccatatcgac gctctcccct atgcgactcc tgcattagga agcagcccag   10800
tactaggttg aggccgttga gcaccgccgc cgcaaggaat ggtgcatgcg taatcaatta   10860
cggggtcatt agttcatagc ccatatatgg agttccgcgt tacataactt acggtaaatg   10920
gcccgcctgg ctgaccgccc aacgaccccc gcccattgac gtcaataatg acgtatgttc   10980
ccatagtaac gccaataggg actttccatt gacgtcaatg ggtggagtat ttacggtaaa   11040
ctgcccactt ggcagtacat caagtgtatc atatgccaag tacgccccct attgacgtca   11100
atgacggtaa atggcccgcc tggcattatg cccagtacat gaccttatgg gactttccta   11160
cttggcagta catctacgta ttagtcatcg ctattaccat ggtgatgcgg ttttggcagt   11220
acatcaatgg gcgtggatag cggtttgact cacggggatt tccaagtctc caccccattg   11280
acgtcaatgg gagtttgttt tggcaccaaa atcaacggga ctttccaaaa tgtcgtaaca   11340
actccgcccc attgacgcaa atgggcggta ggcgtgtacg gtgggaggtc tatataagca   11400
gagctctctg gctaactaga acccactg cttaactggc ttatcgaaat taatacgact   11460
cactataggg agaccggaag cttgaattc                                     11489
```

<210> SEQ ID NO 18
<211> LENGTH: 7518
<212> TYPE: DNA
<213> ORGANISM: Artificial Sequence
<220> FEATURE:
<223> OTHER INFORMATION: synthetic construct

<400> SEQUENCE: 18

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960
accacactgg actagtggat ccatgcatgg agatacacct acattgcatg aatatatgtt   1020
agatttgcaa ccagagacaa ctgatctcta ctgttatgag caattaaatg acagctcaga   1080
ggaggaggat gaaatagatg gtccagctgg acaagcagaa ccggacagag cccattacaa   1140
tattgtaacc ttttgttgca agtgtgactc tacgcttcgg ttgtgcgtac aaagcacaca   1200
cgtagacatt cgtactttgg aagacctgtt aatgggcaca ctaggaattg tgtgcccat    1260
ctgttctcaa ggatccatgg ctcgtgcggt cgggatcgac ctcgggacca ccaactccgt   1320
cgtctcggtt ctggaaggtg gcgacccggt cgtcgtcgcc aactccgagg gctccaggac   1380
caccccgtca attgtcgcgt tcgcccgcaa cggtgaggtg ctggtcggcc agcccgccaa   1440
gaaccaggca gtgaccaacg tcgatcgcac cgtgcgctcg gtcaagcgac acatgggcag   1500
cgactggtcc atagagattg acggcaagaa atacaccgcg ccgagatcca gcgcccgcat   1560
tctgatgaag ctgaagcgcg acgccgaggc ctacctcggt gaggacatta ccgacgcggt   1620
tatcacgacg cccgcctact tcaatgacgc ccagcgtcag gccaccaagg acgccggcca   1680
gatcgccggc ctcaacgtgc tgcggatcgt caacgagccg accgcggccg cgctggccta   1740
cggcctcgac aagggcgaga aggagcagcg aatcctggtc ttcgacttgg gtggtggcac   1800
tttcgacgtt tccctgctgg agatcggcga gggtgtggt gaggtccgtg ccacttcggg   1860
tgacaaccac ctcggcggcg acgactggga ccagcgggtc gtcgattggc tggtggacaa   1920
gttcaagggc accagcggca tcgatctgac caaggacaag atggcgatgc agcggctgcg   1980
ggaagccgcc gagaaggcaa agatcgagct gagttcgagt cagtccacct cgatcaacct   2040
gcctacatc accgtcgacg ccgacaagaa cccgttgttc ttagacgagc agctgacccg   2100
cgcggagttc caacggatca ctcaggacct gctggaccgc actcgcaagc cgttccagtc   2160
ggtgatcgct gacaccggca tttcggtgtc ggagatcgat cacgttgtgc tcgtgggtgg   2220
```

-continued

```
ttcgacccgg atgcccgcgg tgaccgatct ggtcaaggaa ctcaccgcg gcaaggaacc    2280 caacaagggc gtcaaccccg atgaggttgt cgcggtggga gccgctctgc aggccggcgt    2340
cctcaagggc gaggtgaaag acgttctgct gcttgatgtt accccgctga gcctgggtat    2400
cgagaccaag ggcggggtga tgaccaggct catcgagcgc aacaccacga tccccaccaa    2460
gcggtcggag actttcacca ccgccgacga caaccaaccg tcggtgcaga tccaggtcta    2520 tcaggggag cgtgagatcg ccgcgcacaa caagttgctc gggtccttcg agctgaccgg    2580
catcccgccg gcgccgcggg ggattccgca gatcgaggtc actttcgaca tcgacgccaa    2640
cggcattgtg cacgtcaccg ccaaggacaa gggcaccggc aaggagaaca cgatccgaat    2700
ccaggaaggc tcgggcctgt ccaaggaaga cattgaccgc atgatcaagg acgccgaagc    2760
gcacgccgag gaggatcgca agcgtcgcga ggaggccgat gttcgtaatc aagccgagac    2820
attggtctac cagacggaga agttcgtcaa agaacagcgt gaggccgagg gtggttcgaa    2880
ggtacctgaa gacacgctga acaaggttga tgccgcggtg gcggaagcga aggcggcact    2940
tggcggatcg gatatttcgg ccatcaagtc ggcgatggag aagctgggcc aggagtcgca    3000
ggctctgggg caagcgatct acgaagcagc tcaggctgcg tcacaggcca ctggcgctgc    3060
ccaccccggc tcggctgatg aaagcttaag tttaaaccgc tgatcagcct cgactgtgcc    3120
ttctagttgc cagccatctg ttgtttgccc ctccccgtg ccttccttga ccctggaagg    3180
tgccactccc actgtccttt cctaataaaa tgaggaaatt gcatcgcatt gtctgagtag    3240
gtgtcattct attctggggg gtggggtggg gcaggacagc aagggggagg attgggaaga    3300
caatagcagg catgctgggg atgcggtggg ctctatggct tctgaggcgg aaagaaccag    3360
ctggggctct aggggtatc cccacgcgcc ctgtagcggc gcattaagcg cggcgggtgt    3420
ggtggttacg cgcagcgtga ccgctacact tgccagcgcc ctagcgcccg ctcctttcgc    3480
tttcttccct tcctttctcg ccacgttcgc cggctttccc cgtcaagctc taaatcgggg    3540
catcccttta gggttccgat ttagtgcttt acggcacctc gaccccaaaa aacttgatta    3600
gggtgatggt tcacgtagtg ggccatcgcc ctgatagacg gttttcgcc ctttgacgtt    3660 ggagtccacg ttctttaata gtggactctt gttccaaact ggaacaacac tcaaccctat    3720
ctcggtctat tcttttgatt tataagggat tttggggatt tcggcctatt ggttaaaaaa    3780
tgagctgatt taacaaaaat ttaacgcgaa ttaattctgt ggaatgtgtg tcagttaggg    3840
tgtggaaagt ccccaggctc cccaggcagg cagaagtatg caaagcatgc atctcaatta    3900
gtcagcaacc aggtgtggaa agtccccagg ctccccagca ggcagaagta tgcaaagcat    3960
gcatctcaat tagtcagcaa ccatagtccc gcccctaact ccgcccatcc cgcccctaac    4020
tccgcccagt tccgcccatt ctccgcccca tggctgacta ttttttta tttatgcaga    4080 ggccgaggcc gcctctgcct ctgagctatt ccagaagtag tgaggaggct ttttggagg    4140 cctaggcttt tgcaaaaagc tcccgggagc ttgtatatcc attttcggat ctgatcaaga    4200
gacaggatga ggatcgtttc gcatgattga acaagatgga ttgcacgcag gttctccggc    4260
cgcttgggtg gagaggctat tcggctatga ctgggcacaa cagacaatcg gctgctctga    4320
tgccgccgtg ttccggctgt cagcgcaggg gcgcccggtt ctttttgtca agaccgacct    4380
gtccggtgcc ctgaatgaac tgcaggacga ggcagcgcgg ctatcgtggc tggccacgac    4440
gggcgttcct tgcgcagctg tgctcgacgt tgtcactgaa gcgggaaggg actggctgct    4500
attgggcgaa gtgccggggc aggatctcct gtcatctcac cttgctcctg ccagaaaagt    4560
atccatcatg gctgatgcaa tgcggcggct gcatacgctt gatccggcta cctgcccatt    4620
```

```
cgaccaccaa gcgaaacatc gcatcgagcg agcacgtact cggatggaag ccggtcttgt   4680
cgatcaggat gatctggacg aagagcatca ggggctcgcg ccagccgaac tgttcgccag   4740
gctcaaggcg cgcatgcccg acggcgagga tctcgtcgtg acccatggcg atgcctgctt   4800
gccgaatatc atggtggaaa atggccgctt ttctggattc atcgactgtg gccggctggg   4860
tgtggcggac cgctatcagg acatagcgtt ggctacccgt gatattgctg aagagcttgg   4920
cggcgaatgg gctgaccgct tcctcgtgct ttacggtatc gccgctcccg attcgcagcg   4980
catcgccttc tatcgccttc ttgacgagtt cttctgagcg ggactctggg gttcgaaatg   5040
accgaccaag cgacgcccaa cctgccatca cgagatttcg attccaccgc cgccttctat   5100
gaaaggttgg gcttcggaat cgttttccgg gacgccggct ggatgatcct ccagcgcggg   5160
gatctcatgc tggagttctt cgcccacccc aacttgttta ttgcagctta taatggttac   5220
aaataaagca atagcatcac aaatttcaca aataaagcat ttttttcact gcattctagt   5280
tgtggtttgt ccaaactcat caatgtatct tatcatgtct gtataccgtc gacctctagc   5340
tagagcttgg cgtaatcatg gtcatagctg tttcctgtgt gaaattgtta tccgctcaca   5400
attccacaca acatacgagc cggaagcata aagtgtaaag cctggggtgc ctaatgagtg   5460
agctaactca cattaattgc gttgcgctca ctgcccgctt tccagtcggg aaacctgtcg   5520
tgccagctgc attaatgaat cggccaacgc gcggggagag gcggtttgcg tattgggcgc   5580
tcttccgctt cctcgctcac tgactcgctg cgctcggtcg ttcggctgcg gcgagcggta   5640
tcagctcact caaaggcggt aatacggtta tccacagaat caggggataa cgcaggaaag   5700
aacatgtgag caaaaggcca gcaaaaggcc aggaaccgta aaaaggccgc gttgctggcg   5760
ttttttccata ggctccgccc ccctgacgag catcacaaaa atcgacgctc aagtcagagg   5820
tggcgaaacc cgacaggact ataaagatac caggcgtttc ccctggaagc tccctcgtg   5880
cgctctcctg ttccgaccct gccgcttacc ggatacctgt ccgcctttct cccttcggga   5940
agcgtggcgc tttctcaatg ctcacgctgt aggtatctca gttcggtgta ggtcgttcgc   6000
tccaagctgg gctgtgtgca cgaaccccce gttcagcccg accgctgcgc cttatccggt   6060
aactatcgtc ttgagtccaa cccggtaaga cacgacttat cgccactggc agcagccact   6120
ggtaacagga ttagcagagc gaggtatgta ggcggtgcta cagagttctt gaagtggtgg   6180
cctaactacg gctacactag aaggacagta tttggtatct gcgctctgct gaagccagtt   6240
accttcggaa aaagagttgg tagctcttga tccggcaaac aaaccaccgc tggtagcggt   6300
ggttttttg tttgcaagca gcagattacg cgcagaaaaa aaggatctca agaagatcct   6360
ttgatctttt ctacggggtc tgacgctcag tggaacgaaa actcacgtta agggattttg   6420
gtcatgagat tatcaaaaag gatcttcacc tagatccttt taaattaaaa atgaagtttt   6480
aaatcaatct aaagtatata tgagtaaact tggtctgaca gttaccaatg cttaatcagt   6540
gaggcaccta tctcagcgat ctgtctattt cgttcatcca tagttgcctg actccccgtc   6600
gtgtagataa ctacgatacg ggagggctta ccatctggcc ccagtgctgc aatgataccg   6660
cgagacccac gctcaccggc tccagattta tcagcaataa accagccagc cggaagggcc   6720
gagcgcagaa gtggtcctgc aactttatcc gcctccatcc agtctattaa ttgttgccgg   6780
gaagctagag taagtagttc gccagttaat agtttgcgca acgttgttgc cattgctaca   6840
ggcatcgtgg tgtcacgctc gtcgtttggt atggcttcat tcagctccgg ttcccaacga   6900
tcaaggcgag ttacatgatc cccatgttg tgcaaaaaag cggttagctc cttcggtcct   6960
```

-continued

| | |
|---|---|
| ccgatcgttg tcagaagtaa gttggccgca gtgttatcac tcatggttat ggcagcactg | 7020 |
| cataattctc ttactgtcat gccatccgta agatgctttt ctgtgactgg tgagtactca | 7080 |
| accaagtcat tctgagaata gtgtatgcgg cgaccgagtt gctcttgccc ggcgtcaata | 7140 |
| cgggataata ccgcgccaca tagcagaact ttaaaagtgc tcatcattgg aaaacgttct | 7200 |
| tcggggcgaa aactctcaag gatcttaccg ctgttgagat ccagttcgat gtaacccact | 7260 |
| cgtgcaccca actgatcttc agcatctttt actttcacca cgtttctgg gtgagcaaaa | 7320 |
| acaggaaggc aaaatgccgc aaaaaaggga ataaggcga cacggaaatg ttgaatactc | 7380 |
| atactcttcc tttttcaata ttattgaagc atttatcagg gttattgtct catgagcgga | 7440 |
| tacatatttg aatgtattta gaaaaataaa caaatagggg ttccgcgcac atttccccga | 7500 |
| aaagtgccac ctgacgtc | 7518 |

<210> SEQ ID NO 19
<211> LENGTH: 12110
<212> TYPE: DNA
<213> ORGANISM: Artificial Sequence
<220> FEATURE:
<223> OTHER INFORMATION: synthetic construct

<400> SEQUENCE: 19

| | |
|---|---|
| attgacggcg tagtacacac tattgaatca aacagccgac caattgcact accatcacaa | 60 |
| tggagaagcc agtagtaaac gtagacgtag accccccagag tccgtttgtc gtgcaactgc | 120 |
| aaaaaagctt cccgcaattt gaggtagtag cacagcaggt cactccaaat gaccatgcta | 180 |
| atgccagagc attttcgcat ctggccagta aactaatcga gctggaggtt cctaccacag | 240 |
| cgacgatctt ggacataggc agcgcaccgg ctcgtagaat gttttccgag caccagtatc | 300 |
| attgtgtctg ccccatgcgt agtccagaag acccggaccg catgatgaaa tacgccagta | 360 |
| aactggcgga aaaagcgtgc aagattacaa acaagaactt gcatgagaag attaaggatc | 420 |
| tccggaccgt acttgatacg ccggatgctg aaacaccatc gctctgcttt cacaacgatg | 480 |
| ttacctgcaa catgcgtgcc gaatattccg tcatgcagga cgtgtatatc aacgctcccg | 540 |
| gaactatcta tcatcaggct atgaaaggcg tgcggaccct gtactggatt ggcttcgaca | 600 |
| ccacccagtt catgttctcg gctatggcag gttcgtaccc tgcgtacaac accaactggg | 660 |
| ccgacgagaa agtccttgaa gcgcgtaaca tcggactttg cagcacaaag ctgagtgaag | 720 |
| gtaggacagg aaaattgtcg ataatgagga agaaggagtt gaagcccggg tcgcgggttt | 780 |
| atttctccgt aggatcgaca ctttatccag aacacagagc cagcttgcag agctggcatc | 840 |
| ttccatcggt gttccacttg aatggaaagc agtcgtacac ttgccgctgt gatacagtgg | 900 |
| tgagttgcga aggctacgta gtgaagaaaa tcaccatcag tcccgggatc acgggagaaa | 960 |
| ccgtgggata cgcggttaca cacaatagcg agggcttctt gctatgcaaa gttactgaca | 1020 |
| cagtaaaagg agaacgggta tcgttccctg tgtgcacgta catcccggcc accatatgcg | 1080 |
| atcagatgac tggtataatg gccacggata tatcacctga cgatgcacaa aaacttctgg | 1140 |
| ttgggctcaa ccagcgaatt gtcattaacg gtaggactaa caggaacacc aacaccatgc | 1200 |
| aaaattacct tctgccgatc atagcacaag ggttcagcaa atgggctaag gagcgcaagg | 1260 |
| atgatcttga taacgagaaa atgctgggta ctagagaacg caagcttacg tatggctgct | 1320 |
| tgtgggcgtt tcgcactaag aaagtacatt cgttttatcg cccacctgga acgcagacct | 1380 |
| gcgtaaaagt cccagcctct tttagcgctt ttcccatgtc gtccgtatgg acgacctctt | 1440 |
| tgcccatgtc gctgaggcag aaattgaaac tggcattgca accaaagaag gaggaaaaac | 1500 |

-continued

```
tgctgcaggt ctcggaggaa ttagtcatgg aggccaaggc tgcttttgag gatgctcagg    1560
aggaagccag agcggagaag ctccgagaag cacttccacc attagtggca gacaaaggca    1620
tcgaggcagc cgcagaagtt gtctgcgaag tggaggggct ccaggcggac atcggagcag    1680
cattagttga accccgcgc ggtcacgtaa ggataatacc tcaagcaaat gaccgtatga     1740
tcggacagta tatcgttgtc tcgccaaact ctgtgctgaa gaatgccaaa ctcgcaccag    1800
cgcacccgct agcagatcag gttaagatca taacacactc cggaagatca ggaaggtacg    1860
cggtcgaacc atacgacgct aaagtactga tgccagcagg aggtgccgta ccatggccag    1920
aattcctagc actgagtgag agcgccacgt tagtgtacaa cgaaagagag tttgtgaacc    1980
gcaaactata ccacattgcc atgcatggcc ccgccaagaa tacagaagag gagcagtaca    2040
aggttacaaa ggcagagctt gcagaaacag agtacgtgtt tgacgtggac aagaagcgtt    2100
gcgttaagaa ggaagaagcc tcaggtctgg tcctctcggg agaactgacc aaccctccct    2160
atcatgagct agctctggag ggactgaaga cccgacctgc ggtcccgtac aaggtcgaaa    2220
caataggagt gataggcaca ccggggtcgg gcaagtcagc tattatcaag tcaactgtca    2280
cggcacgaga tcttgttacc agcggaaaga aagaaaattg tcgcgaaatt gaggccgacg    2340
tgctaagact gaggggtatg cagattacgt cgaagacagt agattcggtt atgctcaacg    2400
gatgccacaa agccgtagaa gtgctgtacg ttgacgaagc gttcgcgtgc cacgcaggag    2460
cactacttgc cttgattgct atcgtcaggc cccgcaagaa ggtagtacta tgcggagacc    2520
ccatgcaatg cggattcttc aacatgatgc aactaaaggt acatttcaat caccctgaaa    2580
aagacatatg caccaagaca ttctacaagt atatctcccg gcgttgcaca cagccagtta    2640
cagctattgt atcgacactg cattacgatg aaagatgaa aaccacgaac ccgtgcaaga    2700
agaacattga aatcgatatt acaggggcca caaagccgaa gccagggggat atcatcctga    2760
catgtttccg cgggtgggtt aagcaattgc aaatcgacta tcccgggacat gaagtaatga    2820
cagccgcggc ctcacaaggg ctaaccagaa aaggagtgta tgccgtccgg caaaaagtca    2880
atgaaaaccc actgtacgcg atcacatcag agcatgtgaa cgtgttgctc acccgcactg    2940
aggacaggct agtgtggaaa accttgcagg gcgacccatg gattaagcag cccactaaca    3000
tacctaaagg aaactttcag gctactatag aggactggga agctgaacac aagggaataa    3060
ttgctgcaat aaaacagccc actccccgtg ccaatccgtt cagctgcaag accaacgttt    3120
gctgggcgaa agcattggaa ccgatactag ccacggccgg tatcgtactt accggttgcc    3180
agtggagcga actgttccca cagtttgcgg atgacaaacc acattcggcc atttacgcct    3240
tagacgtaat ttgcattaag ttttccggca tggacttgac aagcggactg ttttctaaac    3300
agagcatccc actaacgtac catcccgccg attcagcgag gccggtagct cattgggaca    3360
acagcccagg aacccgcaag tatgggtacg atcacgccat tgccgccgaa ctctcccgta    3420
gatttccggt gttccagcta gctgggaagg gcacacaact tgatttgcag acggggagaa    3480
ccagagttat ctctgcacag cataaacctgg tcccggtgaa ccgcaatctt cctcacgcct    3540
tagtccccga gtacaaggag aagcaacccg gcccggtcaa aaaattcttg aaccagttca    3600
aacaccactc agtacttgtg gtatcagagg aaaaaattga agctcccgt aagagaatcg    3660
aatggatcgc cccgattggc atagccggtg cagataagaa ctacaacctg gctttcgggt    3720
ttccgccgca ggcacggtac gacctggtgt tcatcaacat tggaactaaa tacagaaacc    3780
accactttca gcagtgcgaa gaccatgcgg cgaccttaaa aacccctttcg cgttcggccc    3840
```

-continued

```
tgaattgcct taacccagga ggcaccctcg tggtgaagtc ctatggctac gccgaccgca    3900
acagtgagga cgtagtcacc gctcttgcca gaaagtttgt cagggtgtct gcagcgagac    3960
cagattgtgt ctcaagcaat acagaaatgt acctgatttt ccgacaacta gacaacagcc    4020
gtacacggca attcaccccg caccatctga attgcgtgat ttcgtccgtg tatgagggta    4080
caagagatgg agttggagcc gcgccgtcat accgcaccaa aagggagaat attgctgact    4140
gtcaagagga agcagttgtc aacgcagcca atccgctggg tagaccaggc gaaggagtct    4200
gccgtgccat ctataaacgt tggccgacca gttttaccga ttcagccacg gagacaggca    4260
ccgcaagaat gactgtgtgc ctaggaaaga aagtgatcca cgcggtcggc cctgatttcc    4320
ggaagcaccc agaagcagaa gccttgaaat tgctacaaaa cgcctaccat gcagtggcag    4380
acttagtaaa tgaacataac atcaagtctg tcgccattcc actgctatct acaggcattt    4440
acgcagccgg aaaagaccgc cttgaagtat cacttaactg cttgacaacc gcgctagaca    4500
gaactgacgc ggacgtaacc atctattgcc tggataagaa gtggaaggaa agaatcgacg    4560
cggcactcca acttaaggag tctgtaacag agctgaagga tgaagatatg gagatcgacg    4620
atgagttagt atggattcat ccagacagtt gcttgaaggg aagaaaggga ttcagtacta    4680
caaaaggaaa attgtattcg tacttcgaag gcaccaaatt ccatcaagca gcaaaagaca    4740
tggcggagat aaaggtcctg ttccctaatg accaggaaag taatgaacaa ctgtgtgcct    4800
acatattggg tgagaccatg gaagcaatcc gcgaaaagtg cccggtcgac cataacccgt    4860
cgtctagccc gcccaaaacg ttgccgtgcc tttgcatgta tgccatgacg ccagaaaggg    4920
tccacagact tagaagcaat aacgtcaaag aagttacagt atgctcctcc accccccttc    4980
ctaagcacaa aattaagaat gttcagaagg ttcagtgcac gaaagtagtc ctgtttaatc    5040
cgcacactcc cgcattcgtt cccgcccgta agtacataga agtgccagaa cagcctaccg    5100
ctcctcctgc acaggccgag gaggcccccg aagttgtagc gacaccgtca ccatctacag    5160
ctgataacac ctcgcttgat gtcacagaca tctcactgga tatggatgac agtagcgaag    5220
gctcactttt ttcgagcttt agcggatcgg acaactctat tactagtatg gacagttggt    5280
cgtcaggacc tagttcacta gagatagtag accgaaggca ggtggtggtg gctgacgttc    5340
atgccgtcca agagcctgcc cctattccac cgccaaggct aaagaagatg gcccgcctgg    5400
cagcggcaag aaaagagccc actccaccgg caagcaatag ctctgagtcc ctccacctct    5460
cttttggtgg ggtatccatg tccctcggat caattttcga cggagagacg gcccgccagg    5520
cagcggtaca accccctggca acaggcccca cggatgtgcc tatgtctttc ggatcgtttt    5580
ccgacggaga gattgatgag ctgagccgca gagtaactga gtccgaaccc gtcctgtttg    5640
gatcatttga accgggcgaa gtgaactcaa ttatatcgtc ccgatcagcc gtatcttttc    5700
cactacgcaa gcagagacgt agacgcagga gcaggaggac tgaatactga ctaaccgggg    5760
taggtgggta catattttcg acggacacag gccctgggca cttgcaaaag aagtccgttc    5820
tgcagaacca gcttacagaa ccgaccttgg agcgcaatgt cctggaaaga attcatgccc    5880
cggtgctcga cacgtcgaaa gaggaacaac tcaaactcag gtaccagatg atgcccaccg    5940
aagccaacaa aagtaggtac cagtctcgta agtagaaaaa tcagaaagcc ataaccactg    6000
agcgactact gtcaggacta cgactgtata actctgccac agatcagcca gaatgctata    6060
agatcaccta tccgaaacca ttgtactcca gtagcgtacc ggcgaactac tccgatccac    6120
agttcgctgt agctgtctgt aacaactatc tgcatgagaa ctatccgaca gtagcatctt    6180
atcagattac tgacgagtac gatgcttact tggatatggt agacgggaca gtcgcctgcc    6240
```

```
tggatactgc aaccttctgc cccgctaagc ttagaagtta cccgaaaaaa catgagtata    6300
gagccccgaa tatccgcagt gcggttccat cagcgatgca gaacacgcta caaaatgtgc    6360
tcattgccgc aactaaaaga aattgcaacg tcacgcagat gcgtgaactg ccaacactgg    6420
actcagcgac attcaatgtc gaatgctttc gaaaatatgc atgtaatgac gagtattggg    6480
aggagttcgc tcggaagcca attaggatta ccactgagtt tgtcaccgca tatgtagcta    6540
gactgaaagg ccctaaggcc gccgcactat ttgcaaagac gtataatttg gtcccattgc    6600
aagaagtgcc tatggataga ttcgtcatgg acatgaaaag agacgtgaaa gttacaccag    6660
gcacgaaaca cacagaagaa agaccgaaag tacaagtgat acaagccgca gaacccctgg    6720
cgactgctta cttatgcggg attcaccggg aattagtgcg taggcttacg gccgtcttgc    6780
ttccaaacat tcacacgctt tttgacatgt cggcggagga ttttgatgca atcatagcag    6840
aacacttcaa gcaaggcgac ccggtactgg agacggatat cgcatcattc gacaaaagcc    6900
aagacgacgc tatggcgtta accggtctga tgatcttgga ggacctgggt gtggatcaac    6960
cactactcga cttgatcgag tgcgcctttg gagaaatatc atccacccat ctacctacgg    7020
gtactcgttt taaattcggg gcgatgatga atccggaat gttcctcaca cttttgtca    7080
acacagtttt gaatgtcgtt atcgccagca gagtactaga agagcggctt aaaacgtcca    7140
gatgtgcagc gttcattggc gacgacaaca tcatacatgg agtagtatct gacaaagaaa    7200
tggctgagag gtgcgccacc tggctcaaca tggaggttaa gatcatcgac gcagtcatcg    7260
gtgagagacc accttacttc tgcggcggat ttatcttgca agattcggtt acttccacag    7320
cgtgccgcgt ggcggatccc ctgaaaaggc tgtttaagtt gggtaaaccg ctcccagccg    7380
acgacgagca agacgaagac agaagacgcg ctctgctaga tgaaacaaag gcgtggttta    7440
gagtaggtat aacaggcact ttagcagtgg ccgtgacgac ccggtatgag gtagacaata    7500
ttacacctgt cctactggca ttgagaactt ttgcccagag caaaagagca ttccaagcca    7560
tcagagggga aataaagcat ctctacggtg gtcctaaata gtcagcatag tacatttcat    7620
ctgactaata ctacaacacc accacctcta gactcgagcg gccgccactg tgctggatat    7680
ctgcagaatt ccaccacact ggactagtgg atccatgcat ggagatacac ctacattgca    7740
tgaatatatg ttagatttgc aaccagagac aactgatctc tactgttatg agcaattaaa    7800
tgacagctca gaggaggagg atgaaataga tggtccagct ggacaagcag aaccggacag    7860
agcccattac aatattgtaa cctttttgttg caagtgtgac tctacgcttc ggttgtgcgt    7920
acaaagcaca cacgtagaca ttcgtacttt ggaagacctg ttaatgggca cactaggaat    7980
tgtgtgcccc atctgttctc aaggatccat ggctcgtgcg gtcgggatcg acctcgggac    8040
caccaactcc gtcgtctcgg ttctggaagg tggcgacccg gtcgtcgtcg ccaactccga    8100
gggctccagg accaccccgt caattgtcgc gttcgcccgc aacggtgagg tgctggtcgg    8160
ccagcccgcc aagaaccagg cagtgaccaa cgtcgatcgc accgtgcgct cggtcaagcg    8220
acacatgggc agcgactggt ccatagagat tgacggcaag aaatacaccg cgccggagat    8280
cagcgcccgc attctgatga agctgaagcg cgacgccgag gcctacctcg gtgaggacat    8340
taccgacgcg gttatcacga cgcccgccta cttcaatgac gcccagcgtc aggccaccaa    8400
ggacgccggc cagatcgccg gcctcaacgt gctgcggatc gtcaacgagc cgaccgcggc    8460
cgcgctggcc tacggcctcg acaagggcga aaggagcag cgaatcctgg tcttcgactt    8520
gggtggtggc actttcgacg tttccctgct ggagatcggc gagggtgtgg ttgaggtccg    8580
```

```
tgccacttcg ggtgacaacc acctcggcgg cgacgactgg gaccagcggg tcgtcgattg    8640
gctggtggac aagttcaagg gcaccagcgg catcgatctg accaaggaca agatggcgat    8700
gcagcggctg cgggaagccg ccgagaaggc aaagatcgag ctgagttcga gtcagtccac    8760
ctcgatcaac ctgccctaca tcaccgtcga cgccgacaag aacccgttgt tcttagacga    8820
gcagctgacc cgcgcggagt tccaacggat cactcaggac ctgctggacc gcactcgcaa    8880
gccgttccag tcggtgatcg ctgacaccgg catttcggtg tcggagatcg atcacgttgt    8940
gctcgtgggt ggttcgaccc ggatgcccgc ggtgaccgat ctggtcaagg aactcaccgg    9000
cggcaaggaa cccaacaagg gcgtcaaccc cgatgaggtt gtcgcggtgg agccgctct    9060 gcaggccggc gtcctcaagg gcgaggtgaa agacgttctg ctgcttgatg ttaccccgct    9120
gagcctgggt atcgagacca agggcggggt gatgaccagg ctcatcgagc gcaacaccac    9180
gatccccacc aagcggtcgg agactttcac caccgccgac acaaccaac cgtcggtgca    9240 gatccaggtc tatcaggggg agcgtgagat cgccgcgcac aacaagttgc tcgggtcctt    9300
cgagctgacc ggcatcccgc cggcgccgcg ggggattccg cagatcgagg tcactttcga    9360
catcgacgcc aacggcattg tgcacgtcac cgccaaggac aagggcaccg gcaaggagaa    9420
cacgatccga atccaggaag gctcgggcct gtccaaggaa gacattgacc gcatgatcaa    9480
ggacgccgaa gcgcacgccg aggaggatcg caagcgtcgc gaggaggccg atgttcgtaa    9540
tcaagccgag acattggtct accagacgga gaagttcgtc aaagaacagc gtgaggccga    9600
gggtggttcg aaggtacctg aagacacgct gaacaaggtt gatgccgcgg tggcggaagc    9660
gaaggcggca cttggcggat cggatatttc ggccatcaag tcggcgatgg agaagctggg    9720
ccaggagtcg caggctctgg ggcaagcgat ctacgaagca gctcaggctg cgtcacaggc    9780
cactggcgct gcccaccccg gctcggctga tgaaagctta agtttgtgag catgcaggcc    9840
ttgggcccaa tgatccgacc agcaaaaactc gatgtacttc cgaggaactg atgtgcataa    9900
tgcatcaggc tggtacatta gatccccgct taccgcgggc aatatagcaa cactaaaaac    9960
tcgatgtact tccgaggaag cgcagtgcat aatgctgcgc agtgttgcca cataaccact   10020
atattaacca tttatctagc ggacgccaaa aactcaatgt atttctgagg aagcgtggtg   10080
cataatgcca cgcagcgtct gcataacttt tattatttct tttattaatc aacaaaattt   10140
tgtttttaac atttcaaaaa aaaaaaaaaa aaaaaaaaa aaaaaaaaa aagggaattc   10200 ctcgattaat taagcggccg ctcgagggga attaattctt gaagacgaaa gggccaggtg   10260
gcacttttcg gggaaatgtg cgcggaaccc ctatttgttt attttttctaa atacattcaa   10320 atatgtatcc gctcatgaga caataaccct gataaatgct tcaataatat tgaaaaagga   10380
agagtatgag tattcaacat ttccgtgtcg cccttattcc cttttttgcg cattttgcc   10440 ttcctgtttt tgctcaccca gaaacgctgg tgaaagtaaa agatgctgaa gatcagttgg   10500
gtgcacgagt gggttacatc gaactggatc tcaacagcgg taagatcctt gagagttttc   10560
gccccgaaga acgttttcca atgatgagca cttttaaagt tctgctatgt ggcgcggtat   10620
tatcccgtgt tgacgccggg caagagcaac tcggtcgccg catacactat tctcagaatg   10680
acttggttga gtactcacca gtcacagaaa agcatcttac ggatggcatg acagtaagag   10740
aattatgcag tgctgccata accatgagtg ataacactgc ggccaactta cttctgacaa   10800
cgatcggagg accgaaggag ctaaccgctt ttttgcacaa catgggggat catgtaactc   10860
gccttgatcg ttgggaaccg gagctgaatg aagccatacc aaacgacgag cgtgacacca   10920
cgatgcctgt agcaatggca acaacgttgc gcaaactatt aactggcgaa ctacttactc   10980
```

-continued

```
tagcttcccg gcaacaatta atagactgga tggaggcgga taaagttgca ggaccacttc    11040
tgcgctcggc ccttccggct ggctggttta ttgctgataa atctggagcc ggtgagcgtg    11100
ggtctcgcgg tatcattgca gcactggggc cagatggtaa gccctcccgt atcgtagtta    11160
tctacacgac ggggagtcag gcaactatgg atgaacgaaa tagacagatc gctgagatag    11220
gtgcctcact gattaagcat tggtaactgt cagaccaagt ttactcatat atactttaga    11280
ttgatttaaa acttcatttt taatttaaaa ggatctaggt gaagatcctt tttgataatc    11340
tcatgaccaa aatcccttaa cgtgagtttt cgttccactg agcgtcagac cccgtagaaa    11400
agatcaaagg atcttcttga gatccttttt ttctgcgcgt aatctgctgc ttgcaaacaa    11460
aaaaaccacc gctaccagcg gtggtttgtt tgccggatca agagctacca actctttttc    11520
cgaaggtaac tggcttcagc agagcgcaga taccaaatac tgtccttcta gtgtagccgt    11580
agttaggcca ccacttcaag aactctgtag caccgcctac atacctcgct ctgctaatcc    11640
tgttaccagt ggctgctgcc agtggcgata agtcgtgtct taccgggttg gactcaagac    11700
gatagttacc ggataaggcg cagcggtcgg gctgaacggg gggttcgtgc acacagccca    11760
gcttggagcg aacgacctac accgaactga gatacctaca gcgtgagcat tgagaaagcg    11820
ccacgcttcc cgaagggaga aaggcggaca ggtatccggt aagcggcagg gtcggaacag    11880
gagagcgcac gagggagctt ccaggggaaa acgcctggta tctttatagt cctgtcgggt    11940
ttcgccacct ctgacttgag cgtcgatttt tgtgatgctc gtcaggggg cggagcctat    12000 ggaaaaacgc cagcaacgcg agctcgtatg gacatattgt cgttagaacg cggctacaat    12060
taatacataa ccttatgtat catacacata cgatttaggg gacactatag           12110
```

<210> SEQ ID NO 20
<211> LENGTH: 13599
<212> TYPE: DNA
<213> ORGANISM: Artificial Sequence
<220> FEATURE:
<223> OTHER INFORMATION: synthetic construct
<400> SEQUENCE: 20

```
atggcggatg tgtgacatac acgacgccaa aagattttgt tccagctcct gccacctccg      60
ctacgcgaga gattaaccac ccacgatggc cgccaaagtg catgttgata ttgaggctga     120
cagcccattc atcaagtctt tgcagaaggc atttccgtcg ttcgaggtgg agtcattgca     180
ggtcacacca aatgaccatg caaatgccag agcattttcg cacctggcta ccaaattgat     240
cgagcaggag actgacaaag acacactcat cttggatatc ggcagtgcgc cttccaggag     300
aatgatgtct acgcacaaat accactgcgt atgccctatg cgcagcgcag aagaccccga     360
aaggctcgat agctacgcaa agaaactggc agcggcctcc gggaaggtgc tggatagaga     420
gatcgcagga aaaatcaccg acctgcagac cgtcatggct acgccagacg ctgaatctcc     480 tacctttgc ctgcatacag acgtcacgtg tcgtacggca gccgaagtgg ccgtatacca     540
ggacgtgtat gctgtacatg caccaacatc gctgtaccat caggcgatga aaggtgtcag     600
aacggcgtat tggattgggt tgacaccac cccgtttatg tttgacgcgc tagcaggcgc     660
gtatccaacc tacgccacaa actgggccga cgagcaggtg ttacaggcca ggaacatagg     720
actgtgtgca gcatccttga ctgagggaag actcggcaaa ctgtccattc tccgcaagaa     780
gcaattgaaa ccttgcgaca cagtcatgtt ctcggtagga tctacattgt acactgagag     840
cagaaagcta ctgaggagct ggcacttacc ctccgtattc cacctgaaag gtaaacaatc     900
```

```
ctttacctgt aggtgcgata ccatcgtatc atgtgaaggg tacgtagtta agaaaatcac    960
tatgtgcccc ggcctgtacg gtaaaacggt agggtacgcc gtgacgtatc acgcggaggg   1020
attcctagtg tgcaagacca cagacactgt caaaggagaa agagtctcat tccctgtatg   1080
cacctacgtc ccctcaacca tctgtgatca aatgactggc atactagcga ccgacgtcac   1140
accggaggac gcacagaagt tgttagtggg attgaatcag aggatagttg tgaacgaaag   1200
aacacagcga aacactaaca cgatgaagaa ctatctgctt ccgattgtgg ccgtcgcatt   1260
tagcaagtgg gcgagggaat acaaggcaga ccttgatgat gaaaaacctc tgggtgtccg   1320
agagaggtca cttacttgct gctgcttgtg ggcatttaaa acgaggaaga tgcacaccat   1380
gtacaagaaa ccagacaccc agacaatagt gaaggtgcct tcagagttta actcgttcgt   1440
catcccgagc ctatggtcta caggcctcgc aatcccagtc agatcacgca ttaagatgct   1500
tttggccaag aagaccaagc gagagttaat acctgttctc gacgcgtcgt cagccaggga   1560
tgctgaacaa gaggagaagg agaggttgga ggccgagctg actagagaag ccttaccacc   1620
cctcgtcccc atcgcgccgg cggagacggg agtcgtcgac gtcgacgttg aagaactaga   1680
gtatcacgca ggtgcagggg tcgtggaaac acctcgcagc gcgttgaaag tcaccgcaca   1740
gccgaacgac gtactactag gaaattacgt agttctgtcc ccgcagaccg tgctcaagag   1800
ctccaagttg gcccccgtgc accctctagc agagcaggtg aaaataataa cacataacgg   1860
gagggccggc ggttaccagg tcgacggata tgacggcagg gtcctactac catgtggatc   1920
ggccattccg gtccctgagt ttcaagcttt gagcgagagc gccactatgg tgtacaacga   1980
aagggagttc gtcaacagga aactatacca tattgccgtt cacggaccgt cgctgaacac   2040
cgacgaggag aactacgaga aagtcagagc tgaaagaact gacgccgagt acgtgttcga   2100
cgtagataaa aaatgctgcg tcaagagaga ggaagcgtcg ggtttggtgt tggtgggaga   2160
gctaaccaac ccccgttcc atgaattcgc ctacgaaggg ctgaagatca ggccgtcggc   2220
accatataag actacagtag taggagtctt tggggttccg ggatcaggca agtctgctat   2280
tattaagagc ctcgtgacca aacacgatct ggtcaccagc ggcaagaagg agaactgcca   2340
ggaaatagtt aacgacgtga agaagcaccg cgggaagggg acaagtaggg aaaacagtga   2400
ctccatcctg ctaaacgggt gtcgtcgtgc cgtggacatc ctatatgtgg acgaggcttt   2460
cgctagccat tccggtactc tgctggccct aattgctctt gttaaacctc ggagcaaagt   2520
ggtgttatgc ggagacccca gcaatgcgg attcttcaat atgatgcagc ttaaggtgaa   2580
cttcaaccac aacatctgca ctgaagtatg tcataaaagt atatccagac gttgcacgcg   2640
tccagtcacg gccatcgtgt ctacgttgca ctacggaggc aagatgcgca cgaccaaccc   2700
gtgcaacaaa cccataatca tagacaccac aggacagacc aagcccaagc caggagacat   2760
cgtgttaaca tgcttccgag ctgggcaaa gcagctgcag ttggactacc gtggacacga   2820
agtcatgaca gcagcagcat ctcagggcct caccgcaaa ggggtatacg ccgtaaggca   2880
gaaggtgaat gaaaatccct tgtatgcccc tgcgtcggag cacgtgaatg tactgctgac   2940
gcgcactgag gataggctgg tgtggaaaac gctggccggc gatccctgga ttaaggtcct   3000
atcaaacatt ccacagggta actttacggc cacattggaa gaatggcaag aagaacacga   3060
caaaataatg aaggtgattg aaggaccggc tgcgcctgtg gacgcgttcc agaacaaagc   3120
gaacgtgtgt tgggcgaaaa gcctggtgcc tgtcctggac actgccggaa tcagattgac   3180
agcagaggag tggagcacca taattacagc atttaaggag gacagagctt actctccagt   3240
ggtggccttg aatgaaattt gcaccaagta ctatggagtt gacctggaca gtggcctgtt   3300
```

```
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttgggagaag aaaatccagg aagccattga    4560
catgaggacg gctgtggagt tgctcaatga tgacgtggag ctgaccacag acttggtgag    4620
agtgcacccg gacagcagcc tggtgggtcg taagggctac agtaccactg acgggtcgct    4680
gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
aacaatggac aacatcagat ccaaatgtcc ggtgaacgat tccgattcat caacacctcc    4860
caggacagtg ccctgcctgt gccgctacgc aatgacagca gaacggatcg cccgccttag    4920
gtcacaccaa gttaaaagca tggtggtttg ctcatctttt cccctcccga ataccatgt    4980 agatggggtg cagaaggtaa agtgcgagaa ggttctcctg ttcgacccga cggtaccttc    5040
agtggttagt ccgcggaagt atgccgcatc tacgacggac cactcagatc ggtcgttacg    5100
agggtttgac ttggactgga ccaccgactc gtcttccact gccagcgata ccatgtcgct    5160
acccagtttg cagtcgtgtg acatcgactc gatctacgag ccaatggctc ccatagtagt    5220
gacggctgac gtacaccctg aacccgcagg catcgcggac ctggcggcag atgtgcaccc    5280
tgaacccgca gaccatgtgg acctcgagaa cccgattcct ccaccgcgcc cgaagagagc    5340
tgcatacctt gcctcccgcg cggcggagcg accggtgccg gcgccgagaa agccgacgcc    5400
tgccccaagg actgcgttta ggaacaagct gcctttgacg ttcggcgact ttgacgagca    5460
cgaggtcgat gcgttggcct ccgggattac tttcggagac ttcgacgacg tcctgcgact    5520
aggccgcgcg ggtgcatata ttttctcctc ggacactggc agcggacatt tacaacaaaa    5580
atccgttagg cagcacaatc tccagtgcgc acaactggat gcggtccagg aggagaaaat    5640
```

```
gtacccgcca aaattggata ctgagaggga gaagctgttg ctgctgaaaa tgcagatgca    5700
cccatcggag gctaataaga gtcgatacca gtctcgcaaa gtggagaaca tgaaagccac    5760
ggtggtggac aggctcacat cgggggccag attgtacacg ggagcggacg taggccgcat    5820
accaacatac gcggttcggt accccgcccc cgtgtactcc cctaccgtga tcgaaagatt    5880
ctcaagcccc gatgtagcaa tcgcagcgtg caacgaatac ctatccagaa attacccaac    5940
agtggcgtcg taccagataa cagatgaata cgacgcatac ttggacatgg ttgacgggtc    6000
ggatagttgc ttggacagag cgacattctg cccggcgaag ctccggtgct acccgaaaca    6060
tcatgcgtac caccagccga ctgtacgcag tgccgtcccg tcacccttc agaacacact     6120
acagaacgtg ctagcggccg ccaccaagag aaactgcaac gtcacgcaaa tgcgagaact    6180
acccaccatg gactcggcag tgttcaacgt ggagtgcttc aagcgctatg cctgctccgg    6240
agaatattgg gaagaatatg ctaaacaacc tatccggata accactgaga acatcactac    6300
ctatgtgacc aaattgaaag gcccgaaagc tgctgccttg ttcgctaaga cccacaactt    6360
ggttccgctg caggaggttc ccatggacag attcacggtc gacatgaaac gagatgtcaa    6420
agtcactcca gggacgaaac acacagagga aagacccaaa gtccaggtaa ttcaagcagc    6480
ggagccattg gcgaccgctt acctgtgcgg catccacagg gaattagtaa ggagactaaa    6540
tgctgtgtta cgccctaacg tgcacacatt gtttgatatg tcggccgaag actttgacgc    6600
gatcatcgcc tctcacttcc acccaggaga cccggttcta gagacggaca ttgcatcatt    6660
cgacaaaagc caggacgact ccttggctct tacaggttta atgatcctcg aagatctagg    6720
ggtggatcag tacctgctgg acttgatcga ggcagccttt ggggaaatat ccagctgtca    6780
cctaccaact ggcacgcgct tcaagttcgg agctatgatg aaatcgggca tgttctgac    6840
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
cgacaagctg atggcggaga ggtgcgcgtc gtgggtcaac atggaggtga agatcattga    7020
cgctgtcatg ggcgaaaaac ccccatattt tgtgggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acgaggttag    7200
caagtggttc cggacaggct gggggccga actggaggtg gcactaacat ctaggtatga    7260
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atccatgcat ggagatacac ctacattgca tgaatatatg    7440
ttagatttgc aaccagagac aactgatctc tactgttatg agcaattaaa tgacagctca    7500
gaggaggagg atgaaataga tggtccagct ggacaagcag aaccggacag agcccattac    7560
aatattgtaa cctttgttg caagtgtgac tctacgcttc ggttgtgcgt acaaagcaca    7620
cacgtagaca ttcgtacttt ggaagacctg ttaatgggca cactaggaat tgtgtgcccc    7680
atctgttctc aaggatccat ggctcgtgcg gtcgggatcg acctcgggac caccaactcc    7740
gtcgtctcgg ttctggaagg tggcgacccg gtcgtcgtcg ccaactccga gggctccagg    7800
accaccccgt caattgtcgc gttcgcccgc aacggtgagg tgctggtcgg ccagcccgcc    7860
aagaaccagg cagtgaccaa cgtcgatcgc accgtgcgct cggtcaagcg acacatgggc    7920
agcgactggt ccatagagat tgacggcaag aaatacaccg cgccggagat cagcgcccgc    7980
attctgatga agctgaagcg cgacgccgag gcctacctcg gtgaggacat taccgacgcg    8040
```

```
gttatcacga cgcccgccta cttcaatgac gcccagcgtc aggccaccaa ggacgccggc    8100
cagatcgccg gcctcaacgt gctgcggatc gtcaacgagc cgaccgcggc cgcgctggcc    8160
tacggcctcg acaagggcga gaaggagcag cgaatcctgg tcttcgactt gggtggtggc    8220
actttcgacg tttccctgct ggagatcggc gagggtgtgg ttgaggtccg tgccacttcg    8280
ggtgacaacc acctcggcgg cgacgactgg gaccagcggg tcgtcgattg gctggtggac    8340
aagttcaagg gcaccagcgg catcgatctg accaaggaca gatggcgat  gcagcggctg    8400 cgggaagccg ccgagaaggc aaagatcgag ctgagttcga gtcagtccac ctcgatcaac    8460
ctgccctaca tcaccgtcga cgccgacaag aacccgttgt tcttagacga gcagctgacc    8520
cgcgcggagt tccaacggat cactcaggac ctgctggacc gcactcgcaa gccgttccag    8580
tcggtgatcg ctgacaccgg cattcggtg  tcggagatcg atcacgttgt gctcgtgggt    8640
ggttcgaccc ggatgcccgc ggtgaccgat ctggtcaagg aactcaccgg cggcaaggaa    8700
cccaacaagg gcgtcaaccc cgatgaggtt gtcgcggtgg gagccgctct gcaggccggc    8760
gtcctcaagg gcgaggtgaa agacgttctg ctgcttgatg ttaccccgct gagcctgggt    8820
atcgagacca agggcggggt gatgaccagg ctcatcgagc gcaacaccac gatccccacc    8880
aagcggtcgg agactttcac caccgccgac gacaaccaac cgtcggtgca gatccaggtc    8940
tatcaggggg agcgtgagat cgccgcgcac aacaagttgc tcgggtcctt cgagctgacc    9000
ggcatcccgc cggcgccgcg ggggattccg cagatcgagg tcactttcga catcgacgcc    9060
aacggcattg tgcacgtcac cgccaaggac aagggcaccg gcaaggagaa cacgatccga    9120
atccaggaag gctcgggcct gtccaaggaa gacattgacc gcatgatcaa ggacgccgaa    9180
gcgcacgccg aggaggatcg caagcgtcgc gaggaggccg atgttcgtaa tcaagccgag    9240
acattggtct accagacgga gaagttcgtc aaagaacagc gtgaggccga gggtggttcg    9300
aaggtacctg aagacacgct gaacaaggtt gatgccgcgg tggcggaagc gaaggcggca    9360
cttggcggat cggatatttc ggccatcaag tcggcgatgg agaagctggg ccaggagtcg    9420
caggctctgg ggcaagcgat ctacgaagca gctcaggctg cgtcacaggc cactggcgct    9480
gcccaccccg gctcggctga tgaaagctta agtttgggta attaattgaa ttacatccct    9540
acgcaaacgt tttacggccg ccggtggcgc ccgcgcccgg cggccgtcc  ttggccgttg    9600 caggccactc cggtggctcc cgtcgtcccc gacttccagg cccagcagat gcagcaactc    9660
atcagcgccg taaatgcgct gacaatgaga cagaacgcaa ttgctcctgc taggcctccc    9720
aaaccaaaga agaagaagac aaccaaacca agccgaaaa  cgcagcccaa gaagatcaac    9780
ggaaaaacgc agcagcaaaa gaagaaagac aagcaagccg acaagaagaa gaagaaaccc    9840
ggaaaaagag aaagaatgtg catgaagatt gaaaatgact gtatcttcgt atgcggctag    9900
ccacagtaac gtagtgtttc cagacatgtc gggcaccgca ctatcatggg tgcagaaaat    9960
ctcgggtggt ctgggggcct tcgcaatcgg cgctatcctg gtgctggttg tggtcacttg   10020
cattgggctc cgcagataag ttagggtagg caatggcatt gatatagcaa gaaaattgaa   10080
aacagaaaaa gttagggtaa gcaatggcat ataaccataa ctgtataact tgtaacaaag   10140
cgcaacaaga cctgcgcaat tggccccgtg gtccgcctca cggaaactcg ggcaactca   10200 tattgacaca ttaattggca ataattgaa  gcttacataa gcttaattcg acgaataatt   10260 ggattttat  tttattttgc aattggtttt taatatttcc aaaaaaaaaa aaaaaaaaa    10320 aaaaaaaaaa aaaaaaaaaa aaaaaaaaaa aaaaaaaaaa aaaaaaaaaa ctagtgatca   10380
```

-continued

```
taatcagcca taccacattt gtagaggttt tacttgcttt aaaaaacctc ccacacctcc    10440
ccctgaacct gaaacataaa atgaatgcaa ttgttgttgt taacttgttt attgcagctt    10500
ataatggtta caaataaagc aatagcatca caaatttcac aaataaagca ttttttttcac   10560 tgcattctag ttgtggtttg tccaaactca tcaatgtatc ttatcatgtc tggatctagt    10620
ctgcattaat gaatcggcca acgcgcgggg agaggcggtt tgcgtattgg gcgctcttcc    10680
gcttcctcgc tcactgactc gctgcgctcg gtcgttcggc tgcggcgagc ggtatcagct    10740
cactcaaagg cggtaatacg gttatccaca gaatcagggg ataacgcagg aaagaacatg    10800
tgagcaaaag gccagcaaaa ggccaggaac cgtaaaaagg ccgcgttgct ggcgtttttc    10860
cataggctcc gcccccctga cgagcatcac aaaaatcgac gctcaagtca gaggtggcga    10920
aacccgacag gactataaag ataccaggcg tttccccctg gaagctccct cgtgcgctct    10980
cctgttccga cctgccgct taccggatac ctgtccgcct ttctcccttc gggaagcgtg    11040
gcgctttctc aatgctcgcg ctgtaggtat ctcagttcgg tgtaggtcgt tcgctccaag    11100
ctgggctgtg tgcacgaacc ccccgttcag cccgaccgct gcgccttatc cggtaactat    11160
cgtcttgagt ccaacccggt aagacacgac ttatcgccac tggcagcagc cactggtaac    11220
aggattagca gagcgaggta tgtaggcggt gctacagagt tcttgaagtg gtggcctaac    11280
tacggctaca ctagaaggac agtatttggt atctgcgctc tgctgaagcc agttaccttc    11340
ggaaaaagag ttggtagctc ttgatccggc aaacaaacca ccgctggtag cggtggtttt    11400
tttgtttgca agcagcagat tacgcgcaga aaaaaaggat ctcaagaaga tcctttgatc    11460
ttttctacgg ggcattctga cgctcagtgg aacgaaaact cacgttaagg gattttggtc    11520
atgagattat caaaaaggat cttcacctag atccttttaa attaaaaatg aagttttaaa    11580
tcaatctaaa gtatatatga gtaaacttgg tctgacagtt accaatgctt aatcagtgag    11640
gcacctatct cagcgatctg tctatttcgt tcatccatag ttgcctgact ccccgtcgtg    11700
tagataacta cgatacggga gggcttacca tctggcccca gtgctgcaat gataccgcga    11760
gacccacgct caccggctcc agatttatca gcaataaacc agccagccgg aagggccgag    11820
cgcagaagtg gtcctgcaac tttatccgcc tccatccagt ctattaattg ttgccgggaa    11880
gctagagtaa gtagttcgcc agttaatagt ttgcgcaacg ttgttgccat tgctacaggc    11940
atcgtggtgt cacgctcgtc gtttggtatg gcttcattca gctccggttc ccaacgatca    12000
aggcgagtta catgatcccc catgttgtgc aaaaaagcgg ttagctcctt cggtcctccg    12060
atcgttgtca gaagtaagtt ggccgcagtg ttatcactca tggttatggc agcactgcat    12120
aattctctta ctgtcatgcc atccgtaaga tgcttttctg tgactggtga gtactcaacc    12180
aagtcattct gagaatagtg tatgcggcga ccgagttgct cttgcccggc gtcaatacgg    12240
gataataccg cgccacatag cagaacttta aaagtgctca tcattggaaa acgttcttcg    12300
gggcgaaaac tctcaaggat cttaccgctg ttgagatcca gttcgatgta acccactcgt    12360
gcacccaact gatcttcagc atcttttact ttcaccagcg tttctgggtg agcaaaaaca    12420
ggaaggcaaa atgccgcaaa aaagggaata agggcgacac ggaaatgttg aatactcata    12480
ctcttccttt ttcaatatta ttgaagcatt tatcagggtt attgtctcat gagcggatac    12540
atatttgaat gtatttagaa aaataaacaa ataggggttc cgcgcacatt tccccgaaaa    12600
gtgccacctg acgtctaaga aaccattatt atcatgacat taacctataa aaataggcgt    12660
atcacgaggc cctttcgtct cgcgcgtttc ggtgatgacg tgaaaacct ctgacacatg    12720 cagctcccgg agacggtcac agcttctgtc taagcggatg ccgggagcag acaagcccgt    12780
```

```
cagggcgcgt cagcgggtgt tggcgggtgt cggggctggc ttaactatgc ggcatcagag    12840
cagattgtac tgagagtgca ccatatcgac gctctccctt atgcgactcc tgcattagga    12900
agcagcccag tactaggttg aggccgttga gcaccgccgc cgcaaggaat ggtgcatgcg    12960
taatcaatta cggggtcatt agttcatagc ccatatatgg agttccgcgt tacataactt    13020
acggtaaatg gcccgcctgg ctgaccgccc aacgacccc gcccattgac gtcaataatg     13080
acgtatgttc ccatagtaac gccaataggg actttccatt gacgtcaatg ggtggagtat    13140
ttacggtaaa ctgcccactt ggcagtacat caagtgtatc atatgccaag tacgccccct    13200
attgacgtca atgacggtaa atggcccgcc tggcattatg cccagtacat gaccttatgg    13260
gactttccta cttggcagta catctacgta ttagtcatcg ctattaccat ggtgatgcgg    13320
ttttggcagt acatcaatgg gcgtggatag cggtttgact cacggggatt ccaagtctc     13380 cacccattg acgtcaatgg gagtttgttt tggcaccaaa atcaacggga ctttccaaaa     13440
tgtcgtaaca actccgcccc attgacgcaa atgggcggta ggcgtgtacg gtgggaggtc    13500
tatataagca gagctctctg gctaactaga gaacccactg cttaactggc ttatcgaaat    13560
taatacgact cactataggg agaccggaag cttgaattc                           13599
```

<210> SEQ ID NO 21
<211> LENGTH: 6221
<212> TYPE: DNA
<213> ORGANISM: Artificial Sequence
<220> FEATURE:
<223> OTHER INFORMATION: synthetic construct

<400> SEQUENCE: 21

```
gacggatcgg gagatctccc gatccctat ggtcgactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagaccaa gctggctagc     900 gtttaaacgg gccctctaga atgacagtgc tggcgccagc ctggagccca aattcctccc    960
tgttgctgct gttgctgctg ctgagtcctt gcctgcgggg gacacctgac tgttacttca    1020
gccacagtcc catctcctcc aacttcaaag tgaagtttag agagttgact gaccacctgc    1080
ttaaagatta cccagtcact gtggccgtca atcttcagga cgagaagcac tgcaaggcct    1140 tgtgggagcct cttcctagcc cagcgctgga tagagcaact gaagactgtg gcagggtcta    1200
```

```
agatgcaaac gcttctggag gacgtcaaca ccgagataca ttttgtcacc tcatgtacct   1260
tccagcccct accagaatgt ctgcgattcg tccagaccaa catctcccac ctcctgaagg   1320
acacctgcac acagctgctt gctctgaagc cctgtatcgg gaaggcctgc cagaatttct   1380
ctcggtgcct ggaggtgcag tgccagccgg actcctccac cctgctgccc ccaaggagtc   1440
ccatagccct agaagccacg gagctcccag agcctcggcc caggcaggga tccatgcatg   1500
gagatacacc tacattgcat gaatatatgt tagatttgca accagagaca actgatctct   1560
actgttatga gcaattaaat gacagctcag aggaggagga tgaaatagat ggtccagctg   1620
gacaagcaga accggacaga gcccattaca atattgtaac cttttgttgc aagtgtgact   1680
ctacgcttcg gttgtgcgta caaagcacac acgtagacat tcgtactttg gaagacctgt   1740
taatgggcac actaggaatt gtgtgcccca tctgttctca ggataagctt aagtttaaac   1800
cgctgatcag cctcgactgt gccttctagt tgccagccat ctgttgtttg ccctccccc    1860
gtgccttcct tgaccctgga aggtgccact cccactgtcc tttcctaata aaatgaggaa   1920
attgcatcgc attgtctgag taggtgtcat tctattctgg ggggtggggt ggggcaggac   1980
agcaaggggg aggattggga agacaatagc aggcatgctg gggatgcggt gggctctatg   2040
gcttctgagg cggaaagaac cagctggggc tctagggggt atccccacgc gccctgtagc   2100
ggcgcattaa gcgcggcggg tgtggtggtt acgcgcagcg tgaccgctac acttgccagc   2160
gccctagcgc ccgctccttt cgctttcttc ccttcctttc tcgccacgtt cgccggcttt   2220
ccccgtcaag ctctaaatcg ggcatccct  ttagggttcc gatttagtgc tttacggcac   2280
ctcgacccca aaaaacttga ttagggtgat ggttcacgta gtgggccatc gccctgatag   2340
acggttttc gcccttgac gttggagtcc acgttcttta atagtggact cttgttccaa    2400
actggaacaa cactcaaccc tatctcggtc tattcttttg atttataagg gattttgggg   2460
atttcggcct attggttaaa aaatgagctg atttaacaaa aatttaacgc gaattaattc   2520
tgtggaatgt gtgtcagtta gggtgtggaa agtccccagg ctccccaggc aggcagaagt   2580
atgcaaagca tgcatctcaa ttagtcagca accaggtgtg gaaagtcccc aggctcccca   2640
gcaggcagaa gtatgcaaag catgcatctc aattagtcag caaccatagt cccgccccta   2700
actccgccca tcccgcccct aactccgccc agttccgccc attctccgcc ccatggctga   2760
ctaattttt ttatttatgc agaggccgag gccgcctctg cctctgagct attccagaag   2820
tagtgaggag gcttttttgg aggcctaggc ttttgcaaaa agctcccggg agcttgtata   2880
tccattttcg gatctgatca agagacagga tgaggatcgt ttcgcatgat tgaacaagat   2940
ggattgcacg caggttctcc ggccgcttgg gtggagaggc tattcggcta tgactgggca   3000
caacagacaa tcggctgctc tgatgccgcc gtgttccggc tgtcagcgca ggggcgcccg   3060
gttcttttg tcaagaccga cctgtccggt gccctgaatg aactgcagga cgaggcagcg   3120
cggctatcgt ggctggccac gacgggcgtt ccttgcgcag ctgtgctcga cgttgtcact   3180
gaagcgggaa gggactggct gctattgggc gaagtgccgg gcaggatct cctgtcatct   3240
caccttgctc ctgccgagaa agtatccatc atggctgatg caatgcggcg gctgcatacg   3300
cttgatccgg ctacctgccc attcgaccac caagcgaaac atcgcatcga gcgagcacgt   3360
actcggatga agccggtct tgtcgatcag gatgatctgg acgaagagca tcaggggctc   3420
gcgccagccg aactgttcgc caggctcaag gcgcgcatgc ccgacggcga ggatctcgtc   3480
gtgacccatg gcgatgcctg cttgccgaat atcatggtgg aaaatggccg cttttctgga   3540
ttcatcgact gtggccggct gggtgtggcg gaccgctatc aggacatagc gttggctacc   3600
```

-continued

```
cgtgatattg ctgaagagct tggcggcgaa tgggctgacc gcttcctcgt gctttacggt    3660
atcgccgctc ccgattcgca gcgcatcgcc ttctatcgcc ttcttgacga gttcttctga    3720
gcgggactct ggggttcgaa atgaccgacc aagcgacgcc caacctgcca tcacgagatt    3780
tcgattccac cgccgccttc tatgaaaggt tgggcttcgg aatcgttttc cgggacgccg    3840
gctggatgat cctccagcgc ggggatctca tgctggagtt cttcgcccac cccaacttgt    3900
ttattgcagc ttataatggt tacaaataaa gcaatagcat cacaaatttc acaaataaag    3960
catttttttc actgcattct agttgtggtt tgtccaaact catcaatgta tcttatcatg    4020
tctgtatacc gtcgacctct agctagagct tggcgtaatc atggtcatag ctgtttcctg    4080
tgtgaaattg ttatccgctc acaattccac acaacatacg agccgaagc ataaagtgta    4140 aagcctgggg tgcctaatga gtgagctaac tcacattaat tgcgttgcgc tcactgcccg    4200
ctttccagtc gggaaacctg tcgtgccagc tgcattaatg aatcggccaa cgcgcgggga    4260
gaggcggttt gcgtattggg cgctcttccg cttcctcgct cactgactcg ctgcgctcgg    4320
tcgttcggct gcggcgagcg gtatcagctc actcaaaggc ggtaatacgg ttatccacag    4380
aatcagggga taacgcagga agaacatgt gagcaaaagg ccagcaaaag gccaggaacc    4440
gtaaaaaggc cgcgttgctg cgttttttcc ataggctccg cccccctgac gagcatcaca    4500
aaaatcgacg ctcaagtcag aggtggcgaa acccgacagg actataaaga taccaggcgt    4560
ttccccctgg aagctccctc gtgcgctctc ctgttccgac cctgccgctt accggatacc    4620
tgtccgcctt tctcccttcg ggaagcgtgg cgctttctca atgctcacgc tgtaggtatc    4680
tcagttcggt gtaggtcgtt cgctccaagc tgggctgtgt gcacgaaccc ccgttcagc    4740 ccgaccgctg cgccttatcc ggtaactatc gtcttgagtc aacccggta agacacgact    4800 tatcgccact ggcagcagcc actggtaaca ggattagcag agcgaggtat gtaggcggtg    4860
ctacagagtt cttgaagtgg tggcctaact acggctacac tagaaggaca gtatttggta    4920
tctgcgctct gctgaagcca gttaccttcg gaaaaagagt tggtagctct tgatccggca    4980
aacaaaccac cgctggtagc ggtggttttt tgtttgcaa gcagcagatt acgcgcagaa    5040
aaaaaggatc tcaagaagat cctttgatct tttctacggg gtctgacgct cagtggaacg    5100
aaaactcacg ttaagggatt ttggtcatga gattatcaaa aaggatcttc acctagatcc    5160
ttttaaatta aaaatgaagt tttaaatcaa tctaaagtat atatgagtaa acttggtctg    5220
acagttacca atgcttaatc agtgaggcac ctatctcagc gatctgtcta tttcgttcat    5280
ccatagttgc ctgactcccc gtcgtgtaga taactacgat acgggagggc ttaccatctg    5340
gccccagtgc tgcaatgata ccgcgagacc cacgctcacc ggctccagat ttatcagcaa    5400
taaaccagcc agccggaagg gccgagcgca gaagtggtcc tgcaacttta tccgcctcca    5460
tccagtctat taattgttgc cgggaagcta gagtaagtag ttcgccagtt aatagtttgc    5520
gcaacgttgt tgccattgct acaggcatcg tggtgtcacg ctcgtcgttt ggtatggctt    5580
cattcagctc cggttcccaa cgatcaaggc gagttacatg atcccccatg ttgtgcaaaa    5640
aagcggttag ctccttcggt cctccgatcg ttgtcagaag taagttggcc gcagtgttat    5700
cactcatggt tatggcagca ctgcataatt ctcttactgt catgccatcc gtaagatgct    5760
tttctgtgac tggtgagtac tcaaccaagt cattctgaga atagtgtatg cggcgaccga    5820
gttgctcttg cccggcgtca atacgggata ataccgcgcc acatagcaga actttaaaag    5880
tgctcatcat tggaaaacgt tcttcggggc gaaaactctc aaggatctta ccgctgttga    5940
```

```
gatccagttc gatgtaaccc actcgtgcac ccaactgatc ttcagcatct tttactttca      6000
ccagcgtttc tgggtgagca aaaacaggaa ggcaaaatgc cgcaaaaaag ggaataaggg      6060
cgacacggaa atgttgaata ctcatactct tcctttttca atattattga agcatttatc      6120
agggttattg tctcatgagc ggatacatat ttgaatgtat ttagaaaaat aaacaaatag      6180
gggttccgcg cacatttccc cgaaaagtgc cacctgacgt c                          6221
```

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

<400> SEQUENCE: 22

Arg Ala His Tyr Asn Ile Val Thr Phe
1               5

<210> SEQ ID NO 23
<211> LENGTH: 38
<212> TYPE: PRT
<213> ORGANISM: Artificial Sequence
<220> FEATURE:
<223> OTHER INFORMATION: synthetic peptide

<400> SEQUENCE: 23

Asp Ser Ser Glu Glu Glu Asp Glu Ile Asp Gly Pro Ala Gly Gln Ala
1               5                   10                  15

Glu Pro Asp Arg Ala His Tyr Asn Ile Val Thr Phe Cys Cys Lys Cys
            20                  25                  30

Asp Ser Thr Leu Arg Leu
        35

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24

```
atcggatcca tggtgagcaa gggcgaggag                                         30
```

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25

```
gggaagcttt acttgtacag ctcgtccatg                                         30
```

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26

```
ggggaattca tgcatggaga tacaccta                                           28
```

```
<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
ggtggatcct tgagaacaga tgg                                              23

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
gggtctagaa tgacagtgct ggcgccagc                                        29

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
gggggatccc tgcctgggcc gaggctctgg                                       30

<210> SEQ ID NO 30
<211> LENGTH: 30
<212> TYPE: DNA
<213> ORGANISM: Artificial Sequence
<220> FEATURE:
<223> OTHER INFORMATION: primer

<400> SEQUENCE: 30
atcggatcca tggtgagcaa gggcgaggag                                       30

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
gggaagcttt acttgtacag ctcgtccatg                                       30

<210> SEQ ID NO 32
<211> LENGTH: 28
<212> TYPE: DNA
<213> ORGANISM: Artificial Sequence
<220> FEATURE:
<223> OTHER INFORMATION: primer

<400> SEQUENCE: 32
ggggaattca tgcatggaga tacaccta                                         28

<210> SEQ ID NO 33
<211> LENGTH: 23
<212> TYPE: DNA
<213> ORGANISM: Artificial Sequence
<220> FEATURE:
<223> OTHER INFORMATION: primer
```

-continued

```
<400> SEQUENCE: 33
ggtggatcct tgagaacaga tgg                                              23

<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
gggtctagaa tgacagtgct ggcgccagc                                        29

<210> SEQ ID NO 35
<211> LENGTH: 29
<212> TYPE: DNA
<213> ORGANISM: Artificial Sequence
<220> FEATURE:
<223> OTHER INFORMATION: primer

<400> SEQUENCE: 35
cgagaattcc tgcctgggcc gaggctctg                                        29
```